(12) United States Patent
Min et al.

(10) Patent No.: US 11,094,060 B1
(45) Date of Patent: Aug. 17, 2021

(54) SYSTEMS, METHODS, AND DEVICES FOR MEDICAL IMAGE ANALYSIS, DIAGNOSIS, RISK STRATIFICATION, DECISION MAKING AND/OR DISEASE TRACKING

(71) Applicant: CLEERLY, INC., New York, NY (US)

(72) Inventors: James K. Min, Brooklyn, NY (US); James P. Earls, Fairfax Station, VA (US); Hugo Miguel Rodrigues Marques, Lisbon (PT)

(73) Assignee: Cleerly, Inc., New York, NY (US)

( * ) Notice: Subject to any disclaimer, the term of this patent is extended or adjusted under 35 U.S.C. 154(b) by 0 days.

(21) Appl. No.: 17/213,966

(22) Filed: Mar. 26, 2021

Related U.S. Application Data

(63) Continuation of application No. 17/142,120, filed on Jan. 5, 2021.
(Continued)

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/0066* (2013.01); *A61B 5/0075* (2013.01);
(Continued)

(58) Field of Classification Search
CPC ......... G06T 7/0012; G06T 2207/30101; G06T 2207/10081; G06T 2207/20081;
(Continued)

(56) References Cited

U.S. PATENT DOCUMENTS

| 4,945,478 A | 7/1990 | Merickel et al. |
| 5,722,408 A | 3/1998 | Dehner et al. |

(Continued)

FOREIGN PATENT DOCUMENTS

| CA | 2368390 C | 7/2010 |
| EP | 3431005 A1 | 1/2019 |

(Continued)

OTHER PUBLICATIONS

Abbara et al., "SCCT Guidelines for the performance and acquisition of coronary computed tomographic angiography: A report of the society of Cardiovascular Computed Tomography Guidelines Committee: Endorsed by the North American Society for Cardiovascular Imaging (NASCI)." Journal of cardiovascular computed tomography 2016; 10(6) pp. 435-449.

(Continued)

*Primary Examiner* — Tom Y Lu
(74) *Attorney, Agent, or Firm* — Knobbe, Martens, Olson & Bear, LLP

(57) ABSTRACT

The disclosure herein relates to systems, methods, and devices for medical image analysis, diagnosis, risk stratification, decision making and/or disease tracking. In some embodiments, the systems, devices, and methods described herein are configured to analyze non-invasive medical images of a subject to automatically and/or dynamically identify one or more features, such as plaque and vessels, and/or derive one or more quantified plaque parameters, such as radiodensity, radiodensity composition, volume, radiodensity heterogeneity, geometry, location, and/or the like. In some embodiments, the systems, devices, and methods described herein are further configured to generate one or more assessments of plaque-based diseases from raw medical images using one or more of the identified features and/or quantified parameters.

30 Claims, 66 Drawing Sheets

Related U.S. Application Data

(60) Provisional application No. 62/958,032, filed on Jan. 7, 2020.

(51) Int. Cl.

| | | |
|---|---|---|
| *A61B 8/14* | (2006.01) | |
| *A61B 6/00* | (2006.01) | |
| *A61B 6/03* | (2006.01) | |
| *A61B 5/00* | (2006.01) | |
| *A61B 8/12* | (2006.01) | |
| *G06K 9/62* | (2006.01) | |
| *A61B 5/055* | (2006.01) | |
| *A61K 49/04* | (2006.01) | |

(52) U.S. Cl.
CPC ............ *A61B 5/055* (2013.01); *A61B 5/7267* (2013.01); *A61B 5/742* (2013.01); *A61B 5/7475* (2013.01); *A61B 6/032* (2013.01); *A61B 6/037* (2013.01); *A61B 6/481* (2013.01); *A61B 6/504* (2013.01); *A61B 6/5205* (2013.01); *A61B 8/12* (2013.01); *A61B 8/14* (2013.01); *A61K 49/04* (2013.01); *G06K 9/6298* (2013.01); *G06T 2207/10081* (2013.01); *G06T 2207/10088* (2013.01); *G06T 2207/10101* (2013.01); *G06T 2207/10132* (2013.01); *G06T 2207/20081* (2013.01); *G06T 2207/30048* (2013.01); *G06T 2207/30101* (2013.01)

(58) Field of Classification Search
CPC . G06T 2207/10101; G06T 2207/10132; G06T 2207/30048; G06T 2207/10088; A61B 5/7475; A61B 6/481; A61B 6/037; A61B 6/032; A61B 5/0075; A61B 5/7267; A61B 5/0066; A61B 8/14; A61B 5/742; A61B 5/055; A61B 6/5205; A61B 8/12; A61B 6/504; G06K 9/6298; A61K 49/04
See application file for complete search history.

(56) References Cited

U.S. PATENT DOCUMENTS

| | | | |
|---|---|---|---|
| 5,891,030 | A | 4/1999 | Johnson et al. |
| 6,047,080 | A | 4/2000 | Chen et al. |
| 6,591,004 | B1 | 7/2003 | VanEssen et al. |
| 7,535,986 | B2 | 5/2009 | Hempel |
| 7,558,611 | B2 | 7/2009 | Arnold et al. |
| 7,570,983 | B2 | 8/2009 | Becker et al. |
| 7,711,165 | B2 | 5/2010 | Lesage et al. |
| 7,715,626 | B2 | 5/2010 | Florin et al. |
| 7,805,385 | B2 | 9/2010 | Steck et al. |
| 7,813,549 | B2 | 10/2010 | Buelow et al. |
| 7,840,062 | B2 | 11/2010 | Boroczky et al. |
| 7,860,283 | B2 | 12/2010 | Begelman et al. |
| 7,899,764 | B2 | 3/2011 | Martin et al. |
| 7,904,977 | B1 | 3/2011 | Singh |
| 7,912,528 | B2 | 3/2011 | Krishnan et al. |
| 7,940,974 | B2 | 5/2011 | Skinner et al. |
| 7,940,977 | B2 | 5/2011 | Begelman et al. |
| 7,953,266 | B2 | 5/2011 | Gulsun et al. |
| 7,993,274 | B2 | 8/2011 | Pruvot et al. |
| 8,046,488 | B2 | 10/2011 | Cherukuri et al. |
| 8,068,894 | B2 | 11/2011 | Huizenga et al. |
| 8,144,949 | B2 | 3/2012 | Simon et al. |
| 8,200,466 | B2 | 6/2012 | Spiker et al. |
| 8,386,188 | B2 | 2/2013 | Taylor et al. |
| 8,526,699 | B2 | 9/2013 | Mittal et al. |
| 8,582,854 | B2 | 11/2013 | Zhang et al. |
| 8,605,979 | B2 * | 12/2013 | Arnold ..................... G06T 7/62 382/131 |
| 8,774,479 | B2 | 7/2014 | Madabhushi et al. |
| 8,777,854 | B2 | 7/2014 | Patwardhan et al. |
| 8,885,905 | B2 | 11/2014 | Dey et al. |
| 8,938,106 | B2 | 1/2015 | Aulbach et al. |
| 9,008,392 | B1 | 4/2015 | Bai et al. |
| 9,058,692 | B1 | 6/2015 | Grady et al. |
| 9,070,214 | B1 | 6/2015 | Grady et al. |
| 9,081,721 | B1 | 7/2015 | Grady et al. |
| 9,129,417 | B2 | 9/2015 | Zheng et al. |
| 9,155,512 | B2 | 10/2015 | Choi et al. |
| 9,159,159 | B2 | 10/2015 | Bai et al. |
| 9,195,801 | B1 | 11/2015 | Sankaran et al. |
| 9,220,418 | B2 | 12/2015 | Choi et al. |
| 9,220,419 | B2 | 12/2015 | Choi et al. |
| 9,235,887 | B2 | 1/2016 | Bucker et al. |
| 9,239,905 | B1 | 1/2016 | Sankaran et al. |
| 9,280,639 | B2 | 3/2016 | Sankaran et al. |
| 9,295,397 | B2 | 3/2016 | Liu et al. |
| 9,295,429 | B2 | 3/2016 | Ong et al. |
| 9,378,580 | B2 | 6/2016 | Grady et al. |
| 9,430,827 | B2 | 8/2016 | Kelm et al. |
| 9,538,925 | B2 | 1/2017 | Sharma et al. |
| 9,610,272 | B2 | 4/2017 | Soni |
| 9,642,586 | B2 | 5/2017 | Kelm et al. |
| 9,649,171 | B2 | 5/2017 | Sankaran et al. |
| 9,655,563 | B2 | 5/2017 | Liu et al. |
| 9,700,219 | B2 | 7/2017 | Sharma et al. |
| 9,721,340 | B2 | 8/2017 | Gillies et al. |
| 9,761,004 | B2 | 9/2017 | Mittal et al. |
| 9,767,557 | B1 | 9/2017 | Gulsun et al. |
| 9,770,303 | B2 | 9/2017 | Choi et al. |
| 9,785,748 | B2 | 10/2017 | Koo et al. |
| 9,805,463 | B2 | 10/2017 | Choi et al. |
| 9,805,470 | B2 | 10/2017 | Bhatia et al. |
| 9,836,653 | B2 | 12/2017 | Schnittman |
| 9,839,399 | B2 | 12/2017 | Fonte et al. |
| 9,839,484 | B2 | 12/2017 | Taylor |
| 9,881,372 | B2 | 1/2018 | Gulsun et al. |
| 9,965,891 | B2 | 5/2018 | Grady et al. |
| 10,078,124 | B2 | 9/2018 | Horkay et al. |
| 10,082,553 | B2 | 9/2018 | Boss |
| 10,170,206 | B2 | 1/2019 | Koo et al. |
| 10,176,408 | B2 | 1/2019 | Paik et al. |
| 10,456,094 | B2 | 10/2019 | Fonte et al. |
| 10,478,130 | B2 | 11/2019 | Sharma et al. |
| 10,483,006 | B2 | 11/2019 | Itu et al. |
| 10,517,677 | B2 | 12/2019 | Sankaran et al. |
| 10,776,988 | B2 | 9/2020 | Grady et al. |
| 10,813,612 | B2 | 10/2020 | Min |
| 10,929,828 | B2 | 2/2021 | Fonte et al. |
| 10,939,960 | B2 | 3/2021 | Choi et al. |
| 10,945,606 | B2 | 3/2021 | Sanders et al. |
| 10,951,715 | B2 | 3/2021 | Hart et al. |
| 10,964,071 | B2 | 3/2021 | Grady et al. |
| 10,966,619 | B2 | 4/2021 | Fonte et al. |
| 10,973,583 | B2 | 4/2021 | Taylor et al. |
| 10,978,210 | B2 | 4/2021 | Grady et al. |
| 10,984,535 | B2 | 4/2021 | Grady et al. |
| 10,987,010 | B2 | 4/2021 | Grady et al. |
| 10,990,652 | B2 | 4/2021 | Taylor et al. |
| 10,991,465 | B2 | 4/2021 | Grady |
| 2004/0101181 | A1 | 5/2004 | Giger et al. |
| 2004/0133094 | A1 | 7/2004 | Becker et al. |
| 2004/0136491 | A1 * | 7/2004 | Iatrou .................. A61B 6/4035 378/4 |
| 2005/0043614 | A1 | 2/2005 | Huizenga et al. |
| 2005/0110791 | A1 | 5/2005 | Krishnamoorthy et al. |
| 2005/0118632 | A1 | 6/2005 | Chen et al. |
| 2006/0036167 | A1 | 2/2006 | Shina |
| 2006/0101075 | A1 * | 5/2006 | Lehel ..................... A61B 6/503 |
| 2007/0018558 | A1 | 1/2007 | Chua et al. |
| 2007/0019778 | A1 | 1/2007 | Clouse et al. |
| 2007/0248250 | A1 | 10/2007 | Gulsun et al. |
| 2007/0260141 | A1 * | 11/2007 | Margolis .................. A61B 8/12 600/437 |
| 2008/0100621 | A1 | 5/2008 | Aharon et al. |
| 2008/0103389 | A1 | 5/2008 | Begelman et al. |
| 2008/0119734 | A1 | 5/2008 | Pruvot et al. |
| 2008/0187199 | A1 | 8/2008 | Gulsun et al. |
| 2008/0188962 | A1 | 8/2008 | Suryanarayanan et al. |

(56) References Cited

U.S. PATENT DOCUMENTS

| | | |
|---|---|---|
| 2009/0012382 A1 | 1/2009 | Dutta et al. |
| 2009/0016588 A1 | 1/2009 | Slabaugh et al. |
| 2009/0129673 A1 | 5/2009 | Simon et al. |
| 2009/0276161 A1 | 11/2009 | Cobain |
| 2009/0278846 A1 | 11/2009 | Gulsun et al. |
| 2010/0137711 A1 | 6/2010 | Hamilton et al. |
| 2010/0177945 A1 | 7/2010 | Moriya |
| 2010/0201786 A1 | 8/2010 | Schaefer et al. |
| 2010/0316274 A1* | 12/2010 | Langheinrich ......... A61B 6/032 382/130 |
| 2011/0026798 A1 | 2/2011 | Madabhushi et al. |
| 2011/0206247 A1* | 8/2011 | Dachille ............... G06T 11/001 382/128 |
| 2011/0245650 A1 | 10/2011 | Kerwin et al. |
| 2012/0041323 A1 | 2/2012 | Taylor et al. |
| 2012/0076377 A1* | 3/2012 | Dutta .................... A61B 6/032 382/131 |
| 2012/0128132 A1 | 5/2012 | Coolens et al. |
| 2012/0243764 A1 | 9/2012 | Dey et al. |
| 2012/0263368 A1 | 10/2012 | Nakano et al. |
| 2013/0101187 A1 | 4/2013 | Sundar et al. |
| 2013/0246034 A1 | 9/2013 | Sharma et al. |
| 2014/0058715 A1 | 2/2014 | Sharma et al. |
| 2014/0073976 A1 | 3/2014 | Fonte et al. |
| 2014/0114176 A1 | 4/2014 | Hirschenbain et al. |
| 2015/0066818 A1 | 3/2015 | Choi et al. |
| 2016/0066861 A1* | 3/2016 | Taylor .................. A61B 5/0044 600/485 |
| 2016/0292372 A1 | 10/2016 | Kamen et al. |
| 2016/0296288 A1 | 10/2016 | Sankaran et al. |
| 2016/0300350 A1 | 10/2016 | Choi et al. |
| 2016/0346043 A1 | 12/2016 | Jaquet et al. |
| 2017/0014034 A1 | 1/2017 | Koo et al. |
| 2017/0018081 A1 | 1/2017 | Taylor et al. |
| 2017/0046484 A1 | 2/2017 | Buckler et al. |
| 2017/0103525 A1 | 4/2017 | Hu et al. |
| 2017/0119333 A1 | 5/2017 | Zebaze et al. |
| 2017/0202621 A1 | 7/2017 | Taylor |
| 2017/0245821 A1 | 8/2017 | Itu et al. |
| 2017/0265831 A1 | 9/2017 | Sankaran et al. |
| 2017/0265832 A1 | 9/2017 | Antodiades |
| 2017/0340393 A1 | 11/2017 | Choi et al. |
| 2018/0165811 A1 | 6/2018 | Flohr et al. |
| 2018/0179189 A1 | 6/2018 | MacPhee et al. |
| 2018/0225847 A1 | 8/2018 | Grady et al. |
| 2018/0243033 A1 | 8/2018 | Tran et al. |
| 2018/0330477 A1 | 11/2018 | Paik et al. |
| 2019/0074082 A1 | 3/2019 | Buckler et al. |
| 2019/0159737 A1 | 5/2019 | Buckler et al. |
| 2019/0172197 A1 | 6/2019 | Buckler et al. |
| 2019/0174082 A1 | 6/2019 | Taruki et al. |
| 2019/0180153 A1 | 6/2019 | Buckler et al. |
| 2019/0180438 A1 | 6/2019 | Buckler et al. |
| 2019/0244347 A1 | 8/2019 | Buckler et al. |
| 2019/0244348 A1 | 8/2019 | Buckler et al. |
| 2020/0069262 A1 | 3/2020 | Fonte et al. |
| 2020/0085501 A1 | 3/2020 | Sankaran et al. |
| 2020/0237329 A1 | 7/2020 | Min |
| 2020/0372701 A1 | 11/2020 | Grady et al. |
| 2021/0007807 A1 | 1/2021 | Sankaran et al. |
| 2021/0030478 A1 | 2/2021 | Hart et al. |
| 2021/0042918 A1 | 2/2021 | Bucker |
| 2021/0042927 A1* | 2/2021 | Amis ................... G06T 11/008 |
| 2021/0074435 A1 | 3/2021 | Taylor et al. |
| 2021/0077196 A1 | 3/2021 | Jaquet et al. |
| 2021/0082579 A1 | 3/2021 | Grady et al. |
| 2021/0093384 A1 | 4/2021 | Grady et al. |

FOREIGN PATENT DOCUMENTS

| | | |
|---|---|---|
| FR | 2908976 A1 | 5/2008 |
| JP | 5305821 B2 | 10/2013 |
| JP | 6203410 B2 | 9/2017 |
| WO | WO 2009/105530 | 8/2009 |
| WO | WO 2010/067276 | 6/2010 |
| WO | WO 2014/107402 | 7/2014 |
| WO | WO 2015/095282 | 6/2015 |
| WO | WO 2016/022533 | 2/2016 |
| WO | WO 2016 /024128 | 2/2016 |
| WO | WO 2017/011555 | 1/2017 |
| WO | WO 2017/096407 | 6/2017 |
| WO | WO 2017/106819 | 6/2017 |
| WO | WO 2019/033098 | 2/2019 |

OTHER PUBLICATIONS

Achenbach et al. "Detection of calcified and noncalcified coronary atherosclerotic plaque by contrast-enhanced, submillimeter multidetector spiral computed tomography: a segment-based comparison with intravascular ultrasound." Circulation 2004; 109(1) pp. 14-17.

Ahmadi et al., "Association of Coronary Stenosis and Plaque Morphology with Fractional Flow Reserve and Outcomes." JAMA cardiology 2016; 1 (3): 350-7. doi: 10.1001/jamacardio.2016.0263 [published Online First: Jul. 22, 2016].

Ahmadi A. et al. "Do Plaques rapidly progress prior to myocardial infarction? The interplay between plaque vunerability and progression." Circ Res. 2015; 117(1), pp. 99-104.

Ahmadi et al., "Lesion-Specific and Vessel-Related Determinants of Fractional Flow Reserve Beyond Coronary Artery Stenosis", JACCL Cardiovascular Imaging, vol. 11, No. 4. 2018 pp. 521-530.

Antonopoulos et al., "Detecting Human coronary inflammation by imaging perivascular fat", Sci. Transl. Med. 9, eaal2658 (2017) Jul. 12, 2017.

Al'Aref et al. "Clinical Applications of machine learning in cardiovascular disease and its relevance to cardiac imaging." Eur Heart J. Jul. 27, 2018. [Epub ahead of print].

Al'Aref et al., "High-risk atherosclerotic plaque features for cardiovascular risk assessment in the Prospective Multicenter Imaging Study for Evaluation of Chest Pain trial", Cardiovascular Diagnosis and Therapy,vol. 9, No. 1, Feb. 2019. pp. 89-93.

Arbab-Zadeh et al., "Contemporary Reviews in Cardiovascular Medicine, Acute Coronary Events", Amercan Heart Assocation, Inc., Circulation. 2012;125:1147-1156, Mar. 6, 2012, pp. 1147-1156.

Arbab-Zadeh, et al. "the myth of the vulnerable plaque: transitioning from a focus on individual lesions to atherosclerotic disease burden for coronary artery disease risk assessment." J Am Coll Cardiol. 2015;65: 846-855.

Bakhasi, et al. "Comparative Effectiveness of CT-Derived Atherosclerotic Plaque Metrics for Predicting Myocardial Ischemia." JACC Cardiovasc Imaging. Jul. 13, 2018. doi: 10.2013/j.jcmg.2018. 05.019. [Epub ahead of print].

Baskaran et al., "Dense calcium and lesion-specific ischemia: A comparison of CCTA with fractional flow reserve", Atherosclerosis 260, 2017 pp. 163-168.

Benjamin, et al. "Heart Disease and Stroke Statistics-2018 Update: A Report From the American Heart Association." Circulation. 2018;137: e67-e492.

Bergman "Using Multicoloured Halftsone Screens for Offset Print Quality Monitoring", Linköping Studies in Science and Technology; LiU-TEK-LIC-2005:02.

Blankstein R. et al. "Coronary CTA in the Evaluation of Stable Chest Pain: Clear Benefits, But Not for All." J Am Coll Cardiol 2017; 69 (14): 1771-73. doi: 10.1016/j.jacc.2017.02.011 [published Online First: Apr. 8, 2017].

Boogers, et al. "Automated Quantification of Coronary Plaque with Computed Tomography: Comparison with Intravascular Ultrasound using a Dedicated Registration Algorithm for Fusion-Based Quantification", Epub, (2012).

Budoff MJ, et al. "Diagnostic performance of 64-multidetector row coronary computed tomographic angiography for evaluation of coronary artery stenosis in individuals without know coronary artery disease: results from the prospective multicenter ACCURACY (Assessment by Coronary Computed Tomography of Individuals Undergoing Invasive Coronary Angiography) trial." J Am Coll Cardiol 2008; 52(21): 1724-32.

(56) References Cited

OTHER PUBLICATIONS

Bzdok "Classical Statistics and Statistical Learning in Imaging Neuroscience." Front Neurosci. 2017; 11:543.
Calvert, et al. "Association between IVUS Findings and Adverse Outcomes in Patients with Coronary Artery Disease: the VIVA (VH-IVUS in Vulnerable Atherosclerosis) Study." JACC Cardiovasc Imaging. 2011;4: 894-901.
Celeng, et al. "Non-invasive and Invasive Imaging of Vulnerable Coronary Plaque." trends Cardiovasc Med. 2016;26-538-47.
Cerqueira et al. "Standardized myocardial segmentation and nomenclature for tomographic imaging of the heart. A statement for healthcare professinals from the Cardiac Imaging Committee of the Council on Clinical Cardiology of the American Heart Association." Int J Cardiovasc Imaging 2002; 18(1): 539-42.
Chang et al., "Coronary Atherosclerotic Precursors of Acute Coronary Syndromes", Journal of the American College of Cardiology, vol. 71, No. 22, Jun. 5, 2018. pp. 2511-2522.
Chang et al., "Selective Referral Using CCTA Versus Direct Referral for Individuals Referred to Invasive Coronary Angiography for Suspected CAD", JACC: Cardiovascular Imaging, vol. 12, No. 7, Jul. 2019. pp. 1303-1312.
Chung et al. "Image Segmentation Methods for Detecting Blood Vessels in Angiography", 2006 9th Int. Conf. Control, Automation, Robotics and Vision, Singapore, Dec. 5-8, 2006, ICARCV 2006, pp. 1424-1429.
Costopoulos, et al. "Intravascular Ultrasound and Optical Coherence Tomography Imaging of Coronary Atherosclerosis." Int J Cardiovasc Imaging. 2016;32: 189-200.
Cury, et al. "CAD-RADS ™ Coronary Artery Disease—Reporting and Data System. An Expert consensus documents of the Society of Cardiovascular Computed Tomography (SCCT), the American College of Radiology (ACR) and the North American Society for Cardiovascular Imaging (NASCI)." Endorsed by the American COllege of Cardiology. J Cardiovasc COmput Tomogr. 2016;10: 269-81.
Danad et al. "Comparison of Coronary CT Angiography, SPECT, PET, and Hybrid Imaging for Diagnosis of Ischemic Heart Disease Determined by Fractional Flow Reserve." JAMA Cardiol 2017; 2 (10): 1100-07. doi 10.1001/jamacardio.2017.2471 [published Online First: Aug. 17, 2017].
De Bruyne B. et al. "Fractional flow reserve-guided PCI for stable coronary artery disease." The New England journal of medicine 2014; 371 (13): 1208-17. doi: 10.1056/NEJMoal408758 [published Online First: Sep. 2, 2014].
De Graaf, et al. "Automatic Quantification and Characterization of Coronary Atherosclerosis with Computed Tomography Coronary Angiography: Cross-Correlation with Intravascular Ultrasound Virtual Histology", Int J Cardiovasc, pp. 1177-1190, (2013).
De Graaf, et al. "Feasibility of an Automated Quantitative Computed Tomography Angiography-Derived Risk Stratification of Patients with Suspected CAD." Am J Cardiol (2014).
DeLong ER, et al. "Comparing the areas under two or more correlated receiver operating characteristic curves: a nonparametric approach." Biometrics 1988; 44 (3): 837-45. [published Online First: Sep. 1, 1988].
Dey, et al. "Comparison of Quantitative Atherosclerotic Plaque Burden from Coronary CT Angiography in Patients with First Acute Coronary Syndrome and Stable CAD" J Cardivasc Comput tomogr (2014).
Dey et al., "Direct Quantatitive In Vivo Comparison of Calcified Atherosclerotic Plaque on Vascular MRI and CT by Multimodality Image Registration" Journal of Magnetic Resonance Imaging 23:345-354 (2006).
Dey et al., Integrated prediction of lesion-specific ischemia from quantitative coronary CT Angiography using machine learning: a multicenter study, European Radiology 2018.
Dey, et al. "Non-Invasive Measurement of Coronary Plaque from Coronary CT Angiography and its Clinical Implication", Expert Review of Cardiovascular Therapy (2013).
Diaz-Zamudio, et al. "Automated Quantitiative Plaque Burden from Coronary CT Angiography Non-Invasively Predicts Hemodynamic Significance by Using Fractional Flow Reserve in Intermediate Coronary Lesions." Radiology (2015).
Douglas et al., "Outcomes of Anatomical versus Functional Testing for Coronary Artery Disease", N Engl J Med. Apr. 2, 2015, p. 1291-1300.
Driessen et al., "Adverse Plaque Characteristic Relate More Strongly With Hyperemic Fractional Flow Reserve and Instantenous Wave-Free Ratio Than With Resting Instantaneous Wave-Free Ratio", JACC: Cardiovascular Imaging, 2019, in 11 pages.
Driessen et al., "Effect of Plaque Burden and Morphology on Myocardial Blood Flow and Franctional Flow Reserve", Journal of the American College of Cardiology, vol. 71, No. 5, 2018 p. 499-509.
Dwivedi et al., "Evaluation of Atherosclerotic Plaque in Non-invasice Coronary Imaging", Korean Circulation Journal, Feb. 2018. 48(2), pp. 124-133.
Ehara et al. "Spotty calcification typifies the culprit plaque in patients with acute myocardial infarction: an intravascular ultrasound study." Circulation 2004; 110(22): 3424-9.
Erickson BJ, et al. "Machine Learning for Medical Imaging." Radiographics 2017; 37(2) pp. 505-515.
Ferencik, et al. "Computed Tomography-Based High-Risk Coronary Plaque Score to Predict ACS Among Patients with Acute Chest Pain" Journal of Cardiovascular Computed Tomography, (2015).
Ferencik et al., "Use of High-Risk Coronary Atherosclerotic Plaque Detection for Risk Stratification of Patients With Stable Chest Pain", JAMA Cardiol, Feb. 2018 in 19 pages.
Fihn et al. "2012 ACCF/AHA/ACP/AATS/PCNA/SCAI/STS Guideline for the Diagnosis and the Management of Patients With Statble Ischemic Heart Disease: Executive Summary: A Report of the American College of Cardiology Foundation/American Heart Association Task Force on Practice Guidelines, and the American College of Physicians, American Association for Thoracic Surgery, Preventive Cardiovascular Nurses Association, Society for Cardiovascular Angiography and Interventions, and Society of Thoracic Surgeons." J Am Coll Cardio 2012;60(24):2564-603. doi: 10.1016/c.cacc.2012.07.012 [published Online First: Nov. 28, 2012].
Finh et al. "2014 ACC/AHA/AATS/PCNA/SCAI/STS focused update of the guideline for the diagnosis and management of patients with stable ischemic heart disease: a report of the American College of Cardiology/American Heart Association Task Force on Practice Guidelines, and the American Association for Thoracic Surgery, Preventive Cardiovascular Nurses Association, Society for Cardiovascular Angiography and Interventions, and Society of Thoracic Surgeons." Journal of the American College of Cardiology 2014;64 (18): 1929-49. doi:10.1016/j.jacc.2014.07.017 [published Online First: Aug. 1, 2014].
Friedman et al., "Additive logistic regression: a statistical view of boosting (With discussion and a rejoinder by the authors)." Ann Statist. 2000; 28(2) pp. 337-407.
Funama, Yoshinori, et al. "Improved estimation of coronary plaque and luminal attenuation using a vendor-specific model-based iterative reconstruction algorithm in contrast-enhanced CT coronary angiography." Academic radiology 24.9.
Gaemperli et al. "Cardiac hybrid imaging." Eur Heart J 2011; 32(17): 2100-8.
Gaur et al., "Coronary plaque quantification and fractional flow reserve by coronary computed tomography angiography identify ischaemia-causing lesions", European Heart Journal, 2016 pp. 1220-1227.
Goff, et al. "2013 ACC/AHA Guidelines on the Assessment of Cardiovascular Risk: a Report of the American College of Cardiology/American Heart Association Task Force on Practice Guidelines." J Am Coll Cardiol. 2014;63: 2935-59.
Gogas, et al. "Assessment of Coronary Atherosclerosis by IVUS and IVUS-based Imaging Modalities: Profession and Regression Studies, Tissue Composition and Beyond." Int J Cardiovasc Imaging. 2011;27: 225-37.
Goldstein et al., "Moving beyond regression techniques in cardiovascular risk prediction: applying machine learning to address analytic challenges." Eur Heart J. 2017; 38(23) pp. 1805-1814.

(56) References Cited

OTHER PUBLICATIONS

Greenwood et al. "Effect of Care Guided by Cardiovascular Magnetic Resonance, Myocardial Perfusion Scintigraphy, or NICE Guidelines on Subsequent Unnecessary Angiography Rates: The CE-MARC 2 Randomized Clinical Trial." JAMA 2016; 316(10): 1051-60. doi: 10.1001/jama.2016.12680 [published Online First: Aug. 30, 2016.

Guyon et al., "An introduction to variable and feature selection." J Mach Learn Res. 2003; 3:1157-1182.

Hadamitzky et al., "Optimized Progostic Score for Coronary Computed Tomographic Angiography", Journal of the American College of Cardiology, vol. 62, No. 5, 2013, pp. 468-476.

Hall et al., "The WEKA data mining software: an update." SIGKDD Explor Newsl. 2009; 11(1) pp. 10-18.

Hall et al., "Benchmarking attribute selection techniques for discrete clas data mining." IEEE Transaction on Knowledge and Data Engineering 2003; 15(6): pp. 1437-1447.

Han et al. "Incremental role of resting myocardial computed tomography perfusion for predicting physiologically significant coronary artery disease: A machine learning approach." J Nucl Cardiol. 2018; 25(1) pp. 223-233.

Han et al., "Quantitative measurement of lipid rich plaque by coronary computed tomography angiography: A correlation of histology in sudden cardiac death", Atherosclerosis, 2018 pp. 426-433.

Hausleiter et al. "Estimated radiation dose associated with cardiac CT angiography." JAMA 2009; 301(5): 500-7.

Heo et al., "Optimal boundary detection method and window settings for coronary atherosclerotic plaque volume analysis in coronary computed tomography angiography: comparison with intravascular ultrasound", Eur Radiol, (2016) 26:31, pp. 3190-3198.

Hesse et al. "EANM/ESC procedural guidelines for myocardial perfusion imaging in nuclear cardiology." Eur J Nucl Med Mol Imaging 2005; 32 (7): 855-97. doi: 10.1007/s00259-005-1779-y.

Howard G. et al. "Cigarette smoking and progression of atherosclerosis: The Atherosclerosis Risk in Communities (AIRC) Study." JAMA 1998; 279(2) pp. 119-124.

Hundley WG et al. "Society for Cardiovascular Magnetic Resonance guidelines for reporting cardiovascular magnetic resonance examinations." J Cardiovasc Magn Reson 2009; 11:5.

International Search Report and Written Opinion for Application No. PCT/US20/15035 dated Apr. 14, 2020, in 20 pages.

International Search Report and Written Opinion for Application No. PCT/US2021/012218 dated Mar. 17, 2021, in 11 pages.

Kanamori et al. "Robust Loss Functions for Boosting" Neural Computation. 2007; 19(8) pp. 2183-2244.

Kang, et al. Automated Knowledge-Based Detection of Nonobstructive and Obstructive Arterial Lesions from Coronary CT Angiography. Med Phys.

Kang, et al. "Structured Learning Algorithm for Detection of Nonobstructive and Obstructive Coronary Plaque Lesions from Computed Tomography Angiography", Journal of Medical Imaging, (2015).

Klass O, et al. "Coronary plaque imaging with 256-slice multidetector computed tomography: interobserver ariability of volumetric lesion parameters with semiautomatic plaque analysis software", Int J Cardiovasc Imaging, (2010). 26; pp. 711-720.

Klein et al. :Diagnostic quality of time-averaged ECG-Gated CT data, SPIE medical imaging, 2019.

Knuiman et al. "An Empirical comparison of multivariable methods for estimating risk of death from coronary heart disease." J. Cardiovasc Risk. 1997; 4(2): pp. 127-134.

Kolossvary, et al. "Radiomic Features Are Superior to Conventional Quantitative Computed Tomographic Metrics to Identify Coronary Plaques with Napkin-Ring Sign." Circ Cardiovasc Imaging. 2017;10.

Koo BK, et al. "Diagnosis of ischemia-causing coronary stenoses by noninvasive fractional flow reserve computed from coronary computed tomographic angiograms. Results from the prospective multicenter Discovery-Flow (Diagnosis of Ischemia-Causes Stenoses Obtained Via Noninvasive Fractional Flow Reserve) study." J Am Coll Cardiol 2011; 58 (19): 1989-97. doi: 10.1016/j.jacc.2011.06.066 [published Online First: Oct. 29, 2011].

Kim et al., "Natural History of Diabetic Coronary Atherosclerosis by Quantitiative Measurement of Serial Coronary Computed Tomographic Angiography", JACC: Cardiovascular Imaging, vol. 11, No. 10, 2018 pp. 1461-1471.

Kramer et al. "Standardized cardiovascular magnetic resonance imaging (CMR) protocols, society for cardiovascular magnetic resonance: board of trustees task force on standardized protocols." J Cardiovasc Magn Reson 2008; 10:35. doi: 10.1186/1532-429X-10-35.

Kwan et al., "Bridging the gap for lipid lowering therapy: plaque regression, coronary computed tomographic angiography, and imaging-guided personalized medicine." Expert Rev Cardiovasc Ther. 2017; 15(7): pp. 547-558.

Lee et al., "Differences in Progression to Obstructive Lesions per High-Risk Plaque Features and Plaque Volumes With CCTA", JACC: Cardiovascular Imaging, 2019 in 9 pages.

Lee et al., "Effects of Statins on Coronary Atherosclerotic Plaques—The PARADIGM (Progession of AtheRosclerotic PlAque DetermIned by Computed TomoGraphic Angiography Imaging) Study", JACC: Cardiovascular Imaging, 2018.

Lee et al., "Identification of High-Risk Plaques Destined to Cause Acute Coronary Syndrome Using Coronary Computed Tomographic Angiography and Computational Fluid Dynamics", JACC: Cardiovascular Imaging, vol. 12, No. 6, Jun. 2019. pp. 1032-1043.

Lee et al., "Rationale and design of the Progession of AtheRosclerotic PlAque DetermIned by Computed TomoGraphic Angiography Imaging (PARADIGM) registry: A comprehensive exploration of plaque progression and its impact on clinical outcomes from a multicenter serial coronary computed tomographic angiography study", American Heart Journal, vol. 182. 2016 pp. 72-79.

Lee et al., Rationale and design of the Coronary Computed Tomographic Angiography for Selective Cardiac Catheterization: Relation to Cardiovascular Outcomes, Cost Effectiveness and Quality of Life (CONSERVE) trial:, Am Heart J, 2017; vol. 186, pp. 48-55.

Lee et al., "Reproducibility in the assessment of noncalcified coronary plaque with 256-slice multi-detector CT and automated plaque analysis software", Int J Cardiovasc Imaging; 2010; 26:237-244.

Lee et al., "Quantification of Coronary Atherosclerosis in the Assessment of Coronary Artery Disease." Circ Cardiovasc Imaging. 2018; 11(7): e007562.

Leipsic et al. "SCCT guidelines for the interpretation and reporting of coronary CT angiography: a report of the Society of Cardiovascular Computed Tomography Guidelines Committee" J Cardiovasc Comput Tomogr 2014; 8(5): 342-58.

Libby P. "Mechanisms of acute coronary syndromes and their implications for therapy." N Engl J Med. 2013; 368: 2004-13.

Lu et al., "Central Core Laboratory versus Site Interpretation of Coronary CT Angiography: Agreement and Association with Cardiovascular Events in the PROMISE Trial", Radiology: vol. 287, No. 1, Apr. 2018, pp. 87-95.

Lundberg, et al. "A Unified Approach to Interpreting Model Predictions." 31st Conference on Neural Information Processing Systems (NIPS 2017).

Mancio, Jennifer, et al. "Perivascular adipose tissue and coronary atherosclerosis." Hear 104.20 (2018): 1654-1662. (Year: 2018).

Maurovich-Horvat, et al. "Comprehensive Plaque Assessment by Coronary CT Angiography", Nature Reviews, (2014).

Maurovich-Horvat, et al. "The napkin-ring sign indicates advanced atherosclerotic lesions in coronary CT angiography.", JACC Cardiovasc Imaging 2012; 5(12): 1243-52.

Meijboom et al. "Diagnostic accuracy of 64-slice computed tomography coronary angiography: a prospective, multicenter, multivendor study." J Am Coll Cardiol 2008; 52 (25): 2135-44. doi: 10.1016/j.jacc.2008.08.058.

Melikian et al. "Fractional flow reserve and myocardial perfusion imaging in patients with angiographic multivessel coronary artery disease." JACC Cardiovasc Interv 2010; 3 (3): 307-14. doi: 10.1016/j.jcin.2009.12.010 [published Online First: Mar. 20, 2010].

Mettler et al. "Effective doses in radiology and diagnostic nuclear medicine: a catalog." Radiology 2008; 248(1): 254-63.

(56) References Cited

OTHER PUBLICATIONS

Miller et al. "Diagnostic performance of coronary angiography by 61-row CT." N Engel J Med 2008; 359 (22): 2324-36. doi: 10.1056/NEJMoa0806576 [published Online First: Nov. 29, 2008].
Min, "Atherosclerotic plaque characterization:a need for a paradigm shift for prediction of risk", European Heart Journal—Cardiovascular Imaging, Oct. 2017. pp. 1340-1341.
Min et al., "Atherosclerosis, Stenosis, and Ischemia", JACC: Cardiovascular Imaging, vol. 11, No. 4, Apr. 2018. pp. 531-533.
Min, "Chess and Coronary Artery Ischemia: Clinical Implications of Machine-Learning Applications", Circulation:Cardiovascular Imaging, 2018 in 4 pages.
Min et al., "Diagnostic accuracy of fractional flow reserve from anatomic CT angiography." JAMA 2012; 038 (12): 1237-45. doi: 10.1001/2012.jama.11274 [published Online First: Aug. 28, 2012].
Min et al., "The Immediate Effects of Statins on Coronary Atherosclerosis", JACC:Cardiovascular Imaging, vol. 11, No. 6, Jun. 2018. pp. 839-841.
Min et al. "Prognostic value of multidetector coronary computed tomographic angiography for predication of all-cause mortality" J Am Coll Cardio 2007; 50(12): 1161-70.
Min, et al. "Rationale and Design of the CONFIRM (Coronary CT Angiography Evalution for Clinical Outcomes: An International Multicenter) Registry." J Cardiovasc Comput Tomogr. 2011;5: 84-92.
Mintz GS. "Intravascular Imaging of Coronary Calcification and its Clinical Implications." JACC Cardiovasc Imaging. 2015;8: 461-471.
Montalescot et al. "2013 ESC guidelines on the management of stable coronary artery disease: the Task Force on the management of stable coronary artery disease of the European Society of Cardiology." Eur Heart J 2013;34(35: 2949-3003. doi: 10.1093/eurheartj/eht296 [published Online First: Sep. 3, 2013].
Motoyama et al. "Atherosclerotic plaque characterization by 0.5-mm-slice multislice computed tomographic imaging." Circ J 2009; 71(3): 363-6.
Motoyama et al. "Computed tomographic angiography characteristics of atherosclerotic plaques subsequently resulting in acute coronary syndrome." J Am Coll Cardiol 2009; 54(1): 49-57.
Motoyama et al. "Multislice computed tomographic characteristics of coronary lesions in acute coronary syndromes." J Am Coll Cardiol 2007; 50(4): 319-26.
Motwani et al., "Machine learning for prediction of all-cause mortality in patients with suspected coronary artery disease: a 5-year multicentre prospective registry analysis", European Heart Journal, 2017, pp. 500-507.
Naghavi, et al. From Vulnerable Plaque to Vulnerable Patient: a call for new definitions and risk assessment strategies: Part I. Circulation. 2003; 108: 1664-72.
Nair, et al. "Automated Coronary Plaque Characterisation with intravascular ultrasound backscatter: ex vivo validation." EuroIntervention. 2007; 3: 113-20.
Nakanishi R. et al. "Plaque progression assessed by a novel semi-automated quantitative plaque software on coronary computed tomography angiography between diabetes and non-diabetes patients: A propensity-score matching study." Atherosclerosis 2016; 255 pp. 73-79.
Nakazato et al., "Additive diagnostic value of atherosclerotic plaque characteristics to non-invasive FFR for indentification of lesions causing ischaemia: results from a prospective international multicentre trial", http://www.pcronline.com/eurointervention/ahead_of_print/201509-02/ in 9 pages.
Nakazato et al., "Aggregate Plaque Volume by Coronary Computed Tomography Angiography Is Superior and Incremental to Luminal Narrowing for Diagnosis of Ischemic Lesions of Intermediate Stenosis Severity", Journal of the American College of Cardiology, vol. 62, No. 5, 2013 pp. 460-467.
Nakazato et al., "Atherosclerotic plaque characterization by CT angiography for identification of high-risk coronary artery lesions: a comparison to optical coherence tomography", European Heart Journal—Cardiovascular Imaging, vol. 16, 2015. pp. 373-379.
Nakazato et al., "Quantification and characterisation of coronary artery plaque volume and adverse plaque features by coronary computed tomographic angiography: a direct comparison to intravascular ultrasound", Eur Radiol (2013) 23, pp. 2109-2117.
Nakazato et al., "Relationship of low- and high-density lipoproteins to coronary artery plaque composition by CT angiography", Journal of Cardiovascular Computed Tomography 7, 2013, pp. 83-90.
Neglia et al. "Detection of significant coronary artery disease by noninvasive anatomical and functional imaging." Circ Cardiovasc Imaging 2015; 8 (3) doi: 10.1161/CIRCIMAGING.114.002179 [published Online First: Feb. 26, 2015].
Newby et al., "Coronary CT Angiography and 5-Year Risk of Myocardial Infarction", The New England Journal of Medicine, Aug. 25, 2018, pp. 924-933.
Newby et al., "CT coronary angiography in patients with suspected angina due to coronary heart disease (SCOT-HEART): an open-label, parallel-group, multicentre trial", www.thelancet.com, vol. 385. Jun. 13, 2015, pp. 2383-2391.
Nicholls, et al. "Effect of Evolocumab on Coronary Plaque Composition." J Am Coll Cardiol. 2018;72: 2012-2021.
Nicholls et al. "Intravascular ultrasound-derived measures of coronary atherosclerotic plaque burden and clinical outcome." J Am Coll Cardiol. 2010; 55(21): pp. 2399-2407.
Obaid, D.R., et al. "Atherosclerotic Plaque Composition and Classification Identified by Coronary Computed Tomography: Assessment of CT-Generated Plaque Maps Compared with Virtual Histology Intravascular Ultrasound and Histology." Circulation: Cardiovascular Imaging 6.5 (2013): 655-664. (Year: 2013).
Obaid, Daniel R., et al. "Coronary CT angiography features of ruptured and high-risk atherosclerotic plaques: correlation with intra-vascular ultrasound." Journal of Cardiovascular Computed Tomography 11.6 (2017): 455-461. (Year: 2017).
Okubo, Ryo, et al. "Pericoronary adipose tissue ratio is a stronger associated factor of plaque vulnerability than epicardial adipose tissue on coronary computed tomography angiography." Heart and vessels 32.7 (2017): 813-822. (Year: 2017).
Otsuka et al. "Napkin-ring sign on coronary CT angiography for the prediction of acute coronary syndrome." JACC Cardiovasc Imaging 2013; 6(4): 448-57.
Ovrehus et al., "CT-based total vessel plaque analyses improves prediction of hemodynamic significance lesions as assessed by fractional flow reserve in patients with stable angina pectoris", Journal of Cardiovascular Computed Tomorgraphy 12, 2018 pp. 344-349.
Ovrehus, et al. "Reproducibility of Semi-Automatic Coronary Plaque Quantification in Coronary CT Angiography with Sub-mSv Radiation Dose." J Cardiovasc Comput Toogr, (2016).
Papadopoulou, et al. "Detection and Quantification of Coronary Atherosclerotic plaqie by 64-slice multidetector CT: A systematic head-to-head comparison with intravascular ultrasound." Atherosclerosis. 2011;219: 163-70.
Papadopoulou, et al. Reproductibility of CT Angiography Data Analysis Using Semiautomated Plaque Quantification Software: Implications for the Design of Longitudinal Studies. Int J Cardiovasc Imaging.
Park et al., "Atherosclerotic Plaque Characteristics by CT Angiography Identify Coronary Lesions That Cause Ischemia", JACC: Cardiovascular Imaging, vol. 8, No. 1, 2015 in 10 pages.
Park, et al. "Clinical Feasibility of 3D Automated Coronary Atherosclerotic Plaque Quantification Algorithm on Coronary Computed Tomography Angiography: Comparison with Intravascular Ultrasound" European Radiology (2015), 25: 3073-3083.
Park, et al. "Visual-functional Mismatch between Coronary Angiography and Fractional Flow Reserve." JACC Cardiovasc Interv. 2012; 5: 1029-36.
Pavlou et al., "A note on obtaining correct marginal predictions from a random intercepts model for binary outcomes." BMC Med Res Methodol 2015; 15:59. doi: 10.1186/s12874-015-004606 [published Online First: Aug. 6, 2015].
Pedregosa, et al. "Scikit-learn: Machine Learning in Python." Journal of Machine Learning Research, 2011;12: 2825-2830.

(56) References Cited

OTHER PUBLICATIONS

Picano et al. "The appropriate and justified use of medical radiation in cardiovascular imaging: a position document of the ESC Associations of Cardiovascular Imaging, Percutaneous Cardiovascular Interventions and Electrophysiology." Eur Heart J 2014; 35(10): 665-72.

Puchner, et al. "High-Risk Plaque Detected on Coronary CT Angiography Predicts Acute Coronary Syndrome Independent of Significant Stenosis in Patients with Acute Chest Pain" J Am Coll Cardiol 2014.

Puchner, et al. "High-Risk Coronary Plaque at Coronary CT Angiography is Associated with NAFLD, Independent of Coronary Plaque and Stenosis Burden", J Cardiovasc Comput Tomogr.

Raff, et al. "SCCT guidelines for the interpretation and reporting of coronary computed tomographic angiography" J Cardiovasc Comput Tomogr 2009: 3(2): 122-36.

Rehani et al. "ICRP Publication 117. Radiological protection in fluoroscopically guided procedures performed outside the imaging departement." Ann ICRP 2010; 40(6): 1-102.

Rizvi et al., "Diffuse coronary artery disease among other atherosclerotic plaque characteristics by coronary computed tomography angiography for predicting coronary vessel-specific ischemia by fractional flow reserve", Atherosclerosis 258, 2017 pp. 145-151.

Rizvi et al., "Rationale and Design of the CREDENCE Trial: computed TomogRaphic evaluation of atherosclerotic DEtermiNants of myocardial IsChEmia", BMC Cardiovascular Disorders, 2016, in 10 pages.

Roy-Cardinal et al. "Intravascular Ultrasound Image Segmentation: A Three-Dimentional Fast-Marching Method Based on Grey Level Distributions", IEEE Transactons on Medical Imaging, vol. 25, No. 5, May 2006.

Sabir, A et al. Measuring Noncalcified Coronary Atherosclerotic Plaque Using Voxel Analysis with MDCT Angiography: Phantom Validation: American Journal of Roentgenology, Apr. 2008; vol. 190, No. 4, pp. 242-246.

Samady H. et al. "Coronary artery wall shear is associated with progression and transformation of atherosclerotic plaque and arterial remodeling in patients with coronary artery disease." American Heart Association Circulation, vol. 124, Issue 7, Aug. 16, 2011, pp. 779-788.

Schlett et al. "How to assess non-calcified plaque in CT angiography: delineation methods affect diagnostic accuracy of low-attenuation plaque by CT for lipid-core plaque in history." Euro Heart J Cardiovasc Imaging 2013; 14(11): 1099-105.

Schuurman, et al. "Prognostic Value of Intravascular Ultrasound in Patients with Coronary Artery Disease." J Am Coll Cardiol. 2018;72: 2003-2011.

Seghier et al., "Lesion identification using unified segmentation-normalisation models and fuzzy clustering" NeuroImage 40(2008) 1253-1266.

Seifarth, et al. "Histopathological Correlates of the Napkin-Ring Sign Plaque in Coronary CT Angiography." Send to Atherosclerosis. 2012;224: 90-6.

Sharma et al., "Stress Testing Versus CT Angiography in Patients With Diabetes and Suspected Coronary Artery Disease", Journal of the American College of Cardiology, vol. 73, No. 8, 2019 pp. 893-902.

Shaw et al. "Optimal medical therapy with or without percutaneous coronary intervention to reduce ischemic burden: results from the Clinical Outcomes Utilizing Revascularization and Aggressive Drug Evaluation (COURAGE) trail nuclear substudy." Circulation 2008; 117 (10): 1283-91. doi: 10.116/CIRCULATIONAHA.107.743963.

Shaw et al. "Why all the focus on cardiac imaging?" JAAC Cardiovasc Imaging 2010; 3(7): 789-94 doi: 10.16/j.jcmg.2010.05.004.

Shin S. et al., "Impact of Intensive LDL Cholesterol Lowering on Coronary Artery Atherosclerosis Progression: A Serial CT Angiography Study." JACC Cardiovasc Imaging. 2017; 10(4) pp. 437-446.

Siasos, et al. "Local Low Shear Stress and Endothelial Dysfunction in Patients with Nonobstructive Coronary Atherosclerosis." J Am Coll Cardiol. 2018;71: 2092-2102.

Song et al. "Comparison of machine learning techniques with classical statistical models in predicting health outcomes." Stud Heatlh Technol Inform. 2004; 107(Pt 1) pp. 736-740.

Staruch, et al. "Automated Quantitative Plaque Analysis for Discrimination of Coronary Chronic Total Occlusion and Subtotal Occlusion in Computed Tomography Angiography", J Thoracic Imaging, (2016).

Stone, et al. "A prospective natural-history stucy of coronary atherosclerosis." N Engl J Med 2011; 364(3): 226-35.

Stuijfzand, et al. "Stress Myocardial Perfusion Imaging vs Coronary Computed Tomographic Angiography for Diagnosis of Invasive Vessel-Specific Coronary Physiology Predictive Modeling Results From the Computed Tomographic Evaluation of Atherosclerotic Determinants of Myocardial Ischemia (CREDENCE) Trial", JAMA Cardiology, doi:10.1001/jamacardio.2020.3409, Aug. 19, 2020.

Sun, et al. "Diagnostic Value of Multislice Computed Tomography Angiography in Coronary Artery Disease: a Meta-Analysis." Eur J Radiol. 2006;60: 279-86.

Taylor et al., "Patient-Specific Modeling of Cardiovascular Mechanics", Annu. Rev. Biomed. Eng. 2009.11:109-139.

Thim, et al. "Unreliable Assessment of Necrotic Core by Virtual Histology Intravascular Ultrasound in Porcine Coronary Artery Disease." Circ Cardiovasc Imaging. 2010;3: 384-91.

Thygesen, et al. "Third Universal Definition of Myocardial Infarction." Glob Heart. 2013;7: 275-95.

Tian, et al. "Distinct Morphological Features of Ruptured Culprit Plaque for Acute Coronary Events Compared to those with Silent Rupture and Thin-Cap Fibroatheroma: a Combined Optical Coherence Tomography and Intravascular Ultrasound Study." J Am Coll Cardiol. 2014;63: 2209-16.

Tilkemeier et al., "American Society of Nuclear Cardiology information statement: Standardized reporting matrix for radionuclide myocardial perfusion imaging." J Nucl Cardiol 2006; 13 (6): e157-71. doi: 10.1016/j.nuclcard.2006.08.014.

Tomey Mi, et al. "Advances in the understanding of plaque composition and treatment options: year in review." J AM Coll Cardio. 2014; 63(16) pp. 1604-1616.

Tonino et al., "Angiographic versus functional severity of coronary artery stenoses in the FAME study fractional flow reserve versus angiography in multivessel evaluation." Journal of the American College of Cardiology 2010; 55 (25): 2816-21. doi: 10.1016/j.jacc. 2009.11-096 [published Online First: Jun. 29, 2010].

Van Ooijen, et al. "Coronary Artery Imaging with Multidetector CT: Visualization Issues" RadioGraphics, vol. 23. (2003).

Van Rosendael et al., "Maximization of the usage of coronary CTA derived plaque information using a machine learning based algorithm to improve risk stratification; insights from the CONFIRM registry", Journal of Cardiovascular Computed Tomography 12, 2018, pp. 204-209.

Van Rosendael et al., "Quantitative Evaluation of High-Risk Coronary Plaque by Coronary CTA and Subsequent Acute Coronary Events", JACC: Cardiovascular Imaging, vol. 12, No. 8, Aug. 2019. pp. 1568-1571.

Versteylen MO, et al. "Additive value of semiautomated quantification of coronary artery diseae using cardiac computed tomographic angiography to predict future acute coronary syndrome." J Am Coll Cardiol. 2013; 61(22): pp. 2296-2305.

Virmani, et al. "Atherosclerotic plaque progression and vulnerability to rupture: angiogenesis as a source of intraplaque hemorrage." Arterioscler Thromb Vasc Biol. 2005; 25: 2054-61.

Virmani, et al. "Lessons from sudden coronary death: a comprehensive morphological classification scheme for atherosclerotic lesions." Arterioscler Thromb Vasc Biol. 2000;20: 1262-75.

Virmani, et al. "Pathology of the Vulnerable Plaque." J Am Coll Cardiol. 2006; 47: C13-8.

Wei, et al. "Computerized Detection of Noncalcified Plaques in Coronary CT Angiography: Evaluation of Topological Soft Gradient Prescreening Method and Luminal Analysis" Med Phys, (2014).

(56) References Cited

OTHER PUBLICATIONS

Weir-MacCall et al., "Impact of Non-obstructive left main disease on the progession of coronary artery disease: A PARADIGM substudy", Journal of Cardiovascular Computed Tomography 12, 2018, pp. 231-237.

Weisenfeld et al. "Automatic Segmentation of Newborn Brain MRI", NIH PA Author Manuscript 2010.

Williams et al., "Coronary Artery Plaque Chracteristics Associated With Adverse Outcomes in the SCOT-HEART Study", Journal of the American College of Cardiology, vol. 73, No. 3, Jan. 29, 2019. pp. 291-301.

Williams et al. "Use of Coronary Computed Tomographic Angiography to Guide Management of Patients with Coronary Disease." Journal of American College of Cardiology 2016; 67 (15) : 1759-68. doi: 10.1016/J.Jacc.2016.02.026 [published Online First: Apr. 16, 2016].

Wilson et al. "Prediction of coronary heart disease using risk factor categories" Circulation 1998; 97(18) pp. 1837-1847.

Won et al., "Longitudinal assessment of coronary plaque volume change related to glycemic status using serial coronary computed tomography angiography: A Computed TomoGraphic Angiography Imaging) substudy", Journal of Cardiovascular Computed Tomography 13, 2019 pp. 142-147.

Won et al., "Longitudinal quanititive assessment of coronary plaque progression related to body mass index using serial coronary computed tomography angiography", European Heart Journal—Cardiovascular Imaging, 2019 pp. 591-599.

Yang, et al. "Automatic centerline extraction of coronary arteries in coronary computed tomographic angiography" The International Journal of Cardiocascular Imaging, 28, pp. 921-933. (2012).

Yokoya K, et al. "Process of progression of coronary artery lesions from mild or moderate stenosis to moderate or severe stenosis: A study based on four serial coronary arteriograms per year." Circulation 1999; 100(9); pp. 903-909.

Zeb I et al. "Effect of statin treatment on coronary plaque progression—a serial coronary CT angiography study." Atherosclerosis. 2013; 231(2) pp. 198-204.

Zhao Z., et al. "Dynamic nature of nonculprit coronary artery lesion morphology in STEMI: a serial IVUS analysis from HORIZONS-AMI trial." JACC Cardiovasc Imaging, 2013; 6(1) pp. 86-95.

* cited by examiner

FIG. 5D
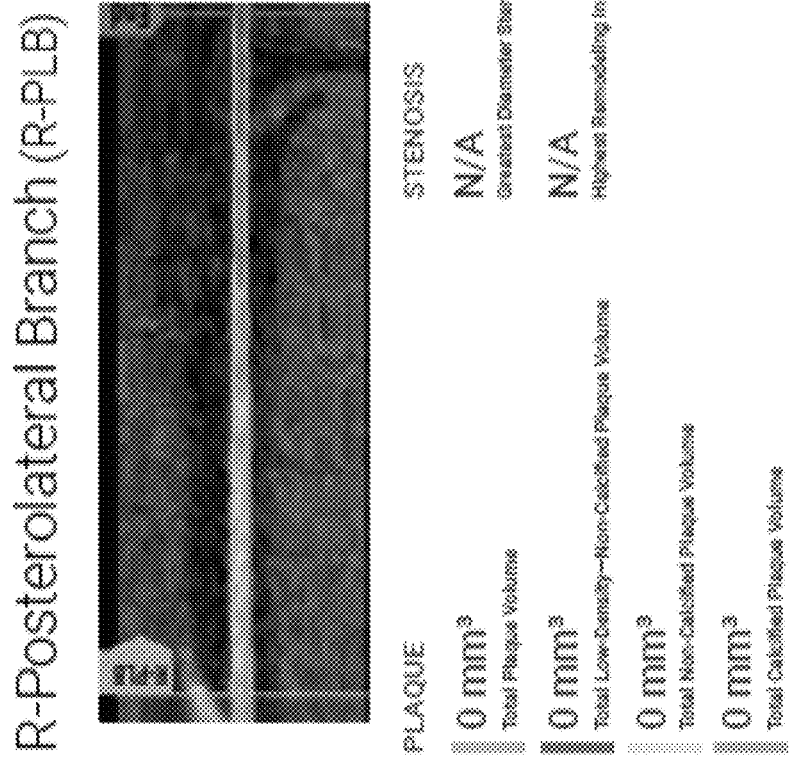
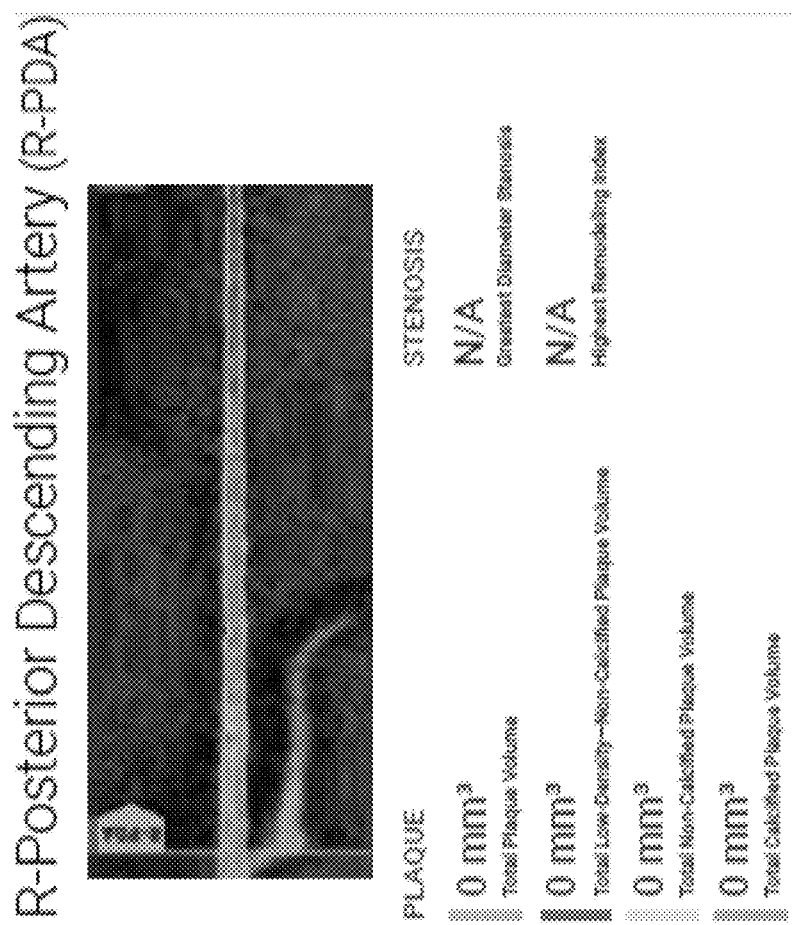

FIG. 5F
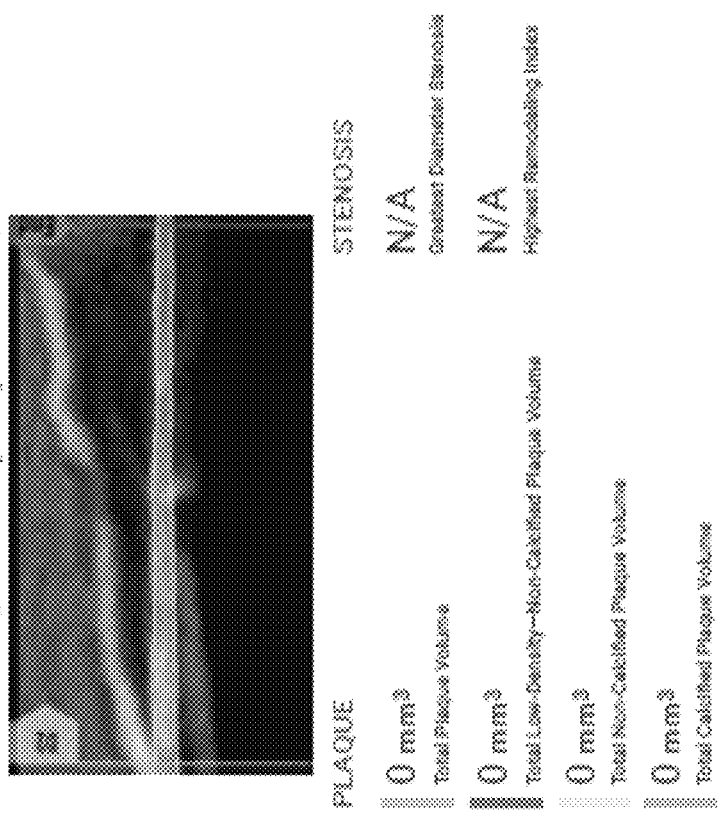
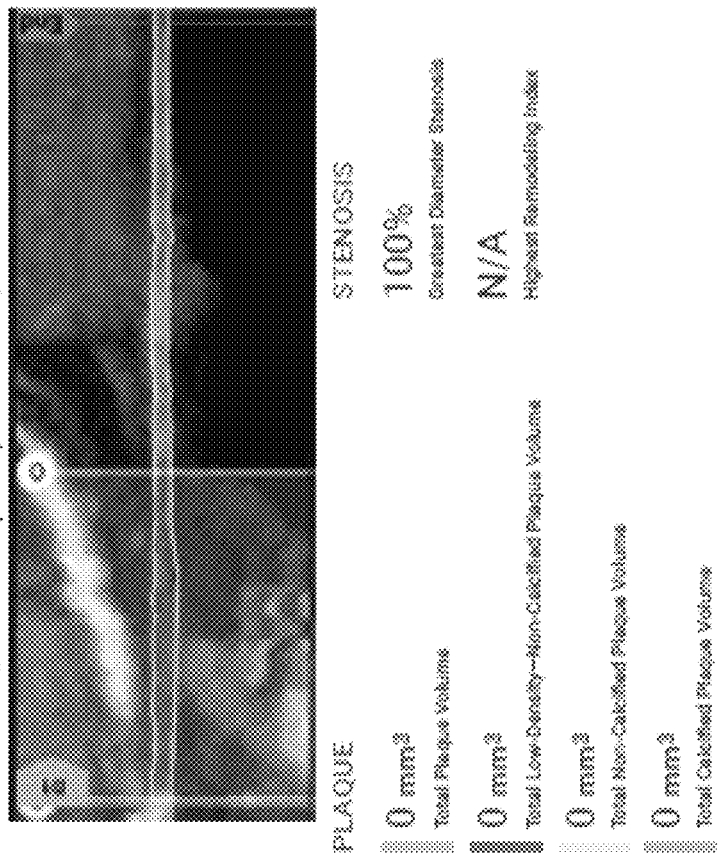

FIG. 5G
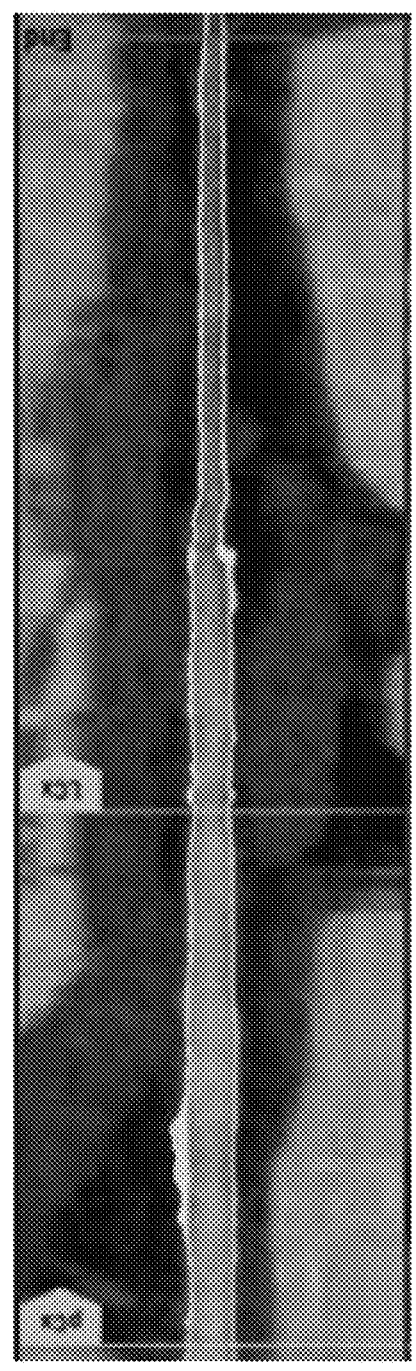
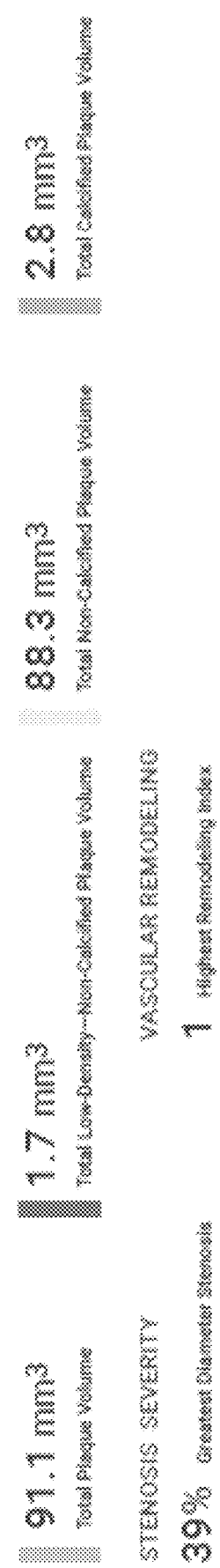

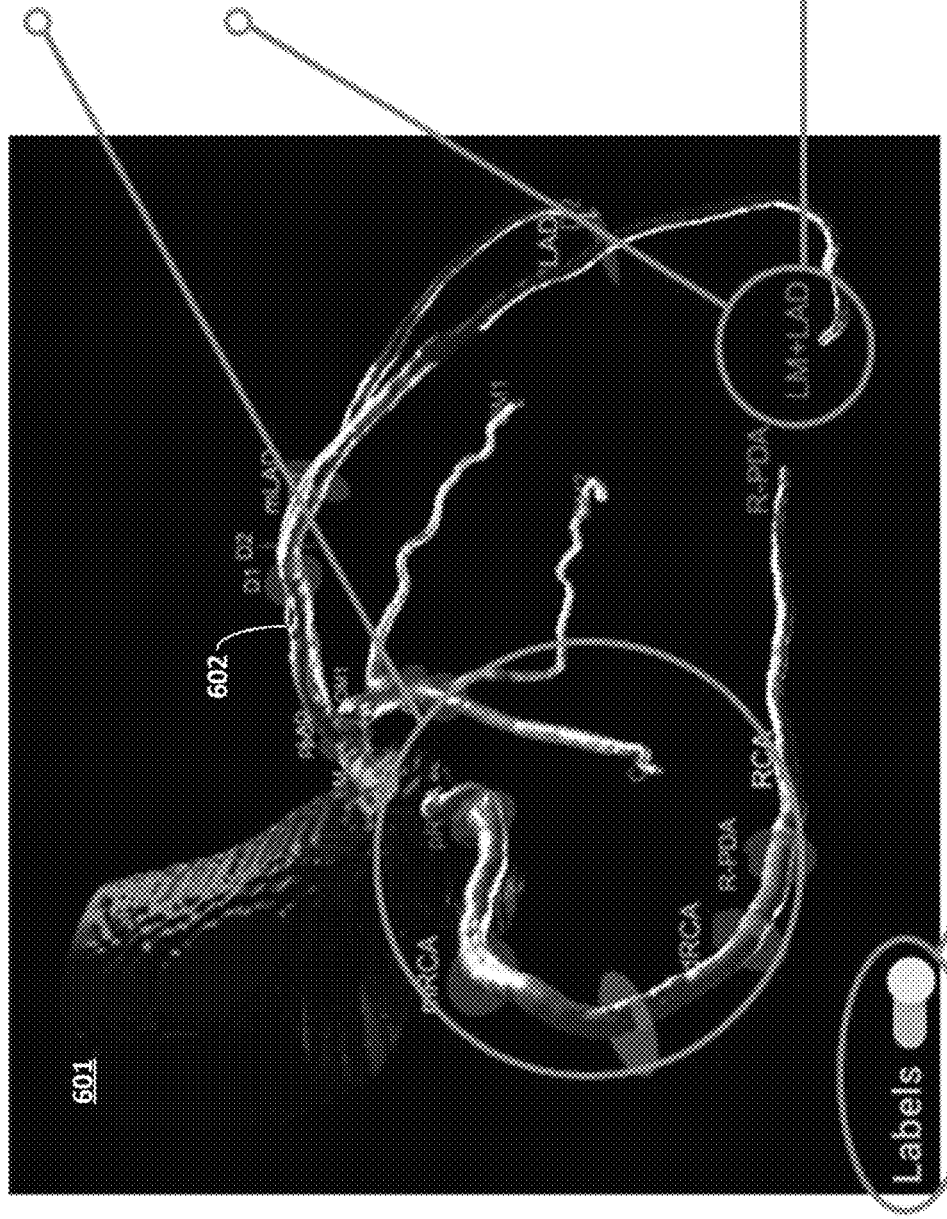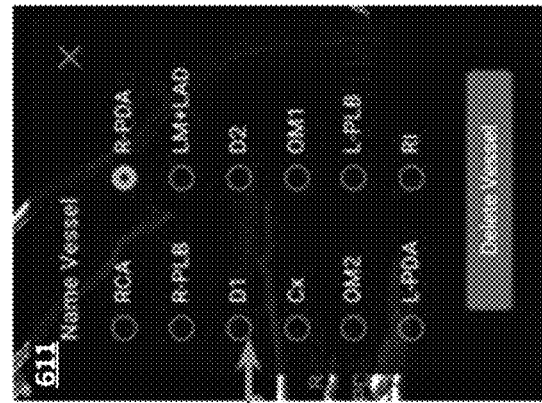
FIG. 6F

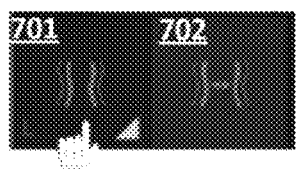 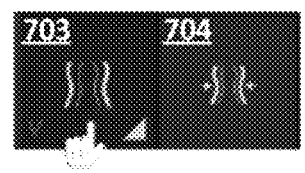
FIG. 7F
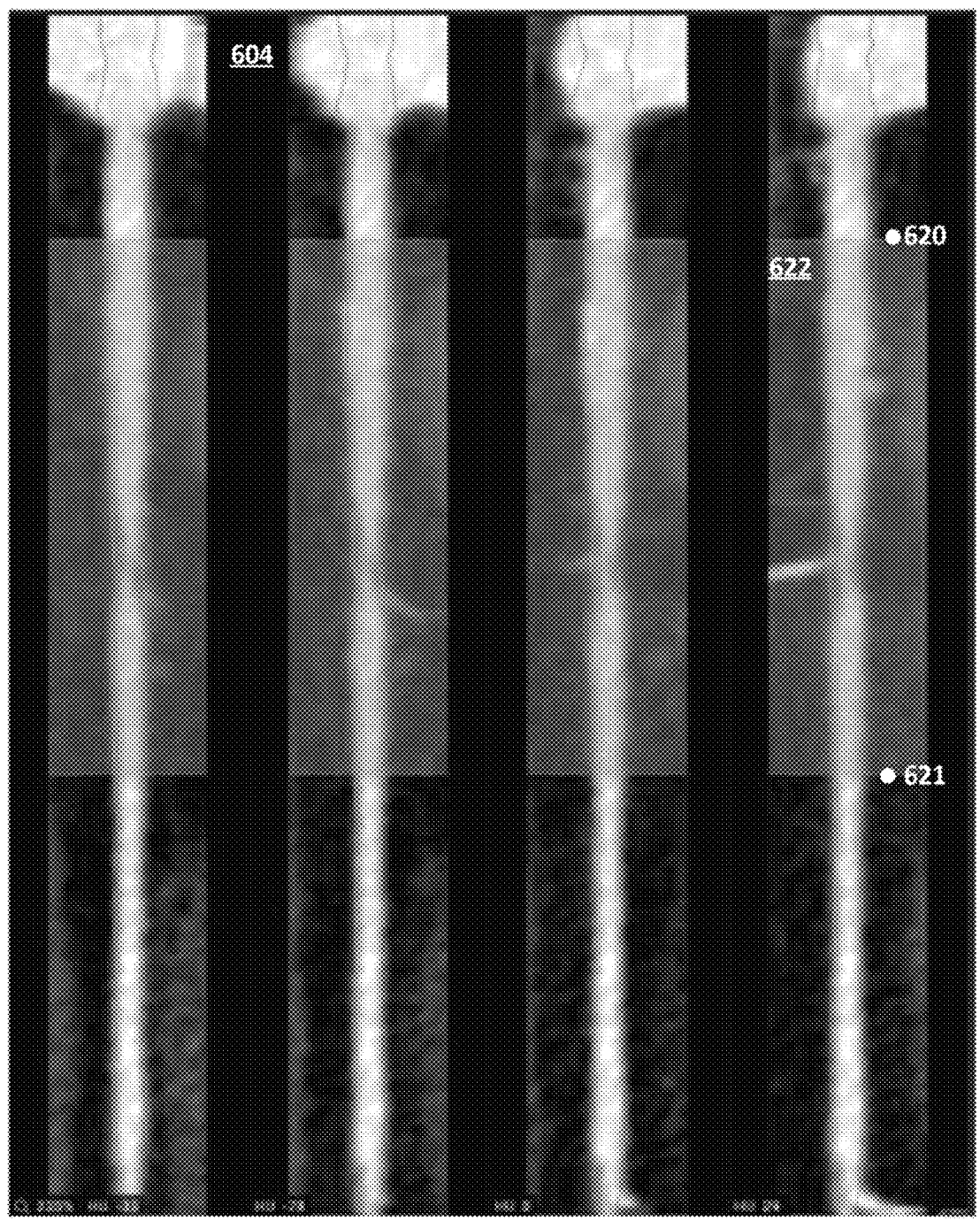
FIG. 7G

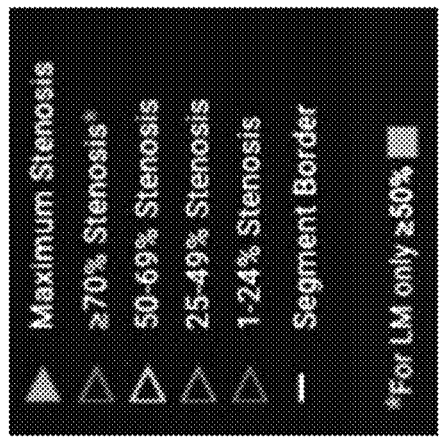
FIG. 9G
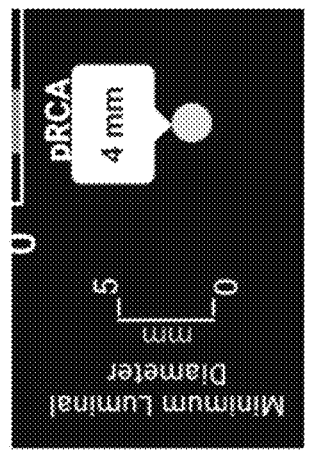
FIG. 9H
FIG. 9J
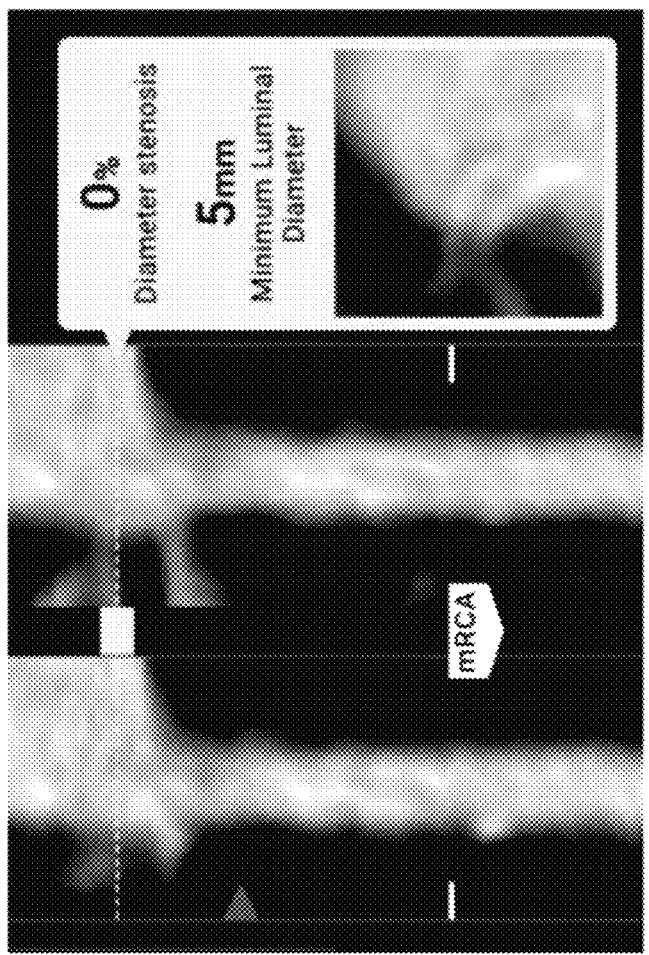
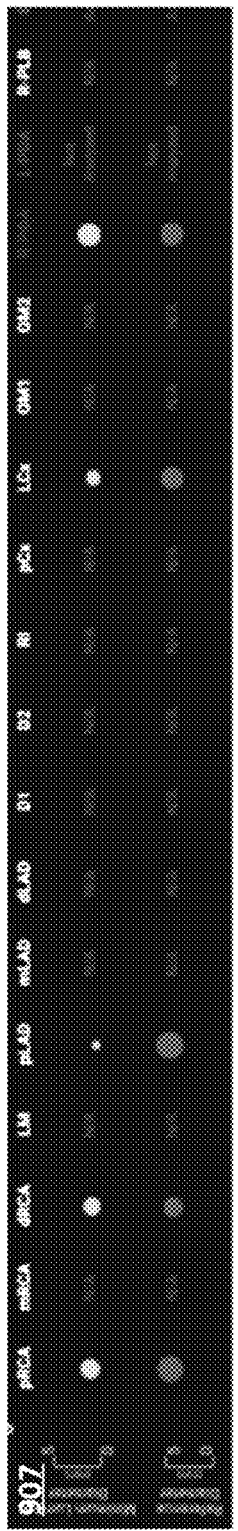
FIG. 9I

SYSTEMS, METHODS, AND DEVICES FOR MEDICAL IMAGE ANALYSIS, DIAGNOSIS, RISK STRATIFICATION, DECISION MAKING AND/OR DISEASE TRACKING

CROSS-REFERENCE TO RELATED APPLICATIONS

The present application is a continuation of U.S. patent application Ser. No. 17/142,120, filed Jan. 5, 2021, and titled SYSTEMS, METHODS, AND DEVICES FOR MEDICAL IMAGE ANALYSIS, DIAGNOSIS, RISK STRATIFICATION, DECISION MAKING AND/OR DISEASE TRACKING, which claims the benefit of U.S. Provisional Patent Application No. 62/958,032, filed Jan. 7, 2020, and titled SYSTEMS, METHODS, AND DEVICES FOR CARDIOVASCULAR IMAGE ANALYSIS, DIAGNOSIS, RISK STRATIFICATION, DECISION MAKING AND/OR DISEASE TRACKING, each of which is incorporated herein by reference in its entirety under 37 C.F.R. § 1.57. Any and all applications for which a foreign or domestic priority claim is identified in the Application Data Sheet as filed with the present application are hereby incorporated by reference under 37 C.F.R. § 1.57.

BACKGROUND

Field

The present application relates to systems, methods, and devices for medical image analysis, diagnosis, risk stratification, decision making and/or disease tracking.

Description

Coronary heart disease affects over 17.6 million Americans. The current trend in treating cardiovascular health issues is generally two-fold. First, physicians generally review a patient's cardiovascular health from a macro level, for example, by analyzing the biochemistry or blood content or biomarkers of a patient to determine whether there are high levels of cholesterol elements in the bloodstream of a patient. In response to high levels of cholesterol, some physicians will prescribe one or more drugs, such as statins, as part of a treatment plan in order to decrease what is perceived as high levels of cholesterol elements in the bloodstream of the patient.

The second general trend for currently treating cardiovascular health issues involves physicians evaluating a patient's cardiovascular health through the use of angiography to identify large blockages in various arteries of a patient. In response to finding large blockages in various arteries, physicians in some cases will perform an angioplasty procedure wherein a balloon catheter is guided to the point of narrowing in the vessel. After properly positioned, the balloon is inflated to compress or flatten the plaque or fatty matter into the artery wall and/or to stretch the artery open to increase the flow of blood through the vessel and/or to the heart. In some cases, the balloon is used to position and expand a stent within the vessel to compress the plaque and/or maintain the opening of the vessel to allow more blood to flow. About 500,000 heart stent procedures are performed each year in the United States.

However, a recent federally funded $100 million study calls into question whether the current trends in treating cardiovascular disease are the most effective treatment for all types of patients. The recent study involved over 5,000 patients with moderate to severe stable heart disease from 320 sites in 37 countries and provided new evidence showing that stents and bypass surgical procedures are likely no more effective than drugs combined with lifestyle changes for people with stable heart disease. Accordingly, it may be more advantageous for patients with stable heart disease to forgo invasive surgical procedures, such as angioplasty and/or heart bypass, and instead be prescribed heart medicines, such as statins, and certain lifestyle changes, such as regular exercise. This new treatment regimen could affect thousands of patients worldwide. Of the estimated 500,000 heart stent procedures performed annually in the United States, it is estimated that a fifth of those are for people with stable heart disease. It is further estimated that 25% of the estimated 100,000 people with stable heart disease, or roughly 23,000 people, are individuals that do not experience any chest pain. Accordingly, over 20,000 patients annually could potentially forgo invasive surgical procedures or the complications resulting from such procedures.

To determine whether a patient should forego invasive surgical procedures and opt instead for a drug regimen, it can be important to more fully understand the cardiovascular disease of a patient. Specifically, it can be advantageous to better understand the arterial vessel health of a patient.

SUMMARY

Various embodiments described herein relate to systems, methods, and devices for medical image analysis, diagnosis, risk stratification, decision making and/or disease tracking.

In particular, in some embodiments, the systems, devices, and methods described herein are configured to utilize non-invasive medical imaging technologies, such as a CT image for example, which can be inputted into a computer system configured to automatically and/or dynamically analyze the medical image to identify one or more coronary arteries and/or plaque within the same. For example, in some embodiments, the system can be configured to utilize one or more machine learning and/or artificial intelligence algorithms to automatically and/or dynamically analyze a medical image to identify, quantify, and/or classify one or more coronary arteries and/or plaque. In some embodiments, the system can be further configured to utilize the identified, quantified, and/or classified one or more coronary arteries and/or plaque to generate a treatment plan, track disease progression, and/or a patient-specific medical report, for example using one or more artificial intelligence and/or machine learning algorithms. In some embodiments, the system can be further configured to dynamically and/or automatically generate a visualization of the identified, quantified, and/or classified one or more coronary arteries and/or plaque, for example in the form of a graphical user interface. Further, in some embodiments, to calibrate medical images obtained from different medical imaging scanners and/or different scan parameters or environments, the system can be configured to utilize a normalization device comprising one or more compartments of one or more materials.

In some embodiments, a normalization device configured to facilitate normalization of medical images of a coronary region of a subject for an algorithm-based medical imaging analysis is provided, wherein the normalization device comprises: a substrate having a width, a length, and a depth dimension, the substrate having a proximal surface and a distal surface, the proximal surface adapted to be placed adjacent to a surface of a body portion of the subject; a plurality of compartments positioned within the substrate, each of the plurality of compartments configured to hold a sample of a known material, wherein: a first subset of the plurality of compartments hold at least one sample of a contrast material, a second subset of the plurality of compartments hold samples of materials representative of materials to be analyzed by the algorithm-based medical imaging analysis, wherein the samples of materials representative of materials comprise at least two of calcium 1000 HU, calcium 220 HU, calcium 150 HU, calcium 130 HU, and a low attenuation material of 30 HU, and a third subset of the plurality of compartments hold at least one sample of phantom material; and an adhesive on the proximal surface of the substrate and configured to adhere the normalization device to the body portion patient.

In some embodiments of the normalization device, wherein samples of materials representative of materials to be analyzed comprise calcium 1000 HU, calcium 220 HU, calcium 150 HU, calcium 130 HU, and a low attenuation material of 30 HU. In some embodiments of the normalization device, the at least one contrast material comprises one or more of iodine, Gad, Tantalum, Tungsten, Gold, Bismuth, or Ytterbium; and the at least one sample of phantom material comprise one or more of water, fat, calcium, uric acid, air, iron, or blood.

In some embodiments of the normalization device, the substrate comprises: a first layer, and at least some of the plurality of compartments are positioned in the first layer in a first arrangement; and a second layer positioned above the first layer, and at least some of the plurality of compartments are positioned in the second layer including in a second arrangement. In some embodiments of the normalization device, at least one of the compartments is configured to be self-sealing such that the sample can be injected into the self-sealing compartment and the compartment seals to contain the injected material.

In some embodiments, a computer-implemented method for normalizing medical images for an algorithm-based medical imaging analysis using a normalization device is provided, wherein normalization of the medical images improves accuracy of the algorithm-based medical imaging analysis, the method comprising: accessing, by a computer system, a first medical image of a coronary region of a subject and the normalization device, wherein the first medical image is obtained non-invasively; accessing, by the computer system, a second medical image of a coronary region of a subject and the normalization device, wherein the second medical image is obtained non-invasively, and wherein the first medical image and the second medical image comprise at least one of the following: one or more first variable acquisition parameters associated with capture of the first medical image differ from a corresponding one or more second variable acquisition parameters associated with capture of the second medical image, a first image capture technology used to capture the first medical image differs from a second image capture technology used to capture the second medical image, or a first contrast agent used during the capture of the first medical image differs from a second contrast agent used during the capture of the second medical image; identifying, by the computer system, first image parameters of the normalization device within the first medical image; generating a normalized first medical image for the algorithm-based medical imaging analysis based in part on the first identified image parameters of the normalization device within the first medical image; identifying, by the computer system, second image parameters of the normalization device within the second medical image; and generating a normalized second medical image for the algorithm-based medical imaging analysis based in part on the second identified image parameters of the normalization device within the second medical image, wherein the computer system comprises a computer processor and an electronic storage medium. In some embodiments of a computer-implemented method for normalizing medical images for an algorithm-based medical imaging analysis using a normalization device, the algorithm-based medical imaging analysis comprises an artificial intelligence or machine learning imaging analysis algorithm, wherein the artificial intelligence or machine learning imaging analysis algorithm was trained using images that included the normalization device.

In some embodiments, a computer-implemented method of quantifying and classifying coronary plaque within a coronary region of a subject based on non-invasive medical image analysis is provided, the method comprising: accessing, by a computer system, a medical image of a coronary region of a subject, wherein the medical image of the coronary region of the subject is obtained non-invasively; identifying, by the computer system utilizing a coronary artery identification algorithm, one or more coronary arteries within the medical image of the coronary region of the subject, wherein the coronary artery identification algorithm is configured to utilize raw medical images as input; identifying, by the computer system utilizing a plaque identification algorithm, one or more regions of plaque within the one or more coronary arteries identified from the medical image of the coronary region of the subject, wherein the plaque identification algorithm is configured to utilize raw medical images as input; determining, by the computer system, one or more vascular morphology parameters and a set of quantified plaque parameters of the one or more identified regions of plaque from the medical image of the coronary region of the subject, wherein the set of quantified plaque parameters comprises a ratio or function of volume to surface area, heterogeneity index, geometry, and radiodensity of the one or more regions of plaque within the medical image; generating, by the computer system, a weighted measure of the determined one or more vascular morphology parameters and the set of quantified plaque parameters of the one or more regions of plaque; and classifying, by the computer system, the one or more regions of plaque within the medical image as stable plaque or unstable plaque based at least in part on the generated weighted measure of the determined one or more vascular morphology parameters and the determined set of quantified plaque parameters, wherein the computer system comprises a computer processor and an electronic storage medium.

In some embodiments of a computer-implemented method of quantifying and classifying coronary plaque within a coronary region of a subject based on non-invasive medical image analysis, a ratio of volume to surface area of the one or more regions of plaque below a predetermined threshold is indicative of stable plaque. In some embodiments of a computer-implemented method of quantifying and classifying coronary plaque within a coronary region of a subject based on non-invasive medical image analysis, a heterogeneity of the one or more regions of plaque below a predetermined threshold is indicative of stable plaque. In some embodiments of a computer-implemented method of quantifying and classifying coronary plaque within a coronary region of a subject based on non-invasive medical image analysis, the heterogeneity index of one or more regions of plaque is determined by generating spatial mapping of radiodensity values across the one or more regions of plaque.

In some embodiments of a computer-implemented method of quantifying and classifying coronary plaque within a coronary region of a subject based on non-invasive medical image analysis, the method further comprises generating, by the computer system, an assessment of the subject for one or more of atherosclerosis, stenosis, or ischemia based at least in part on the classified one or more regions of plaque. In some embodiments of a computer-implemented method of quantifying and classifying coronary plaque within a coronary region of a subject based on non-invasive medical image analysis, the medical image is obtained using an imaging technique comprising one or more of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS). In some embodiments of a computer-implemented method of quantifying and classifying coronary plaque within a coronary region of a subject based on non-invasive medical image analysis, the one or more vascular morphology parameters comprises a classification of arterial remodeling.

In some embodiments, a method for analyzing CT images and corresponding information is provided, the method comprising: storing computer-executable instructions, a set of computed tomography (CT) images of a patient's coronary vessels, vessel labels, and artery information associated with the set of CT images including information indicative of stenosis and plaque of segments of the coronary vessels, and indicative of locations of the coronary vessels; generating and displaying in a user interface a first panel including an artery tree comprising a three-dimensional (3D) representation of coronary vessels based on the CT images and depicting coronary vessels identified in the CT images, and depicting segment labels, the artery tree not including heart tissue between branches of the artery tree; receiving a first input indicating a selection of a coronary vessel in the artery tree in the first panel; in response to the first input, generating and displaying on the user interface a second panel illustrating at least a portion of the selected coronary vessel in at least one straightened multiplanar vessel (SMPR) view; generating and displaying on the user interface a third panel showing a cross-sectional view of the selected coronary vessel, the cross-sectional view generated using one of the set of CT images of the selected coronary vessel, wherein locations along the at least one SMPR view are each associated with one of the CT images in the set of CT images such that a selection of a particular location along the coronary vessel in the at least one SMPR view displays the associated CT image in the cross-sectional view in the third panel; generating and displaying on the user interface a fourth panel showing at least one anatomical plane view of the selected coronary vessel based on the set of stored CT images, wherein the method is performed by one or more computer hardware processors executing computer-executable instructions stored on one or more non-transitory computer storage mediums.

In some embodiments of a method for analyzing CT images and corresponding information, one or more anatomical plane views include an axial plane view, a coronal plane view, and a sagittal plane view each corresponding to the selected coronary vessel. In some embodiments of a method for analyzing CT images and corresponding information, the method further comprises receiving a second input on the second panel of the user interface indicating a first location along the selected coronary vessel in the at least one SMPR view, and in response to the second input, generating and displaying in the cross-sectional view in the third panel a CT image associated with the first location of the selected coronary vessel, and generating and displaying in the fourth panel an axial plane view, a coronal plane view, and a sagittal plane view of the selected coronary vessel that correspond to the selected coronary vessel at the first location. In some embodiments of a method for analyzing CT images and corresponding information, the method further comprises receiving a third input on the second panel pf the user interface indicating a second location along the selected coronary vessel in the at least one SMPR view, and in response to the third input, generating and displaying in the cross-sectional view in the third panel a CT image associated with the second location of the selected coronary vessel, and generating and displaying in the fourth panel an axial plane view, a coronal plane view, and a sagittal plane view of the selected coronary vessel that correspond to the selected coronary vessel at the second location.

In some embodiments of a method for analyzing CT images and corresponding information, the method further comprises generating and displaying segment name labels, proximal to a respective segment on the artery tree, indicative of the name of the segment, using the artery information, and in response to an input selection of a first segment name label displayed on the user interface, generating and displaying on the user interface a panel having a list of vessel segment names and indicating the current name of the selected vessel segment, and in response to an input selection of a second segment name label on the list, replacing the first segment name label with the second segment name label of the displayed artery tree in the user interface. In some embodiments of a method for analyzing CT images and corresponding information, the method further comprises generating and displaying on the user interface in a cartoon artery tree, the cartoon artery tree comprising a non-patient specific graphical representation of a coronary artery tree, and wherein in response to a selection of a vessel segment in the cartoon artery tree, a view of the selected vessel segment is displayed in the user interface in a SMPR view, and upon selection of a location of the vessel segment displayed in the SMPR view, generating and displaying in the user interface a panel that displays information related to stenosis or plaque of the selected vessel segment at the selected location. In some embodiments of a method for analyzing CT images and corresponding information, the method further comprises generating and displaying a tool bar on a the user interface, the tool bar comprising at least one of the following tools: a lumen wall tool, a snap to vessel wall tool, a snap to lumen wall tool, vessel wall tool, a segment tool, a stenosis tool, a plaque overlay tool a snap to centerline tool, chronic total occlusion tool, stent tool, an exclude tool, a tracker tool, or a distance measurement tool.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

The disclosed aspects will hereinafter be described in conjunction with the accompanying drawings, which are incorporated in and constitute a part of this specification, and are provided to illustrate and provide a further understanding of example embodiments, and not to limit the disclosed aspects. In the drawings, like designations denote like elements unless otherwise stated.

FIGS. 5B-5I illustrate example embodiment(s) of a patient-specific medical report generated based on medical image analysis.

FIG. 6F illustrates an example of a three-dimensional (3D) rendering of a coronary artery tree that allows a user to view the vessels and modify the labels of a vessel.

FIG. 7F illustrates the lumen snap tool button (left) in the vessel snap tool button (right) on a user interface which can be used to activate these tools.

FIG. 7G illustrates an example of a panel that can be displayed on the user interface while using the lumen snap tool in the vessel snap tool.

FIG. 7U is an example of a view that can be displayed when extending the centerline of a vessel. FIG. 7V illustrates an example of a view that can be displayed when saving or canceling centerline edits. FIG. 7W is an example of a CMPR view that can be displayed when editing the vessel centerline.

FIGS. 7Z and 7AA illustrates examples of panels that can be displayed while using the exclude tool, which allows a portion of the vessel to be excluded from the analysis, for example, due to image aberrations. A row FIGS. 7AB and 7AC illustrate examples of additional panels that can be displayed while using the exclude tool. FIG. 7 AB illustrates a panel that can be used to add a new exclusion. FIG. 7AC illustrates a panel that can be used to add a reason for the exclusion.

FIGS. 7AD, 7AE, 7AF, and 7AG illustrate examples of panels that can be displayed while using the distance tool, which can be used to measure the distance between two points on an image. For example, FIG. 7AD illustrates the distance tool being used to measure a distance on an SMPR view. FIG. 7AE illustrates the distance tool being used to measure a distance on an CMPR view. FIG. 7AF illustrates the distance will be used to measure a distance on a cross-sectional view of the vessel. FIG. 7AG illustrates the distance tool being used to measure a distance on an axial view.

FIG. 7AH illustrates a "vessel statistics" portion (button) of a panel which can be selected to display the vessel statistics tab.

FIG. 7AI illustrates the vessel statistics tab.

FIG. 7AJ illustrates functionality on the vessel statistics tab that allows a user to click through the details of multiple lesions.

FIG. 7AK further illustrates an example of the vessel panel which the user can use to toggle between vessels.

FIG. 9G illustrates another example of a panel that can be displayed on the user interface showing information of the vessel, for example, diameter stenosis and minimum luminal diameter.

FIG. 9H illustrates an example of a portion of a panel that can be displayed on the user interface indicating a diameter stenosis legend.

FIG. 9I illustrates an example of a panel that can be displayed on the user interface indicating minimum and reference lumen diameters.

FIG. 9J illustrates a portion of the panel shown in FIG. 9I, and shows how specific minimum lumen diameter details can be quickly and efficiently displayed by selecting (e.g., by hovering over) a desired graphic of a lumen.

FIG. 11A illustrates a CT image reconstructed using filtered back projection, while FIG. 11B illustrates the same CT image reconstructed using iterative reconstruction.

FIG. 11C illustrates a CT image reconstructed by using iterative reconstruction, while FIG. 11D illustrates the same image reconstructed using machine learning.

DETAILED DESCRIPTION

Figure 1:
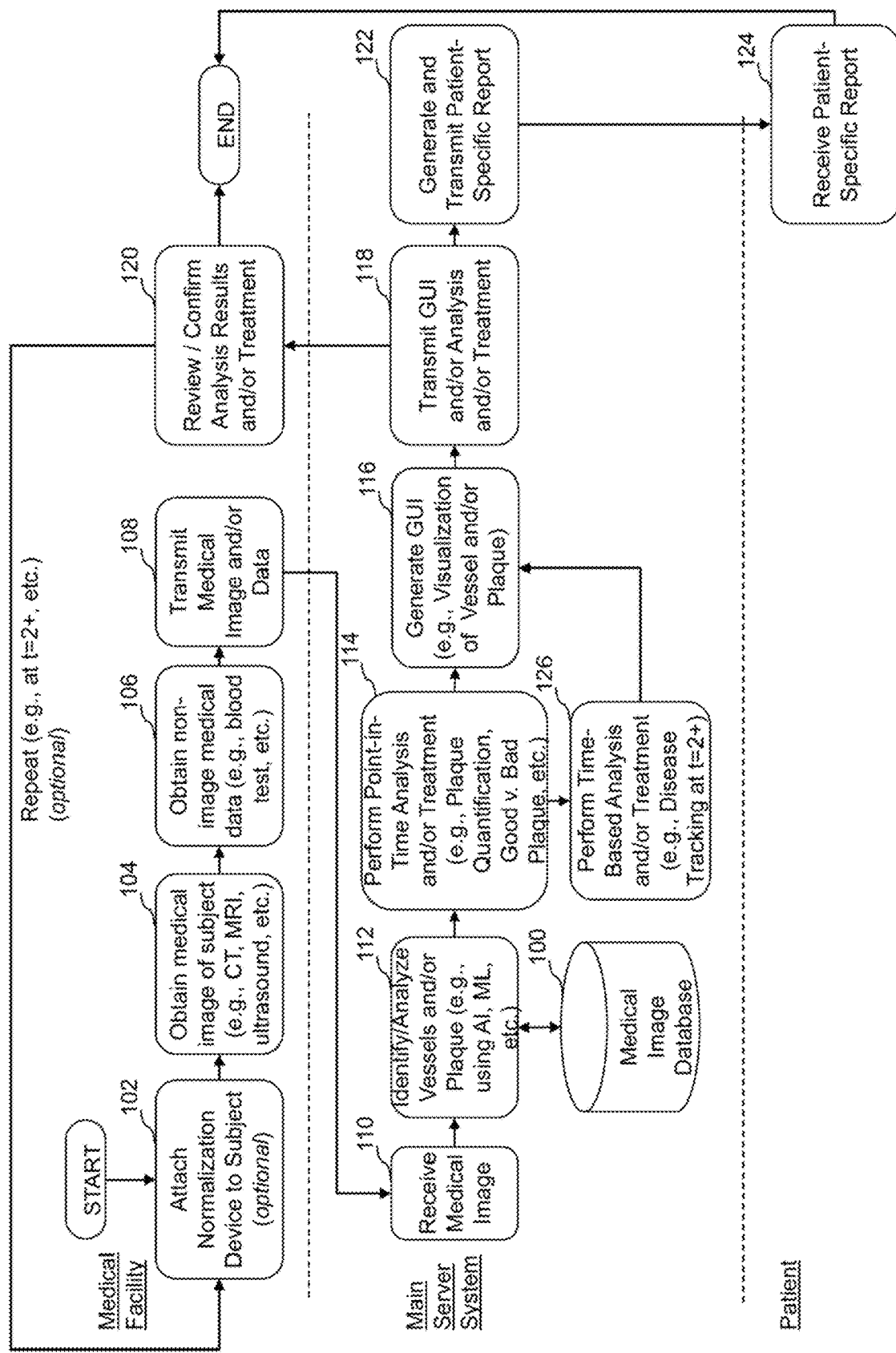
FIG. 1 is a flowchart illustrating an overview of an example embodiment(s) of a method for medical image analysis, visualization, risk assessment, disease tracking, treatment generation, and/or patient report generation.

Although several embodiments, examples, and illustrations are disclosed below, it will be understood by those of ordinary skill in the art that the inventions described herein extend beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

INTRODUCTION

Disclosed herein are systems, methods, and devices for medical image analysis, diagnosis, risk stratification, decision making and/or disease tracking. Coronary heart disease affects over 17.6 million Americans. The current trend in treating cardiovascular health issues is generally two-fold. First, physicians generally review a patient's cardiovascular health from a macro level, for example, by analyzing the biochemistry or blood content or biomarkers of a patient to determine whether there are high levels of cholesterol elements in the bloodstream of a patient. In response to high levels of cholesterol, some physicians will prescribe one or more drugs, such as statins, as part of a treatment plan in order to decrease what is perceived as high levels of cholesterol elements in the bloodstream of the patient.

The second general trend for currently treating cardiovascular health issues involves physicians evaluating a patient's cardiovascular health through the use of angiography to identify large blockages in various arteries of a patient. In response to finding large blockages in various arteries, physicians in some cases will perform an angioplasty procedure wherein a balloon catheter is guided to the point of narrowing in the vessel. After properly positioned, the balloon is inflated to compress or flatten the plaque or fatty matter into the artery wall and/or to stretch the artery open to increase the flow of blood through the vessel and/or to the heart. In some cases, the balloon is used to position and expand a stent within the vessel to compress the plaque and/or maintain the opening of the vessel to allow more blood to flow. About 500,000 heart stent procedures are performed each year in the United States.

However, a recent federally funded $100 million study calls into question whether the current trends in treating cardiovascular disease are the most effective treatment for all types of patients. The recent study involved over 5,000 patients with moderate to severe stable heart disease from 320 sites in 37 countries and provided new evidence showing that stents and bypass surgical procedures are likely no more effective than drugs combined with lifestyle changes for people with stable heart disease. Accordingly, it may be more advantageous for patients with stable heart disease to forgo invasive surgical procedures, such as angioplasty and/or heart bypass, and instead be prescribed heart medicines, such as statins, and certain lifestyle changes, such as regular exercise. This new treatment regimen could affect thousands of patients worldwide. Of the estimated 500,000 heart stent procedures performed annually in the United States, it is estimated that a fifth of those are for people with stable heart disease. It is further estimated that 25% of the estimated 100,000 people with stable heart disease, or roughly 23,000 people, are individuals that do not experience any chest pain. Accordingly, over 20,000 patients annually could potentially forgo invasive surgical procedures or the complications resulting from such procedures.

To determine whether a patient should forgo invasive surgical procedures and opt instead for a drug regimen and/or to generate a more effective treatment plan, it can be important to more fully understand the cardiovascular disease of a patient. Specifically, it can be advantageous to better understand the arterial vessel health of a patient. For example, it is helpful to understand whether plaque build-up in a patient is mostly fatty matter build-up or mostly calcified matter build-up, because the former situation may warrant treatment with heart medicines, such as statins, whereas in the latter situation a patient should be subject to further periodic monitoring without prescribing heart medicine or implanting any stents. However, if the plaque build-up is significant enough to cause severe stenosis or narrowing of the arterial vessel such that blood flow to heart muscle might be blocked, then an invasive angioplasty procedure to implant a stent may likely be required because heart attack or sudden cardiac death (SCD) could occur in such patients without the implantation of a stent to enlarge the vessel opening. Sudden cardiac death is one of the largest causes of natural death in the United States, accounting for approximately 325,000 adult deaths per year and responsible for nearly half of all deaths from cardiovascular disease. For males, SCD is twice as common as compared to females. In general, SCD strikes people in the mid-30 to mid-40 age range. In over 50% of cases, sudden cardiac arrest occurs with no warning signs.

With respect to the millions suffering from heart disease, there is a need to better understand the overall health of the artery vessels within a patient beyond just knowing the blood chemistry or content of the blood flowing through such artery vessels. For example, in some embodiments of systems, devices, and methods disclosed herein, arteries with "good" or stable plaque or plaque comprising hardened calcified content are considered non-life threatening to patients whereas arteries containing "bad" or unstable plaque or plaque comprising fatty material are considered more life threatening because such bad plaque may rupture within arteries thereby releasing such fatty material into the arteries. Such a fatty material release in the blood stream can cause inflammation that may result in a blood clot. A blood clot within an artery can prevent blood from traveling to heart muscle thereby causing a heart attack or other cardiac event. Further, in some instances, it is generally more difficult for blood to flow through fatty plaque buildup than it is for blood to flow through calcified plaque build-up. Therefore, there is a need for better understanding and analysis of the arterial vessel walls of a patient.

Further, while blood tests and drug treatment regimens are helpful in reducing cardiovascular health issues and mitigating against cardiovascular events (for example, heart attacks), such treatment methodologies are not complete or perfect in that such treatments can misidentify and/or fail to pinpoint or diagnose significant cardiovascular risk areas. For example, the mere analysis of the blood chemistry of a patient will not likely identify that a patient has artery vessels having significant amounts of fatty deposit material bad plaque buildup along a vessel wall. Similarly, an angiogram, while helpful in identifying areas of stenosis or vessel narrowing, may not be able to clearly identify areas of the artery vessel wall where there is significant buildup of bad plaque. Such areas of buildup of bad plaque within an artery vessel wall can be indicators of a patient at high risk of suffering a cardiovascular event, such as a heart attack. In certain circumstances, areas where there exist areas of bad plaque can lead to a rupture wherein there is a release of the fatty materials into the bloodstream of the artery, which in turn can cause a clot to develop in the artery. A blood clot in the artery can cause a stoppage of blood flow to the heart tissue, which can result in a heart attack. Accordingly, there is a need for new technology for analyzing artery vessel walls and/or identifying areas within artery vessel walls that comprise a buildup of plaque whether it be bad or otherwise.

Various systems, methods, and devices disclosed herein are directed to embodiments for addressing the foregoing issues. In particular, various embodiments described herein relate to systems, methods, and devices for medical image analysis, diagnosis, risk stratification, decision making and/or disease tracking. In some embodiments, the systems, devices, and methods described herein are configured to utilize non-invasive medical imaging technologies, such as a CT image for example, which can be inputted into a computer system configured to automatically and/or dynamically analyze the medical image to identify one or more coronary arteries and/or plaque within the same. For example, in some embodiments, the system can be configured to utilize one or more machine learning and/or artificial intelligence algorithms to automatically and/or dynamically analyze a medical image to identify, quantify, and/or classify one or more coronary arteries and/or plaque. In some embodiments, the system can be further configured to utilize the identified, quantified, and/or classified one or more coronary arteries and/or plaque to generate a treatment plan, track disease progression, and/or a patient-specific medical report, for example using one or more artificial intelligence and/or machine learning algorithms. In some embodiments, the system can be further configured to dynamically and/or automatically generate a visualization of the identified, quantified, and/or classified one or more coronary arteries and/or plaque, for example in the form of a graphical user interface. Further, in some embodiments, to calibrate medical images obtained from different medical imaging scanners and/or different scan parameters or environments, the system can be configured to utilize a normalization device comprising one or more compartments of one or more materials.

As will be discussed in further detail, the systems, devices, and methods described herein allow for automatic and/or dynamic quantified analysis of various parameters relating to plaque, cardiovascular arteries, and/or other structures. More specifically, in some embodiments described herein, a medical image of a patient, such as a coronary CT image, can be taken at a medical facility. Rather than having a physician eyeball or make a general assessment of the patient, the medical image is transmitted to a backend main server in some embodiments that is configured to conduct one or more analyses thereof in a reproducible manner. As such, in some embodiments, the systems, methods, and devices described herein can provide a quantified measurement of one or more features of a coronary CT image using automated and/or dynamic processes. For example, in some embodiments, the main server system can be configured to identify one or more vessels, plaque, and/or fat from a medical image. Based on the identified features, in some embodiments, the system can be configured to generate one or more quantified measurements from a raw medical image, such as for example radiodensity of one or more regions of plaque, identification of stable plaque and/or unstable plaque, volumes thereof, surface areas thereof, geometric shapes, heterogeneity thereof, and/or the like. In some embodiments, the system can also generate one or more quantified measurements of vessels from the raw medical image, such as for example diameter, volume, morphology, and/or the like. Based on the identified features and/or quantified measurements, in some embodiments, the system can be configured to generate a risk assessment and/or track the progression of a plaque-based disease or condition, such as for example atherosclerosis, stenosis, and/or ischemia, using raw medical images. Further, in some embodiments, the system can be configured to generate a visualization of GUI of one or more identified features and/or quantified measurements, such as a quantized color mapping of different features. In some embodiments, the systems, devices, and methods described herein are configured to utilize medical image-based processing to assess for a subject his or her risk of a cardiovascular event, major adverse cardiovascular event (MACE), rapid plaque progression, and/or non-response to medication. In particular, in some embodiments, the system can be configured to automatically and/or dynamically assess such health risk of a subject by analyzing only non-invasively obtained medical images. In some embodiments, one or more of the processes can be automated using an AI and/or ML algorithm. In some embodiments, one or more of the processes described herein can be performed within minutes in a reproducible manner. This is stark contrast to existing measures today which do not produce reproducible prognosis or assessment, take extensive amounts of time, and/or require invasive procedures.

As such, in some embodiments, the systems, devices, and methods described herein are able to provide physicians and/or patients specific quantified and/or measured data relating to a patient's plaque that do not exist today. For example, in some embodiments, the system can provide a specific numerical value for the volume of stable and/or unstable plaque, the ratio thereof against the total vessel volume, percentage of stenosis, and/or the like, using for example radiodensity values of pixels and/or regions within a medical image. In some embodiments, such detailed level of quantified plaque parameters from image processing and downstream analytical results can provide more accurate and useful tools for assessing the health and/or risk of patients in completely novel ways.

General Overview

In some embodiments, the systems, devices, and methods described herein are configured to automatically and/or dynamically perform medical image analysis, diagnosis, risk stratification, decision making and/or disease tracking. FIG. 1 is a flowchart illustrating an overview of an example embodiment(s) of a method for medical image analysis, visualization, risk assessment, disease tracking, treatment generation, and/or patient report generation. As illustrated in FIG. 1, in some embodiments, the system is configured to access and/or analyze one or more medical images of a subject, such as for example a medical image of a coronary region of a subject or patient.

In some embodiments, before obtaining the medical image, a normalization device is attached to the subject and/or is placed within a field of view of a medical imaging scanner at block 102. For example, in some embodiments, the normalization device can comprise one or more compartments comprising one or more materials, such as water, calcium, and/or the like. Additional detail regarding the normalization device is provided below. Medical imaging scanners may produce images with different scalable radiodensities for the same object. This, for example, can depend not only on the type of medical imaging scanner or equipment used but also on the scan parameters and/or environment of the particular day and/or time when the scan was taken. As a result, even if two different scans were taken of the same subject, the brightness and/or darkness of the resulting medical image may be different, which can result in less than accurate analysis results processed from that image. To account for such differences, in some embodiments, a normalization device comprising one or more known elements is scanned together with the subject, and the resulting image of the one or more known elements can be used as a basis for translating, converting, and/or normalizing the resulting image. As such, in some embodiments, a normalization device is attached to the subject and/or placed within the field of view of a medical imaging scan at a medical facility.

In some embodiments, at block 104, the medical facility then obtains one or more medical images of the subject. For example, the medical image can be of the coronary region of the subject or patient. In some embodiments, the systems disclosed herein can be configured to take in CT data from the image domain or the projection domain as raw scanned data or any other medical data, such as but not limited to: x-ray; Dual-Energy Computed Tomography (DECT), Spectral CT, photon-counting detector CT, ultrasound, such as echocardiography or intravascular ultrasound (IVUS); magnetic resonance (MR) imaging; optical coherence tomography (OCT); nuclear medicine imaging, including positron-emission tomography (PET) and single photon emission computed tomography (SPECT); near-field infrared spectroscopy (NIRS); and/or the like. As used herein, the term CT image data or CT scanned data can be substituted with any of the foregoing medical scanning modalities and process such data through an artificial intelligence (AI) algorithm system in order to generate processed CT image data. In some embodiments, the data from these imaging modalities enables determination of cardiovascular phenotype, and can include the image domain data, the projection domain data, and/or a combination of both.

In some embodiments, at block 106, the medical facility can also obtain non-imaging data from the subject. For example, this can include blood tests, biomarkers, panomics and/or the like. In some embodiments, at block 108, the medical facility can transmit the one or more medical images and/or other non-imaging data at block 108 to a main server system. In some embodiments, the main server system can be configured to receive and/or otherwise access the medical image and/or other non-imaging data at block 110.

In some embodiments, at block 112, the system can be configured to automatically and/or dynamically analyze the one or more medical images which can be stored and/or accessed from a medical image database 100. For example, in some embodiments, the system can be configured to take in raw CT image data and apply an artificial intelligence (AI) algorithm, machine learning (ML) algorithm, and/or other physics-based algorithm to the raw CT data in order to identify, measure, and/or analyze various aspects of the identified arteries within the CT data. In some embodiments, the inputting of the raw medical image data involves uploading the raw medical image data into cloud-based data repository system. In some embodiments, the processing of the medical image data involves processing the data in a cloud-based computing system using an AI and/or ML algorithm. In some embodiments, the system can be configured to analyze the raw CT data in about 1 minute, about 2 minutes, about 3 minutes, about 4 minutes, about 5 minutes, about 6 minutes, about 7 minutes, about 8 minutes, about 9 minutes, about 10 minutes, about 15 minutes, about 20 minutes, about 30 minutes, about 35 minutes, about 40 minutes, about 45 minutes, about 50 minutes, about 55 minutes, about 60 minutes, and/or within a range defined by two of the aforementioned values.

In some embodiments, the system can be configured to utilize a vessel identification algorithm to identify and/or analyze one or more vessels within the medical image. In some embodiments, the system can be configured to utilize a coronary artery identification algorithm to identify and/or analyze one or more coronary arteries within the medical image. In some embodiments, the system can be configured to utilize a plaque identification algorithm to identify and/or analyze one or more regions of plaque within the medical image. In some embodiments, the vessel identification algorithm, coronary artery identification algorithm, and/or plaque identification algorithm comprises an AI and/or ML algorithm. For example, in some embodiments, the vessel identification algorithm, coronary artery identification algorithm, and/or plaque identification algorithm can be trained on a plurality of medical images wherein one or more vessels, coronary arteries, and/or regions of plaque are pre-identified. Based on such training, for example by use of a Convolutional Neural Network in some embodiments, the system can be configured to automatically and/or dynamically identify from raw medical images the presence and/or parameters of vessels, coronary arteries, and/or plaque.

As such, in some embodiments, the processing of the medical image or raw CT scan data can comprise analysis of the medical image or CT data in order to determine and/or identify the existence and/or nonexistence of certain artery vessels in a patient. As a natural occurring phenomenon, certain arteries may be present in certain patients whereas such certain arteries may not exist in other patients.

In some embodiments, at block 112, the system can be further configured to analyze the identified vessels, coronary arteries, and/or plaque, for example using an AI and/or ML algorithm. In particular, in some embodiments, the system can be configured to determine one or more vascular morphology parameters, such as for example arterial remodeling, curvature, volume, width, diameter, length, and/or the like. In some embodiments, the system can be configured to determine one or more plaque parameters, such as for example volume, surface area, geometry, radiodensity, ratio or function of volume to surface area, heterogeneity index, and/or the like of one or more regions of plaque shown within the medical image. "Radiodensity" as used herein is a broad term that refers to the relative inability of electromagnetic relation (e.g., X-rays) to pass through a material. In reference to an image, radiodensity values refer to values indicting a density in image data (e.g., film, print, or in an electronic format) where the radiodensity values in the image corresponds to the density of material depicted in the image.

In some embodiments, at block 114, the system can be configured to utilize the identified and/or analyzed vessels, coronary arteries, and/or plaque from the medical image to perform a point-in-time analysis of the subject. In some embodiments, the system can be configured to use automatic and/or dynamic image processing of one or more medical images taken from one point in time to identify and/or analyze one or more vessels, coronary arteries, and/or plaque and derive one or more parameters and/or classifications thereof. For example, as will be described in more detail herein, in some embodiments, the system can be configured to generate one or more quantification metrics of plaque and/or classify the identified regions of plaque as good or bad plaque. Further, in some embodiments, at block 114, the system can be configured to generate one or more treatment plans for the subject based on the analysis results. In some embodiments, the system can be configured to utilize one or more AI and/or ML algorithms to identify and/or analyze vessels or plaque, derive one or more quantification metrics and/or classifications, and/or generate a treatment plan.

In some embodiments, if a previous scan or medical image of the subject exists, the system can be configured to perform at block 126 one or more time-based analyses, such as disease tracking. For example, in some embodiments, if the system has access to one or more quantified parameters or classifications derived from previous scans or medical images of the subject, the system can be configured to compare the same with one or more quantified parameters or classifications derived from a current scan or medical image to determine the progression of disease and/or state of the subject.

In some embodiments, at block 116, the system is configured to automatically and/or dynamically generate a Graphical User Interface (GUI) or other visualization of the analysis results at block 116, which can include for example identified vessels, regions of plaque, coronary arteries, quantified metrics or parameters, risk assessment, proposed treatment plan, and/or any other analysis result discussed herein. In some embodiments, the system is configured to analyze arteries present in the CT scan data and display various views of the arteries present in the patient, for example within 10-15 minutes or less. In contrast, as an example, conducting a visual assessment of a CT to identify stenosis alone, without consideration of good or bad plaque or any other factor, can take anywhere between 15 minutes to more than an hour depending on the skill level, and can also have substantial variability across radiologists and/or cardiac imagers.

In some embodiments, at block 118, the system can be configured to transmit the generated GUI or other visualization, analysis results, and/or treatment to the medical facility. In some embodiments, at block 120, a physician at the medical facility can then review and/or confirm and/or revise the generated GUI or other visualization, analysis results, and/or treatment.

In some embodiments, at block 122, the system can be configured to further generate and transmit a patient-specific medical report to a patient, who can receive the same at block 124. In some embodiments, the patient-specific medical report can be dynamically generated based on the analysis results derived from and/or other generated from the medical image processing and analytics. For example, the patient-specific report can include identified vessels, regions of plaque, coronary arteries, quantified metrics or parameters, risk assessment, proposed treatment plan, and/or any other analysis result discussed herein.

In some embodiments, one or more of the process illustrated in FIG. 1 can be repeated, for example for the same patient at a different time to track progression of a disease and/or the state of the patient.

Image Processing-Based Classification of Good v. Bad Plaque

As discussed, in some embodiments, the systems, methods, and devices described herein are configured to automatically and/or dynamically identify and/or classify good v. bad plaque or stable v. unstable plaque based on medical image analysis and/or processing. For example, in some embodiments, the system can be configured to utilize an AI and/or ML algorithm to identify areas in an artery that exhibit plaque buildup within, along, inside and/or outside the arteries. In some embodiments, the system can be configured to identify the outline or boundary of plaque buildup associated with an artery vessel wall. In some embodiments, the system can be configured to draw or generate a line that outlines the shape and configuration of the plaque buildup associated with the artery. In some embodiments, the system can be configured to identify whether the plaque buildup is a certain kind of plaque and/or the composition or characterization of a particular plaque buildup. In some embodiments, the system can be configured to characterize plaque binarily, ordinally and/or continuously. In some embodiments, the system can be configured to determine that the kind of plaque buildup identified is a "bad" kind of plaque due to the dark color or dark gray scale nature of the image corresponding to the plaque area, and/or by determination of its attenuation density (e.g., using a Hounsfield unit scale or other). For example, in some embodiments, the system can be configured to identify certain plaque as "bad" plaque if the brightness of the plaque is darker than a pre-determined level. In some embodiments, the system can be configured to identify good plaque areas based on the white coloration and/or the light gray scale nature of the area corresponding to the plaque buildup. For example, in some embodiments, the system can be configured to identify certain plaque as "good" plaque if the brightness of the plaque is lighter than a pre-determined level. In some embodiments, the system can be configured to determine that dark areas in the CT scan are related to "bad" plaque, whereas the system can be configured to identify good plaque areas corresponding to white areas. In some embodiments, the system can be configured to identify and determine the total area and/or volume of total plaque, good plaque, and/or bad plaque identified within an artery vessel or plurality of vessels. In some embodiments, the system can be configured to determine the length of the total plaque area, good plaque area, and/or bad plaque area identified. In some embodiments, the system can be configured to determine the width of the total plaque area, good plaque area, and/or bad plaque area identified. The "good" plaque may be considered as such because it is less likely to cause heart attack, less likely to exhibit significant plaque progression, and/or less likely to be ischemia, amongst others. Conversely, the "bad" plaque be considered as such because it is more likely to cause heart attack, more likely to exhibit significant plaque progression, and/or more likely to be ischemia, amongst others. In some embodiments, the "good" plaque may be considered as such because it is less likely to result in the no-reflow phenomenon at the time of coronary revascularization. Conversely, the "bad" plaque may be considered as such because it is more likely to cause the no-reflow phenomenon at the time of coronary revascularization.

Figure 2A:
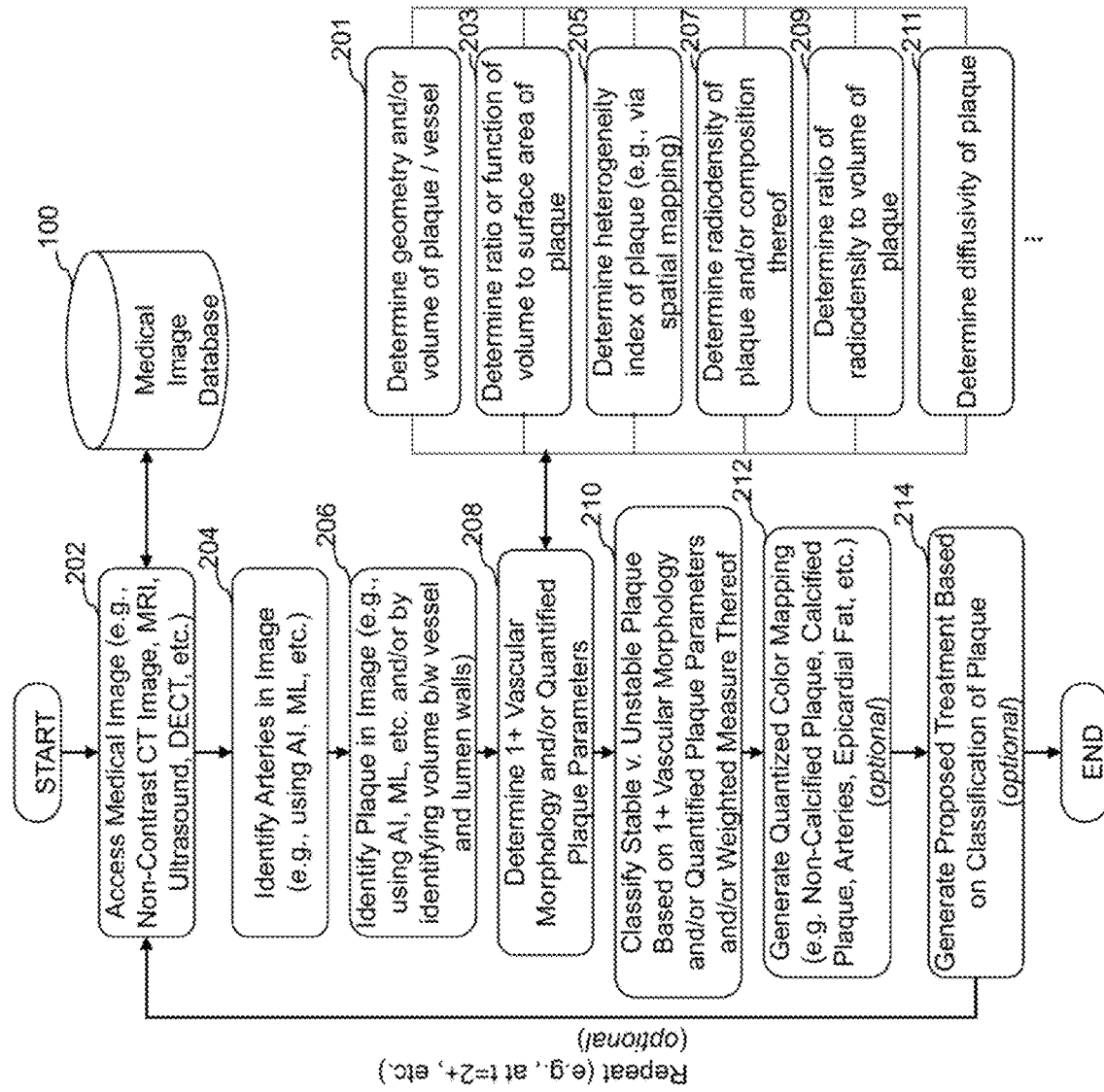
FIG. 2A is a flowchart illustrating an overview of an example embodiment(s) of a method for analysis and classification of plaque from a medical image.

FIG. 2A is a flowchart illustrating an overview of an example embodiment(s) of a method for analysis and classification of plaque from a medical image, which can be obtained non-invasively. As illustrated in FIG. 2A, at block 202, in some embodiments, the system can be configured to access a medical image, which can include a coronary region of a subject and/or be stored in a medical image database 100. The medical image database 100 can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 204, the system can be configured to identify one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 206, the system can be configured to identify one or more regions of plaque in the medical image. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system can be configured to identify a vessel wall and a lumen wall for each of the identified coronary arteries in the medical image. In some embodiments, the system is then configured to determine the volume in between the vessel wall and the lumen wall as plaque. In some embodiments, the system can be configured to identify regions of plaque based on the radiodensity values typically associated with plaque, for example by setting a predetermined threshold or range of radiodensity values that are typically associated with plaque with or without normalizing using a normalization device.

In some embodiments, the system is configured to automatically and/or dynamically determine one or more vascular morphology parameters and/or plaque parameters at block 208 from the medical image. In some embodiments, the one or more vascular morphology parameters and/or plaque parameters can comprise quantified parameters derived from the medical image. For example, in some embodiments, the system can be configured to utilize an AI and/or ML algorithm or other algorithm to determine one or more vascular morphology parameters and/or plaque parameters. As another example, in some embodiments, the system can be configured to determine one or more vascular morphology parameters, such as classification of arterial remodeling due to plaque, which can further include positive arterial remodeling, negative arterial remodeling, and/or intermediate arterial remodeling. In some embodiments, the classification of arterial remodeling is determined based on a ratio of the largest vessel diameter at a region of plaque to a normal reference vessel diameter of the same region which can be retrieved from a normal database. In some embodiments, the system can be configured to classify arterial remodeling as positive when the ratio of the largest vessel diameter at a region of plaque to a normal reference vessel diameter of the same region is more than 1.1. In some embodiments, the system can be configured to classify arterial remodeling as negative when the ratio of the largest vessel diameter at a region of plaque to a normal reference vessel diameter is less than 0.95. In some embodiments, the system can be configured to classify arterial remodeling as intermediate when the ratio of the largest vessel diameter at a region of plaque to a normal reference vessel diameter is between 0.95 and 1.1.

Further, as part of block 208, in some embodiments, the system can be configured to determine a geometry and/or volume of one or more regions of plaque and/or one or more vessels or arteries at block 201. For example, the system can be configured to determine if the geometry of a particular region of plaque is round or oblong or other shape. In some embodiments, the geometry of a region of plaque can be a factor in assessing the stability of the plaque. As another example, in some embodiments, the system can be configured to determine the curvature, diameter, length, volume, and/or any other parameters of a vessel or artery from the medical image.

In some embodiments, as part of block 208, the system can be configured to determine a volume and/or surface area of a region of plaque and/or a ratio or other function of volume to surface area of a region of plaque at block 203, such as for example a diameter, radius, and/or thickness of a region of plaque. In some embodiments, a plaque having a low ratio of volume to surface area can indicate that the plaque is stable. As such, in some embodiments, the system can be configured to determine that a ratio of volume to surface area of a region of plaque below a predetermined threshold is indicative of stable plaque.

In some embodiments, as part of block 208, the system can be configured to determine a heterogeneity index of a region of plaque at block 205. For instance, in some embodiments, a plaque having a low heterogeneity or high homogeneity can indicate that the plaque is stable. As such, in some embodiments, the system can be configured to determine that a heterogeneity of a region of plaque below a predetermined threshold is indicative of stable plaque. In some embodiments, heterogeneity or homogeneity of a region of plaque can be determined based on the heterogeneity or homogeneity of radiodensity values within the region of plaque. As such, in some embodiments, the system can be configured to determine a heterogeneity index of plaque by generating spatial mapping, such as a three-dimensional histogram, of radiodensity values within or across a geometric shape or region of plaque. In some embodiments, if a gradient or change in radiodensity values across the spatial mapping is above a certain threshold, the system can be configured to assign a high heterogeneity index. Conversely, in some embodiments, if a gradient or change in radiodensity values across the spatial mapping is below a certain threshold, the system can be configured to assign a low heterogeneity index.

In some embodiments, as part of block 208, the system can be configured to determine a radiodensity of plaque and/or a composition thereof at block 207. For example, a high radiodensity value can indicate that a plaque is highly calcified or stable, whereas a low radiodensity value can indicate that a plaque is less calcified or unstable. As such, in some embodiments, the system can be configured to determine that a radiodensity of a region of plaque above a predetermined threshold is indicative of stable stabilized plaque. In addition, different areas within a region of plaque can be calcified at different levels and thereby show different radiodensity values. As such, in some embodiments, the system can be configured to determine the radiodensity values of a region of plaque and/or a composition or percentage or change of radiodensity values within a region of plaque. For instance, in some embodiments, the system can be configured to determine how much or what percentage of plaque within a region of plaque shows a radiodensity value within a low range, medium range, high range, and/or any other classification.

Similarly, in some embodiments, as part of block 208, the system can be configured to determine a ratio of radiodensity value of plaque to a volume of plaque at block 209. For instance, it can be important to assess whether a large or small region of plaque is showing a high or low radiodensity value. As such, in some embodiments, the system can be configured to determine a percentage composition of plaque comprising different radiodensity values as a function or ratio of volume of plaque.

In some embodiments, as part of block 208, the system can be configured to determine the diffusivity and/or assign a diffusivity index to a region of plaque at block 211. For example, in some embodiments, the diffusivity of a plaque can depend on the radiodensity value of plaque, in which a high radiodensity value can indicate low diffusivity or stability of the plaque.

In some embodiments, at block 210, the system can be configured to classify one or regions of plaque identified from the medical image as stable v. unstable or good v. bad based on the one or more vascular morphology parameters and/or quantified plaque parameters determined and/or derived from raw medical images. In particular, in some embodiments, the system can be configured to generate a weighted measure of one or more vascular morphology parameters and/or quantified plaque parameters determined and/or derived from raw medical images. For example, in some embodiments, the system can be configured weight one or more vascular morphology parameters and/or quantified plaque parameters equally. In some embodiments, the system can be configured weight one or more vascular morphology parameters and/or quantified plaque parameters differently. In some embodiments, the system can be configured weight one or more vascular morphology parameters and/or quantified plaque parameters logarithmically, algebraically, and/or utilizing another mathematical transform. In some embodiments, the system is configured to classify one or more regions of plaque at block 210 using the generated weighted measure and/or using only some of the vascular morphology parameters and/or quantified plaque parameters.

In some embodiments, at block 212, the system is configured to generate a quantized color mapping based on the analyzed and/or determined parameters. For example, in some embodiments, the system is configured to generate a visualization of the analyzed medical image by generating a quantized color mapping of calcified plaque, non-calcified plaque, good plaque, bad plaque, stable plaque, and/or unstable plaque as determined using any of the analytical techniques described herein. Further, in some embodiments, the quantified color mapping can also include arteries and/or epicardial fat, which can also be determined by the system, for example by utilizing one or more AI and/or ML algorithms.

In some embodiments, at block 214, the system is configured to generate a proposed treatment plan for the subject based on the analysis, such as for example the classification of plaque derived automatically from a raw medical image. In particular, in some embodiments, the system can be configured to assess or predict the risk of atherosclerosis, stenosis, and/or ischemia of the subject based on a raw medical image and automated image processing thereof.

In some embodiments, one or more processes described herein in connection with FIG. 2A can be repeated. For example, if a medical image of the same subject is taken again at a later point in time, one or more processes described herein can be repeated and the analytical results thereof can be used for disease tracking and/or other purposes.

Determination of Non-Calcified Plaque from a Non-Contrast CT Image(s)

As discussed herein, in some embodiments, the system can be configured to utilize a CT or other medical image of a subject as input for performing one or more image analysis techniques to assess a subject, including for example risk of a cardiovascular event. In some embodiments, such CT image can comprise a contrast-enhanced CT image, in which case some of the analysis techniques described herein can be directly applied, for example to identify or classify plaque. However, in some embodiments, such CT image can comprise a non-contrast CT image, in which case it can be more difficult to identify and/or determine non-calcified plaque due to its low radiodensity value and overlap with other low radiodensity values components, such as blood for example. As such, in some embodiments, the systems, devices, and methods described herein provide a novel approach to determining non-calcified plaque from a non-contrast CT image, which can be more widely available.

Also, in some embodiments, in addition to or instead of analyzing a contrast-enhanced CT scan, the system can also be configured to examine the attenuation densities within the arteries that are lower than the attenuation density of the blood flowing within them in a non-contrast CT scan. In some embodiments, these "low attenuation" plaques may be differentiated between the blood attenuation density and the fat that sometimes surrounds the coronary artery and/or may represent non-calcified plaques of different materials. In some embodiments, the presence of these non-calcified plaques may offer incremental prediction for whether a previously calcified plaque is stabilizing or worsening or progressing or regressing. These findings that are measurable through these embodiments may be linked to the prognosis of a patient, wherein calcium stabilization (that is, higher attenuation densities) and lack of non-calcified plaque by may associated with a favorable prognosis, while lack of calcium stabilization (that is, no increase in attenuation densities), or significant progression or new calcium formation may be associated with a poorer prognosis, including risk of rapid progression of disease, heart attack or other major adverse cardiovascular event.

Figure 2B:
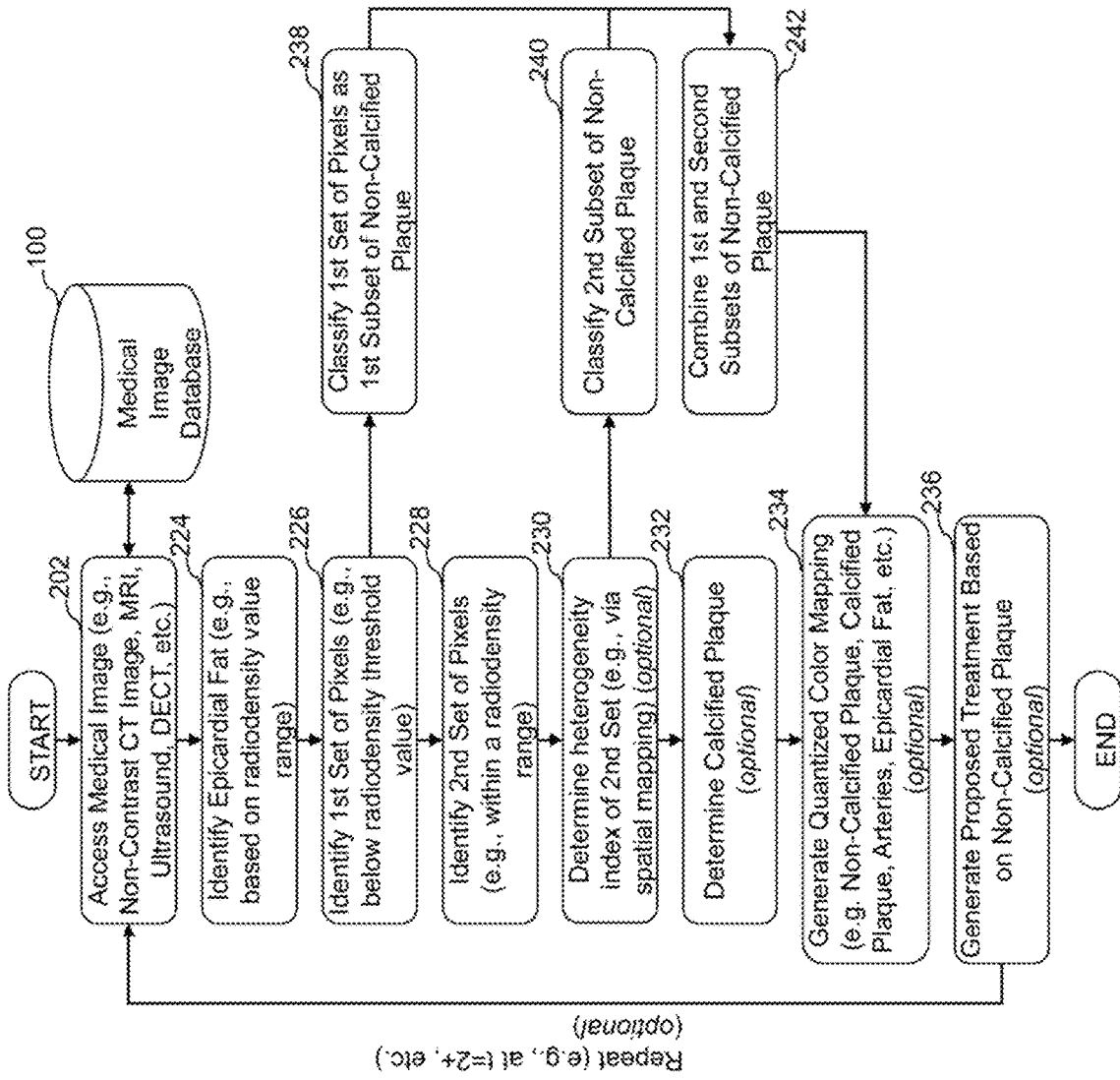
FIG. 2B is a flowchart illustrating an overview of an example embodiment(s) of a method for determination of non-calcified plaque from a non-contrast CT image(s).

FIG. 2B is a flowchart illustrating an overview of an example embodiment(s) of a method for determination of non-calcified and/or low-attenuated plaque from a medical image, such as a non-contrast CT image. As discussed herein and as illustrated in FIG. 2B, in some embodiments, the system can be configured to determine non-calcified and/or low-attenuated plaque from a medical image. In some embodiments, the medical image can be of the coronary region of the subject or patient. In some embodiments, the medical image can be obtained using one or more modalities such as CT, Dual-Energy Computed Tomography (DECT), Spectral CT, x-ray, ultrasound, echocardiography, IVUS, MR, OCT, nuclear medicine imaging, PET, SPECT, NIRS, and/or the like. In some embodiments, the system can be configured to access one or more medical images at block 202, for example from a medical image database 100.

In some embodiments, in order to determine non-calcified and/or low-attenuated plaque from the medical image or non-contrast CT image, the system can be configured to utilize a stepwise approach to first identify areas within the medical image that are clearly non-calcified plaque. In some embodiments, the system can then conduct a more detailed analysis of the remaining areas in the image to identify other regions of non-calcified and/or low-attenuated plaque. By utilizing such compartmentalized or a stepwise approach, in some embodiments, the system can identify or determine non-calcified and/or low-attenuated plaque from the medical image or non-contrast CT image with a faster turnaround rather than having to apply a more complicated analysis to every region or pixel of the image.

In particular, in some embodiments, at block 224, the system can be configured to identify epicardial fat from the medical image. In some embodiments, the system can be configured to identify epicardial fat by determining every pixel or region within the image that has a radiodensity value below a predetermined threshold and/or within a predetermined range. The exact predetermined threshold value or range of radiodensity for identifying epicardial fat can depend on the medical image, scanner type, scan parameters, and/or the like, which is why a normalization device can be used in some instances to normalize the medical image. For example, in some embodiments, the system can be configured to identify as epicardial fat pixels and/or regions within the medical image or non-contrast CT image with a radiodensity value that is around −100 Hounsfield units and/or within a range that includes −100 Hounsfield units. In particular, in some embodiments, the system can be configured to identify as epicardial fat pixels and/or regions within the medical image or non-contrast CT image with a radiodensity value that is within a range with a lower limit of about −100 Hounsfield units, about −110 Hounsfield units, about −120 Hounsfield units, about −130 Hounsfield units, about −140 Hounsfield units, about −150 Hounsfield units, about −160 Hounsfield units, about −170 Hounsfield units, about −180 Hounsfield units, about −190 Hounsfield units, or about −200 Hounsfield units, and an upper limit of about 30 Hounsfield units, about 20 Hounsfield units, about 10 Hounsfield units, about 0 Hounsfield units, about −10 Hounsfield units, about −20 Hounsfield units, about −30 Hounsfield units, about −40 Hounsfield units, about −50 Hounsfield units, about −60 Hounsfield units, about −70 Hounsfield units, about −80 Hounsfield units, or about −90 Hounsfield units.

In some embodiments, the system can be configured to identify and/or segment arteries on the medical image or non-contrast CT image using the identified epicardial fat as outer boundaries of the arteries. For example, the system can be configured to first identify regions of epicardial fat on the medical image and assign a volume in between epicardial fat as an artery, such as a coronary artery.

In some embodiments, at block 226, the system can be configured to identify a first set of pixels or regions within the medical image, such as within the identified arteries, as non-calcified or low-attenuated plaque. More specifically, in some embodiments, the system can be configured to identify as an initial set low-attenuated or non-calcified plaque by identifying pixels or regions with a radiodensity value that is below a predetermined threshold or within a predetermined range. For example, the predetermined threshold or predetermined range can be set such that the resulting pixels can be confidently marked as low-attenuated or non-calcified plaque without likelihood of confusion with another matter such as blood. In particular, in some embodiments, the system can be configured to identify the initial set of low-attenuated or non-calcified plaque by identifying pixels or regions with a radiodensity value below around 30 Hounsfield units. In some embodiments, the system can be configured to identify the initial set of low-attenuated or non-calcified plaque by identifying pixels or regions with a radiodensity value at or below around 60 Hounsfield units, around 55 Hounsfield units, around 50 Hounsfield units, around 45 Hounsfield units, around 40 Hounsfield units, around 35 Hounsfield units, around 30 Hounsfield units, around 25 Hounsfield units, around 20 Hounsfield units, around 15 Hounsfield units, around 10 Hounsfield units, around 5 Hounsfield units, and/or with a radiodensity value at or above around 0 Hounsfield units, around 5 Hounsfield units, around 10 Hounsfield units, around 15 Hounsfield units, around 20 Hounsfield units, around 25 Hounsfield units, and/or around 30 Hounsfield units. In some embodiments, the system can be configured classify pixels or regions that fall within or below this predetermined range of radiodensity values as a first set of identified non-calcified or low-attenuated plaque at block 238.

In some embodiments, the system at block 228 can be configured to identify a second set of pixels or regions within the medical image, such as within the identified arteries, that may or may not represent low-attenuated or non-calcified plaque. As discussed, in some embodiments, this second set of candidates of pixels or regions may require additional analysis to confirm that they represent plaque. In particular, in some embodiments, the system can be configured to identify this second set of pixels or regions that may potentially be low-attenuated or non-calcified plaque by identifying pixels or regions of the image with a radiodensity value within a predetermined range. In some embodiments, the predetermined range for identifying this second set of pixels or regions can be between around 30 Hounsfield units and 100 Hounsfield units. In some embodiments, the predetermined range for identifying this second set of pixels or regions can have a lower limit of around 0 Hounsfield units, 5 Hounsfield units, 10 Hounsfield units, 15 Hounsfield units, 20 Hounsfield units, 25 Hounsfield units, 30 Hounsfield units, 35 Hounsfield units, 40 Hounsfield units, 45 Hounsfield units, 50 Hounsfield units, and/or an upper limit of around 55 Hounsfield units, 60 Hounsfield units, 65 Hounsfield units, 70 Hounsfield units, 75 Hounsfield units, 80 Hounsfield units, 85 Hounsfield units, 90 Hounsfield units, 95 Hounsfield units, 100 Hounsfield units, 110 Hounsfield units, 120 Hounsfield units, 130 Hounsfield units, 140 Hounsfield units, 150 Hounsfield units.

In some embodiments, at block 230, the system can be configured conduct an analysis of the heterogeneity of the identified second set of pixels or regions. For example, depending on the range of radiodensity values used to identify the second set of pixels, in some embodiments, the second set of pixels or regions may include blood and/or plaque. Blood can typically show a more homogeneous gradient of radiodensity values compared to plaque. As such, in some embodiments, by analyzing the homogeneity or heterogeneity of the pixels or regions identified as part of the second set, the system can be able to distinguish between blood and non-calcified or low attenuated plaque. As such, in some embodiments, the system can be configured to determine a heterogeneity index of the second set of regions of pixels identified from the medical image by generating spatial mapping, such as a three-dimensional histogram, of radiodensity values within or across a geometric shape or region of plaque. In some embodiments, if a gradient or change in radiodensity values across the spatial mapping is above a certain threshold, the system can be configured to assign a high heterogeneity index and/or classify as plaque. Conversely, in some embodiments, if a gradient or change in radiodensity values across the spatial mapping is below a certain threshold, the system can be configured to assign a low heterogeneity index and/or classify as blood.

In some embodiments, at block 240, the system can be configured to identify a subset of the second set of regions of pixels identified from the medical image as plaque or non-calcified or low-attenuated plaque. In some embodiments, at block 242, the system can be configured to combine the first set of identified non-calcified or low-attenuated plaque from block 238 and the second set of identified non-calcified or low-attenuated plaque from block 240. As such, even using non-contrast CT images, in some embodiments, the system can be configured to identify low-attenuated or non-calcified plaque which can be more difficult to identify compared to calcified or high-attenuated plaque due to possible overlap with other matter such as blood.

In some embodiments, the system can also be configured to determine calcified or high-attenuated plaque from the medical image at block 232. This process can be more straightforward compared to identifying low-attenuated or non-calcified plaque from the medical image or non-contrast CT image. In particular, in some embodiments, the system can be configured to identify calcified or high-attenuated plaque from the medical image or non-contrast CT image by identifying pixels or regions within the image that have a radiodensity value above a predetermined threshold and/or within a predetermined range. For example, in some embodiments, the system can be configured to identify as calcified or high-attenuated plaque regions or pixels from the medical image or non-contrast CT image having a radiodensity value above around 100 Hounsfield units, around 150 Hounsfield units, around 200 Hounsfield units, around 250 Hounsfield units, around 300 Hounsfield units, around 350 Hounsfield units, around 400 Hounsfield units, around 450 Hounsfield units, around 500 Hounsfield units, around 600 Hounsfield units, around 700 Hounsfield units, around 800 Hounsfield units, around 900 Hounsfield units, around 1000 Hounsfield units, around 1100 Hounsfield units, around 1200 Hounsfield units, around 1300 Hounsfield units, around 1400 Hounsfield units, around 1500 Hounsfield units, around 1600 Hounsfield units, around 1700 Hounsfield units, around 1800 Hounsfield units, around 1900 Hounsfield units, around 2000

Hounsfield units, around 2500 Hounsfield units, around 3000 Hounsfield units, and/or any other minimum threshold.

In some embodiments, at block 234, the system can be configured to generate a quantized color mapping of one or more identified matters from the medical image. For example, in some embodiments, the system can be configured assign different colors to each of the different regions associated with different matters, such as non-calcified or low-attenuated plaque, calcified or high-attenuated plaque, all plaque, arteries, epicardial fat, and/or the like. In some embodiments, the system can be configured to generate a visualization of the quantized color map and/or present the same to a medical personnel or patient via a GUI. In some embodiments, at block 236, the system can be configured to generate a proposed treatment plan for a disease based on one or more of the identified non-calcified or low-attenuated plaque, calcified or high-attenuated plaque, all plaque, arteries, epicardial fat, and/or the like. For example, in some embodiments, the system can be configured to generate a treatment plan for an arterial disease, renal artery disease, abdominal atherosclerosis, carotid atherosclerosis, and/or the like, and the medical image being analyzed can be taken from any one or more regions of the subject for such disease analysis.

In some embodiments, one or more processes described herein in connection with FIG. 2B can be repeated. For example, if a medical image of the same subject is taken again at a later point in time, one or more processes described herein can be repeated and the analytical results thereof can be used for disease tracking and/or other purposes.

Further, in some embodiments, the system can be configured to identify and/or determine non-calcified plaque from a DECT or spectral CT image. Similar to the processes described above, in some embodiments, the system can be configured to access a DECT or spectral CT image, identify epicardial fat on the DECT image or spectral CT and/or segment one or more arteries on the DECT image or spectral CT, identify and/or classify a first set of pixels or regions within the arteries as a first set of low-attenuated or non-calcified plaque, and/or identify a second set of pixels or regions within the arteries as a second set of low-attenuated or non-calcified plaque. However, unlike the techniques described above, in some embodiments, such as for example where a DECT or spectral CT image is being analyzed, the system can be configured to identify a subset of those second set of pixels without having to perform a heterogeneity and/or homogeneity analysis of the second set of pixels. Rather, in some embodiments, the system can be configured to distinguish between blood and low-attenuated or non-calcified plaque directly from the image, for example by utilizing the dual or multispectral aspect of a DECT or spectral CT image. In some embodiments, the system can be configured to combine the first set of identified pixels or regions and the subset of the second set of pixels or regions identified as low-attenuated or non-calcified plaque to identify a whole set of the same on the medical image. In some embodiments, even if analyzing a DECT or spectral CT image, the system can be configured to further analyze the second set of pixels or regions by performing a heterogeneity or homogeneity analysis, similar to that described above in relation to block 230. For example, even if analyzing a DECT or spectral CT image, in some embodiments, the distinction between certain areas of blood and/or low-attenuated or non-calcified plaque may not be complete and/or accurate.

Imaging Analysis-Based Risk Assessment

In some embodiments, the systems, devices, and methods described herein are configured to utilize medical image-based processing to assess for a subject his or her risk of a cardiovascular event, major adverse cardiovascular event (MACE), rapid plaque progression, and/or non-response to medication. In particular, in some embodiments, the system can be configured to automatically and/or dynamically assess such health risk of a subject by analyzing only non-invasively obtained medical images, for example using AI and/or ML algorithms, to provide a full image-based analysis report within minutes.

In particular, in some embodiments, the system can be configured to calculate the total amount of plaque (and/or amounts of specific types of plaque) within a specific artery and/or within all the arteries of a patient. In some embodiments, the system can be configured to determine the total amount of bad plaque in a particular artery and/or within a total artery area across some or all of the arteries of the patient. In some embodiments, the system can be configured to determine a risk factor and/or a diagnosis for a particular patient to suffer a heart attack or other cardiac event based on the total amount of plaque in a particular artery and/or a total artery area across some or all of the arteries of a patient. Other risk factors that can be determined from the amount of "bad" plaque, or the relative amount of "bad" versus "good" plaque, can include the rate of disease progression and/or the likelihood of ischemia. In some embodiments, plaques can be measured by total volume (or area on cross-sectional imaging) as well as by relative amount when normalized to the total vessel volumes, total vessel lengths or subtended myocardium.

In some embodiments, the imaging data of the coronary arteries can include measures of atherosclerosis, stenosis and vascular morphology. In some embodiments, this information can be combined with other cardiovascular disease phenotyping by quantitative characterization of left and right ventricles, left and right atria; aortic, mitral, tricuspid and pulmonic valves; aorta, pulmonary artery, pulmonary vein, coronary sinus and inferior and superior vena cava; epicardial or pericoronary fat; lung densities; bone densities; pericardium and others. As an example, in some embodiments, the imaging data for the coronary arteries may be integrated with the left ventricular mass, which can be segmented according to the amount and location of the artery it is subtended by. This combination of left ventricular fractional myocardial mass to coronary artery information may enhance the prediction of whether a future heart attack will be a large one or a small one. As another example, in some embodiments, the vessel volume of the coronary arteries can be related to the left ventricular mass as a measure of left ventricular hypertrophy, which can be a common finding in patients with hypertension. Increased left ventricular mass (relative or absolute) may indicate disease worsening or uncontrolled hypertension. As another example, in some embodiments, the onset, progression, and/or worsening of atrial fibrillation may be predicted by the atrial size, volume, atrial free wall mass and thickness, atrial function and fat surrounding the atrium. In some embodiments, these predictions may be done with a ML or AI algorithm or other algorithm type.

Sequentially, in some embodiments, the algorithms that allow for segmentation of atherosclerosis, stenosis and vascular morphology—along with those that allow for segmentation of other cardiovascular structures, and thoracic structures—may serve as the inputs for the prognostic algorithms. In some embodiments, the outputs of the prognostic algorithms, or those that allow for image segmentation, may be leveraged as inputs to other algorithms that may then guide clinical decision making by predicting future events. As an example, in some embodiments, the integrated scoring of atherosclerosis, stenosis, and/or vascular morphology may identify patients who may benefit from coronary revascularization, that is, those who will achieve symptom benefit, reduced risk of heart attack and death. As another example, in some embodiments, the integrated scoring of atherosclerosis, stenosis and vascular morphology may identify individuals who may benefit from specific types of medications, such as lipid lowering medications (such as statin medications, PCSK-9 inhibitors, icosopent ethyl, and others); Lp(a) lowering medications; anti-thrombotic medications (such as clopidogrel, rivoroxaban and others). In some embodiments, the benefit that is predicted by these algorithms may be for reduced progression, determination of type of plaque progression (progression, regression or mixed response), stabilization due to the medical therapy, and/or need for heightened intensified therapy. In some embodiments, the imaging data may be combined with other data to identify areas within a coronary vessel that are normal and without plaque now but may be at higher likelihood of future plaque formation.

In some embodiments, an automated or manual co-registration method can be combined with the imaging segmentation data to compare two or more images over time. In some embodiments, the comparison of these images can allow for determination of differences in coronary artery atherosclerosis, stenosis and vascular morphology over time, and can be used as an input variable for risk prediction.

In some embodiments, the imaging data of the coronary arteries for atherosclerosis, stenosis, and vascular morphology—coupled or not coupled to thoracic and cardiovascular disease measurements—can be integrated into an algorithm that determines whether a coronary vessel is ischemia, or exhibits reduced blood flow or pressure (either at rest or hyperemic states).

In some embodiments, the algorithms for coronary atherosclerosis, stenosis and ischemia can be modified by a computer system and/or other to remove plaque or "seal" plaque. In some embodiments, a comparison can be made before or after the system has removed or sealed the plaque to determine whether any changes have occurred. For example, in some embodiments, the system can be configured to determine whether coronary ischemia is removed with the plaque sealing.

In some embodiments, the characterization of coronary atherosclerosis, stenosis and/or vascular morphology can enable relating a patient's biological age to their vascular age, when compared to a population-based cohort of patients who have undergone similar scanning. As an example, a 60-year old patient may have X units of plaque in their coronary arteries that is equivalent to the average 70-year old patient in the population-based cohort. In this case, the patient's vascular age may be 10 years older than the patient's biological age.

In some embodiments, the risk assessment enabled by the image segmentation prediction algorithms can allow for refined measures of disease or death likelihood in people being considered for disability or life insurance. In this scenario, the risk assessment may replace or augment traditional actuarial algorithms.

In some embodiments, imaging data may be combined with other data to augment risk assessment for future adverse events, such as heart attacks, strokes, death, rapid progression, non-response to medical therapy, no-reflow phenomenon and others. In some embodiments, other data may include a multi-omic approach wherein an algorithm integrates the imaging phenotype data with genotype data, proteomic data, transcriptomic data, metabolomic data, microbiomic data and/or activity and lifestyle data as measured by a smart phone or similar device.

Figure 3A:
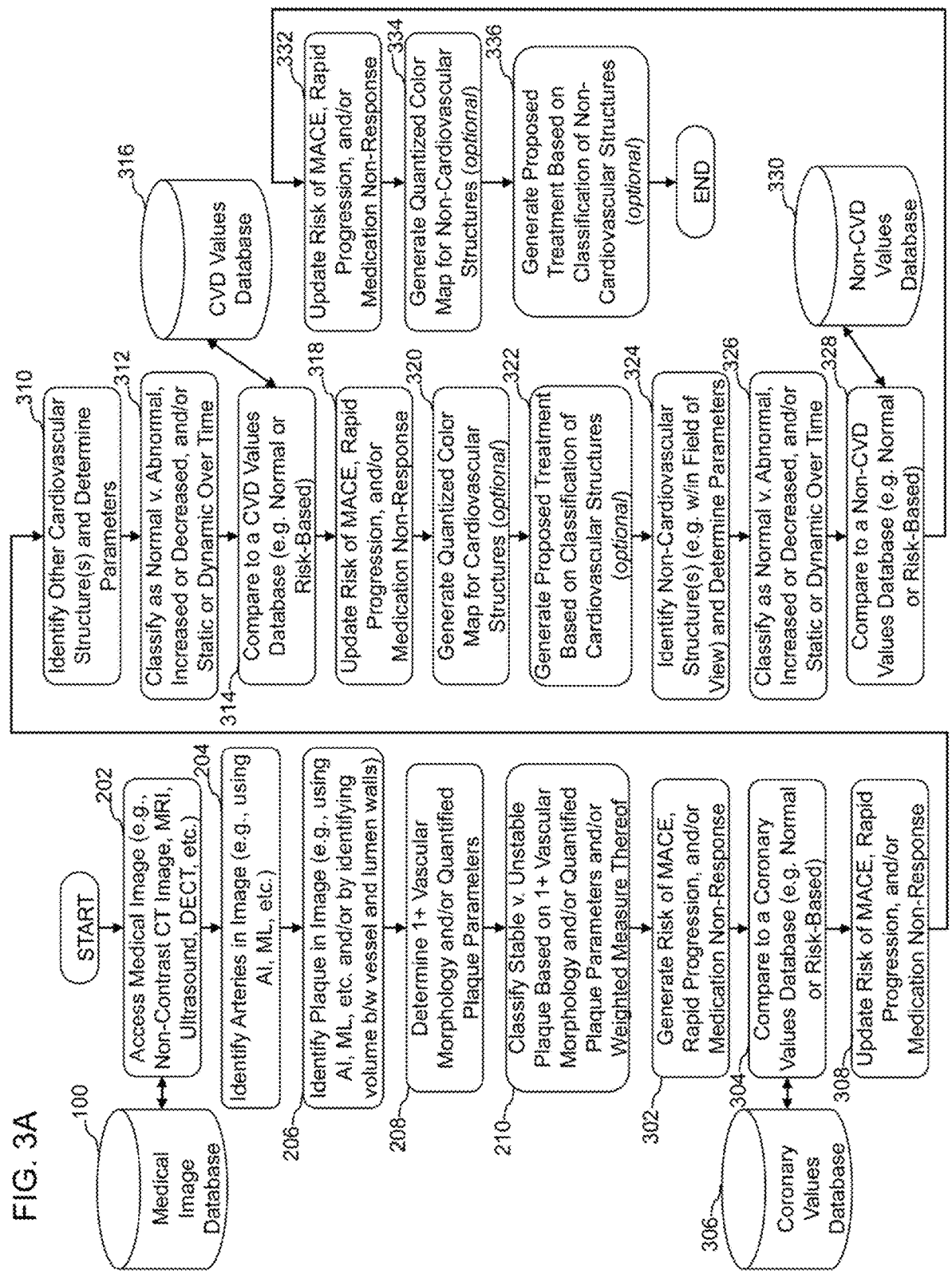
FIG. 3A is a flowchart illustrating an overview of an example embodiment(s) of a method for risk assessment based on medical image analysis.

FIG. 3A is a flowchart illustrating an overview of an example embodiment(s) of a method for risk assessment based on medical image analysis. As illustrated in FIG. 3A, in some embodiments, the system can be configured to access a medical image at block 202. Further, in some embodiments, the system can be configured to identify one or more arteries at block 204 and/or one or more regions of plaque at block 206. In addition, in some embodiments, the system can be configured to determine one or more vascular morphology and/or quantified plaque parameters at block 208 and/or classify stable or unstable plaque based on the determined one or more vascular morphology and/or quantified plaque parameters and/or a weighted measure thereof at block 210. Additional detail regarding the processes and techniques represented in blocks 202, 204, 206, 208, and 210 can be found in the description above in relation to FIG. 2A.

In some embodiments, the system can automatically and/or dynamically determine and/or generate a risk of cardiovascular event for the subject at block 302, for example using the classified stable and/or unstable regions of plaque. More specifically, in some embodiments, the system can utilize an AI, ML, or other algorithm to generate a risk of cardiovascular event, MACE, rapid plaque progression, and/or non-response to medication at block 302 based on the image analysis.

In some embodiments, at block 304, the system can be configured to compare the determined one or more vascular morphology parameters, quantified plaque parameters, and/or classified stable v. unstable plaque and/or values thereof, such as volume, ratio, and/or the like, to one or more known datasets of coronary values derived from one or more other subjects. The one or more known datasets can comprise one or more vascular morphology parameters, quantified plaque parameters, and/or classified stable v. unstable plaque and/or values thereof, such as volume, ratio, and/or the like, derived from medical images taken from other subjects, including healthy subjects and/or subjects with varying levels of risk. For example, the one or more known datasets of coronary values can be stored in a coronary values database 306 that can be locally accessible by the system and/or remotely accessible via a network connection by the system.

In some embodiments, at block 308, the system can be configured to update the risk of cardiovascular event for the subject based on the comparison to the one or more known datasets. For example, based on the comparison, the system may increase or decrease the previously generated risk assessment. In some embodiments, the system may maintain the previously generated risk assessment even after comparison. In some embodiments, the system can be configured to generate a proposed treatment for the subject based on the generated and/or updated risk assessment after comparison with the known datasets of coronary values.

In some embodiments, at block 310, the system can be configured to further identify one or more other cardiovascular structures from the medical image and/or determine one or more parameters associated with the same. For example, the one or more additional cardiovascular structures can include the left ventricle, right ventricle, left atrium, right atrium, aortic valve, mitral valve, tricuspid valve, pulmonic valve, aorta, pulmonary artery, inferior and superior vena cava, epicardial fat, and/or pericardium.

In some embodiments, parameters associated with the left ventricle can include size, mass, volume, shape, eccentricity, surface area, thickness, and/or the like. Similarly, in some embodiments, parameters associated with the right ventricle can include size, mass, volume, shape, eccentricity, surface area, thickness, and/or the like. In some embodiments, parameters associated with the left atrium can include size, mass, volume, shape, eccentricity, surface area, thickness, pulmonary vein angulation, atrial appendage morphology, and/or the like. In some embodiments, parameters associated with the right atrium can include size, mass, volume, shape, eccentricity, surface area, thickness, and/or the like.

Further, in some embodiments, parameters associated with the aortic valve can include thickness, volume, mass, calcifications, three-dimensional map of calcifications and density, eccentricity of calcification, classification by individual leaflet, and/or the like. In some embodiments, parameters associated with the mitral valve can include thickness, volume, mass, calcifications, three-dimensional map of calcifications and density, eccentricity of calcification, classification by individual leaflet, and/or the like. In some embodiments, parameters associated with the tricuspid valve can include thickness, volume, mass, calcifications, three-dimensional map of calcifications and density, eccentricity of calcification, classification by individual leaflet, and/or the like. In some embodiments, parameters associated with the pulmonic valve can include thickness, volume, mass, calcifications, three-dimensional map of calcifications and density, eccentricity of calcification, classification by individual leaflet, and/or the like.

In some embodiments, parameters associated with the aorta can include dimensions, volume, diameter, area, enlargement, outpouching, and/or the like. In some embodiments, parameters associated with the pulmonary artery can include dimensions, volume, diameter, area, enlargement, outpouching, and/or the like. In some embodiments, parameters associated with the inferior and superior vena cava can include dimensions, volume, diameter, area, enlargement, outpouching, and/or the like.

In some embodiments, parameters associated with epicardial fat can include volume, density, density in three dimensions, and/or the like. In some embodiments, parameters associated with the pericardium can include thickness, mass, and/or the like.

In some embodiments, at block 312, the system can be configured to classify one or more of the other identified cardiovascular structures, for example using the one or more determined parameters thereof. In some embodiments, for one or more of the other identified cardiovascular structures, the system can be configured to classify each as normal v. abnormal, increased or decreased, and/or static or dynamic over time.

In some embodiments, at block 314, the system can be configured to compare the determined one or more parameters of other cardiovascular structures to one or more known datasets of cardiovascular structure parameters derived from one or more other subjects. The one or more known datasets of cardiovascular structure parameters can include any one or more of the parameters mentioned above associated with the other cardiovascular structures. In some embodiments, the cardiovascular structure parameters of the one or more known datasets can be derived from medical images taken from other subjects, including healthy subjects and/or subjects with varying levels of risk. In some embodiments, the one or more known datasets of cardiovascular structure parameters can be stored in a cardiovascular structure values or cardiovascular disease (CVD) database 316 that can be locally accessible by the system and/or remotely accessible via a network connection by the system.

In some embodiments, at block 318, the system can be configured to update the risk of cardiovascular event for the subject based on the comparison to the one or more known datasets of cardiovascular structure parameters. For example, based on the comparison, the system may increase or decrease the previously generated risk assessment. In some embodiments, the system may maintain the previously generated risk assessment even after comparison.

In some embodiments, at block 320, the system can be configured to generate a quantified color map, which can include color coding for one or more other cardiovascular structures identified from the medical image, stable plaque, unstable plaque, arteries, and/or the like. In some embodiments, at block 322, the system can be configured to generate a proposed treatment for the subject based on the generated and/or updated risk assessment after comparison with the known datasets of cardiovascular structure parameters.

In some embodiments, at block 324, the system can be configured to further identify one or more non-cardiovascular structures from the medical image and/or determine one or more parameters associated with the same. For example, the medical image can include one or more non-cardiovascular structures that are in the field of view. In particular, the one or more non-cardiovascular structures can include the lungs, bones, liver, and/or the like.

In some embodiments, parameters associated with the non-cardiovascular structures can include volume, surface area, ratio or function of volume to surface area, heterogeneity of radiodensity values, radiodensity values, geometry (such as oblong, spherical, and/or the like), spatial radiodensity, spatial scarring, and/or the like. In addition, in some embodiments, parameters associated with the lungs can include density, scarring, and/or the like. For example, in some embodiments, the system can be configured to associate a low Hounsfield unit of a region of the lungs with emphysema. In some embodiments, parameters associated with bones, such as the spine and/or ribs, can include radiodensity, presence and/or extent of fractures, and/or the like. For example, in some embodiments, the system can be configured to associate a low Hounsfield unit of a region of bones with osteoporosis. In some embodiments, parameters associated with the liver can include density for non-alcoholic fatty liver disease which can be assessed by the system by analyzing and/or comparing to the Hounsfield unit density of the liver.

In some embodiments, at block 326, the system can be configured to classify one or more of the identified non-cardiovascular structures, for example using the one or more determined parameters thereof. In some embodiments, for one or more of the identified non-cardiovascular structures, the system can be configured to classify each as normal v. abnormal, increased or decreased, and/or static or dynamic over time.

In some embodiments, at block 328, the system can be configured to compare the determined one or more parameters of non-cardiovascular structures to one or more known datasets of non-cardiovascular structure parameters or non-CVD values derived from one or more other subjects. The one or more known datasets of non-cardiovascular structure parameters or non-CVD values can include any one or more of the parameters mentioned above associated with non-cardiovascular structures. In some embodiments, the non-cardiovascular structure parameters or non-CVD values of the one or more known datasets can be derived from medical images taken from other subjects, including healthy subjects and/or subjects with varying levels of risk. In some embodiments, the one or more known datasets of non-cardiovascular structure parameters or non-CVD values can be stored in a non-cardiovascular structure values or non-CVD database 330 that can be locally accessible by the system and/or remotely accessible via a network connection by the system.

In some embodiments, at block 332, the system can be configured to update the risk of cardiovascular event for the subject based on the comparison to the one or more known datasets of non-cardiovascular structure parameters or non-CVD values. For example, based on the comparison, the system may increase or decrease the previously generated risk assessment. In some embodiments, the system may maintain the previously generated risk assessment even after comparison.

In some embodiments, at block 334, the system can be configured to generate a quantified color map, which can include color coding for one or more non-cardiovascular structures identified from the medical image, as well as for the other cardiovascular structures identified from the medical image, stable plaque, unstable plaque, arteries, and/or the like. In some embodiments, at block 336, the system can be configured to generate a proposed treatment for the subject based on the generated and/or updated risk assessment after comparison with the known datasets of non-cardiovascular structure parameters or non-CVD values.

In some embodiments, one or more processes described herein in connection with FIG. 3A can be repeated. For example, if a medical image of the same subject is taken again at a later point in time, one or more processes described herein can be repeated and the analytical results thereof can be used for tracking of risk assessment of the subject based on image processing and/or other purposes.

Quantification of Atherosclerosis

In some embodiments, the system is configured to analyze one or more arteries present in a medical image, such as CT scan data, to automatically and/or dynamically quantify atherosclerosis. In some embodiments, the system is configured to quantify atherosclerosis as the primary disease process, while stenosis and/or ischemia can be considered surrogates thereof. Prior to the embodiments described herein, it was not feasible to quantify the primary disease due to the lengthy manual process and manpower needed to do so, which could take anywhere from 4 to 8 or more hours. In contrast, in some embodiments, the system is configured to quantify atherosclerosis based on analysis of a medical image and/or CT scan using one or more AI, ML, and/or other algorithms that can segment, identify, and/or quantify atherosclerosis in less than about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 20 minutes, about 25 minutes, about 30 minutes, about 40 minutes, about 50 minutes, and/or about 60 minutes. In some embodiments, the system is configured to quantify atherosclerosis within a time frame defined by two of the aforementioned values. In some embodiments, the system is configured to calculate stenosis rather than simply eyeballing, thereby allowing users to better understand whole heart atherosclerosis and/or guaranteeing the same calculated stenosis result if the same medical image is used for analysis. Importantly, the type of atherosclerosis can also be quantified and/or classified by this method. Types of atherosclerosis can be determined binarily (calcified vs. non-calcified plaque), ordinally (dense calcified plaque, calcified plaque, fibrous plaque, fibrofatty plaque, necrotic core, or admixtures of plaque types), or continuously (by attenuation density on a Hounsfield unit scale or similar).

Figure 3B:
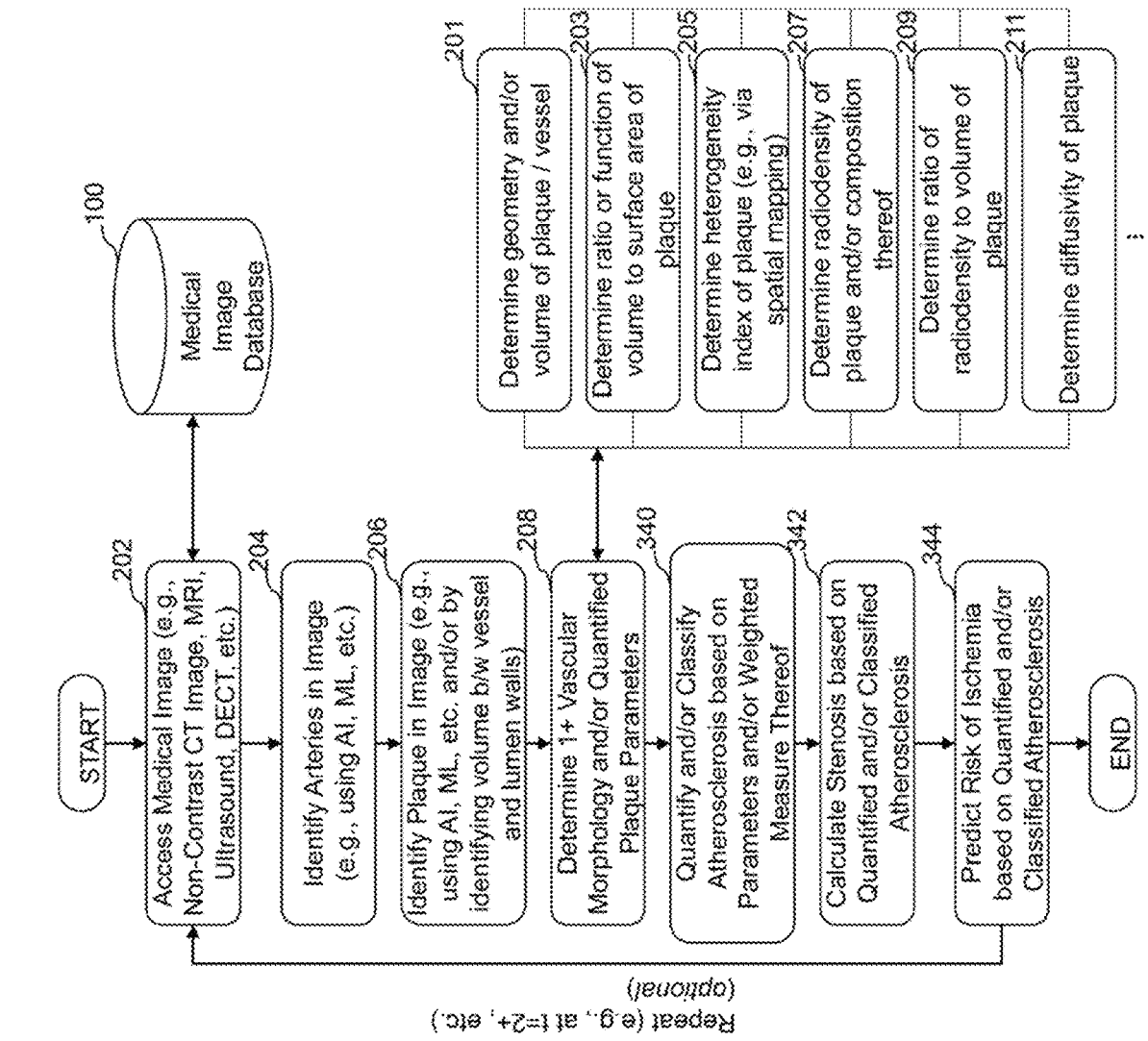
FIG. 3B is a flowchart illustrating an overview of an example embodiment(s) of a method for quantification of atherosclerosis based on medical image analysis.

FIG. 3B is a flowchart illustrating an overview of an example embodiment(s) of a method for quantification and/or classification of atherosclerosis based on medical image analysis. As illustrated in FIG. 3B, in some embodiments, the system can be configured to access a medical image at block 202, such as a CT scan of a coronary region of a subject. Further, in some embodiments, the system can be configured to identify one or more arteries at block 204 and/or one or more regions of plaque at block 206. In addition, in some embodiments, the system can be configured to determine one or more vascular morphology and/or quantified plaque parameters at block 208. For example, in some embodiments, the system can be configured to determine a geometry and/or volume of a region of plaque and/or a vessel at block 201, a ratio or function of volume to surface area of a region of plaque at block 203, a heterogeneity or homogeneity index of a region of plaque at block 205, radiodensity of a region of plaque and/or a composition thereof by ranges of radiodensity values at block 207, a ratio of radiodensity to volume of a region of plaque at block 209, and/or a diffusivity of a region of plaque at block 211. Additional detail regarding the processes and techniques represented in blocks 202, 204, 206, 208, 201, 203, 205, 207, 209, and 211 can be found in the description above in relation to FIG. 2A.

In some embodiments, the system can be configured quantify and/or classify atherosclerosis at block 340 based on the determined one or more vascular morphology and/or quantified plaque parameters. In some embodiments, the system can be configured to generate a weighted measure of one or more vascular morphology parameters and/or quantified plaque parameters determined and/or derived from raw medical images. For example, in some embodiments, the system can be configured to weight one or more vascular morphology parameters and/or quantified plaque parameters equally. In some embodiments, the system can be configured weight one or more vascular morphology parameters and/or quantified plaque parameters differently. In some embodiments, the system can be configured weight one or more vascular morphology parameters and/or quantified plaque parameters logarithmically, algebraically, and/or utilizing another mathematical transform. In some embodiments, the system is configured to quantify and/or classify atherosclerosis at block 340 using the weighted measure and/or using only some of the vascular morphology parameters and/or quantified plaque parameters.

In some embodiments, the system is configured to generate a weighted measure of the one or more vascular morphology parameters and/or quantified plaque parameters by comparing the same to one or more known vascular morphology parameters and/or quantified plaque parameters that are derived from medical images of other subjects. For example, the one or more known vascular morphology parameters and/or quantified plaque parameters can be derived from one or more healthy subjects and/or subjects at risk of coronary vascular disease.

In some embodiments, the system is configured to classify atherosclerosis of a subject based on the quantified atherosclerosis as one or more of high risk, medium risk, or low risk. In some embodiments, the system is configured to classify atherosclerosis of a subject based on the quantified atherosclerosis using an AI, ML, and/or other algorithm. In some embodiments, the system is configured to classify atherosclerosis of a subject by combining and/or weighting one or more of a ratio of volume of surface area, volume, heterogeneity index, and radiodensity of the one or more regions of plaque.

In some embodiments, a plaque having a low ratio of volume to surface area or a low absolute volume itself can indicate that the plaque is stable. As such, in some embodiments, the system can be configured to determine that a ratio of volume to surface area of a region of plaque below a predetermined threshold is indicative of a low risk atherosclerosis. Thus, in some embodiments, the system can be configured to take into account the number and/or sides of a plaque. For example, if there are a higher number of plaques with smaller sides, then that can be associated with a higher surface area or more irregularity, which in turn can be associated with a higher surface area to volume ratio. In contrast, if there are fewer number of plaques with larger sides or more regularity, then that can be associated with a lower surface area to volume ratio or a higher volume to surface area ratio. In some embodiments, a high radiodensity value can indicate that a plaque is highly calcified or stable, whereas a low radiodensity value can indicate that a plaque is less calcified or unstable. As such, in some embodiments, the system can be configured to determine that a radiodensity of a region of plaque above a predetermined threshold is indicative of a low risk atherosclerosis. In some embodiments, a plaque having a low heterogeneity or high homogeneity can indicate that the plaque is stable. As such, in some embodiments, the system can be configured to determine that a heterogeneity of a region of plaque below a predetermined threshold is indicative of a low risk atherosclerosis.

In some embodiments, at block 342, the system is configured to calculate or determine a numerical calculation or representation of coronary stenosis based on the quantified and/or classified atherosclerosis derived from the medical image. In some embodiments, the system is configured to calculate stenosis using the one or more vascular morphology parameters and/or quantified plaque parameters derived from the medical image of a coronary region of the subject.

In some embodiments, at block 344, the system is configured to predict a risk of ischemia for the subject based on the quantified and/or classified atherosclerosis derived from the medical image. In some embodiments, the system is configured to calculate a risk of ischemia using the one or more vascular morphology parameters and/or quantified plaque parameters derived from the medical image of a coronary region of the subject.

In some embodiments, the system is configured to generate a proposed treatment for the subject based on the quantified and/or classified atherosclerosis, stenosis, and/or risk of ischemia, wherein all of the foregoing are derived automatically and/or dynamically from a raw medical image using image processing algorithms and techniques.

In some embodiments, one or more processes described herein in connection with FIG. 3A can be repeated. For example, if a medical image of the same subject is taken again at a later point in time, one or more processes described herein can be repeated and the analytical results thereof can be used for tracking of quantified atherosclerosis for a subject and/or other purposes.

Quantification of Plaque, Stenosis, and/or CAD-RADS Score

As discussed herein, in some embodiments, the system is configured to take the guesswork out of interpretation of medical images and provide substantially exact and/or substantially accurate calculations or estimates of stenosis percentage, atherosclerosis, and/or Coronary Artery Disease-Reporting and Data System (CAD-RADS) score as derived from a medical image. As such, in some embodiments, the system can enhance the reads of the imagers by providing comprehensive quantitative analyses that can improve efficiency, accuracy, and/or reproducibility.

Figure 3C:
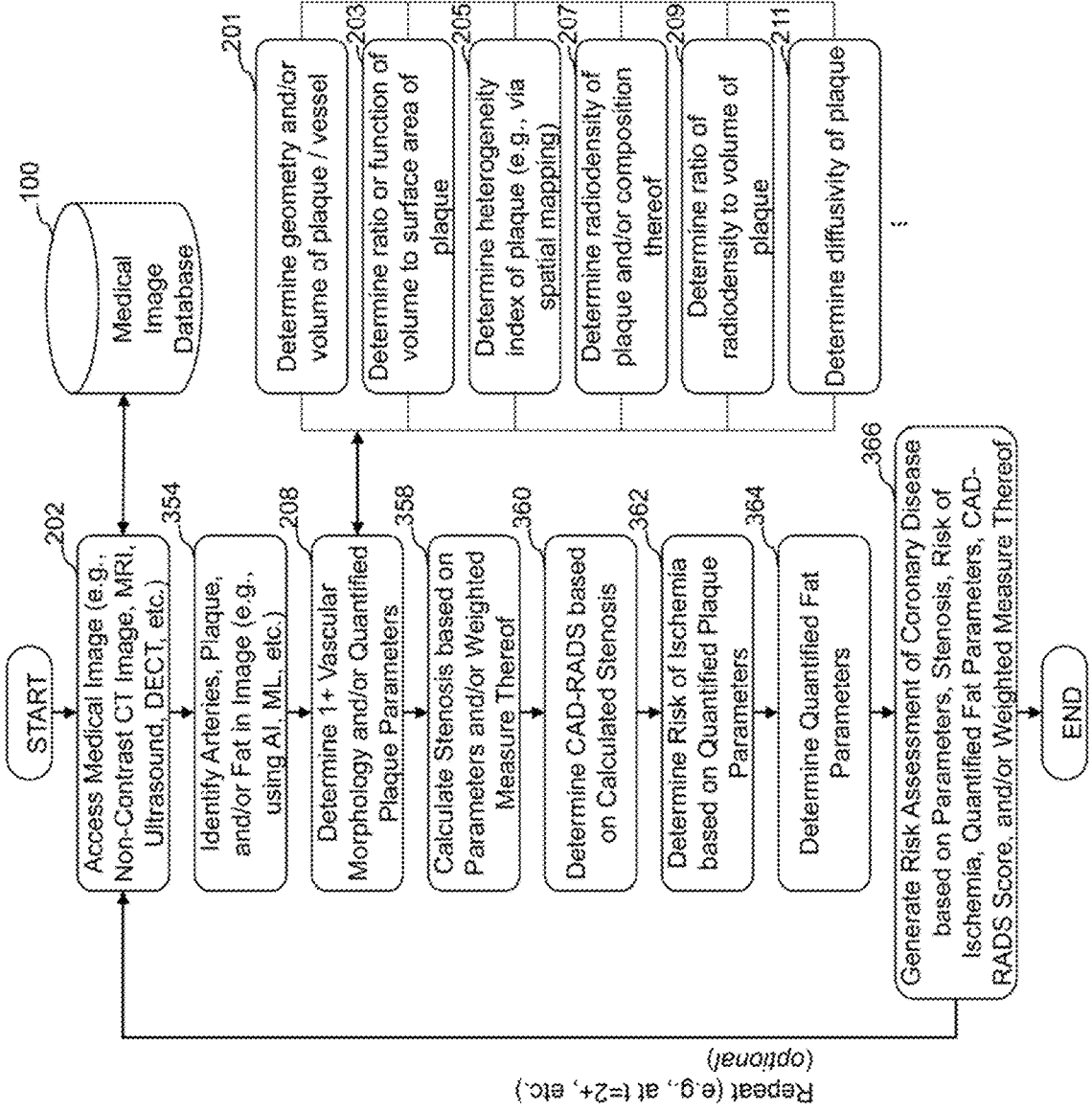
FIG. 3C is a flowchart illustrating an overview of an example embodiment(s) of a method for quantification of stenosis and generation of a CAD-RADS score based on medical image analysis.

FIG. 3C is a flowchart illustrating an overview of an example embodiment(s) of a method for quantification of stenosis and generation of a CAD-RADS score based on medical image analysis. As illustrated in FIG. 3A, in some embodiments, the system can be configured to access a medical image at block 202. Additional detail regarding the types of medical images and other processes and techniques represented in block 202 can be found in the description above in relation to FIG. 2A.

In some embodiments, at block 354, the system is configured to identify one or more arteries, plaque, and/or fat in the medical image, for example using AI, ML, and/or other algorithms. The processes and techniques for identifying one or more arteries, plaque, and/or fat can include one or more of the same features as described above in relation to blocks 204 and 206. In particular, in some embodiments, the system can be configured to utilize one or more AI and/or ML algorithms to automatically and/or dynamically identify one or more arteries, including for example coronary arteries, carotid arteries, aorta, renal artery, lower extremity artery, and/or cerebral artery. In some embodiments, one or more AI and/or ML algorithms can be trained using a Convolutional Neural Network (CNN) on a set of medical images on which arteries have been identified, thereby allowing the AI and/or ML algorithm automatically identify arteries directly from a medical image. In some embodiments, the arteries are identified by size and/or location.

Further, in some embodiments, the system can be configured to identify one or more regions of plaque in the medical image, for example using one or more AI and/or ML algorithms to automatically and/or dynamically identify one or more regions of plaque. In some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system can be configured to identify a vessel wall and a lumen wall for each of the identified coronary arteries in the medical image. In some embodiments, the system is then configured to determine the volume in between the vessel wall and the lumen wall as plaque. In some embodiments, the system can be configured to identify regions of plaque based on the radiodensity values typically associated with plaque, for example by setting a predetermined threshold or range of radiodensity values that are typically associated with plaque with or without normalizing using a normalization device.

Similarly, in some embodiments, the system can be configured to identify one or more regions of fat, such as epicardial fat, in the medical image, for example using one or more AI and/or ML algorithms to automatically and/or dynamically identify one or more regions of fat. In some embodiments, the one or more AI and/or ML algorithms can be trained using a Convolutional Neural Network (CNN) on a set of medical images on which regions of fat have been identified, thereby allowing the AI and/or ML algorithm automatically identify regions of fat directly from a medical image. In some embodiments, the system can be configured to identify regions of fat based on the radiodensity values typically associated with fat, for example by setting a predetermined threshold or range of radiodensity values that are typically associated with fat with or without normalizing using a normalization device.

In some embodiments, the system can be configured to determine one or more vascular morphology and/or quantified plaque parameters at block 208. For example, in some embodiments, the system can be configured to determine a geometry and/or volume of a region of plaque and/or a vessel at block 201, a ratio or function of volume to surface area of a region of plaque at block 203, a heterogeneity or homogeneity index of a region of plaque at block 205, radiodensity of a region of plaque and/or a composition thereof by ranges of radiodensity values at block 207, a ratio of radiodensity to volume of a region of plaque at block 209, and/or a diffusivity of a region of plaque at block 211. Additional detail regarding the processes and techniques represented in blocks 208, 201, 203, 205, 207, 209, and 211 can be found in the description above in relation to FIG. 2A.

In some embodiments, at block 358, the system is configured to calculate or determine a numerical calculation or representation of coronary stenosis based on the one or more vascular morphology parameters and/or quantified plaque parameters derived from the medical image of a coronary region of the subject. In some embodiments, the system can be configured to generate a weighted measure of one or more vascular morphology parameters and/or quantified plaque parameters determined and/or derived from raw medical images. For example, in some embodiments, the system can be configured weight one or more vascular morphology parameters and/or quantified plaque parameters equally. In some embodiments, the system can be configured to weight one or more vascular morphology parameters and/or quantified plaque parameters differently. In some embodiments, the system can be configured weight one or more vascular morphology parameters and/or quantified plaque parameters logarithmically, algebraically, and/or utilizing another mathematical transform. In some embodiments, the system is configured to calculate stenosis at block 358 using the weighted measure and/or using only some of the vascular morphology parameters and/or quantified plaque parameters. In some embodiments, the system can be configured to calculate stenosis on a vessel-by-vessel basis or a region-by-region basis.

In some embodiments, based on the calculated stenosis, the system is configured to determine a CAD-RADS score at block 360. This is in contrast to preexisting methods of determining a CAD-RADS based on eyeballing or general assessment of a medical image by a physician, which can result in unreproducible results. In some embodiments described herein, however, the system can be configured to generate a reproducible and/or objective calculated CAD-RADS score based on automatic and/or dynamic image processing of a raw medical image.

In some embodiments, at block 362, the system can be configured to determine a presence or risk of ischemia based on the calculated stenosis, one or more quantified plaque parameters and/or vascular morphology parameters derived from the medical image. For example, in some embodiments, the system can be configured to determine a presence or risk of ischemia by combining one or more of the foregoing parameters, either weighted or not, or by using some or all of these parameters on an individual basis. In some embodiments, the system can be configured to determine a presence of risk of ischemia by comparing one or more of the calculated stenosis, one or more quantified plaque parameters and/or vascular morphology parameters to a database of known such parameters derived from medical images of other subjects, including for example healthy subjects and/or subjects at risk of a cardiovascular event. In some embodiments, the system can be configured to calculate presence or risk of ischemia on a vessel-by-vessel basis or a region-by-region basis.

In some embodiments, at block 364, the system can be configured to determine one or more quantified parameters of fat for one or more regions of fat identified from the medical image. For example, in some embodiments, the system can utilize any of the processes and/or techniques discussed herein in relation to deriving quantified parameters of plaque, such as those described in connection with blocks 208, 201, 203, 205, 207, 209, and 211. In particular, in some embodiments, the system can be configured to determine one or more parameters of fat, including volume, geometry, radiodensity, and/or the like of one or more regions of fat within the medical image.

In some embodiments, at block 366, the system can be configured to generate a risk assessment of cardiovascular disease or event for the subject. In some embodiments, the generated risk assessment can comprise a risk score indicating a risk of coronary disease for the subject. In some embodiments, the system can generate a risk assessment based on an analysis of one or more vascular morphology parameters, one or more quantified plaque parameters, one or more quantified fat parameters, calculated stenosis, risk of ischemia, CAD-RADS score, and/or the like. In some embodiments, the system can be configured to generate a weighted measure of one or more vascular morphology parameters, one or more quantified plaque parameters, one or more quantified fat parameters, calculated stenosis, risk of ischemia, and/or CAD-RADS score of the subject. For example, in some embodiments, the system can be configured weight one or more of the foregoing parameters equally. In some embodiments, the system can be configured weight one or more of these parameters differently. In some embodiments, the system can be configured weight one or more of these parameters logarithmically, algebraically, and/or utilizing another mathematical transform. In some embodiments, the system is configured to generate a risk assessment of coronary disease or cardiovascular event for the subject at block 366 using the weighted measure and/or using only some of these parameters.

In some embodiments, the system can be configured to generate a risk assessment of coronary disease or cardiovascular event for the subject by combining one or more of the foregoing parameters, either weighted or not, or by using some or all of these parameters on an individual basis. In some embodiments, the system can be configured to generate a risk assessment of coronary disease or cardiovascular event by comparing one or more vascular morphology parameters, one or more quantified plaque parameters, one or more quantified fat parameters, calculated stenosis, risk of ischemia, and/or CAD-RADS score of the subject to a database of known such parameters derived from medical images of other subjects, including for example healthy subjects and/or subjects at risk of a cardiovascular event.

Further, in some embodiments, the system can be configured to automatically and/or dynamically generate a CAD-RADS modifier based on one or more of the determined one or more vascular morphology parameters, the set of quantified plaque parameters of the one or more regions of plaque, the quantified coronary stenosis, the determined presence or risk of ischemia, and/or the determined set of quantified fat parameters. In particular, in some embodiments, the system can be configured to automatically and/or dynamically generate one or more applicable CAD-RADS modifiers for the subject, including for example one or more of nondiagnostic (N), stent (S), graft (G), or vulnerability (V), as defined by and used by CAD-RADS. For example, N can indicate that a study is non-diagnostic, S can indicate the presence of a stent, G can indicate the presence of a coronary artery bypass graft, and V can indicate the presence of vulnerable plaque, for example showing a low radiodensity value.

In some embodiments, the system can be configured to generate a proposed treatment for the subject based on the generated risk assessment of coronary disease, one or more vascular morphology parameters, one or more quantified plaque parameters, one or more quantified fat parameters, calculated stenosis, risk of ischemia, CAD-RADS score, and/or CAD-RADS modifier derived from the raw medical image using image processing.

In some embodiments, one or more processes described herein in connection with FIG. 3B can be repeated. For example, if a medical image of the same subject is taken again at a later point in time, one or more processes described herein can be repeated and the analytical results thereof can be used for tracking of quantified plaque, calculated stenosis, CAD-RADS score and/or modifier derived from a medical image(s), risk determined risk of ischemia, quantified fat parameters, generated risk assessment of coronary disease for a subject, and/or other purposes.

Disease Tracking

In some embodiments, the systems, methods, and devices described herein can be configured to track the progression and/or regression of an arterial and/or plaque-based disease, such as a coronary disease. For example, in some embodiments, the system can be configured to track the progression and/or regression of a disease by automatically and/or dynamically analyzing a plurality of medical images obtained from different times using one or more techniques discussed herein and comparing different parameters derived therefrom. As such, in some embodiments, the system can provide an automated disease tracking tool using non-invasive raw medical images as an input, which does not rely on subjective assessment.

In particular, in some embodiments, the system can be configured to utilize a four-category system to determine whether plaque stabilization or worsening is occurring in a subject. For example, in some embodiments, these categories can include: (1) "plaque progression" or "rapid plaque progression"; (2) "mixed response—calcium dominant" or "non-rapid calcium dominant mixed response"; (3) "mixed response—non-calcium dominant" or "non-rapid non-calcium dominant mixed response"; or (4) "plaque regression."

In some embodiments, in "plaque progression" or "rapid plaque progression," the overall volume or relative volume of plaque increases. In some embodiments, in "mixed response—calcium dominant" or "non-rapid calcium dominant mixed response," the plaque volume remains relatively constant or does not increase to the threshold level of "rapid plaque progression" but there is a general progression of calcified plaque and a general regression of non-calcified plaque. In some embodiments, in "mixed response—non-calcium dominant" or "non-rapid non-calcium dominant mixed response," the plaque volume remains relatively constant but there is a general progression of non-calcified plaque and a general regression of calcified plaque. In some embodiments, in "plaque regression," the overall volume or relative volume of plaque decreases.

In some embodiments, these 4 categories can be expanded to be more granular, for example including for higher vs. lower density calcium plaques (e.g., for those >vs. <1000 Hounsfield units) and/or to categorize more specifically in calcium-dominant and non-calcified plaque-dominant mixed response. For example, for the non-calcified plaque-dominant mixed response, the non-calcified plaque can further include necrotic core, fibrofatty plaque and/or fibrous plaque as separate categories within the overall umbrella of non-calcified plaque. Similarly, calcified plaques can be categorized as lower density calcified plaques, medium density calcified plaques and high density calcified plaques.

Figure 3D:
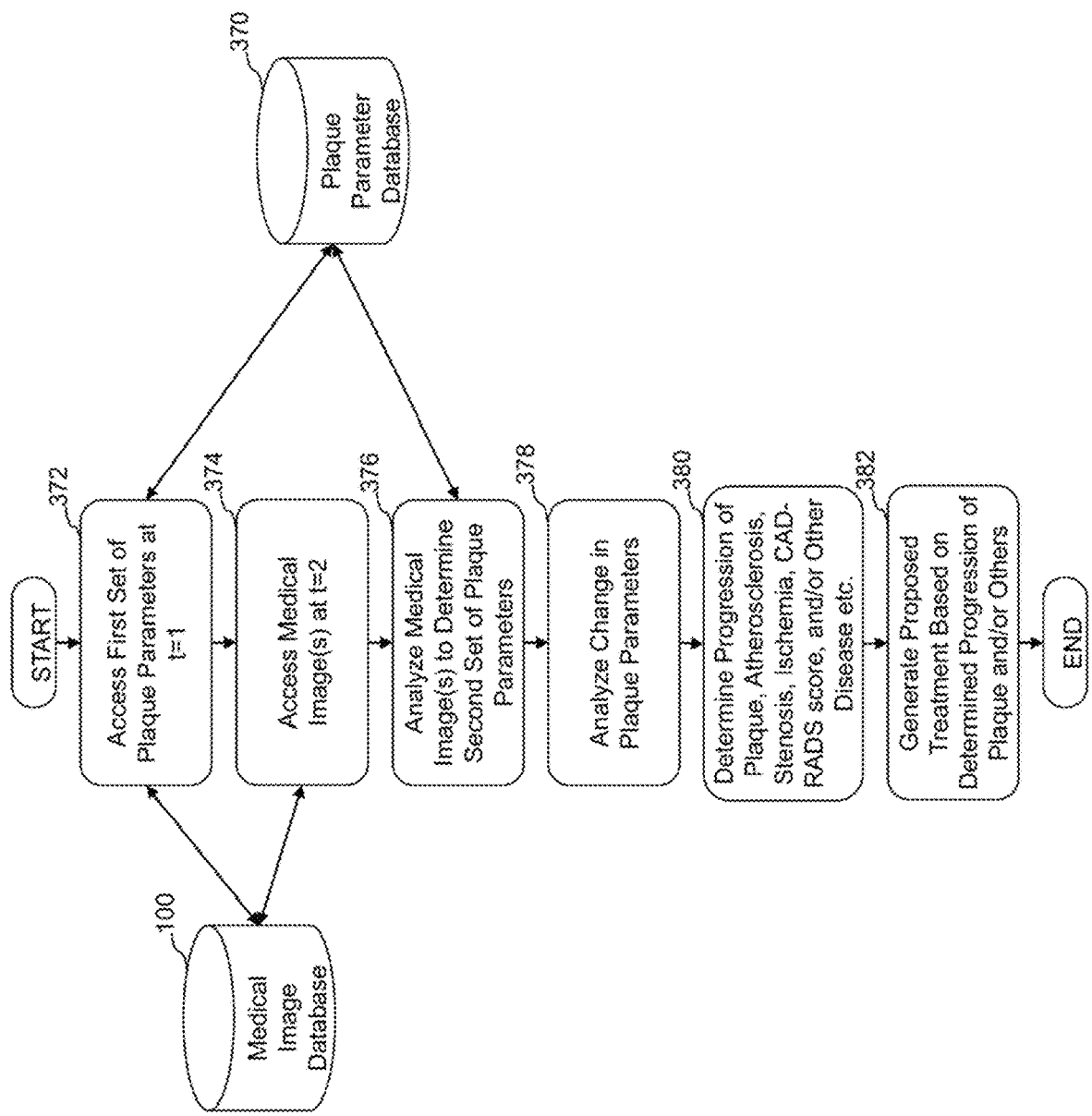
FIG. 3D is a flowchart illustrating an overview of an example embodiment(s) of a method for disease tracking based on medical image analysis.

FIG. 3D is a flowchart illustrating an overview of an example embodiment(s) of a method for disease tracking based on medical image analysis. For example, in some embodiments, the system can be configured to track the progression and/or regression of a plaque-based disease or condition, such as a coronary disease relating to or involving atherosclerosis, stenosis, ischemia, and/or the like, by analyzing one or more medical images obtained non-invasively.

As illustrated in FIG. 3D, in some embodiments, the system at block 372 is configured to access a first set of plaque parameters derived from a medical image of a subject at a first point in time. In some embodiments, the medical image can be stored in a medical image database 100 and can include any of the types of medical images described above, including for example CT, non-contrast CT, contrast-enhanced CT, MR, DECT, Spectral CT, and/or the like. In some embodiments, the medical image of the subject can comprise the coronary region, coronary arteries, carotid arteries, renal arteries, abdominal aorta, cerebral arteries, lower extremities, and/or upper extremities of the subject. In some embodiments, the set of plaque parameters can be stored in a plaque parameter database 370, which can include any of the quantified plaque parameters discussed above in relation to blocks 208, 201, 203, 205, 207, 209, and/or 211.

In some embodiments, the system can be configured to directly access the first set of plaque parameters that were previously derived from a medical image(s) and/or stored in a plaque parameter database 370. In some embodiments, the plaque parameter database 370 can be locally accessible and/or remotely accessible by the system via a network connection. In some embodiments, the system can be configured to dynamically and/or automatically derive the first set of plaque parameters from a medical image taken from a first point in time.

In some embodiments, at block 374, the system can be configured to access a second medical image(s) of the subject, which can be obtained from the subject at a later point in time than the medical image from which the first set of plaque parameters were derived. In some embodiments, the medical image can be stored in a medical image database 100 and can include any of the types of medical images described above, including for example CT, non-contrast CT, contrast-enhanced CT, MR, DECT, Spectral CT, and/or the like.

In some embodiments, at block 376, the system can be configured to dynamically and/or automatically derive a second set of plaque parameters from the second medical image taken from the second point in time. In some embodiments, the second set of plaque parameters can include any of the quantified plaque parameters discussed above in relation to blocks 208, 201, 203, 205, 207, 209, and/or 211. In some embodiments, the system can be configured to store the derived or determined second set of plaque parameters in the plaque parameter database 370.

In some embodiments, at block 378, the system can be configured to analyze changes in one or more plaque parameters between the first set derived from a medical image taken at a first point in time to the second set derived from a medical image taken at a later point in time. For example, in some embodiments, the system can be configured to compare a quantified plaque parameter between the two scans, such as for example radiodensity, volume, geometry, location, ratio or function of volume to surface area, heterogeneity index, radiodensity composition, radiodensity composition as a function of volume, ratio of radiodensity to volume, diffusivity, any combinations or relations thereof, and/or the like of one or more regions of plaque. In some embodiments, the system can be configured to determine the heterogeneity index of one or more regions of plaque by generating a spatial mapping or a three-dimensional histogram of radiodensity values across a geometric shape of one or more regions of plaque. In some embodiments, the system is configured to analyze changes in one or more non-image based metrics, such as for example serum biomarkers, genetics, omics, transcriptomics, microbiomics, and/or metabolomics.

In some embodiments, the system is configured to determine a change in plaque composition in terms of radiodensity or stable v. unstable plaque between the two scans. For example, in some embodiments, the system is configured to determine a change in percentage of higher radiodensity or stable plaques v. lower radiodensity or unstable plaques between the two scans. In some embodiments, the system can be configured to track a change in higher radiodensity plaques v. lower radiodensity plaques between the two scans. In some embodiments, the system can be configured to define higher radiodensity plaques as those with a Hounsfield unit of above 1000 and lower radiodensity plaques as those with a Hounsfield unit of below 1000.

In some embodiments, at block 380, the system can be configured to determine the progression or regression of plaque and/or any other related measurement, condition, assessment, or related disease based on the comparison of the one or more parameters derived from two or more scans and/or change in one or more non-image based metrics, such as serum biomarkers, genetics, omics, transcriptomics, microbiomics, and/or metabolomics. For example, in some embodiments, the system can be configured to determine the progression and/or regression of plaque in general, atherosclerosis, stenosis, risk or presence of ischemia, and/or the like. Further, in some embodiments, the system can be configured to automatically and/or dynamically generate a CAD-RADS score of the subject based on the quantified or calculated stenosis, as derived from the two medical images. Additional detail regarding generating a CAD-RADS score is described herein in relation to FIG. 3C. In some embodiments, the system can be configured to determine a progression or regression in the CAD-RADS score of the subject. In some embodiments, the system can be configured to compare the plaque parameters individually and/or combining one or more of them as a weighted measure. For example, in some embodiments, the system can be configured to weight the plaque parameters equally, differently, logarithmically, algebraically, and/or utilizing another mathematical transform. In some embodiments, the system can be configured to utilize only some or all of the quantified plaque parameters.

In some embodiments, the state of plaque progression as determined by the system can include one of four categories, including rapid plaque progression, non-rapid calcium dominant mixed response, non-rapid non-calcium dominant mixed response, or plaque regression. In some embodiments, the system is configured to classify the state of plaque progression as rapid plaque progression when a percent atheroma volume increase of the subject is more than 1% per year. In some embodiments, the system is configured to classify the state of plaque progression as non-rapid calcium dominant mixed response when a percent atheroma volume increase of the subject is less than 1% per year and calcified plaque represents more than 50% of total new plaque formation. In some embodiments, the system is configured to classify the state of plaque progression as non-rapid non-calcium dominant mixed response when a percent atheroma volume increase of the subject is less than 1% per year and non-calcified plaque represents more than 50% of total new plaque formation. In some embodiments, the system is configured to classify the state of plaque progression as plaque regression when a decrease in total percent atheroma volume is present.

In some embodiments, at block 382, the system can be configured to generate a proposed treatment plan for the subject. For example, in some embodiments, the system can be configured to generate a proposed treatment plan for the subject based on the determined progression or regression of plaque and/or any other related measurement, condition, assessment, or related disease based on the comparison of the one or more parameters derived from two or more scans.

In some embodiments, one or more processes described herein in connection with FIG. 3D can be repeated. For example, one or more processes described herein can be repeated and the analytical results thereof can be used for continued tracking of a plaque-based disease and/or other purposes.

Determination of Cause of Change in Calcium Score

In some embodiments, the systems, methods and devices disclosed herein can be configured to generate analysis and/or reports that can determine the likely cause of an increased calcium score. A high or increased calcium score alone is not representative of any specific cause, either positive or negative. Rather, in general, there can be various possible causes for a high or increased calcium score. For example, in some cases, a high or increased calcium score can be an indicator of significant heart disease and/or that the patient is at increased risk of a heart attack. Also, in some cases, a high or increased calcium score can be an indicator that the patient is increasing the amount of exercise performed, because exercise can convert fatty material plaque within the artery vessel. In some cases, a high or increased calcium score can be an indicator of the patient beginning a statin regimen wherein the statin is converting the fatty material plaque into calcium. Unfortunately, a blood test alone cannot be used to determine which of the foregoing reasons is the likely cause of an increased calcium score. In some embodiments, by utilizing one or more techniques described herein, the system can be configured to determine the cause of an increased or high calcium score.

More specifically, in some embodiments, the system can be configured to track a particular segment of an artery wall vessel of a patient in such a way to monitor the conversion of a fatty deposit material plaque lesion to a mostly calcified plaque deposit, which can be helpful in determining the cause of an increase calcium score, such as one or more of the causes identified above. In addition, in some embodiments, the system can be configured to determine and/or use the location, size, shape, diffusivity and/or the attenuation radiodensity of one or more regions of calcified plaque to determine the cause of an increase in calcium score. As a non-limiting example, if a calcium plaque increases in density, this may represent a stabilization of plaque by treatment or lifestyle, whereas if a new calcium plaque forms where one was not there before (particularly with a lower attenuation density), this may represent an adverse finding of disease progression rather than stabilization. In some embodiments, one or more processes and techniques described herein may be applied for non-contrast CT scans (such as an ECG gated coronary artery calcium score or non-ECG gated chest CT) as well as contrast-enhanced CT scans (such as a coronary CT angiogram).

As another non-limiting example, the CT scan image acquisition parameters can be altered to improve understanding of calcium changes over time. As an example, traditional coronary artery calcium imaging is done using a 2.5-3.0 mm slice thickness and detecting voxels/pixels that are 130 Hounsfield units or greater. An alternative may be to do "thin" slice imaging with 0.5 mm slice thickness or similar; and detecting all Hounsfield units densities below 130 and above a certain threshold (e.g., 100) that may identify less dense calcium that may be missed by an arbitrary 130 Hounsfield unit threshold.

Figure 3E:
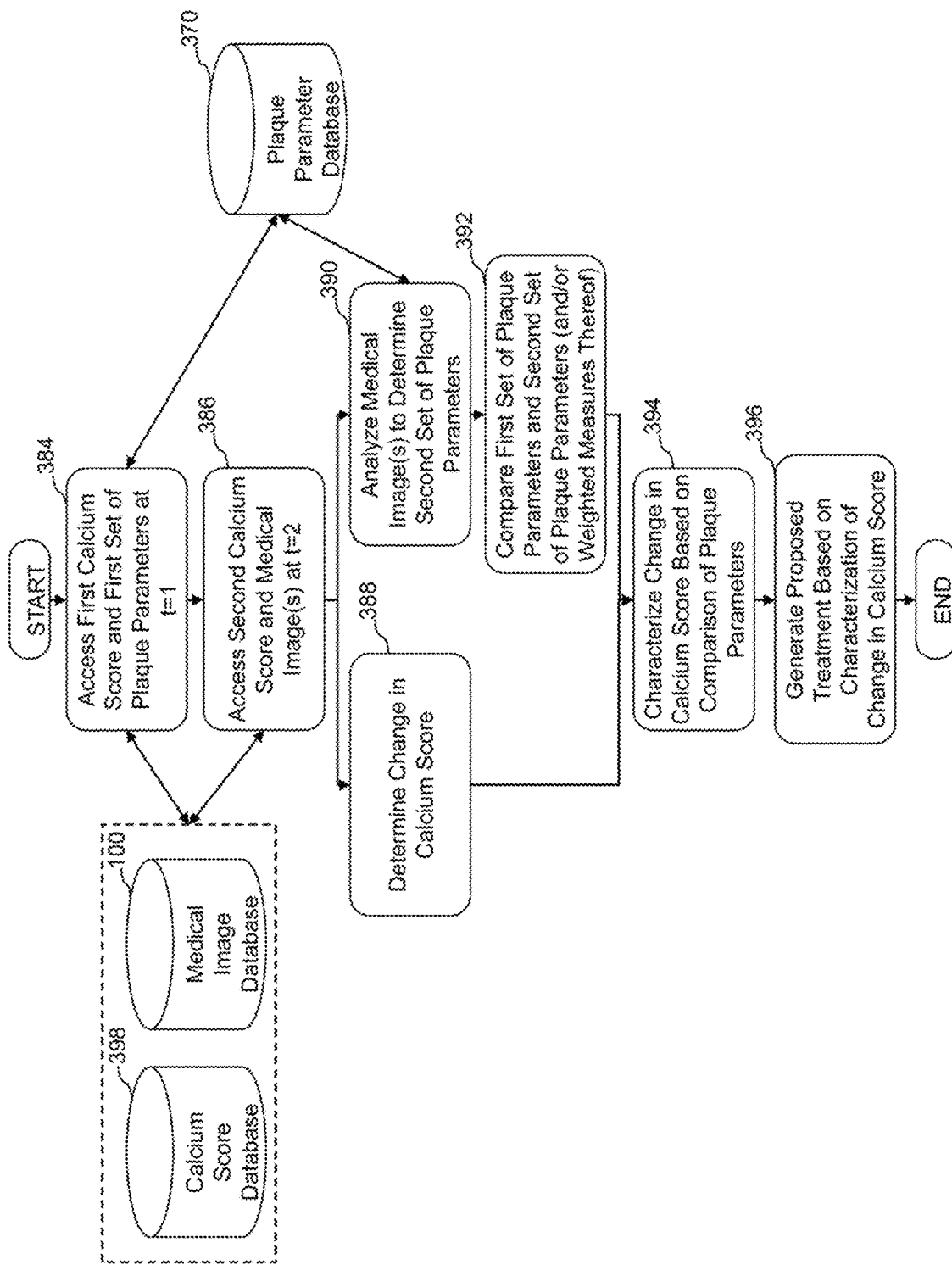
FIG. 3E is a flowchart illustrating an overview of an example embodiment(s) of a method for determination of cause of change in calcium score based on medical image analysis.

FIG. 3E is a flowchart illustrating an overview of an example embodiment(s) of a method for determination of cause of change in calcium score, whether an increase or decrease, based on medical image analysis.

As illustrated in FIG. 3E, in some embodiments, the system can be configured to access a first calcium score and/or a first set of plaque parameters of a subject at block 384. The first calcium score and/or a first set of plaque parameters can be derived from a medical image of a subject and/or from a blood test at a first point in time. In some embodiments, the medical image can be stored in a medical image database 100 and can include any of the types of medical images described above, including for example CT, non-contrast CT, contrast-enhanced CT, MR, DECT, Spectral CT, and/or the like. In some embodiments, the medical image of the subject can comprise the coronary region, coronary arteries, carotid arteries, renal arteries, abdominal aorta, cerebral arteries, lower extremities, and/or upper extremities of the subject. In some embodiments, the set of plaque parameters can be stored in a plaque parameter database 370, which can include any of the quantified plaque parameters discussed above in relation to blocks 208, 201, 203, 205, 207, 209, and/or 211.

In some embodiments, the system can be configured to directly access and/or retrieve the first calcium score and/or first set of plaque parameters that are stored in a calcium score database 398 and/or plaque parameter database 370 respectively. In some embodiments, the plaque parameter database 370 and/or calcium score database 298 can be locally accessible and/or remotely accessible by the system via a network connection. In some embodiments, the system can be configured to dynamically and/or automatically derive the first set of plaque parameters and/or calcium score from a medical image and/or blood test of the subject taken from a first point in time.

In some embodiments, at block 386, the system can be configured to access a second calcium score and/or second medical image(s) of the subject, which can be obtained from the subject at a later point in time than the first calcium score and/or medical image from which the first set of plaque parameters were derived. For example, in some embodiments, the second calcium score can be derived from the second medical image and/or a second blood test taken of the subject at a second point in time. In some embodiments, the second calcium score can be stored in the calcium score database 398. In some embodiments, the medical image can be stored in a medical image database 100 and can include any of the types of medical images described above, including for example CT, non-contrast CT, contrast-enhanced CT, MR, DECT, Spectral CT, and/or the like.

In some embodiments, at block 388, the system can be configured to compare the first calcium score to the second calcium score and determine a change in the calcium score. However, as discussed above, this alone typically does not provide insight as to the cause of the change in calcium score, if any. In some embodiments, if there is no statistically significant change in calcium score between the two readings, for example if any difference is below a predetermined threshold value, then the system can be configured to end the analysis of the change in calcium score. In some embodiments, if there is a statistically significant change in calcium score between the two readings, for example if the difference is above a predetermined threshold value, then the system can be configured to continue its analysis.

In particular, in some embodiments, at block 390, the system can be configured to dynamically and/or automatically derive a second set of plaque parameters from the second medical image taken from the second point in time. In some embodiments, the second set of plaque parameters can include any of the quantified plaque parameters discussed above in relation to blocks 208, 201, 203, 205, 207, 209, and/or 211. In some embodiments, the system can be configured to store the derived or determined second set of plaque parameters in the plaque parameter database 370.

In some embodiments, at block 392, the system can be configured to analyze changes in one or more plaque parameters between the first set derived from a medical image taken at a first point in time to the second set derived from a medical image taken at a later point in time. For example, in some embodiments, the system can be configured to compare a quantified plaque parameter between the two scans, such as for example radiodensity, volume, geometry, location, ratio or function of volume to surface area, heterogeneity index, radiodensity composition, radiodensity composition as a function of volume, ratio of radiodensity to volume, diffusivity, any combinations or relations thereof, and/or the like of one or more regions of plaque and/or one or more regions surrounding plaque. In some embodiments, the system can be configured to determine the heterogeneity index of one or more regions of plaque by generating a spatial mapping or a three-dimensional histogram of radiodensity values across a geometric shape of one or more regions of plaque. In some embodiments, the system is configured to analyze changes in one or more non-image based metrics, such as for example serum biomarkers, genetics, omics, transcriptomics, microbiomics, and/or metabolomics.

In some embodiments, the system is configured to determine a change in plaque composition in terms of radiodensity or stable v. unstable plaque between the two scans. For example, in some embodiments, the system is configured to determine a change in percentage of higher radiodensity or stable plaques v. lower radiodensity or unstable plaques between the two scans. In some embodiments, the system can be configured to track a change in higher radiodensity plaques v. lower radiodensity plaques between the two scans. In some embodiments, the system can be configured to define higher radiodensity plaques as those with a Hounsfield unit of above 1000 and lower radiodensity plaques as those with a Hounsfield unit of below 1000.

In some embodiments, the system can be configured to compare the plaque parameters individually and/or combining one or more of them as a weighted measure. For example, in some embodiments, the system can be configured to weight the plaque parameters equally, differently, logarithmically, algebraically, and/or utilizing another mathematical transform. In some embodiments, the system can be configured to utilize only some or all of the quantified plaque parameters.

In some embodiments, at block 394, the system can be configured to characterize the change in calcium score of the subject based on the comparison of the one or more plaque parameters, whether individually and/or combined or weighted. In some embodiments, the system can be configured to characterize the change in calcium score as positive, neutral, or negative. For example, in some embodiments, if the comparison of one or more plaque parameters reveals that plaque is stabilizing or showing high radiodensity values as a whole for the subject without generation of any new plaque, then the system can report that the change in calcium score is positive. In contrast, if the comparison of one or more plaque parameters reveals that plaque is destabilizing as a whole for the subject, for example due to generation of new unstable regions of plaque with low radiodensity values, without generation of any new plaque, then the system can report that the change in calcium score is negative. In some embodiments, the system can be configured to utilize any or all techniques of plaque quantification and/or tracking of plaque-based disease analysis discussed herein, include those discussed in connection with FIGS. 3A, 3B, 3C, and 3D.

As a non-limiting example, in some embodiments, the system can be configured to characterize the cause of a change in calcium score based on determining and comparing a change in ratio between volume and radiodensity of one or more regions of plaque between the two scans. Similarly, in some embodiments, the system can be configured to characterize the cause of a change in calcium score based on determining and comparing a change in diffusivity and/or radiodensity of one or more regions of plaque between the two scans. For example, if the radiodensity of a region of plaque has increased, the system can be configured to characterize the change or increase in calcium score as positive. In some embodiments, if the system identifies one or more new regions of plaque in the second image that were not present in the first image, the system can be configured to characterize the change in calcium score as negative. In some embodiments, if the system determines that the volume to surface area ratio of one or more regions of plaque has decreased between the two scans, the system can be configured to characterize the change in calcium score as positive. In some embodiments, if the system determines that a heterogeneity or heterogeneity index of a region is plaque has decreased between the two scans, for example by generating and/or analyzing spatial mapping of radiodensity values, then the system can be configured to characterize the change in calcium score as positive.

In some embodiments, the system is configured to utilize an AI, ML, and/or other algorithm to characterize the change in calcium score based on one or more plaque parameters derived from a medical image. For example, in some embodiments, the system can be configured to utilize an AI and/or ML algorithm that is trained using a CNN and/or using a dataset of known medical images with identified plaque parameters combined with calcium scores. In some embodiments, the system can be configured to characterize a change in calcium score by accessing known datasets of the same stored in a database. For example, the known dataset may include datasets of changes in calcium scores and/or medical images and/or plaque parameters derived therefrom of other subjects in the past. In some embodiments, the system can be configured to characterize a change in calcium score and/or determine a cause thereof on a vessel-by-vessel basis, segment-by-segment basis, plaque-by-plaque basis, and/or a subject basis.

In some embodiments, at block 396, the system can be configured to generate a proposed treatment plan for the subject. For example, in some embodiments, the system can be configured to generate a proposed treatment plan for the subject based on the change in calcium score and/or characterization thereof for the subject.

In some embodiments, one or more processes described herein in connection with FIG. 3E can be repeated. For example, one or more processes described herein can be repeated and the analytical results thereof can be used for continued tracking and/or characterization of changes in calcium score for a subject and/or other purposes.

Prognosis of Cardiovascular Event

In some embodiments, the systems, devices, and methods described herein are configured to generate a prognosis of a cardiovascular event for a subject based on one or more of the medical image-based analysis techniques described herein. For example, in some embodiments, the system is configured to determine whether a patient is at risk for a cardiovascular event based on the amount of bad plaque buildup in the patient's artery vessels. For this purpose, a cardiovascular event can include clinical major cardiovascular events, such as heart attack, stroke or death, as well as disease progression and/or ischemia.

In some embodiments, the system can identify the risk of a cardiovascular event based on a ratio of the amount and/or volume of bad plaque buildup versus the total surface area and/or volume of some or all of the artery vessels in a patient. In some embodiments, if the foregoing ratio exceeds a certain threshold, the system can be configured to output a certain risk factor and/or number and/or level associated with the patient. In some embodiments, the system is configured to determine whether a patient is at risk for a cardiovascular event based on an absolute amount or volume or a ratio of the amount or volume bad plaque buildup in the patient's artery vessels compared to the total volume of some or all of the artery vessels. In some embodiments, the system is configured to determine whether a patient is at risk for a cardiovascular event based on results from blood chemistry or biomarker tests of the patient, for example whether certain blood chemistry or biomarker tests of the patient exceed certain threshold levels. In some embodiments, the system is configured to receive as input from the user or other systems and/or access blood chemistry or biomarker tests data of the patient from a database system. In some embodiments, the system can be configured to utilize not only artery information related to plaque, vessel morphology, and/or stenosis but also input from other imaging data about the non-coronary cardiovascular system, such as subtended left ventricular mass, chamber volumes and size, valvular morphology, vessel (e.g., aorta, pulmonary artery) morphology, fat, and/or lung and/or bone health. In some embodiments, the system can utilize the outputted risk factor to generate a treatment plan proposal. For example, the system can be configured to output a treatment plan that involves the administration of cholesterol reducing drugs, such as statins, in order to transform the soft bad plaque into hard plaque that is safer and more stable for a patient. In general, hard plaque that is largely calcified can have a significant lower risk of rupturing into the artery vessel thereby decreasing the chances of a clot forming in the artery vessel which can decrease a patient's risk of a heart attack or other cardiac event.

Figure 4A:
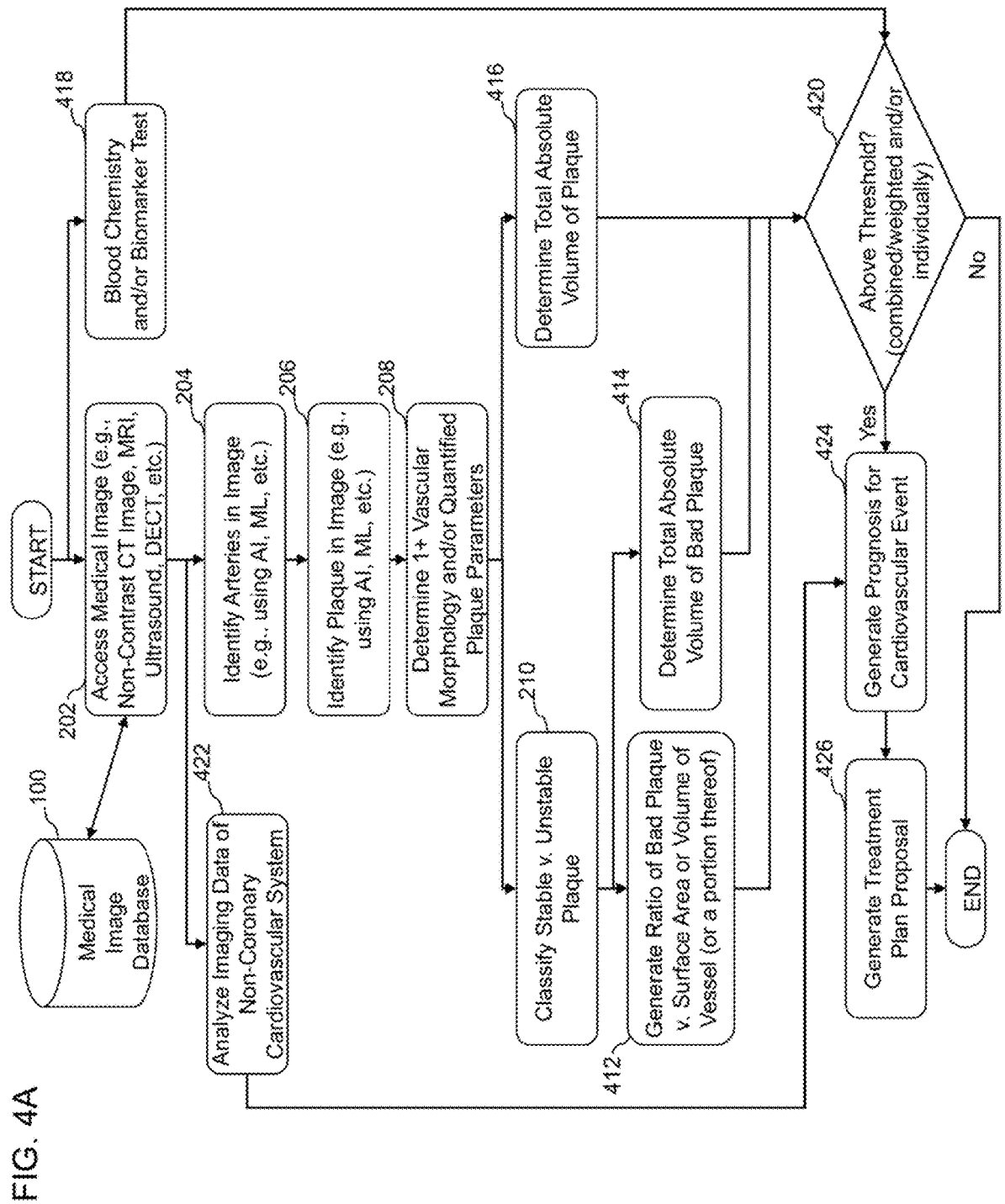
FIG. 4A is a flowchart illustrating an overview of an example embodiment(s) of a method for prognosis of a cardiovascular event based on medical image analysis.

FIG. 4A is a flowchart illustrating an overview of an example embodiment(s) of a method for prognosis of a cardiovascular event based on and/or derived from medical image analysis.

As illustrated in FIG. 4A, in some embodiments, the system can be configured to access a medical image at block 202, such as a CT scan of a coronary region of a subject, which can be stored in a medical image database 100. Further, in some embodiments, the system can be configured to identify one or more arteries at block 204 and/or one or more regions of plaque at block 206. In addition, in some embodiments, the system can be configured to determine one or more vascular morphology and/or quantified plaque parameters at block 208. For example, in some embodiments, the system can be configured to determine a geometry and/or volume of a region of plaque and/or a vessel, a ratio or function of volume to surface area of a region of plaque, a heterogeneity or homogeneity index of a region of plaque, radiodensity of a region of plaque and/or a composition thereof by ranges of radiodensity values, a ratio of radiodensity to volume of a region of plaque, and/or a diffusivity of a region of plaque. In addition, in some embodiments, at block 210, the system can be configured to classify one or more regions of plaque as stable v. unstable or good v. bad based on the one or more vascular morphology parameters and/or quantified plaque parameters determined and/or derived from raw medical images. Additional detail regarding the processes and techniques represented in blocks 202, 204, 206, 208, and 210 can be found in the description above in relation to FIG. 2A.

In some embodiments, the system at block 412 is configured to generate a ratio of bad plaque to the vessel on which the bad plaque appears. More specifically, in some embodiments, the system can be configured to determine a total surface area of a vessel identified on a medical image and a surface area of all regions of bad or unstable plaque within that vessel. Based on the foregoing, in some embodiments, the system can be configured to generate a ratio of surface area of all bad plaque within a particular vessel to the surface area of the entire vessel or a portion thereof shown in a medical image. Similarly, in some embodiments, the system can be configured to determine a total volume of a vessel identified on a medical image and a volume of all regions of bad or unstable plaque within that vessel. Based on the foregoing, in some embodiments, the system can be configured to generate a ratio of volume of all bad plaque within a particular vessel to the volume of the entire vessel or a portion thereof shown in a medical image.

In some embodiments, at block 414, the system is further configured to determine a total absolute volume and/or surface area of all bad or unstable plaque identified in a medical image. Also, in some embodiments, at block 416, the system is configured to determine a total absolute volume of all plaque, including good plaque and bad plaque, identified in a medical image. Further, in some embodiments, at block 418, the system can be configured to access or retrieve results from a blood chemistry and/or biomarker test of the patient and/or other non-imaging test results. Furthermore, in some embodiments, at block 422, the system can be configured to access and/or analyze one or more non-coronary cardiovascular system medical images.

In some embodiments, at block 420, the system can be configured to analyze one or more of the generated ratio of bad plaque to a vessel, whether by surface area or volume, total absolute volume of bad plaque, total absolute volume of plaque, blood chemistry and/or biomarker test results, and/or analysis results of one or more non-coronary cardiovascular system medical images to determine whether one or more of these parameters, either individually and/or combined, is above a predetermined threshold. For example, in some embodiments, the system can be configured to analyze one or more of the foregoing parameters individually by comparing them to one or more reference values of healthy subjects and/or subjects at risk of a cardiovascular event. In some embodiments, the system can be configured to analyze a combination, such as a weighted measure, of one or more of the foregoing parameters by comparing the combined or weighted measure thereof to one or more reference values of healthy subjects and/or subjects at risk of a cardiovascular event. In some embodiments, the system can be configured to weight one or more of these parameters equally. In some embodiments, the system can be configured to weight one or more of these parameters differently. In some embodiments, the system can be configured to weight one or more of these parameters logarithmically, algebraically, and/or utilizing another mathematical transform. In some embodiments, the system can be configured to utilize only some of the aforementioned parameters, either individually, combined, and/or as part of a weighted measure.

In some embodiments, at block 424, the system is configured to generate a prognosis for a cardiovascular event for the subject. In particular, in some embodiments, the system is configured to generate a prognosis for cardiovascular event based on one or more of the analysis results of the generated ratio of bad plaque to a vessel, whether by surface area or volume, total absolute volume of bad plaque, total absolute volume of plaque, blood chemistry and/or biomarker test results, and/or analysis results of one or more non-coronary cardiovascular system medical images. In some embodiments, the system is configured to generate the prognosis utilizing an AI, ML, and/or other algorithm. In some embodiments, the generated prognosis comprises a risk score or risk assessment of a cardiovascular event for the subject. In some embodiments, the cardiovascular event can include one or more of atherosclerosis, stenosis, ischemia, heart attack, and/or the like.

In some embodiments, at block 426, the system can be configured to generate a proposed treatment plan for the subject. For example, in some embodiments, the system can be configured to generate a proposed treatment plan for the subject based on the change in calcium score and/or characterization thereof for the subject. In some embodiments, the generated treatment plan can include use of statins, lifestyle changes, and/or surgery.

In some embodiments, one or more processes described herein in connection with FIG. 4A can be repeated. For example, one or more processes described herein can be repeated and the analytical results thereof can be used for continued prognosis of a cardiovascular event for a subject and/or other purposes.

Patient-Specific Stent Determination

In some embodiments, the systems, methods, and devices described herein can be used to determine and/or generate one or more parameters for a patient-specific stent and/or selection or guidance for implantation thereof. In particular, in some embodiments, the systems disclosed herein can be used to dynamically and automatically determine the necessary stent type, length, diameter, gauge, strength, and/or any other stent parameter for a particular patient based on processing of the medical image data, for example using AI, ML, and/or other algorithms.

In some embodiments, by determining one or more patient-specific stent parameters that are best suited for a particular artery area, the system can reduce the risk of patient complications and/or insurance risks because if too large of a stent is implanted, then the artery wall can be stretched too thin resulting in a possible rupture, or undesirable high flow, or other issues. On the other hand, if too small of a stent is implanted, then the artery wall might not be stretched open enough resulting in too little blood flow or other issues.

In some embodiments, the system is configured to dynamically identify an area of stenosis within an artery, dynamically determine a proper diameter of the identified area of the artery, and/or automatically select a stent from a plurality of available stent options. In some embodiments, the selected stent can be configured to prop open the artery area after implantation to the determined proper artery diameter. In some embodiments, the proper artery diameter is determined to be equivalent or substantially equivalent to what the diameter would naturally be without stenosis. In some embodiments, the system can be configured to dynamically generate a patient-specific surgical plan for implanting the selected stent in the identified artery area. For example, the system can be configured to determine whether a bifurcation of the artery is near the identified artery area and generate a patient-specific surgical plan for inserting two guidewires for handling the bifurcation and/or determining the position for jailing and inserting a second stent into the bifurcation.

Figure 4B:
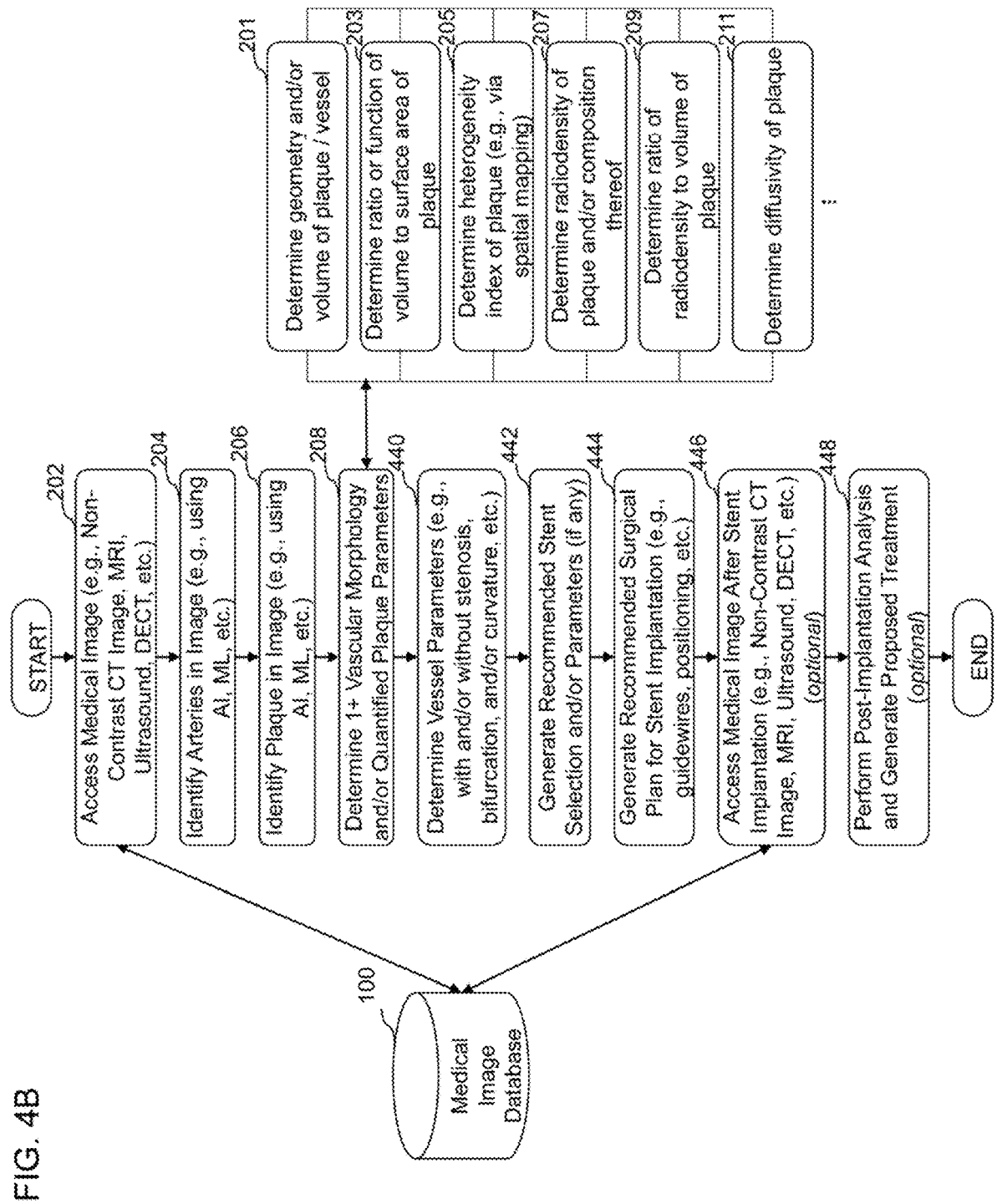
FIG. 4B is a flowchart illustrating an overview of an example embodiment(s) of a method for determination of patient-specific stent parameters based on medical image analysis.

FIG. 4B is a flowchart illustrating an overview of an example embodiment(s) of a method for determination of patient-specific stent parameters based on medical image analysis.

As illustrated in FIG. 4B, in some embodiments, the system can be configured to access a medical image at block 202, such as a CT scan of a coronary region of a subject. Further, in some embodiments, the system can be configured to identify one or more arteries at block 204 and/or one or more regions of plaque at block 206. In addition, in some embodiments, the system can be configured to determine one or more vascular morphology and/or quantified plaque parameters at block 208. For example, in some embodiments, the system can be configured to determine a geometry and/or volume of a region of plaque and/or a vessel at block 201, a ratio or function of volume to surface area of a region of plaque at block 203, a heterogeneity or homogeneity index of a region of plaque at block 205, radiodensity of a region of plaque and/or a composition thereof by ranges of radiodensity values at block 207, a ratio of radiodensity to volume of a region of plaque at block 209, and/or a diffusivity of a region of plaque at block 211. Additional detail regarding the processes and techniques represented in blocks 202, 204, 206, 208, 201, 203, 205, 207, 209, and 211 can be found in the description above in relation to FIG. 2A.

In some embodiments, at block 440, the system can be configured to analyze the medical image to determine one or more vessel parameters, such as the diameter, curvature, vascular morphology, vessel wall, lumen wall, and/or the like. In some embodiments, the system can be configured to determine or derive from the medical image one or more vessel parameters as shown in the medical image, for example with stenosis at certain regions along the vessel. In some embodiments, the system can be configured to determine one or more vessel parameters without stenosis. For example, in some embodiments, the system can be configured to graphically and/or hypothetically remove stenosis or plaque from a vessel to determine the diameter, curvature, and/or the like of the vessel if stenosis did not exist.

In some embodiments, at block 442, the system can be configured to determine whether a stent is recommended for the subject and, if so, one or more recommended parameters of a stent specific for that patient based on the medical analysis. For example, in some embodiments, the system can be configured to analyze one or more of the identified vascular morphology parameters, quantified plaque parameters, and/or vessel parameters. In some embodiments, the system can be configured to utilize an AI, ML, and/or other algorithm. In some embodiments, the system is configured to analyze one or more of the aforementioned parameters individually, combined, and/or as a weighted measure. In some embodiments, one or more of these parameters derived from a medical image, either individually or combined, can be compared to one or more reference values derived or collected from other subjects, including those who had a stent implanted and those who did not. In some embodiments, based on the determined parameters of a patient-specific stent, the system can be configured to determine a selection of a preexisting stent that matches those parameters and/or generate manufacturing instructions to manufacture a patient-specific stent with stent parameters derived from a medical image. In some embodiments, the system can be configured to recommend a diameter of a stent that is less than or substantially equal to the diameter of an artery if stenosis did not exist.

In some embodiments, at block 444, the system can be configured to generate a recommended surgical plan for stent implantation based on the analyzed medical image. For example, in some embodiments, the system can be configured to determine whether a bifurcation exists based on the medical image and/or generate guidelines for the positioning of guidewires and/or stent for the patient prior to surgery. As such, in some embodiments, the system can be configured to generate a detailed surgical plan that is specific to a particular patient based on medical image analysis of plaque and/or other parameters.

In some embodiments, at block 446, the system is configured to access or retrieve one or more medical images after stent implantation. In some embodiments, at block 448, the system can be configured to analyze the accessed medical image to perform post-implantation analysis. For example, in some embodiments, the system can be configured to derive one or more vascular morphology and/or plaque parameters, including any of those discussed herein in relation to block 208, after stent implantation. Based on analysis of the foregoing, in some embodiments, the system can generate further proposed treatment in some embodiments, such as for example recommended use of statins or other medications, lifestyle change, further surgery or stent implantation, and/or the like.

In some embodiments, one or more processes described herein in connection with FIG. 4B can be repeated. For example, one or more processes described herein can be repeated and the analytical results thereof can be used to determine the need for and/or parameters of an additional patient-specific stent for a patient and/or other purposes.

Patient-Specific Report

In some embodiments, the system is configured to dynamically generate a patient-specific report based on the analysis of the processed data generated from the raw CT scan data. In some embodiments, the patient specific report is dynamically generated based on the processed data. In some embodiments, the written report is dynamically generated based on selecting and/or combining certain phrases from a database, wherein certain words, terms, and/or phrases are altered to be specific to the patient and the identified medical issues of the patient. In some embodiments, the system is configured to dynamically select one or more images from the image scanning data and/or the system generated image views described herein, wherein the selected one or more images are dynamically inserted into the written report in order to generate a patient-specific report based on the analysis of the processed data.

In some embodiments, the system is configured to dynamically annotate the selected one or more images for insertion into the patient specific report, wherein the annotations are specific to patient and/or are annotations based on the data processing performed by the devices, methods, and systems disclosed herein, for example, annotating the one or more images to include markings or other indicators to show where along the artery there exists bad plaque buildup that is significant.

In some embodiments, the system is configured to dynamically generate a report based on past and/or present medical data. For example, in some embodiments, the system can be configured to show how a patient's cardiovascular health has changed over a period. In some embodiments, the system is configured to dynamically generate phrases and/or select phrases from a database to specifically describe the cardiovascular health of the patient and/or how the cardiovascular disease has changed within a patient.

In some embodiments, the system is configured to dynamically select one or more medical images from prior medical scanning and/or current medical scanning for insertion into the medical report in order to show how the cardiovascular disease has changed over time in a patient, for example, showing past and present images juxtaposed to each other, or for example, showing past images that are superimposed on present images thereby allowing a user to move or fade or toggle between past and present images.

In some embodiments, the patient-specific report is an interactive report that allows a user to interact with certain images, videos, animations, augmented reality (AR), virtual reality (VR), and/or features of the report. In some embodiments, the system is configured to insert into the patient-specific report dynamically generated illustrations or images of patient artery vessels in order to highlight specific vessels and/or portions of vessels that contain or are likely to contain vascular disease that require review or further analysis. In some embodiments, the dynamically generated patient-specific report is configured to show a user the vessel walls using AR and/or VR.

In some embodiments, the system is configured to insert into the dynamically generated report any ratios and/or dynamically generated data using the methods, systems, and devices disclosed herein. In some embodiments, the dynamically generated report comprises a radiology report. In some embodiments, the dynamically generated report is in an editable document, such as Microsoft Word®, in order to allow the physician to make edits to the report. In some embodiments, the dynamically generated report is saved into a PACS (Picture Archiving and Communication System) or other EMR (electronic medical records) system.

In some embodiments, the system is configured to transform and/or translate data from the imaging into drawings or infographics in a video format, with or without audio, in order to transmit accurately the information in a way that is better understandable to any patient to improve literacy. In some embodiments, this method of improving literacy is coupled to a risk stratification tool that defines a lower risk with higher literacy, and a higher risk with lower literacy. In some embodiments, these report outputs may be patient-derived and/or patient-specific. In some embodiments, real patient imaging data (for example, from their CT) can be coupled to graphics from their CT and/or drawings from the CT to explain the findings further. In some embodiments, real patient imaging data, graphics data and/or drawings data can be coupled to an explaining graphic that is not from the patient but that can help the patient better understand (for example, a video about lipid-rich plaque).

In some embodiments, these patient reports can be imported into an application that allows for following disease over time in relation to control of heart disease risk factors, such as diabetes or hypertension. In some embodiments, an app and/or user interface can allow for following of blood glucose and blood pressure over time and/or relate the changes of the image over time in a way that augments risk prediction.

In some embodiments, the system can be configured to generate a video report that is specific to the patient based on the processed data generated from the raw CT data. In some embodiments, the system is configured to generate and/or provide a personalized cinematic viewing experience for a user, which can be programmed to automatically and dynamically change content based upon imaging findings, associated auto-calculated diagnoses, and/or prognosis algorithms. In some embodiments, the method of viewing, unlike traditional reporting, is through a movie experience which can be in the form of a regular 2D movie and/or through a mixed reality movie experience through AR or VR. In some embodiments, in the case of both 2D and mixed reality, the personalized cinematic experience can be interactive with the patient to predict their prognosis, such as risk of heart attack, rate of disease progression, and/or ischemia.

In some embodiments, the system can be configured to dynamically generate a video report that comprises both cartoon images and/or animation along with audio content in combination with actual CT image data from the patient. In some embodiments, the dynamically generated video medical report is dynamically narrated based on selecting phrases, terms and/or other content from a database such that a voice synthesizer or pre-made voice content can be used for playback during the video report. In some embodiments, the dynamically generated video medical report is configured to comprise any of the images disclosed herein. In some embodiments, the dynamically generated video medical report can be configured to dynamically select one or more medical images from prior medical scanning and/or current medical scanning for insertion into the video medical report in order to show how the cardiovascular disease has changed over time in a patient. For example, in some embodiments, the report can show past and present images juxtaposed next to each other. In some embodiments, the repot can show past images that are superimposed on present images thereby allowing a user to toggle or move or fade between past and present images. In some embodiments, the dynamically generated video medical report can be configured to show actual medical images, such as a CT medical image, in the video report and then transition to an illustrative view or cartoon view (partial or entirely an illustrative or cartoon view) of the actual medical images, thereby highlighting certain features of the patient's arteries. In some embodiments, the dynamically generated video medical report is configured to show a user the vessel walls using AR and/or VR.

Figure 5A:
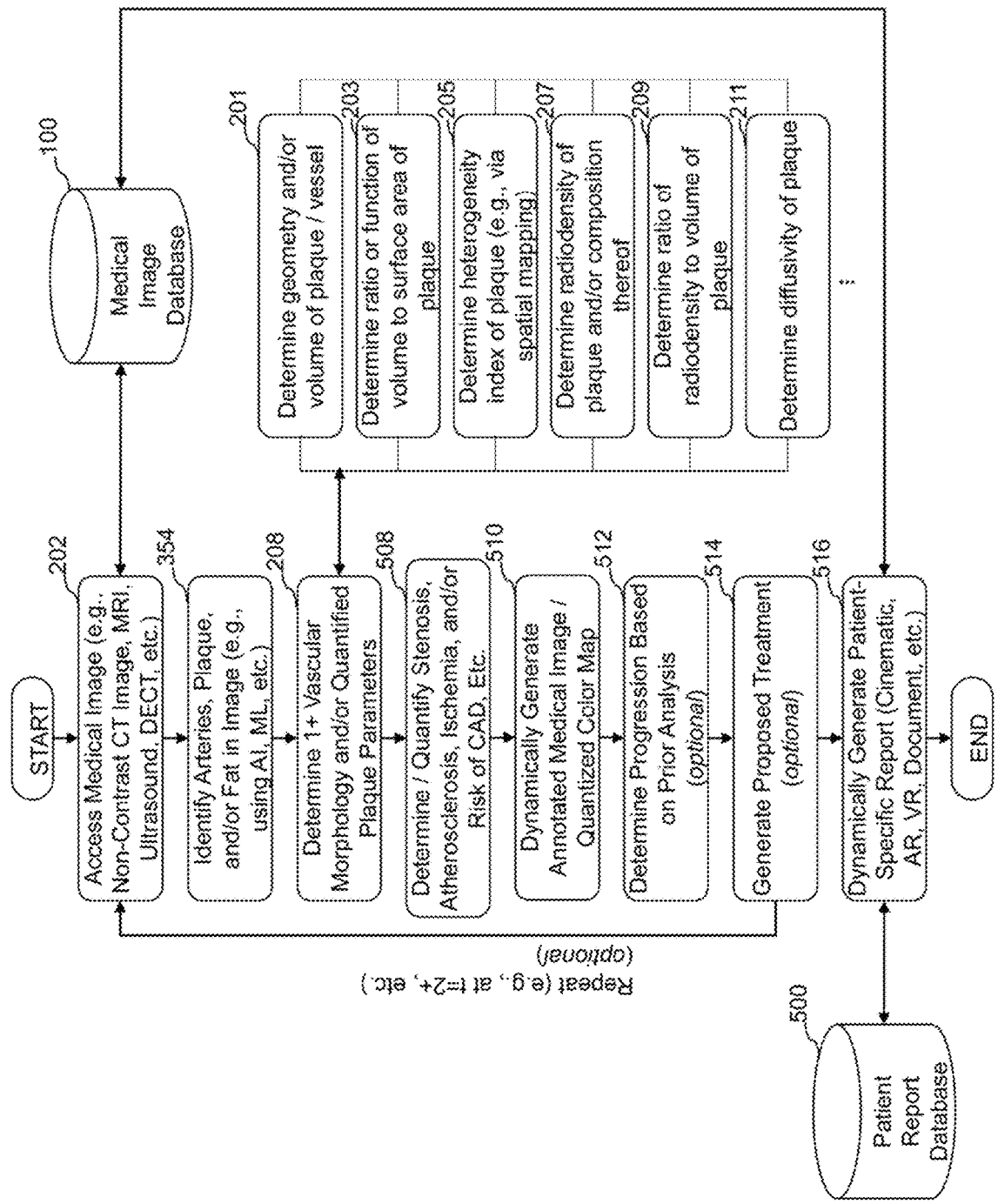
FIG. 5A is a flowchart illustrating an overview of an example embodiment(s) of a method for generation of a patient-specific medical report based on medical image analysis.

FIG. 5A is a flowchart illustrating an overview of an example embodiment(s) of a method for generation of a patient-specific medical report based on medical image analysis. As illustrated in FIG. 5A, in some embodiments, the system can be configured to access a medical image at block 202. In some embodiments, the medical image can be stored in a medical image database 100. Additional detail regarding the types of medical images and other processes and techniques represented in block 202 can be found in the description above in relation to FIG. 2A.

In some embodiments, at block 354, the system is configured to identify one or more arteries, plaque, and/or fat in the medical image, for example using AI, ML, and/or other algorithms. Additional detail regarding the types of medical images and other processes and techniques represented in block 354 can be found in the description above in relation to FIG. 3C.

In some embodiments, at block 208, the system can be configured to determine one or more vascular morphology and/or quantified plaque parameters. For example, in some embodiments, the system can be configured to determine a geometry and/or volume of a region of plaque and/or a vessel at block 201, a ratio or function of volume to surface area of a region of plaque at block 203, a heterogeneity or homogeneity index of a region of plaque at block 205, radiodensity of a region of plaque and/or a composition thereof by ranges of radiodensity values at block 207, a ratio of radiodensity to volume of a region of plaque at block 209, and/or a diffusivity of a region of plaque at block 211. Additional detail regarding the processes and techniques represented in blocks 208, 201, 203, 205, 207, 209, and 211 can be found in the description above in relation to FIG. 2A.

In some embodiments, at block 508, the system can be configured to determine and/or quantify stenosis, atherosclerosis, risk of ischemia, risk of cardiovascular event or disease, and/or the like. The system can be configured to utilize any techniques and/or algorithms described herein, including but not limited to those described above in connection with block 358 and block 366 of FIG. 3C.

In some embodiments, at block 510, the system can be configured to generate an annotated medical image and/or quantized color map using the analysis results derived from the medical image. For example, in some embodiments, the system can be configured to generate a quantized map showing one or more arteries, plaque, fat, good plaque, bad plaque, vascular morphologies, and/or the like.

In some embodiments, at block 512, the system can be configured to determine a progression of plaque and/or disease of the patient, for example based on analysis of previously obtained medical images of the subject. In some embodiments, the system can be configured to utilize any algorithms or techniques described herein in relation to disease tracking, including but not limited to those described in connection with block 380 and/or FIG. 3D generally.

In some embodiments, at block 514, the system can be configured to generate a proposed treatment plan for the patient based on the determined progression of plaque and/or disease. In some embodiments, the system can be configured to utilize any algorithms or techniques described herein in relation to disease tracking and treatment generation, including but not limited to those described in connection with block 382 and/or FIG. 3D generally.

In some embodiments, at block 516, the system can be configured to generate a patient-specific report. The patient-specific report can include one or more medical images of the patient and/or derived graphics thereof. For example, in some embodiments, the patient report can include one or more annotated medical images and/or quantized color maps. In some embodiments, the patient-specific report can include one or more vascular morphology and/or quantified plaque parameters derived from the medical image. In some embodiments, the patient-specific report can include quantified stenosis, atherosclerosis, ischemia, risk of cardiovascular event or disease, CAD-RADS score, and/or progression or tracking of any of the foregoing. In some embodiments, the patient-specific report can include a proposed treatment, such as statins, lifestyle changes, and/or surgery.

In some embodiments, the system can be configured to access and/or retrieve from a patient report database 500 one or more phrases, characterizations, graphics, videos, audio files, and/or the like that are applicable and/or can be used to generate the patient-specific report. In generating the patient-specific report, in some embodiments, the system can be configured to compare one or more parameters, such as those mentioned above and/or derived from a medical image of the patient, with one or more parameters previously derived from other patients. For example, in some embodiments, the system can be configured to compare one or more quantified plaque parameters derived from the medical image of the patient with one or more quantified plaque parameters derived from medical images of other patients in the similar or same age group. Based on the comparison, in some embodiments, the system can be configured to determine which phrases, characterizations, graphics, videos, audio files, and/or the like to include in the patient-specific report, for example by identifying similar previous cases. In some embodiments, the system can be configured to utilize an AI and/or ML algorithm to generate the patient-specific report. In some embodiments, the patient-specific report can include a document, AR experience, VR experience, video, and/or audio component.

Figure 5B:
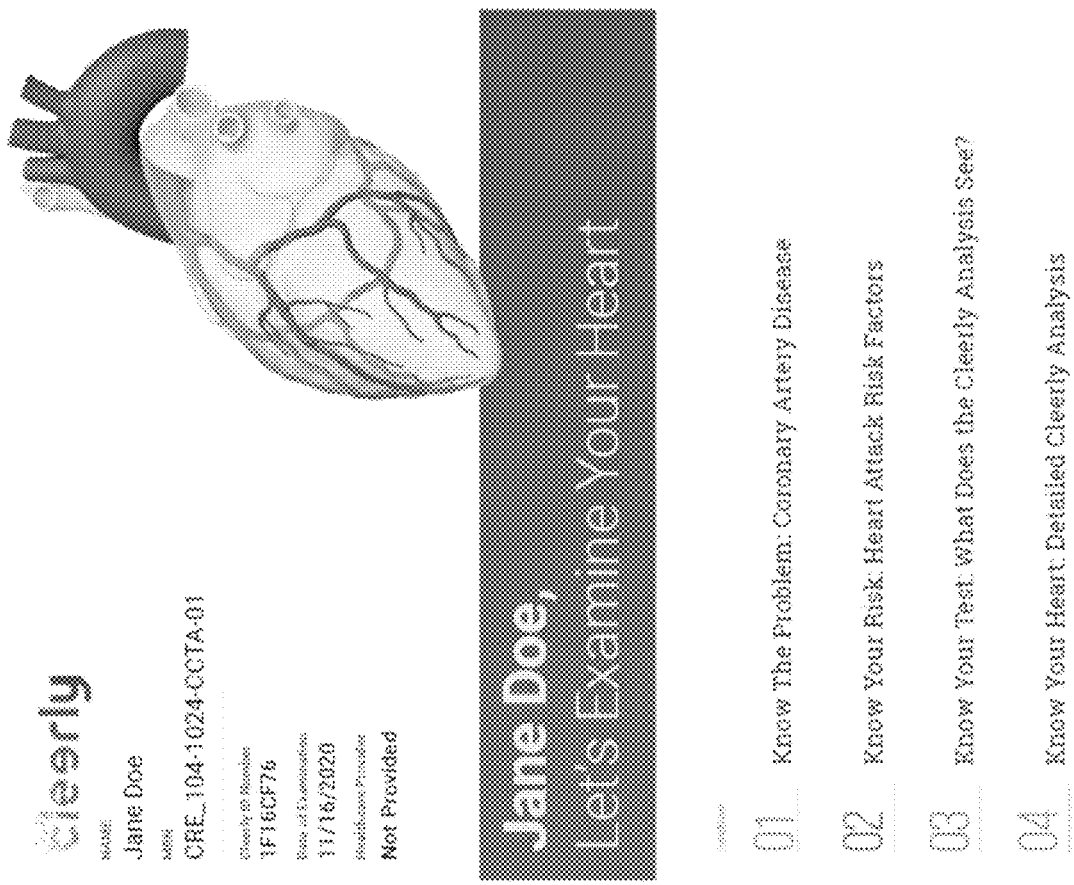
Figure 5C:
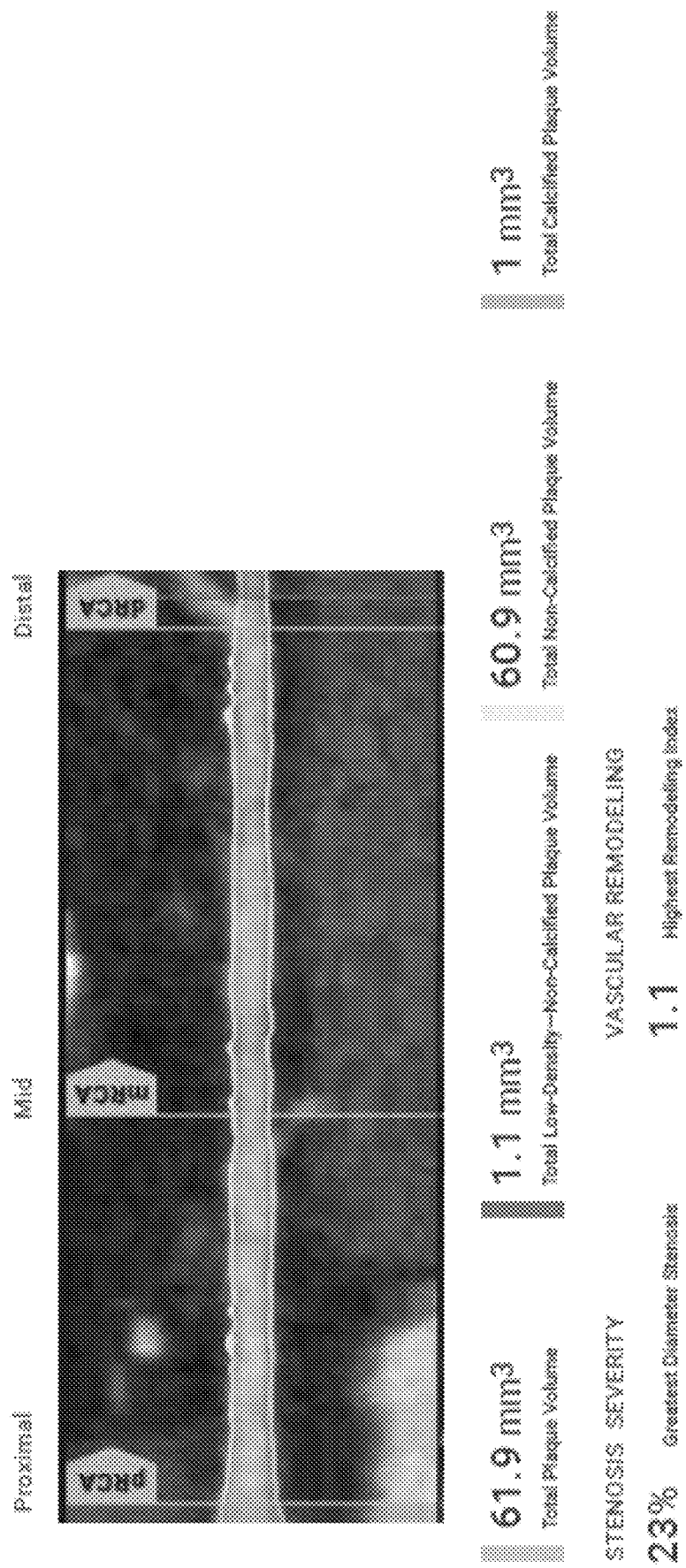
Figure 5E:
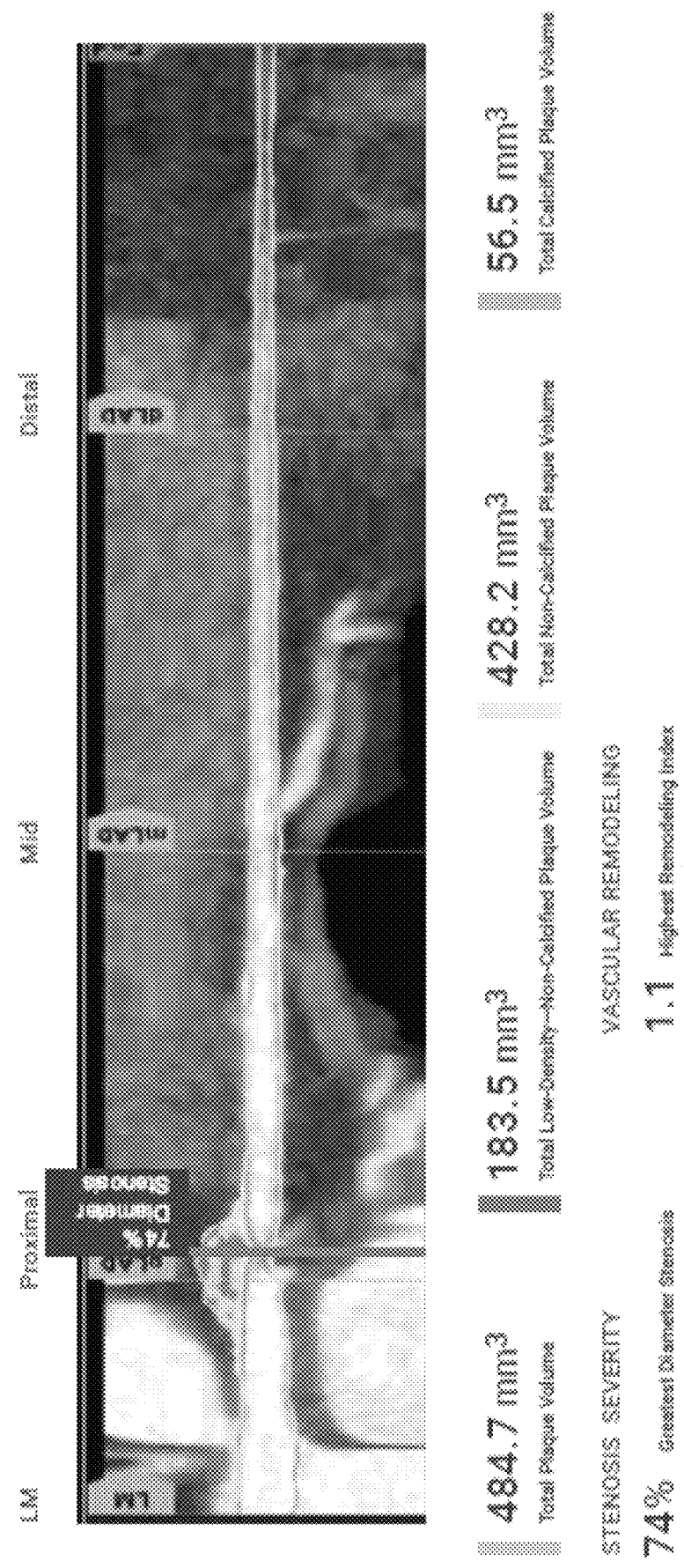
Figure 5H:
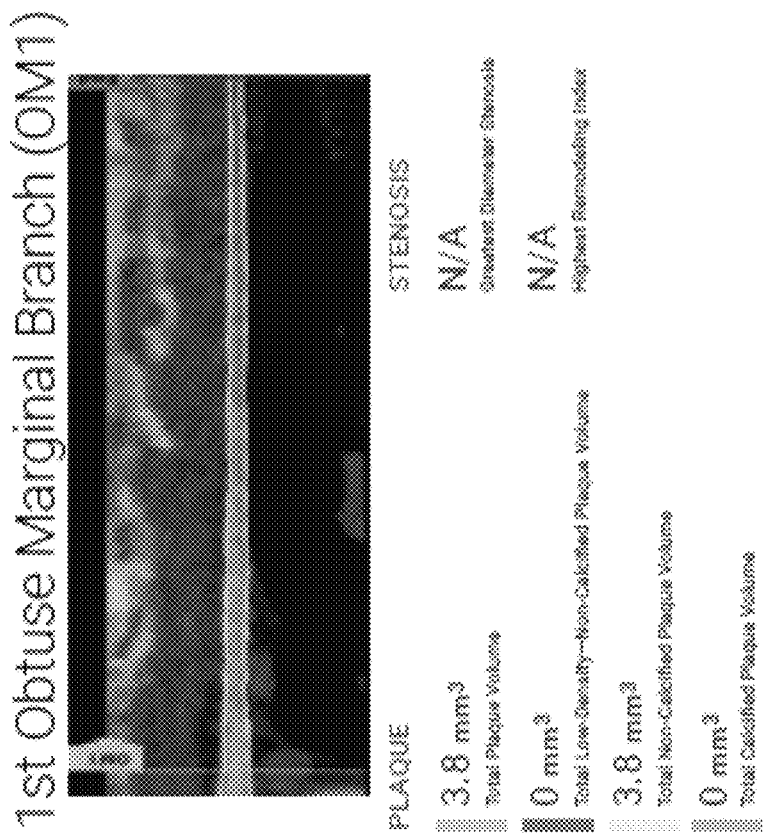
Figure 51:
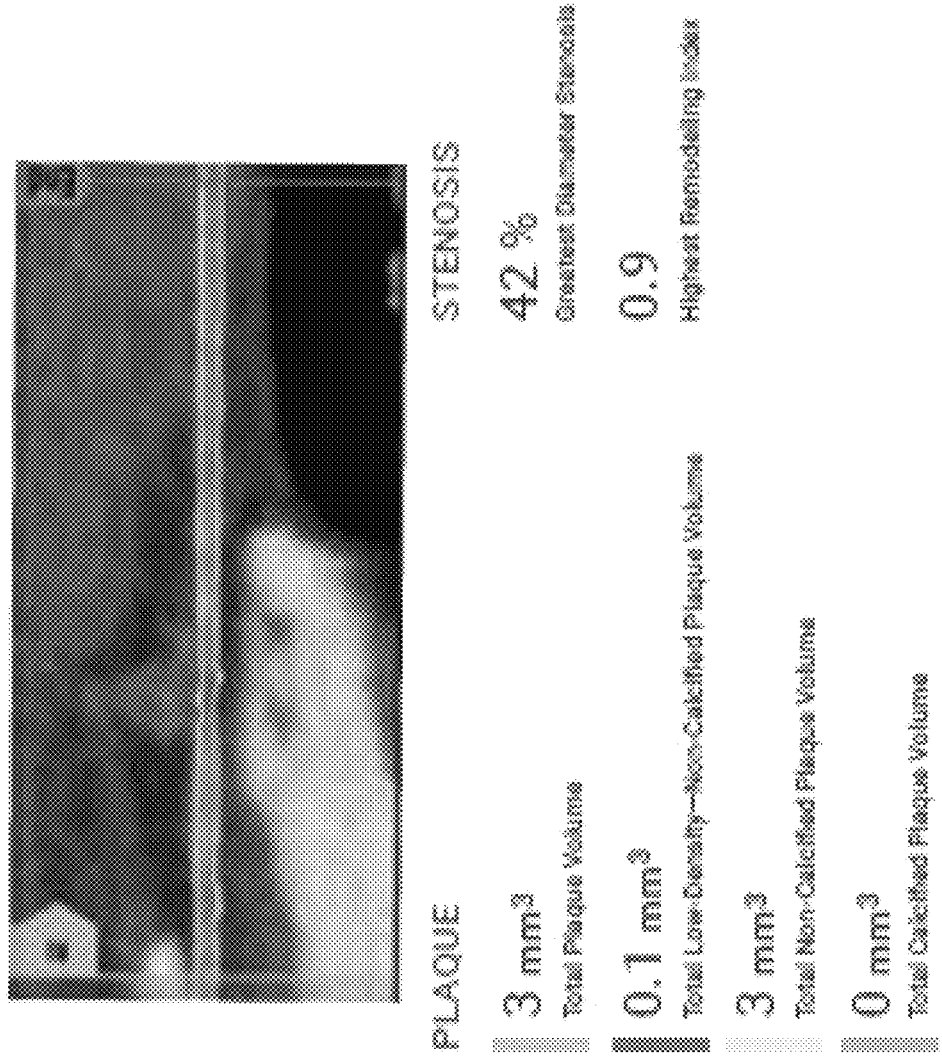

FIGS. 5B-5I illustrate example embodiment(s) of a patient-specific medical report generated based on medical image analysis. In particular, FIG. 5B illustrates an example cover page of a patient-specific report.

FIGS. 5C-5I illustrate portions of an example patient-specific report(s). In some embodiments, a patient-specific report generated by the system may include only some or all of these illustrated portions. As illustrated in FIGS. 5C-5I, in some embodiments, the patient-specific report includes a visualization of one or more arteries and/or portions thereof, such as for example, the Right Coronary Artery (RCA), R-Posterior Descending Artery (R-PDA), R-Posterolateral Branch (R-PLB), Left Main (LM) and Left Anterior Descending (LAD) Artery, 1st Diagonal (D1) Artery, 2nd Diagonal (D2) Artery, Circumflex (Cx) Artery, 1st Obtuse Marginal Branch (OM1), 2nd Obtuse Marginal Branch (OM2), Ramus Intermedius (RI), and/or the like. In some embodiments, for each of the arteries included in the report, the system is configured to generate a straightened view for easy tracking along the length of the vessel, such as for example at the proximal, mid, and/or distal portions of an artery.

In some embodiments, a patient-specific report generated by the system includes a quantified measure of various plaque and/or vascular morphology-related parameters shown within the vessel. In some embodiments, for each or some of the arteries included in the report, the system is configured to generate and/or derive from a medical image of the patient and include in a patient-specific report a quantified measure of the total plaque volume, total low-density or non-calcified plaque volume, total non-calcified plaque value, and/or total calcified plaque volume. Further, in some embodiments, for each or some of the arteries included in the report, the system is configured to generate and/or derive from a medical image of the patient and include in a patient-specific report a quantified measure of stenosis severity, such as for example a percentage of the greatest diameter stenosis within the artery. In some embodiments, for each or some of the arteries included in the patient-specific report, the system is configured to generate and/or derive from a medical image of the patient and include in a patient-specific report a quantified measure of vascular remodeling, such as for example the highest remodeling index.

Visualization/GUI

Atherosclerosis, the buildup of fats, cholesterol and other substances in and on your artery walls (e.g., plaque), which can restrict blood flow. The plaque can burst, triggering a blood clot. Although atherosclerosis is often considered a heart problem, it can affect arteries anywhere in the body. However, determining information about plaque in coronary arteries can be difficult due in part to imperfect imaging data, aberrations that can be present in coronary artery images (e.g., due to movement of the patient), and differences in the manifestation of plaque in different patients. Accordingly, neither calculated information derived from CT images, or visual inspection of the CT images, alone provide sufficient information to determine conditions that exist in the patient's coronary arteries. Portions of this disclosure describe information they can be determined from CT images using automatic or semiautomatic processes. For example, using a machine learning process has been trained on thousands of CT scans determine information depicted in the CT images, and/or utilizing analyst to review and enhance the results of the machine learning process, and the example user interfaces described herein can provide the determined information to another analyst or a medical practitioner. While the information determined from the CT images is invaluable in assessing the condition of a patient's coronary arteries, visual analysis of the coronary arteries by skilled medical practitioner, with the information determined from the CT images in-hand, allows a more comprehensive assessment of the patient's coronary arteries. As indicated herein, embodiments of the system facilitate the analysis and visualization of vessel lumens, vessel walls, plaque and stenosis in and around coronary vessels. This system can display vessels in multi-planar formats, cross-sectional views, 3D coronary artery tree view, axial, sagittal, and coronal views based on a set of computerized tomography (CT) images, e.g., generated by a CT scan of a patient's vessels. The CT images can be Digital Imaging and Communications in Medicine (DICOM) images, a standard for the communication and management of medical imaging information and related data. CT images, or CT scans, as used herein, is a broad term that refers to pictures of structures within the body created by computer controlled scanner. For example, by a scanner that uses an X-ray beam. However, it is appreciated that other radiation sources and/or imaging systems may produce a set of CT-like images. Accordingly, the use of the term "CT images" herein may refer to any type of imaging system having any type of imaging source that produces a set of images depicting "slices" of structures within a body, unless otherwise indicated. One key aspect of the user interface described herein is the precise correlation of the views and information that is displayed of the CT images. Locations in the CT images displayed on portions (or "panels") of the user interface are correlated precisely by the system such that the same locations are displayed concurrently in a different views. By simultaneously displaying a portion of the coronary vessel in, for example, two, three, four, five or six views simultaneously, and allowing a practitioner to explore particular locations of a coronary vessel in one view while the other 2-6 views correspondingly show the exact same location provides an enormous amount of insight into the condition of the vessel and allows the practitioner/analyst to quickly and easily visually integrate the presented information to gain a comprehensive and accurate understanding of the condition of the coronary vessel being examined.

Advantageously, the present disclosure allows CT images and data to be analyzed in a more useful and accurate way, for users to interact and analyze images and data in a more analytically useful way and/or for computation analysis to be performed in a more useful way, for example to detect conditions requiring attention. The graphical user interfaces in the processing described herein allow a user to visualize otherwise difficult to define relationships between different information and views of coronary arteries. In an example, displaying a portion of a coronary artery simultaneously in a CMPR view, a SMPR view, and a cross-sectional view can provide insight to an analyst of plaque or stenosis associated with the coronary artery that may not otherwise be perceivable using a fewer number of views. Similarly, displaying the portion of the coronary artery in an axial view, a sagittal view, and a coronal view, in addition to the CMPR view, the SMPR view, and the cross-sectional view can provide further information to the analyst that would not otherwise be perceivable with a fewer number of views of the coronary artery. In various embodiments, any of the information described or illustrated herein, determined by the system or an analyst interacting with the system, and other information (for example, from another outside source, e.g., an analyst) that relates to coronary arteries/vessels associated with the set of CT images ("artery information") including information indicative of stenosis and plaque of segments of the coronary vessels in the set of CT images, and information indicative of identification and location of the coronary vessels in the set of CT images, can be stored on the system and presented in various panels of the user interface and in reports. The present disclosure allows for easier and quicker analysis of a patient's coronary arteries and features associate with coronary arteries. The present disclosure also allows faster analysis of coronary artery data by allowing quick and accurate access to selected portions of coronary artery data. Without using the present system and methods of the disclosure, quickly selecting, displaying, and analyzing CT images and coronary artery information, can be cumbersome and inefficient, and may lead to analyst missing critical information in their analysis of a patient's coronary arteries, which may lead to inaccurate evaluation of a patient's condition.

In various embodiments, the system can identify a patient's coronary arteries either automatically (e.g., using a machine learning algorithm during the preprocessing step of set of CT images associated with a patient), or interactively (e.g., by receiving at least some input form a user) by an analyst or practitioner using the system. As described herein, in some embodiments, the processing of the raw CT scan data can comprise analysis of the CT data in order to determine and/or identify the existence and/or nonexistence of certain artery vessels in a patient. As a natural occurring phenomenon, certain arteries may be present in certain patients whereas such certain arteries may not exist in other patients. In some embodiments, the system can be configured to identify and label the artery vessels detected in the scan data. In certain embodiments, the system can be configured to allow a user to click upon a label of an identified artery within the patient, and thereby allowing that artery to be highlighted in an electronic representation of a plurality of artery vessels existing in the patient. In some embodiments, the system is configured to analyze arteries present in the CT scan data and display various views of the arteries present in the patient, for example within 10-15 minutes or less. In contrast, as an example, conducting a visual assessment of a CT to identify stenosis alone, without consideration of good or bad plaque or any other factor, can take anywhere between 15 minutes to more than an hour depending on the skill level, and can also have substantial variability across radiologists and/or cardiac imagers.

Although some systems may allow an analyst to view the CT images associated with a patient, they lack the ability to display all of the necessary views, in real or near real-time, with correspondence between 3-D artery tree views of coronary arteries specific to a patient, multiple SMPR views, and a cross-sectional, as well as an axial view, a sagittal view, and/or the coronal view. Embodiments of the system can be configured this display one or more of the use, or all of the use, which provides unparalleled visibility of a patient's coronary arteries, and allows an analyst or practitioner to perceive features and information that is simply may not be perceivable without these views. That is, a user interface configured to show all of these views, as well as information related to the displayed coronary vessel, allows an analyst or practitioner to use their own experience in conjunction with the information that the system is providing, to better identify conditions of the arteries which can help them make a determination on treatments for the patient. In addition, the information that is determined by the system and displayed by the user interface that cannot be perceived by an analyst or practitioner is presented in such a manner that is easy to understand and quick to assimilate. As an example, the knowledge of actual radiodensity values of plaque is not something that analyst and determine simply by looking at the CT image, but the system can and present a full analysis of all plaque is found.

In general, arteries vessels are curvilinear in nature. Accordingly, the system can be configured to straighten out such curvilinear artery vessels into a substantially straight-line view of the artery, and in some embodiments, the foregoing is referred to as a straight multiplanar reformation (MPR) view. In some embodiments, the system is configured to show a dashboard view with a plurality of artery vessels showing in a straight multiplanar reformation view. In some embodiments, the linear view of the artery vessels shows a cross-sectional view along a longitudinal axis (or the length of the vessel or a long axis) of the artery vessel. In some embodiments, the system can be configured to allow the user to rotate in a 360° fashion about the longitudinal axis of the substantially linear artery vessels in order for the user to review the vessel walls from various views and angles. In some embodiments, the system is configured to not only show the narrowing of the inner vessel diameter but also characteristics of the inner and/or outer vessel wall itself. In some embodiments, the system can be configured to display the plurality of artery vessels in a multiple linear views, e.g., in an SMPR view.

In some embodiments, the system can be configured to display the plurality of artery vessels in a perspective view in order to better show the user the curvatures of the artery vessels. In some embodiments, the perspective view is referred to as a curved multiplanar reformation view. In some embodiments, the perspective view comprises the CT image of the heart and the vessels, for example, in an artery tree view. In some embodiments, the perspective view comprises a modified CT image showing the artery vessels without the heart tissue displayed in order to better highlight the vessels of the heart. In some embodiments, the system can be configured to allow the user to rotate the perspective view in order to display the various arteries of the patient from different perspectives. In some embodiments, the system can be configured to show a cross-sectional view of an artery vessel along a latitudinal axis (or the width of the vessel or short axis). In contrast to the cross-sectional view along a longitudinal axis, in some embodiments, the system can allow a user to more clearly see the stenosis or vessel wall narrowing by viewing the artery vessel from a cross-sectional view across a latitudinal axis.

In some embodiments, the system is configured to display the plurality of artery vessels in an illustrative view or cartoon view. In the illustrative view of the artery vessels, in some embodiments, the system can utilize solid coloring or grey scaling of the specific artery vessels or sections of specific artery vessels to indicate varying degrees of risk for a cardiovascular event to occur in a particular artery vessel or section of artery vessel. For example, the system can be configured to display a first artery vessel in yellow to indicate a medium risk of a cardiovascular event occurring in the first artery vessel while displaying a second artery vessel in red to indicate a high risk of a cardiovascular event occurring in the second artery vessel. In some embodiments, the system can be configured to allow the user to interact with the various artery vessels and/or sections of artery vessels in order to better understand the designated risk associated with the artery vessel or section of artery vessel. In some embodiments, the system can allow the user to switch from the illustrative view to a CT view of the arteries of the patient.

In some embodiments, the system can be configured to display in a single dashboard view all or some of the various views described herein. For example, the system can be configured to display the linear view with the perspective view. In another example, the system can be configured to display the linear view with the illustrative view.

In some embodiments, the processed CT image data can result in allowing the system to utilize such processed data to display to a user various arteries of a patient. As described above, the system can be configured to utilize the processed CT data in order to generate a linear view of the plurality of artery vessels of a patient. In some embodiments, the linear view displays the arteries of a patient as in a linear fashion to resemble a substantially straight line. In some embodiments, the generating of the linear view requires the stretching of the image of one or more naturally occurring curvilinear artery vessels. In some embodiments, the system can be configured to utilize such processed data to allow a user to rotate a displayed linear view of an artery in a 360° rotatable fashion. In some embodiments, the processed CT image data can visualize and compare the artery morphologies over time, i.e., throughout the cardiac cycle. The dilation of the arteries, or lack thereof, may represent a healthy versus sick artery that is not capable of vasodilation. In some embodiments, a prediction algorithm can be made to determine the ability of the artery to dilate or not, by simply examining a single point in time.

As mentioned above, aspects of the system can help to visualize a patient's coronary arteries. In some embodiments, the system can be configured to utilize the processed data from the raw CT scans in order to dynamically generate a visualization interface for a user to interact with and/or analyze the data for a particular patient. The visualization system can display multiple arteries associated with a patient's heart. The system can be configured to display multiple arteries in a substantially linear fashion even though the arteries are not linear within the body of the patient. In some embodiments, the system can be configured to allow the user to scroll up and down or left to right along the length of the artery in order to visualize different areas of the artery. In some embodiments, the system can be configured to allow a user to rotate in a 360° fashion an artery in order to allow the user to see different portions of the artery at different angles.

Advantageously, the system can be configured to comprise or generate markings in areas where there is an amount of plaque buildup that exceeds a threshold level. In some embodiments, the system can be configured to allow the user to target a particular area of the artery for further examination. The system can be configured to allow the user to click on one or more marked areas of the artery in order to display the underlying data associated with the artery at a particular point along the length of the artery. In some embodiments, the system can be configured to generate a cartoon rendition of the patient's arteries. In some embodiments, the cartoon or computer-generated representation of the arteries can comprise a color-coded scheme for highlighting certain areas of the patient's arteries for the user to examine further. In some embodiments, the system can be configured to generate a cartoon or computer-generated image of the arteries using a red color, or any other graphical representation, to signify arteries that require further analysis by the user. In some embodiments, the system can label the cartoon representation of the arteries, and the 3D representation of the arteries described above, with stored coronary vessel labels according to the labeling scheme. If a user desires, the labeling scheme can be changed or refined and preferred labels may be stored and used label coronary arteries.

In some embodiments, the system can be configured to identify areas in the artery where ischemia is likely to be found. In some embodiments, the system can be configured to identify the areas of plaque in which bad plaque exists. In some embodiments, the system can be configured to identify bad plaque areas by determining whether the coloration and/or the gray scale level of the area within the artery exceeds a threshold level. In an example, the system can be configured to identify areas of plaque where the image of a plaque area is black or substantially black or dark gray. In an example, the system can be configured to identify areas of "good" plaque by the designation of whiteness or light grey in a plaque area within the artery.

In some embodiments, the system is configured to identify portions of an artery vessel where there is high risk for a cardiac event and/or draw an outline following the vessel wall or profiles of plaque build-up along the vessel wall. In some embodiments, the system is further configured to display this information to a user and/or provide editing tools for the user to change the identified portions or the outline designations if the user thinks that the AI algorithm incorrectly drew the outline designations. In some embodiments, the system comprises an editing tool referred to as "snap-to-lumen," wherein the user selects a region of interest by drawing a box around a particular area of the vessel and selecting the snap-to-lumen option and the system automatically redraws the outline designation to more closely track the boundaries of the vessel wall and/or the plaque build-up, wherein the system is using image processing techniques, such as but not limited to edge detection. In some embodiments, the AI algorithm does not process the medical image data with complete accuracy and therefore editing tools are necessary to complete the analysis of the medical image data. In some embodiments, the final user editing of the medical image data allows for faster processing of the medical image data than using solely AI algorithms to process the medical image data.

In some embodiments, the system is configured to replicate images from higher resolution imaging. As an example, in CT, partial volume artifacts from calcium are a known artifact of CT that results in overestimation of the volume of calcium and the narrowing of an artery. By training and validating a CT artery appearance to that of intravascular ultrasound or optical coherence tomography or histopathology, in some embodiments, the CT artery appearance may be replicated to be similar to that of IVUS or OCT and, in this way, de-bloom the coronary calcium artifacts to improve the accuracy of the CT image.

In some embodiments, the system is configured to provide a graphical user interface for displaying a vessel from a beginning portion to an ending portion and/or the tapering of the vessel over the course of the vessel length. Many examples of panels that can be displayed in a graphical user interface are illustrated and described in reference to FIGS. 6A-9N. In some embodiments, portions of the user interface, panels, buttons, or information displayed on the user interface be arranged differently than what is described herein and illustrated in the Figures. For example, a user may have a preference for arranging different views of the arteries in different portions of the user interface.

In some embodiments, the graphical user interface is configured to annotate the displayed vessel view with plaque build-up data obtained from the AI algorithm analysis in order to show the stenosis of the vessel or a stenosis view. In some embodiments, the graphical user interface system is configured to annotate the displayed vessel view with colored markings or other markings to show areas of high risk or further analysis, areas of medium risk, and/or areas of low risk. For example, the graphical user interface system can be configured to annotate certain areas along the vessel length in red markings, or other graphical marking, to indicate that there is significant bad fatty plaque build-up and/or stenosis. In some embodiments, the annotated markings along the vessel length are based on one or more variable such as but not limited to stenosis, biochemistry tests, biomarker tests, AI algorithm analysis of the medical image data, and/or the like. In some embodiments, the graphical user interface system is configured to annotate the vessel view with an arthrosclerosis view. In some embodiments, the graphical user interface system is configured to annotate the vessel view with an ischemia view. In some embodiments, the graphical user interface is configured to allow the user to rotate the vessel 180 degrees or 360 degrees in order to display the vessel and the annotated plaque build-up views from different angles. From this view, the user can manually determine the stent length and diameter for addressing the stenosis, and in some embodiments, the system is configured to analyze the medical image information to determine the recommended stent length and diameter, and display the proposed stent for implantation in the graphical user interface to illustrate to the user how the stent would address the stenosis within the identified area of the vessel. In some embodiments, the systems, methods, and devices disclosed herein can be applied to other areas of the body and/or other vessels and/or organs of a subject, whether the subject is human or other mammal.

Illustrative Example

One of the main uses of such systems can be to determine the presence of plaque in vessels, for example but not limited to coronary vessels. Plaque type can be visualized based on Hounsfield Unit density for enhanced readability for the user. Embodiments of the system also provide quantification of variables related to stenosis and plaque composition at both the vessel and lesion levels for the segmented coronary artery.

In some embodiments, the system is configured as a web-based software application that is intended to be used by trained medical professionals as an interactive tool for viewing and analyzing cardiac CT data for determining the presence and extent of coronary plaques (i.e., atherosclerosis) and stenosis in patients who underwent Coronary Computed Tomography Angiography (CCTA) for evaluation of coronary artery disease (CAD), or suspected CAD. This system post processes CT images obtained using a CT scanner. The system is configured to generate a user interface that provides tools and functionality for the characterization, measurement, and visualization of features of the coronary arteries.

Features of embodiments of the system can include, for example, centerline and lumen/vessel extraction, plaque composition overlay, user identification of stenosis, vessel statistics calculated in real time, including vessel length, lesion length, vessel volume, lumen volume, plaque volume (non-calcified, calcified, low-density-non-calcified plaque and total), maximum remodeling index, and area/diameter stenosis (e.g., a percentage), two dimensional (2D) visualization of multi-planar reformatted vessel and cross-sectional views, interactive three dimensional (3D) rendered coronary artery tree, visualization of a cartoon artery tree that corresponds to actual vessels that appear in the CT images, semi-automatic vessel segmentation that is user modifiable, and user identification of stents and Chronic Total Occlusion (CTO).

In an embodiment, the system uses 18 coronary segments within the coronary vascular tree (e.g., in accordance with the guidelines of the Society of Cardiovascular Computed Tomography). The coronary segment labels include:
pRCA—proximal right coronary artery
mRCA—mid right coronary artery
dRCA—distal right coronary artery
R-PDA—right posterior descending artery
LM—left main artery
pLAD—proximal left descending artery
mLAD—mid left anterior descending artery
dLAD—distal left anterior descending artery
D1—first diagonal
D2—second diagonal
pCx—proximal left circumflex artery
OM1—first obtuse marginal
LCx—distal left circumflex
OM2—second obtuse marginal
L-PDA—left posterior descending artery
R-PLB—right posterior lateral branch
RI—ramus intermedius artery
L-PLB—left posterior lateral branch Other embodiments can include more, or fewer, coronary segment labels. The coronary segments present in an individual patient are dependent on whether they are right or left coronary dominant. Some segments are only present when there is right coronary dominance, and some only when there is a left coronary dominance. Therefore, in many, if not all instances, no single patient may have all 18 segments. The system will account for most known variants.

In one example of performance of the system, CT scans were processed by the system, and the resulting data was compared to ground truth results produced by expert readers. Pearson Correlation Coefficients and Bland-Altman Agreements between the systems results and the expert reader results is shown in the table below:

| Output | Pearson Correlation | Bland-Altman Agreement |
|---|---|---|
| Lumen Volume | 0.91 | 96% |
| Vessel Volume | 0.93 | 97% |
| Total Plaque Volume | 0.85 | 95% |
| Calcified Plaque Volume | 0.94 | 95% |
| Non-Calcified Plaque Volume | 0.74 | 95% |
| Low-Density-Non-Calcified Plaque Volume | 0.53 | 97% |

FIGS. 6A-9N illustrate an embodiment of the user interface of the system, and show examples of panels, graphics, tools, representations of CT images, and characteristics, structure, and statistics related to coronary vessels found in a set of CT images. In various embodiments, the user interface is flexible and that it can be configured to show various arrangements of the panels, images, graphics representations of CT images, and characteristics, structure, and statistics. For example, based on an analyst's preference. The system has multiple menus and navigational tools to assist in visualizing the coronary arteries. Keyboard and mouse shortcuts can also be used to navigate through the images and information associated with a set of CT images for patient.

Figure 6A:
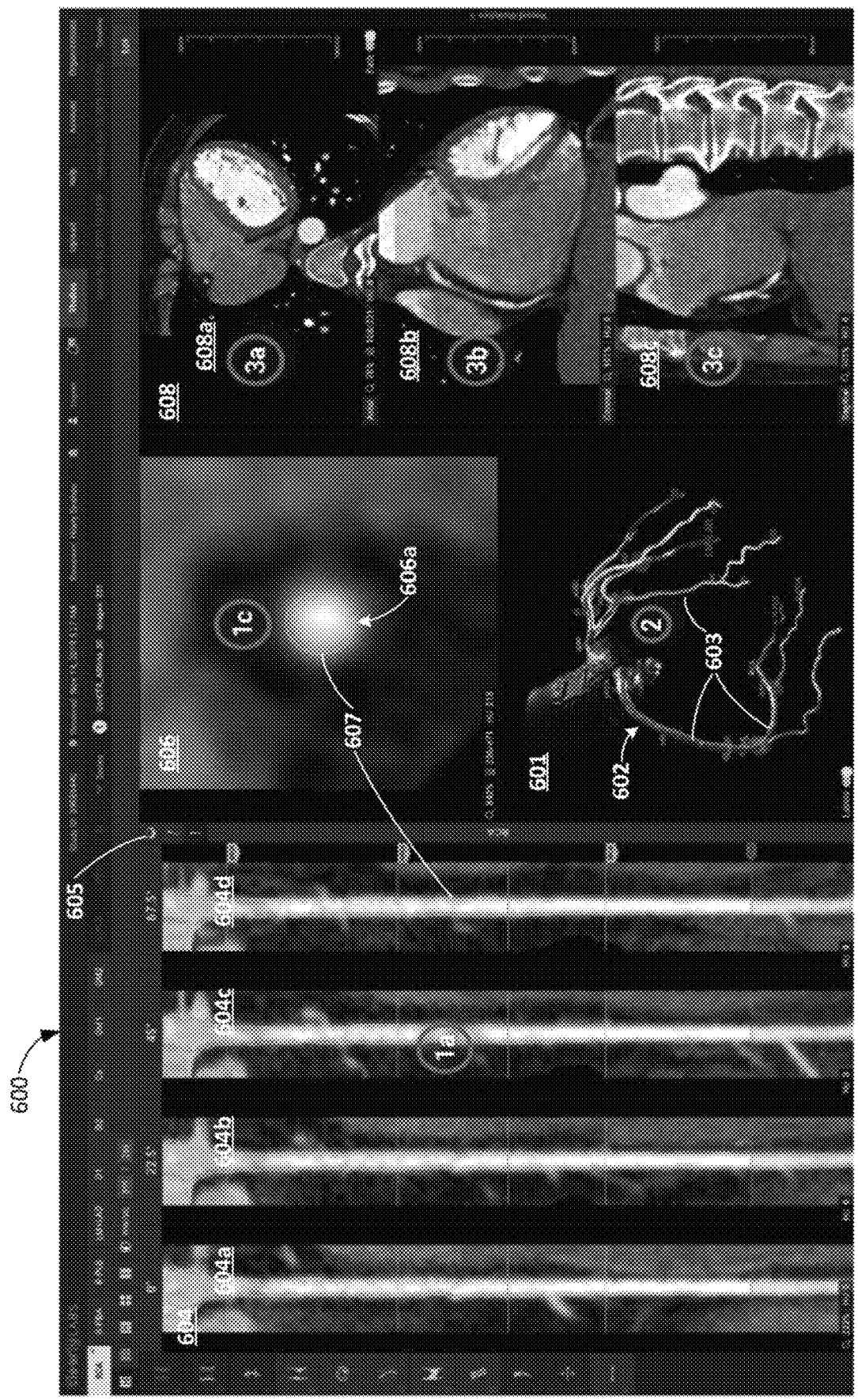
FIG. 6A illustrates an example of a user interface that can be generated and displayed on the system, the user interface having multiple panels (views) that can show various corresponding views of a patient's arteries.

FIG. 6A illustrates an example of a user interface 600 that can be generated and displayed on a CT image analysis system described herein, the user interface 600 having multiple panels (views) that can show various corresponding views of a patient's arteries and information about the arteries. In an embodiment, the user interface 600 shown in FIG. 6A can be a starting point for analysis of the patient's coronary arteries, and is sometimes referred to herein as the "Study Page" (or the Study Page 600). In some embodiments, the Study Page can include a number of panels that can be arranged in different positions on the user interface 600, for example, based on the preference the analyst. In various instances of the user interface 600, certain panels of the possible panels that may be displayed can be selected to be displayed (e.g., based on a user input).

The example of the Study Page 600 shown in FIG. 6A includes a first panel 601 (also shown in the circled "2") including an artery tree 602 comprising a three-dimensional (3D) representation of coronary vessels based on the CT images and depicting coronary vessels identified in the CT images, and further depicting respective segment labels. While processing the CT images, the system can determine the extent of the coronary vessels are determined and the artery tree is generated. Structure that is not part of the coronary vessels (e.g., heart tissue and other tissue around the coronary vessels) are not included in the artery tree 602. Accordingly, the artery tree 602 in FIG. 6A does not include any heart tissue between the branches (vessels) 603 of the artery tree 602 allowing visualization of all portions of the artery tree 602 without them being obscured by heart tissue.

This Study Page 600 example also includes a second panel 604 (also shown in the circled "1a") illustrating at least a portion of the selected coronary vessel in at least one straightened multiplanar reformat (SMPR) vessel view. A SMPR view is an elevation view of a vessel at a certain rotational aspect. When multiple SMPR views are displayed in the second panel 604 each view can be at a different rotational aspect. For example, at any whole degree, or at a half degree, from 0° to 259.5°, where 360° is the same view as 0°. In this example, the second panel 604 includes four straightened multiplanar vessels 604*a-d* displayed in elevation views at a relative rotation of 0°, 22.5°, 45°, and 67.5°, the rotation indicated that the upper portion of the straightened multiplanar vessel. In some embodiments, the rotation of each view can be selected by the user, for example, at the different relative rotation interval. The user interface includes the rotation tool 605 that is configured to receive an input from a user, and can be used to adjust rotation of a SMPR view (e.g., by one or more degrees). One or more graphics related to the vessel shown in the SMPR view can also be displayed. For example, a graphic representing the lumen of the vessel, a graphic representing the vessel wall, and/or a graphic representing plaque.

This Study Page 600 example also includes the third panel 606 (also indicated by the circled "1c"), which is configured to show a cross-sectional view of a vessel 606*a* generated based on a CT image in the set of CT images of the patient. The cross-sectional view corresponds to the vessel shown in the SMPR view. The cross-sectional view also corresponds to a location indicated by a user (e.g., with a pointing device) on a vessel in the SMPR view. The user interfaces configured such that a selection of a particular location along the coronary vessel in the second panel 604 displays the associated CT image in a cross-sectional view in the third panel 606. In this example, a graphic 607 is displayed on the second panel 604 and the third panel 606 indicating the extent of plaque in the vessel.

This Study Page 600 example also includes a fourth panel 608 that includes anatomical plane views of the selected coronary vessel. In this embodiment, the Study Page 600 includes an axial plane view 608*a* (also indicated by the circled "3a"), a coronal plane view 608*b* (also indicated by the circled "3b"), and a sagittal plane view 608*c* (also indicated by the circled "3c"). The axial plane view is a transverse or "top" view. The coronal plane view is a front view. The sagittal plane view is a side view. The user interface is configured to display corresponding views of the selected coronary vessel. For example, views of the selected coronary vessel at a location on the coronary vessel selected by the user (e.g., on one of the SMPR views in the second panel 604.

Figure 6B:
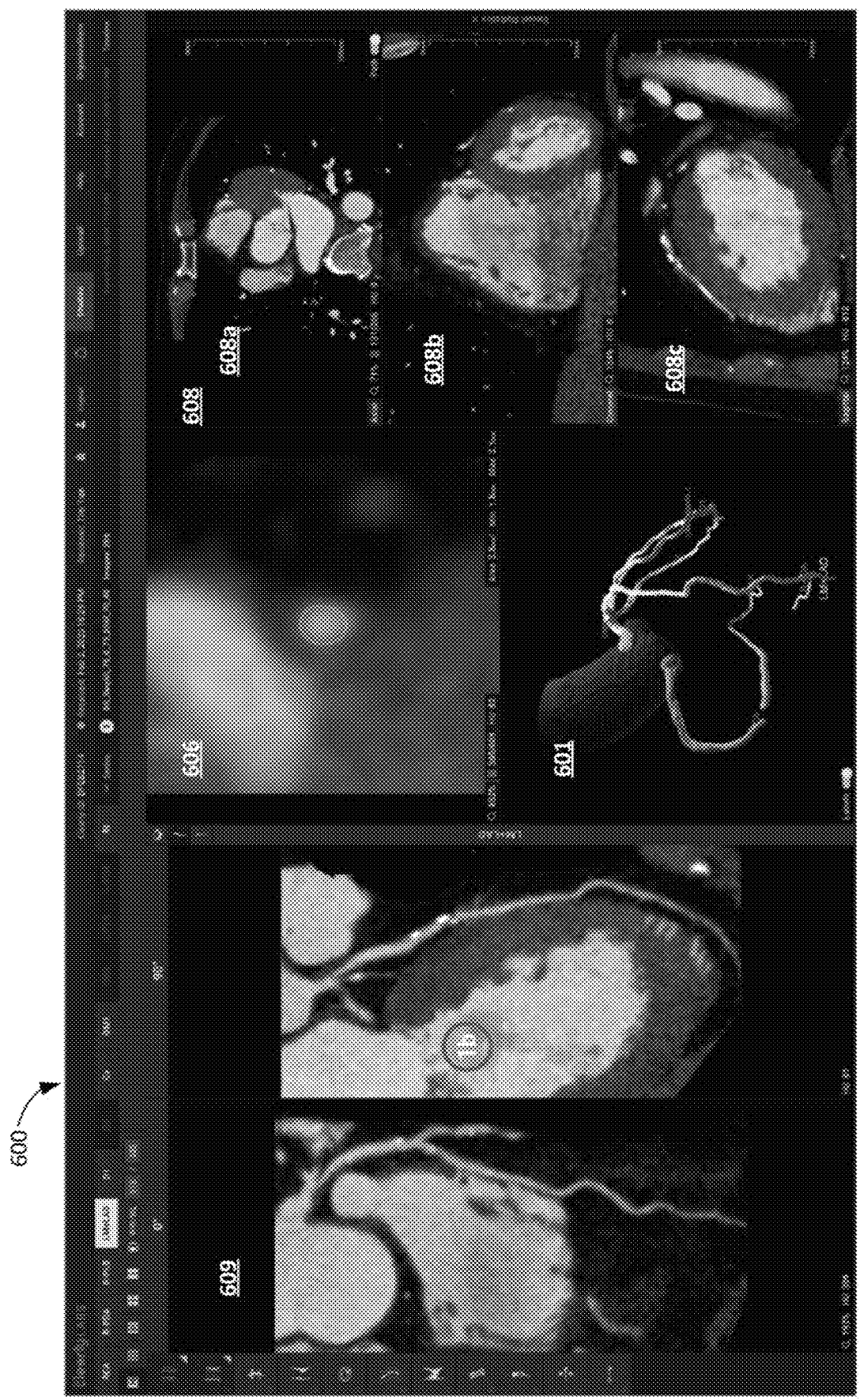
FIG. 6B illustrates an example of a user interface that can be generated and displayed on the system, the user interface having multiple panels that can show various corresponding views of a patient's arteries.

FIG. 6B illustrates another example of the Study Page (user interface) 600 that can be generated and displayed on the system, the user interface 600 having multiple panels that can show various corresponding views of a patient's arteries. In this example, the user interface 600 displays an 3D artery tree in the first panel 601, the cross-sectional view in the third panel 606, and axial, coronal, and sagittal plane views in the fourth panel 608. Instead of the second panel 604 shown in FIG. 6A, the user interface 600 includes a fifth panel 609 showing curved multiplanar reformat (CMPR) vessel views of a selected coronary vessel. The fifth panel 609 can be configured to show one or more CMPR views. In this example, two CMPR views were generated and are displayed, a first CMPR view 609*a* at 0° and a second CMPR view 609*b* at 90°. The CMPR views can be generated and displayed at various relative rotations, for example, from 0° to 259.5°. The coronary vessel shown in the CMPR view corresponds to the selected vessel, and corresponds to the vessel displayed in the other panels. When a location on the vessel in one panel is selected (e.g., the CMPR view), the views in the other panels (e.g., the cross-section, axial, sagittal, and coronal views) can be automatically updated to also show the vessel at that the selected location in the respective views, thus greatly enhancing the information presented to a user and increasing the efficiency of the analysis.

Figure 6C:
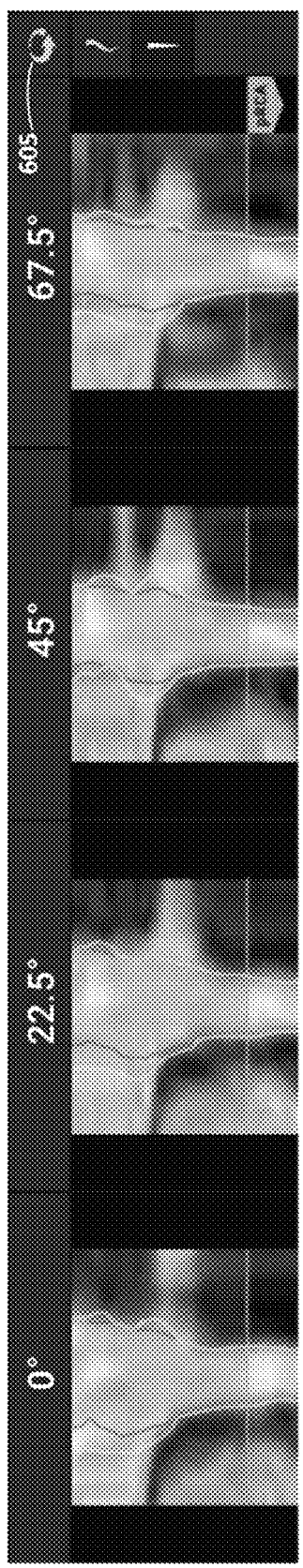
FIGS. 6C, 6D, and 6E illustrate certain details of a multiplanar reformat (MPR) vessel view in the second panel, and certain functionality associated with this view.
Figure 6D:
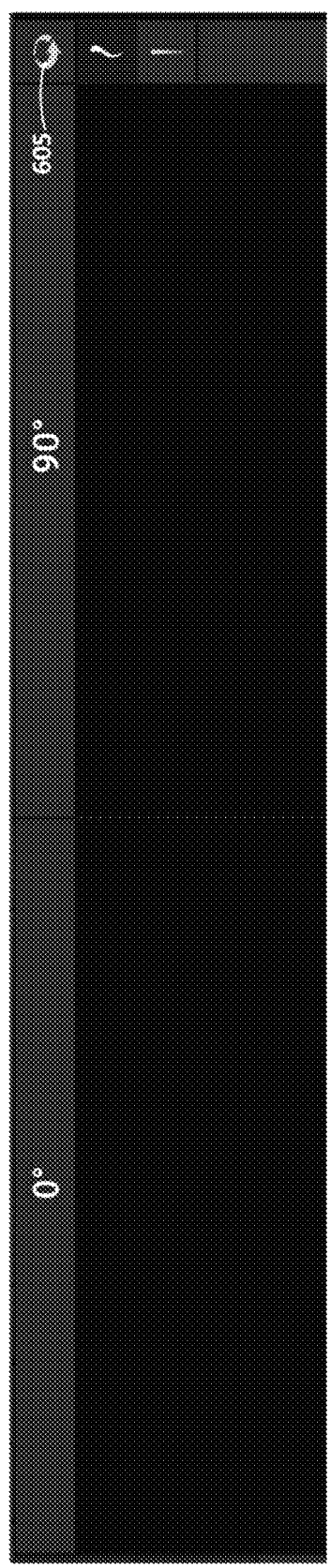
Figure 6E:

FIGS. 6C, 6D, and 6E illustrate certain details of a multiplanar reformat (MPR) vessel view in the second panel, and certain functionality associated with this view. After a user verifies the accuracy of the segmentation of the coronary artery tree in panel 602, they can proceed to interact with the MPR views where edits can be made to the individual vessel segments (e.g., the vessel walls, the lumen, etc.) In the SMPR and CMPR views, the vessel can be rotated in increments (e.g., 22.5°) by using the arrow icon 605, illustrated in FIGS. 6C and 6D. Alternatively, the vessel can be rotated continuously by 1 degree increments in 360 degrees by using the rotation command 610, as illustrated in FIG. 6E. The vessels can also be rotated by pressing the COMMAND or CTRL button and left clicking+dragging the mouse on the user interface 600.

Figure 6G:
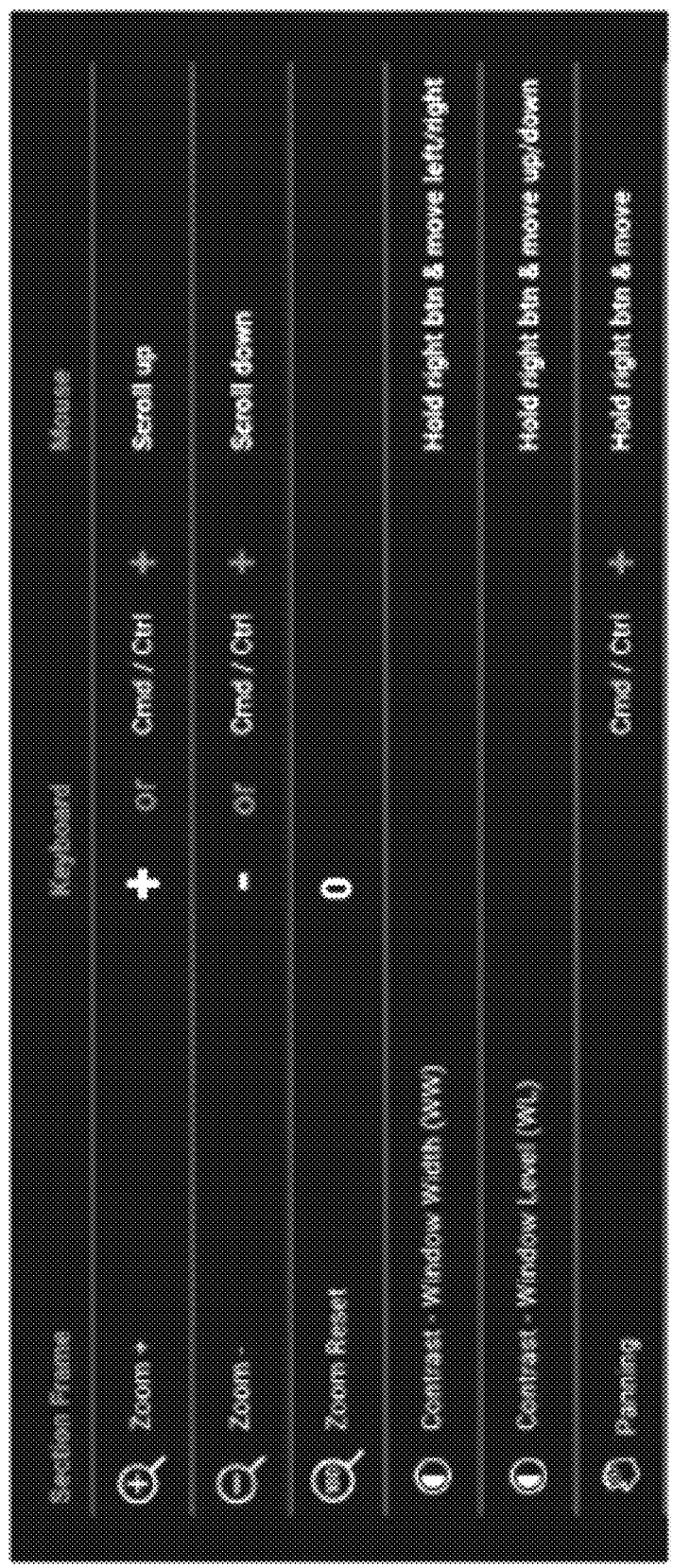
FIG. 6G illustrates an example of a panel of the user interface that provides shortcut commands that a user may employ while analyzing information in the user interface in a coronary artery tree view, an axial view, a sagittal view, and a coronal view.
Figure 6I:
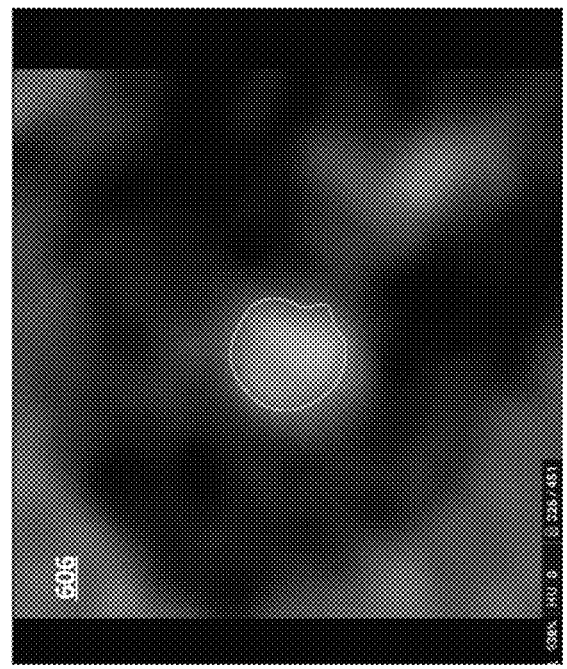
FIG. 6I illustrates an example of a panel of the user interface showing a cross-sectional view of a vessel, in the graphical overlay of an extracted feature of the vessel.
Figure 6H:
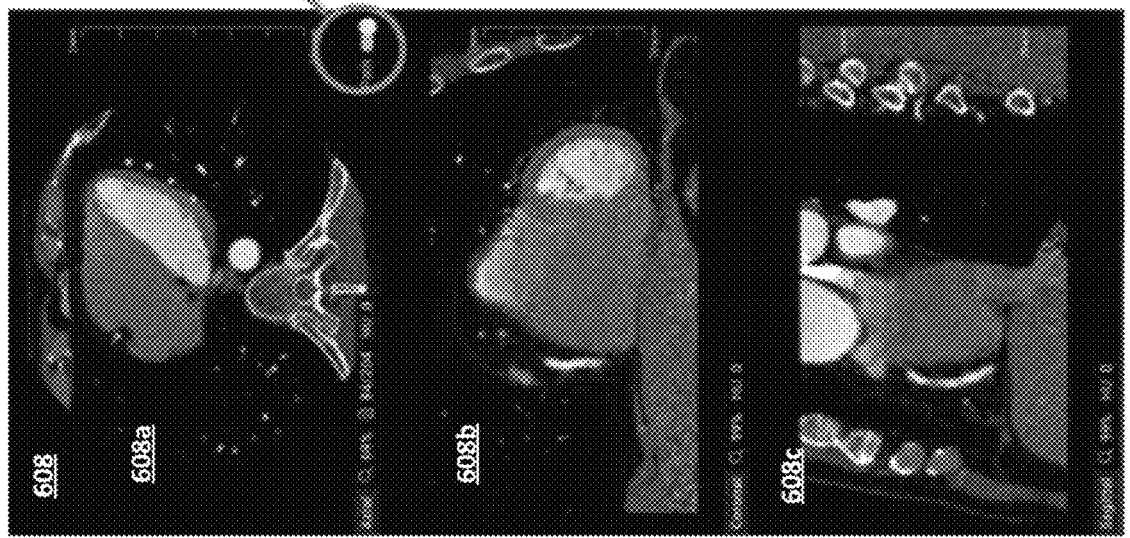
FIG. 6H illustrates examples of panels of the user interface for viewing DICOM images in three anatomical planes: axial, coronal, and sagittal.

FIG. 6F illustrates additional information of the three-dimensional (3D) rendering of the coronary artery tree 602 on the first panel 601 that allows a user to view the vessels and modify the labels of a vessel. FIG. 6G illustrates shortcut commands for the coronary artery tree 602, axial view 608*a*, sagittal view 608*b*, and coronal view 608*c*. In panel 601 shown in FIG. 6F, a user can rotate the artery tree as well as zoom in and out of the 3D rendering using commands selected in the user interface illustrated in FIG. 6G. Clicking on a vessel will turn it yellow which indicates that is the vessel that is currently being reviewed. In this view, users can rename or delete a vessel by right-clicking on the vessel name which opens panel 611, which is configured to receive an input from a user to rename the vessel. Panel 601 also includes a control that can be activated to turn the displayed labels "on" or "off." FIG. 6H further illustrates panel 608 of the user interface for viewing DICOM images in three anatomical planes: axial, coronal, and sagittal. FIG. 6I illustrates panel 606 showing a cross-sectional view of a vessel. The scroll, zoom in/out, and pan commands can also be used on these views.

Figure 6J:
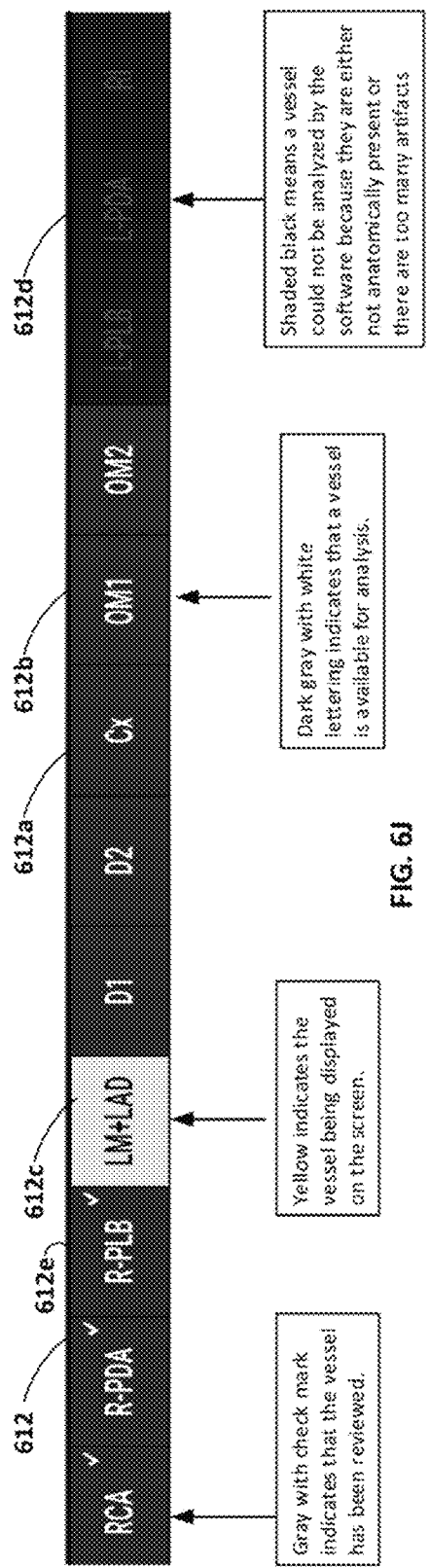
FIG. 6J illustrates an example of a toolbar that allows a user to select different vessels for review and analysis.
Figure 6K:
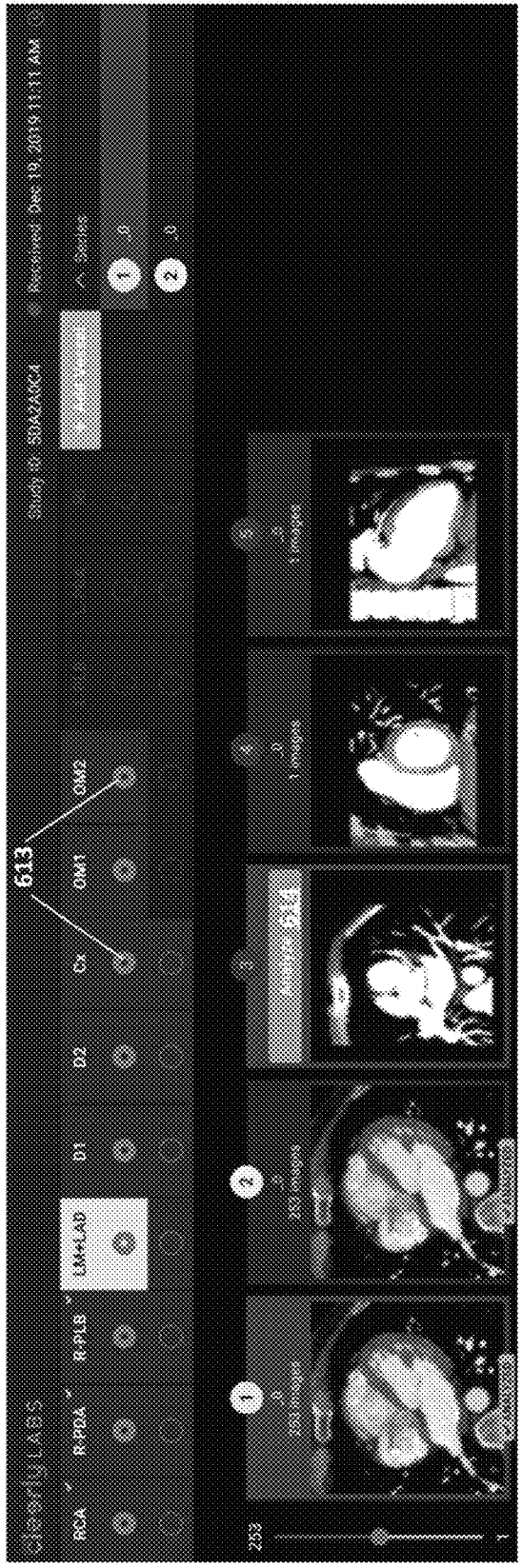
FIG. 6K illustrates an example of a series selection panel of the user interface in an expanded view of the toolbar illustrated in FIG. 6J, which allows a user to expand the menu to view all the series (set of images) that are available for review and analysis for a particular patient.

FIGS. 6J and 6K illustrate certain aspects of the toolbar 612 and menu navigation functionality of the user interface 600. FIG. 6J illustrates a toolbar of the user interface for navigating the vessels. The toolbar 612 includes a button 612*a*, 612*b* etc. for each of the vessels displayed on the screen. The user interface 600 is configured to display the buttons 612*a-n* to indicate various information to the user. In an example, when a vessel is selected, the corresponding button is highlighted (e.g., displayed in yellow), for example, button 612*c*. In another example, a button being dark gray with white lettering indicates that a vessel is available for analysis. In an example, a button 612*d* that is shaded black means a vessel could not be analyzed by the software because they are either not anatomically present or there are too many artifacts. A button 612*e* that is displayed as gray with check mark indicates that the vessel has been reviewed.

Figure 6L:
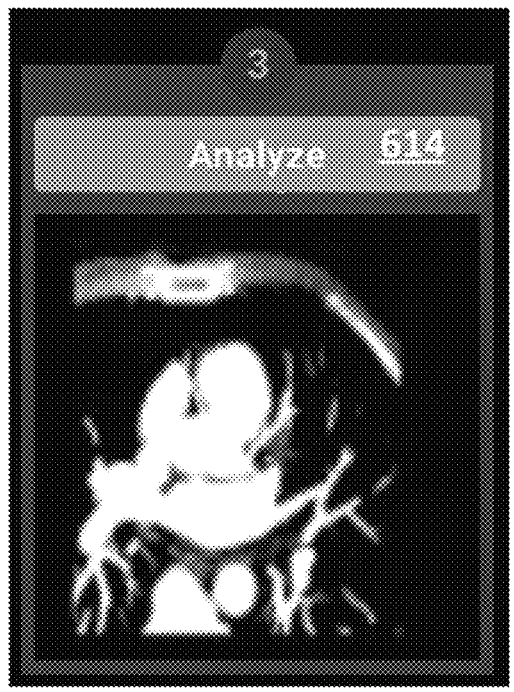
FIG. 6L illustrates an example of a selection panel that can be displayed on the user interface that may be uses to select a vessel segment for analysis.

FIG. 6K illustrates a view of the user interface 600 with an expanded menu to view all the series (of images) that are available for review and analysis. If the system has provided more than one of the same vessel segment from different series of images for analysis, the user interface is configured to receive a user input to selected the desired series for analysis. In an example, an input can be received indicating a series for review by a selection on one of the radio buttons 613 from the series of interest. The radio buttons will change from gray to purple when it is selected for review. In an embodiment, the software, by default, selects the two series of highest diagnostic quality for analysis however, all series are available for review. The user can use clinical judgment to determine if the series selected by the system is of diagnostic quality that is required for the analysis, and should select a different series for analysis if desired. The series selected by the system is intended to improve workflow by prioritizing diagnostic quality images. The system is not intended to replace the user's review of all series and selection of a diagnostic quality image within a study. Users can send any series illustrated in FIG. 6K for the system to suggest vessel segmentations by hovering the mouse over the series and select an "Analyze" button 614 as illustrated in FIG. 6L.

Figure 6M:
FIG. 6M illustrates an example of a panel that can be displayed on the user interface to add a new vessel on the image.
Figure 6N:
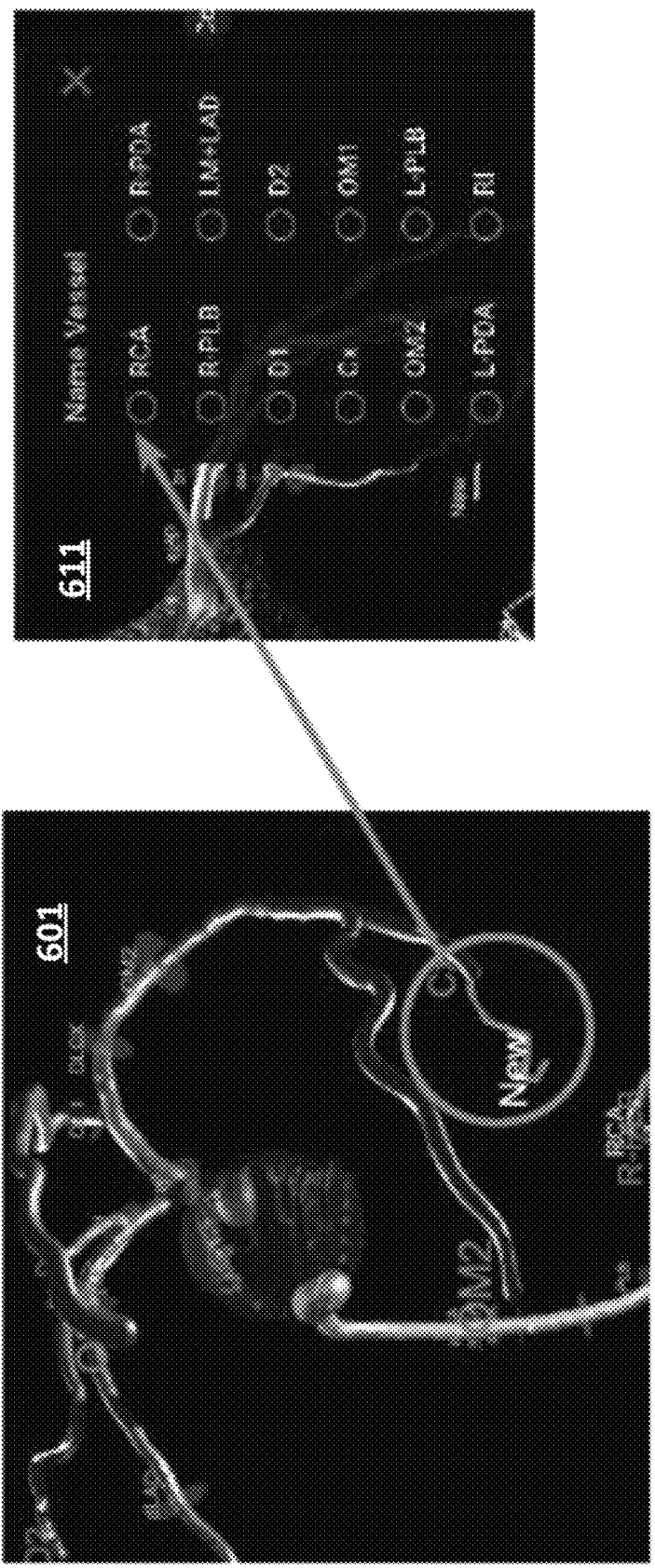
FIG. 6N illustrates examples of two panels that can be displayed on the user interface to name, or to rename, a vessel in the 3-D artery tree view.

FIG. 6M illustrates a panel that can be displayed on the user interface 600 to add a new vessel on the image, according to one embodiment. To add a new vessel on the image, the user interface 600 can receive a user input via a "+Add Vessel" button on the toolbar 612. The user interface will display a "create Mode" 615 button appear in the fourth panel 608 on the axial, coronal and sagittal view. Then the vessel can be added on the image by scrolling and clicking the left mouse button to create multiple dots (e.g., green dots). As the new vessel is being added, it will preview as a new vessel in the MPR, cross-section, and 3D artery tree view. The user interface is configured to receive a "Done" command to indicate adding the vessel has been completed. Then, to segment the vessels utilizing the system's semi-automatic segmentation tool, click "Analyze" on the tool bar and the user interface displays suggested segmentation for review and modification. The name of the vessel can be chosen by selecting "New" in the 3D artery tree view in the first panel 601, which activates the name panel 611 and the name of the vessel can be selected from panel 611, which then stores the new vessel and its name. In an embodiment, if the software is unable to identify the vessel which has been added by the user, it will return straight vessel lines connecting the user-added green dots, and the user can adjust the centerline. The pop-up menu 611 of the user interface allows new vessels to be identified and named according to a standard format quickly and consistently.

Figure 7A:
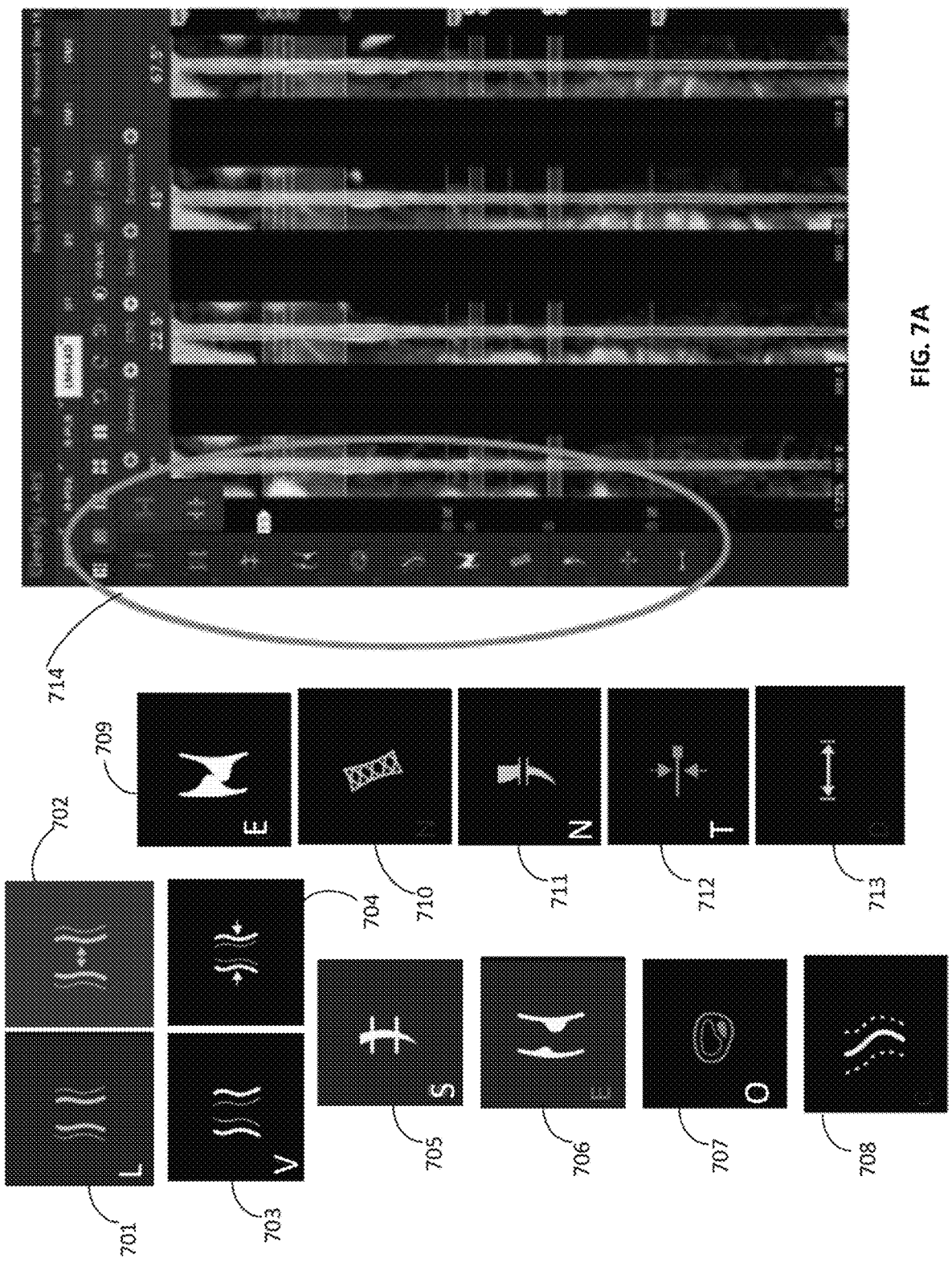
FIG. 7A illustrates an example of an editing toolbar which allows users to modify and improve the accuracy of the findings resulting from processing CT scans with a machine learning algorithm and then by an analyst.

FIG. 7A illustrates an example of an editing toolbar 714 that includes editing tools which allow users to modify and improve the accuracy of the findings resulting from processing CT scans with a machine learning algorithm, and then processing the CT scans, and information generated by the machine learning algorithm, by an analyst. In some embodiments, the user interface includes editing tools that can be used to modify and improve the accuracy of the findings. In some embodiments, the editing tools are located on the left-hand side of the user interface, as shown in FIG. 7A. The following is a listing and description of the available editing tools. Hovering over each button (icon) will display the name of each tool. These tools can be activated and deactivated by clicking on it. If the color of the tool is gray, it is deactivated. If the software has identified any of these characteristics in the vessel, the annotations will already be on the image when the tool is activated. The editing tools in the toolbar can include one or more of the following tools: Lumen Wall 701, Snap to Vessel Wall 702, Vessel Wall 703, Snap to Lumen Wall 704, Segments 705, Stenosis 706, Plaque Overlay 707, Centerline 708, Chronic Total Occlusion (CTO) 709, Stent 710, Exclude By 711, Tracker 712, and Distance 713. The user interface 600 is configured to activate each of these tools by receiving a user selection on the respective toll icon (shown in the table below and in FIG. 7A) and are configured to provide functionality described in the Editing Tools Description Table below:

| | | Editing Tools Description Table |
|---|---|---|
| L👤 | LUMEN WALL | USERS CAN ADJUST OR DRAW NEW LUMEN WALL CONTOURS TO IMPROVE THE ACCURACY OF THE LOCATION AND MEASUREMENTS OF THE LUMEN |
| 👤 | SNAP TO VESSEL WALL | USERS CAN DRAG A SHADED AREA AND RELEASE IT IN ORDER TO SNAP THE LUMEN WALL TO THE VESSEL WALL FOR HEALTHY VESSELS AREAS |
| V👤 | VESSEL WALL | USERS CAN ADJUST OR DRAW NEW VESSEL WALL CONTOURS TO REFINE THE EXTEROR OF THE VESSEL WALL |
| 👤 | SNAP TO LUMEN WALL | USERS CAN DRAG A SHADEID AREA AND RELEASE IT IN ORDER TO SNAP THE VESSEL WALL TO THE LUMEN WALL FOR HEALTHY VESSELS AREAS |
| S👤 | SEGMENTS | USERS CAN ADD SEGMENT MARKERS TO DEFINE THE BOUNDARIES OF EACH OF THE 18 CORONARY SEGMENTS. NEW OR ALREADY EXISTING MARKERS CAN BE DRAGGED UP AND DOWN TO ADJUST TO THE EXACT SEGMENT BOUNDARIES. |
| E👤 | STENOSIS | THIS TOOL CONSISTS OF 5 MARKERS THAT ALLOW USERS TO MARK REGIONS OF STENOSIS ON THE VESSEL. USERS CAN ADD NEW STENOSIS MARKERS AND NEW OR ALREADY EXISTING MARKERS CAN BE DRAGGED UP/DOWN. |
| P👤 | PLAQUE OVERLAY | THIS TOOL OVERLAYS THE SMPR AND THE CROSS SECTION VIEWS. WITH COLORIZED AREAS OF PLAQUE BASED UPON THE PLAQUES HOUNSFIELD ATTENUATION |
| C👤 | CENTERLINE | USERS CAN ADJUST THE CENTERLINE OF THE VESSEL IN THE CMPR OR CROSS-SECTION VIEW, ADJUSTMENTS WILL BE PROPAGATED TO THE SMPR VIEW. |
| O👤 | CTO | CHRONIC TOTAL OCCLUSION TOOL CONSISTS OF TWO MARKERS THAT IDENTIFY THE START AND END OF A SECTION OF AN ARTERY THAT ISTOTALLY OCCLUDED. MULTIPLE CTOS CAN BE ADDED AND DRAGGED TO THE AREA OF INTEREST. |
| N👤 | STENT | THE STENT TOOL ALLOW USERS TO IDENTIFY THE PRESENCE OF STENT(S) IN THE CORNARY ARTERIES. USERS CAN ADD STENT MARKERS AND DRAG EXISTING MARKERS UP OR DOWN TO THE EXACT STENT BOUNDARIES. |

| Editing Tools Description Table | | |
|---|---|---|
| X⊁ | EXCLUDE | BY USING THIS TOOL, SECTIONS OF A VESSEL CAN BE REMOVED FROM THE FINAL CALCULATIONS/ANALYSIS. REMOVAL OF THESE SECTIONS IS OFTEN DUE TO THE PRESENCE OF ARTIFACTS, USUALLY DUE TO MOTION OR MISALIGNMENT ISSUES, AMONG OTHERS. |
| T⊁ | TRACKER | THE TRACKER ORIENTS AND ALLOWS USERS TO CORRELATE THE MPR, CROSS-SECTION, AXIAL, CORONAL, SAGITTAL, AND 3D ARTERY TREE VIEWS. |
| D⊢—⊣ | DISTANCE | THE TOOL IS USED ON THE MPR, CROSS-SECTION, AXIAL, CORONAL, OR SAGITTAL VIEWS TO MEASURE DISTANCES BETWEEN POINTS. THE TOOL PROVIDES ACCURATE READINGS IN MILLIMETERS ALLOWING FOR QUICK REVIEW AND ESTIMATION ON AREAS OF INTEREST |

Figure 7B:
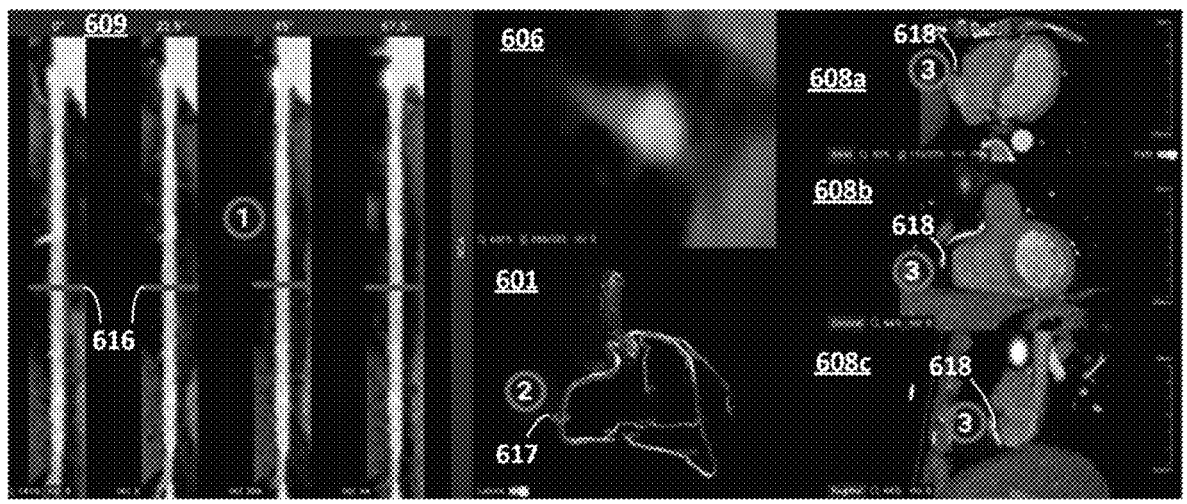
FIGS. 7B and 7C illustrate examples of certain functionality of the tracker tool.
Figure 7C:
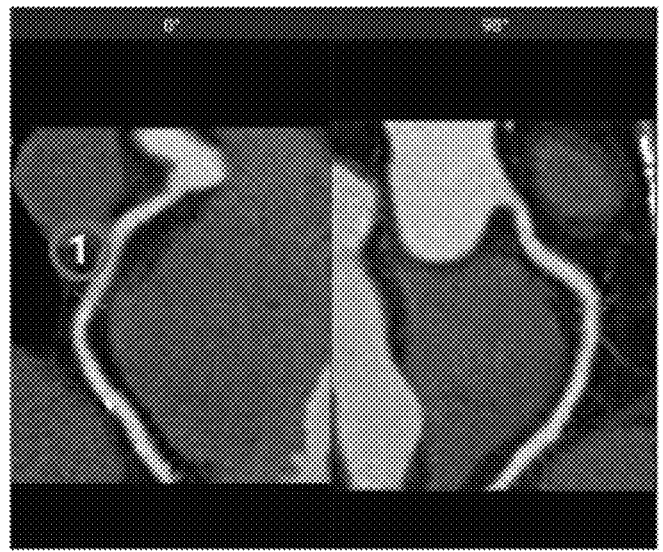

FIGS. 7B and 7C illustrate certain functionality of the Tracker tool. The Tracker tool 712 orients and allows user to correlate the views shown in the various panels of the user interface 600, for example, in the SMPR, CMPR, cross-section, axial, coronal, sagittal, and the 3D artery tree views. To activate, the tracker icon is selected on the editing toolbar. When the Tracker tool 712 is activated, the user interface generates and displays a line 616 (e.g., a red line) on the SMPR or CMPR view. The system generates on the user interface a corresponding (red) disc 617 which is displayed on the 3D artery tree in the first panel 601 in a corresponding location as the line 616. The system generates on the user interface a corresponding (red) dot which his displayed on the axial, sagittal and coronal views in the fourth panel 608 in a corresponding location as the line 616. The line 616, disc 617, and dots 618 are location indicators all referencing the same location in the different views, such that scrolling any of the trackers up and down will also result in the same movement of the location indicator in other views. Also, the user interface 600 displays the cross-sectional image in panel 606 corresponding to the location indicated by the location indicators.

Figure 7D:
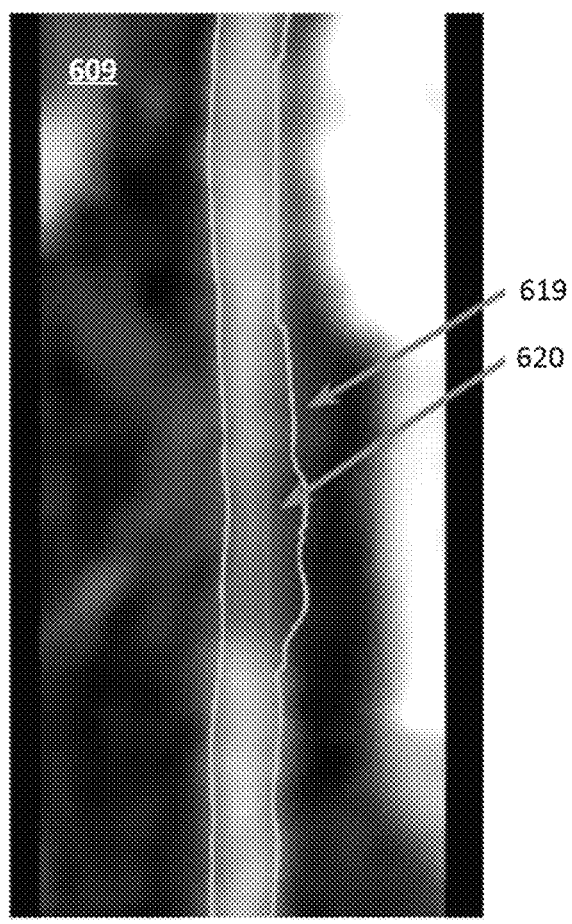
FIGS. 7D and 7E illustrate certain functionality of the vessel and lumen wall tools, which are used to modify the lumen and vessel wall contours.
Figure 7E:
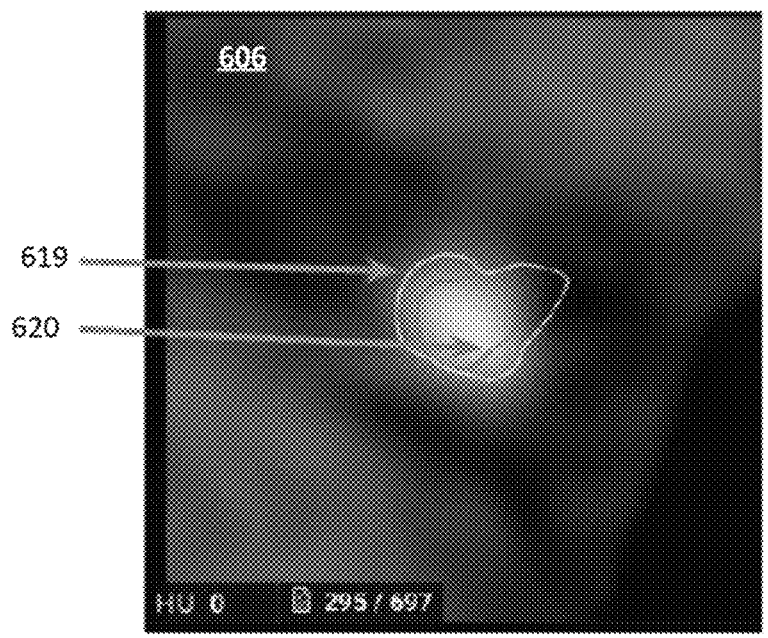

FIGS. 7D and 7E illustrate certain functionality of the vessel and lumen wall tools, which are used to modify the lumen and vessel wall contours. The Lumen Wall tool 701 and the Vessel Wall tool 703 are configured to modify the lumen and vessel walls (also referred to herein as contours, boundaries, or features) that were previously determined for a vessel (e.g., determined by processing the CT images using a machine learning process. These tool are used by the system for determining measurements that are output or displayed. By interacting with the contours generated by the system with these tools, a user can refine the accuracy of the location of the contours, and any measurements that are derived from those contours. These tools can be used in the SMPR and cross-section view. The tools are activated by selecting the vessel and lumen icons 701, 703 on the editing toolbar. The vessel wall 619 will be displayed in the MPR view and the cross-section view in a graphical "trace" overlay in a color (e.g., yellow). The lumen wall 629 will be displayed in a graphical "trace" overly in a different color (e.g., purple). In an embodiment, the user interface is configured to refine the contours through interactions with a user. For example, to refine the contours, the user can hover above the contour with a pointing device (e.g., mouse, stylus, finger) so it highlights the contour, click on the contour for the desired vessel or lumen wall and drag the displayed trace to a different location setting a new boundary. The user interface 600 is configured to automatically save any changes to these tracings. The system re-calculates any measurements derived from the changes contours in real time, or near real time. Also, the changes made in one panel on one view are displayed correspondingly in the other views/panels.

FIG. 7F illustrates the lumen wall button 701 and the snap to vessel wall button 702 (left) and the vessel wall button 703 and the snap to lumen wall button 704 (right) of the user interface 600 which can be used to activate the Lumen Wall/Snap to Vessel tools 701, 702, and the Vessel Wall/Snap to Lumen Wall 703, 704 tools, respectively. The user interface provides these tools to modify lumen and vessel wall contours that were previously determined. The Snap to Vessel/Lumen Wall tools are used to easily and quickly close the gap between lumen and vessel wall contours, that is, move a trace of the lumen contour and a trace of the vessel contour to be the same, or substantially the same, saving interactive editing time. The user interface 600 is configured to activate these tools when a user hovers of the tools with a pointing device, which reveals the snap to buttons. For example, hovering over the Lumen Wall button 701 reveals the Snap to Vessel button 702 to the right-side of the Lumen wall button, and hovering over the Vessel Wall button 703 reveals the Snap to Lumen Wall button 704 beside the Vessel Wall button 703. A button is selected to activate the desired tool. In reference to Figure G, a pointing device can be used to click at a first point 620 and drag along the intended part of the vessel to edit to a second point 621, and an area 622 will appear indicating where the tool will run. Once the end of the desired area 622 is drawn, releasing the selection will snap the lumen and vessel walls together.

Figure 7H:
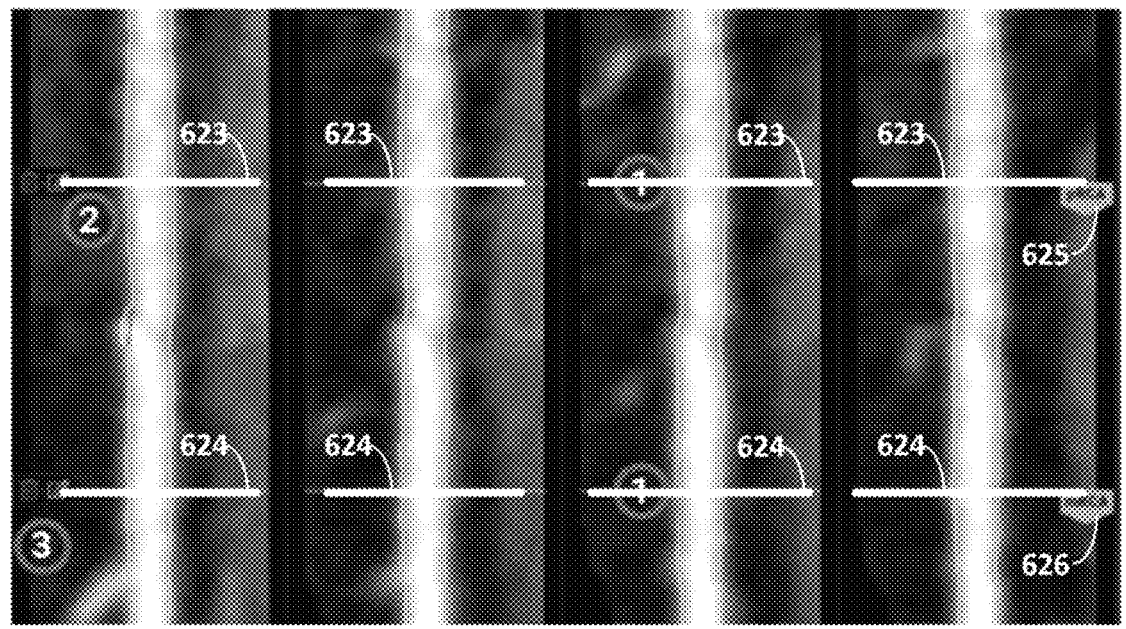
FIG. 7H illustrates an example of a panel of the user interface that can be displayed while using the segment tool which allows for marking the boundaries between individual coronary segments on the MPR.
Figure 7I:
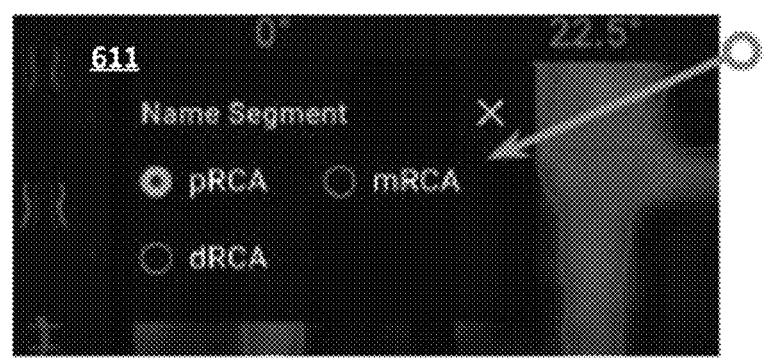
FIG. 7I illustrates an example of a panel of the user interface that allows a different name to be selected for a segment.

FIG. 7H illustrates an example of the second panel 602 that can be displayed while using the Segment tool 705 which allows for marking the boundaries between individual coronary segments on the MPR. The user interface 600 is configured such that when the Segment tool 705 is selected, lines (e.g., lines 623, 624) appear on the vessel image in the second panel 602 on the vessels in the SMPR view. The lines indicate segment boundaries that were determined by the system. The names are displayed in icons 625, 626 adjacent to the respective line 623, 624. To edit the name of the segment, click on an icon 625, 626 and label appropriately using the name panel 611, illustrated in FIG. 7I. A segment can also be deleted, for example, by selecting a trashcan icon. The lines 623, 624 can be moved up and down to define the segment of interest. If a segment is missing, the user can add a new segment using a segment addition button, and labeled using the labeling feature in the segment labeling pop-up menu 611.

Figure 7J:
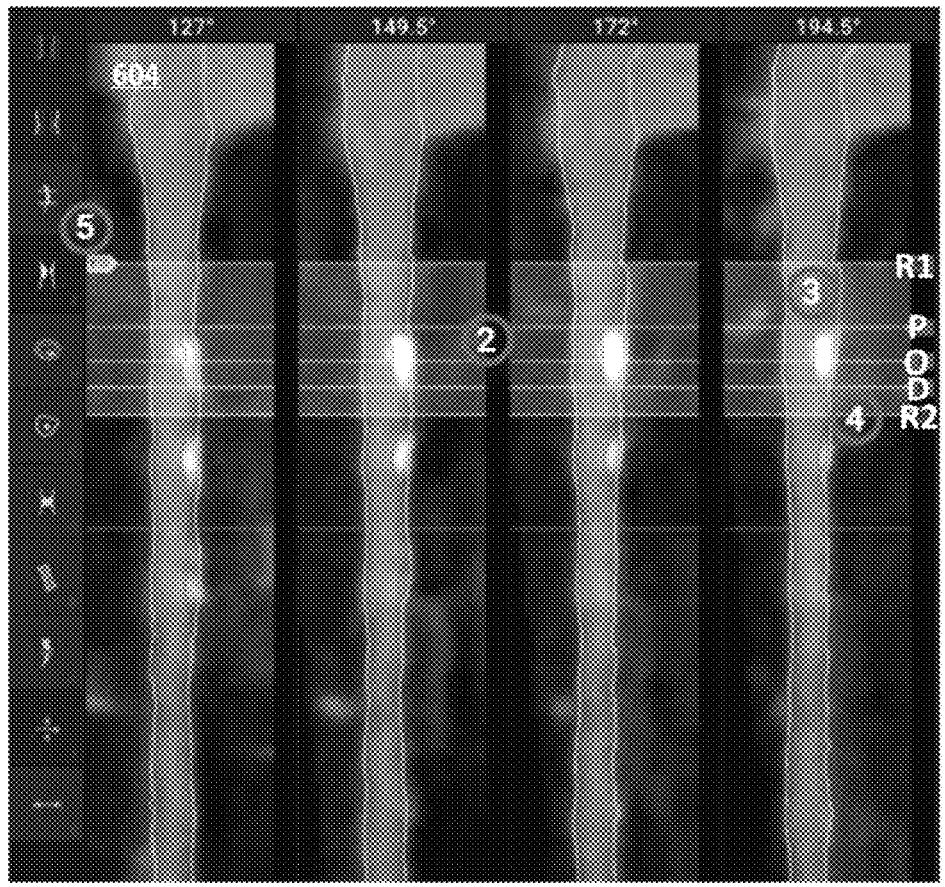
FIG. 7J illustrates an example of a panel of the user interface that can be displayed while using the stenosis tool, which allows a user to indicate markers to mark areas of stenosis on a vessel.
Figure 7K:
FIG. 7K illustrates an example of a stenosis button of the user interface which can be used to drop five evenly spaced stenosis markers.
Figure 7L:
FIG. 7L illustrates an example of a stenosis button of the user interface which can be used to drop stenosis markers based on the user edited lumen and vessel wall contours.
Figure 7M:
FIG. 7M illustrates the stenosis markers on segments on a curved multiplanar vessel (CMPR) view.

FIGS. 7J-7M illustrate an example of using the stenosis tool 706 on the user interface 600. For example, FIG. 7L illustrates a stenosis button which can be used to drop stenosis markers based on the user edited lumen and vessel wall contours. FIG. 7M illustrates the stenosis markers on segments on a curved multiplanar vessel (CMPR) view. The second panel 604 can be displayed while using the stenosis tool 706 which allows a user to indicate markers to mark areas of stenosis on a vessel. In an embodiment, the stenosis tool contains a set of five markers that are used to mark areas of stenosis on the vessel. These markers are defined as:

R1: Nearest proximal normal slice to the stenosis/lesion
P: Most proximal abnormal slice of the stenosis/lesion
O: Slice with the maximum occlusion
D: Most distal abnormal slice of the stenosis/lesion
R2: Nearest distal normal slice to the stenosis/lesion In an embodiment, there are two ways to add stenosis markers to the multiplanar view (straightened and curved). After selecting the stenosis tool 706, a stenosis can be added by activating the stenosis button shown in FIG. 7K or FIG. 7L: to drop 5 evenly spaced stenosis markers (i) click on the Stenosis "+" button (FIG. 7K); (ii) a series of 5 evenly spaced yellow lines will appear on the vessel; the user must edit these markers to the applicable position; (iii) move all 5 markers at the same time by clicking inside the highlighted area encompassed by the markers and dragging them up/down; (iv) move the individual markers by clicking on the individual yellow lines or tags and move up and down; (v) to delete a stenosis, click on the red trashcan icon. To drop stenosis markers based on the user-edited lumen and vessel wall contours, click on the stenosis "⟳" button (see FIG. 7L). A series of 5 yellow lines will appear on the vessel. The positions are based on the user-edited contours. The user interface 600 provides functionality for a user to edit the stenosis markers, e.g., can move the stenosis markers FIG. 7J illustrates the stenosis markers R1, P, O, D, and R2 placed on vessels in a SMPR view. FIG. 7M illustrates the markers R1, P, O, D, and R2 placed on vessels in a CMPR view.

Figure 7N:
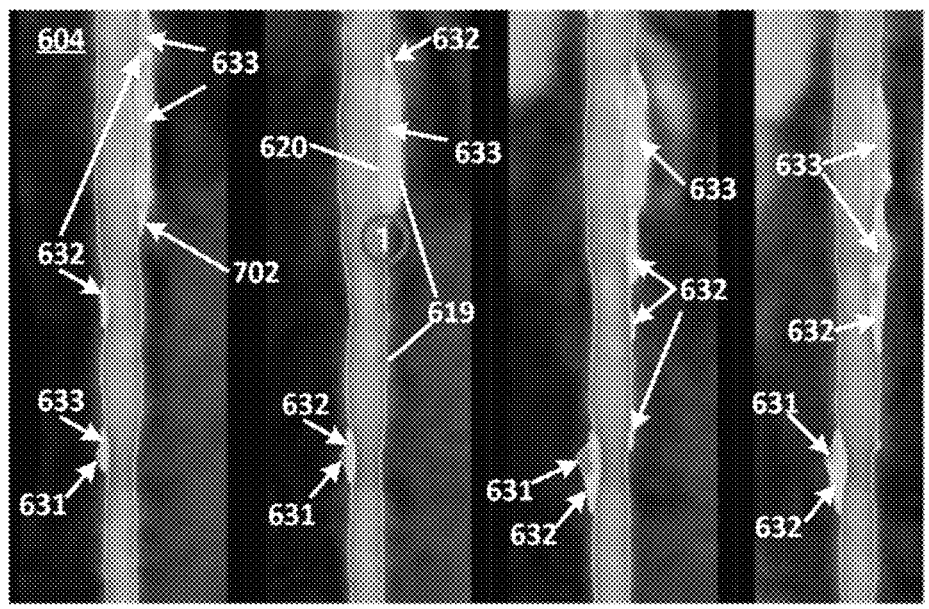
FIG. 7N illustrates an example of a panel of the user interface that can be displayed while using the plaque overlay tool.
Figure 7O:
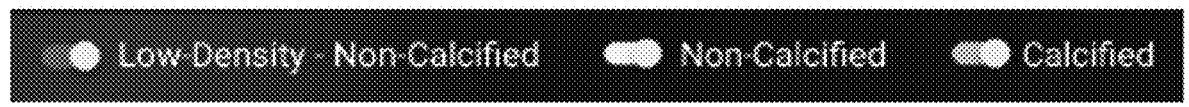
FIGS. 7O and 7P illustrate a button on the user interface that can be selected to the plaque thresholds.
Figure 7P:
Figure 7Q:
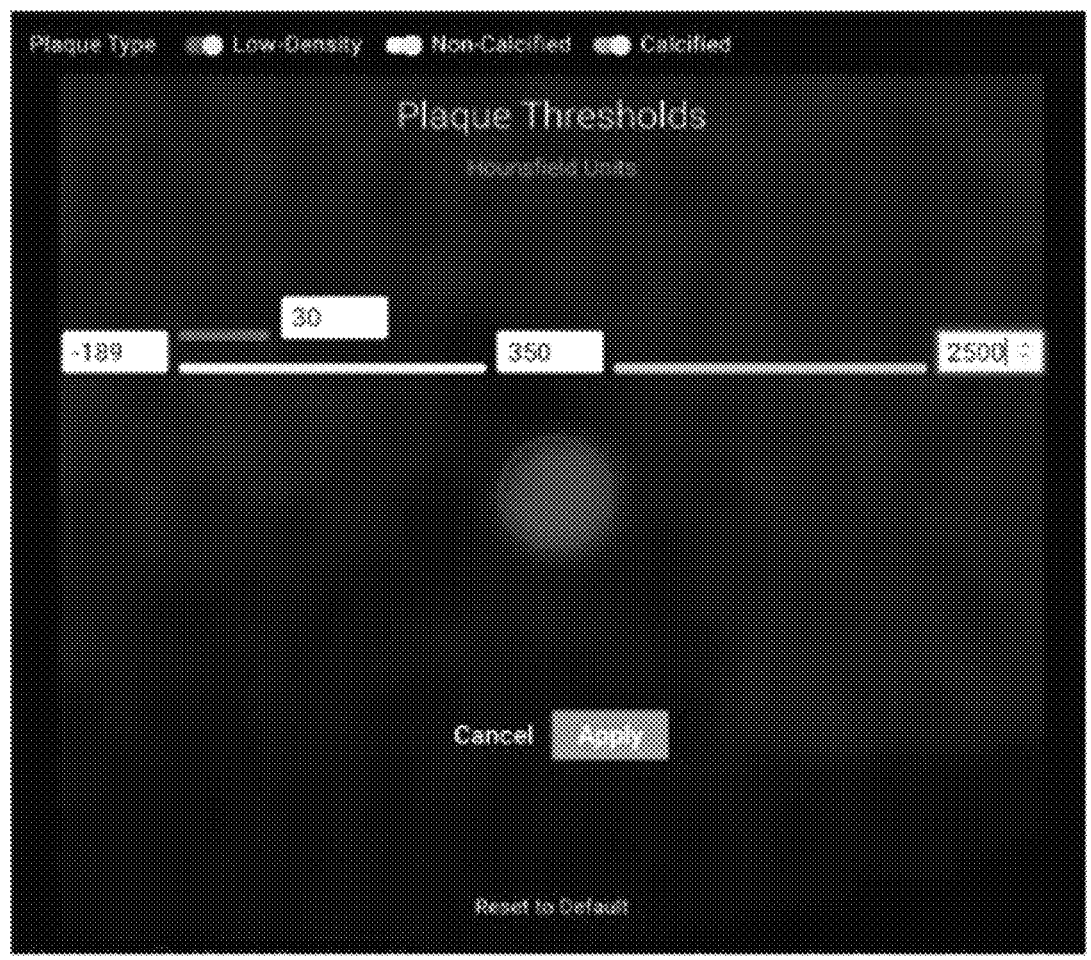
FIG. 7Q illustrates a panel of the user interface which can receive a user input to adjust plaque threshold levels for low-density plaque, non-calcified plaque, and calcified plaque.

FIG. 7N illustrates an example of a panel that can be displayed while using the Plaque Overlay tool 707 of the user interface. In an embodiment and in reference to FIG. 7N, "Plaque" is categorized as: low-density-non-calcified plaque (LD-NCP) 701, non-calcified plaque (NCP) 632, or calcified plaque (CP) 633. Selecting the Plaque Overlay tool 707 on the editing toolbar activates the tool. When activated, the Plaque Overlay tool 707 overlays different colors on vessels in the SMPR view in the second panel 604, and in the cross-section the SMPR, and cross-section view in the third panel 606 (see for example, FIG. 7R) with areas of plaque based on Hounsfield Unit (HU) density. In addition, a legend opens in the cross-section view corresponding to plaque type to plaque overlay color as illustrated in FIGS. 7O and 7Q. Users can select different HU ranges for the three different types of plaque by clicking on the "Edit Thresholds" button located in the top right corner of the cross-section view as illustrated in FIG. 7P. In one embodiment, plaque thresholds default to the values shown in the table below:

| Plaque Type | Hounsfield Unit (HU) |
|---|---|
| LD-NCP | −189 to 30 |
| NCP | −189 to 350 |
| CP | 350 to 2500 |

The default values can be revised, if desired, for example, using the Plaque Threshold interface shown in FIG. 7Q. Although default values are provided, users can select different plaque thresholds based on their clinical judgment. Users can use the cross-section view of the third panel 606, illustrated in FIG. 7R, to further examine areas of interest.

Figure 7S:
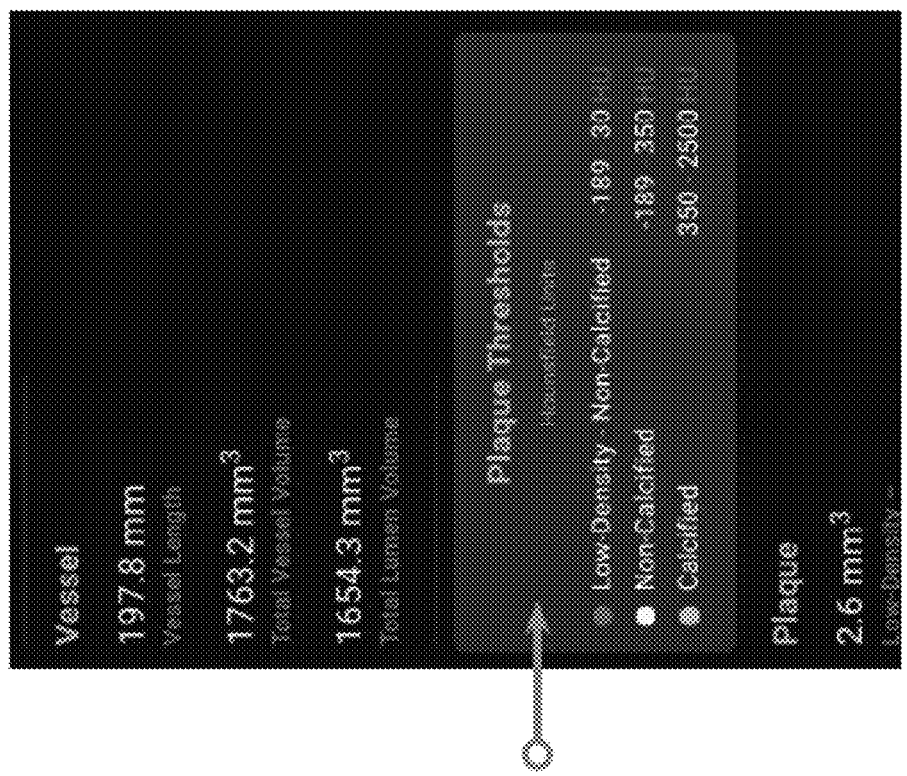
FIG. 7S illustrates a panel can be displayed showing plaque thresholds in a vessel statistics panel that includes information on the vessel being viewed.
Figure 7R:
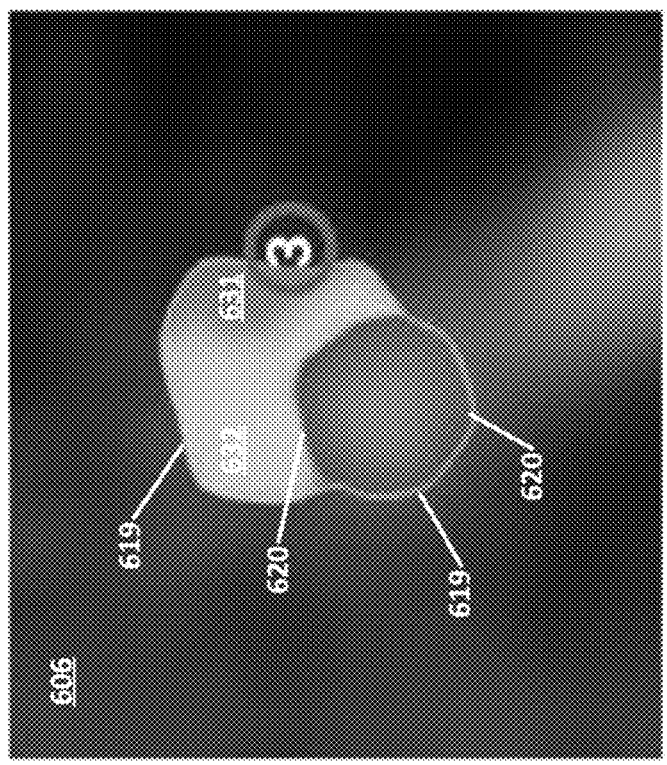
FIG. 7R illustrates a cross-sectional view of a vessel indicating areas of plaque which are displayed in the user interface in accordance with the plaque thresholds.
Figure 7U:
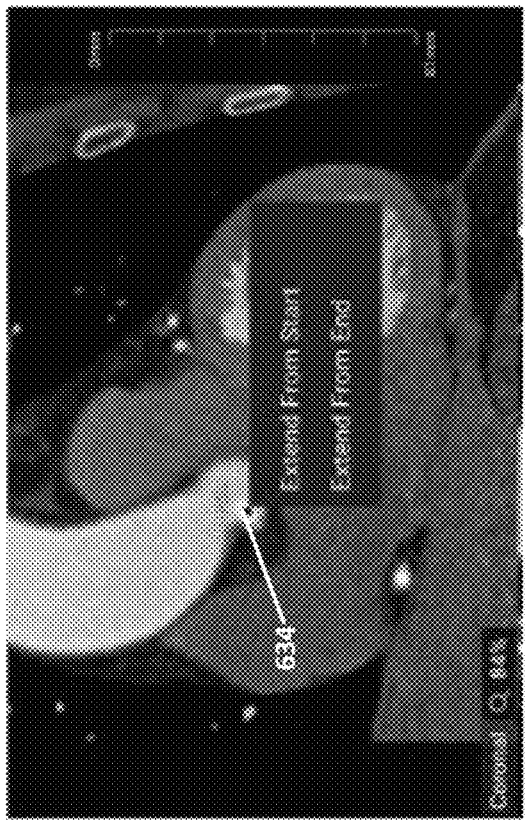
FIGS. 7U, 7V, 7W illustrate examples of panels showing other views of a vessel that can be displayed when using the centerline tool.
Figure 7W:
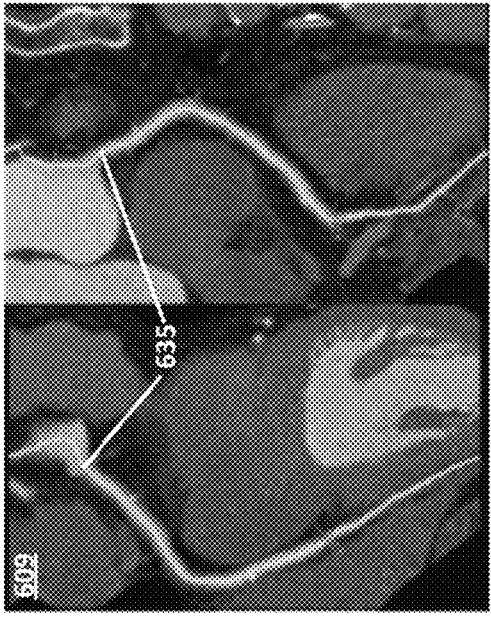
Figure 7T:
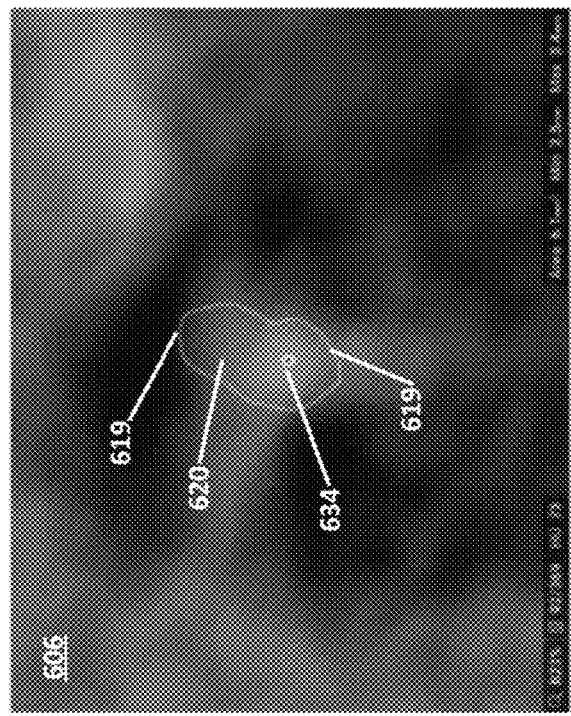
FIG. 7T illustrates a panel showing a cross-sectional view of a vessel that can be displayed while using the centerline tool, which allows adjustment of the center of the lumen.
Figure 7V:

Users can also view the selected plaque thresholds in a vessel statistics panel of the user interface 600, illustrated in FIG. 7S.

The Centerline tool 708 allows users to adjust the center of the lumen. Changing a center point (of the centerline) may change the lumen and vessel wall and the plaque quantification. if present. The Centerline tool 708 is activated by selecting it on the user interface 600. A line 635 (e.g., a yellow line) will appear on the CMPR view 609 and a point 634 (e.g., a yellow point) will appear in the cross-section view on the third panel 606. The centerline can be adjusted as necessary by clicking and dragging the line/point. Any changes made in the CMPR view will be reflected in the cross-section view, and vice-versa. The user interface 600 provides for several ways to extend the centerline of an existing vessel. For example, a user can extend the centerline by: (1) right-clicking on the dot 634 delineated vessel on the axial, coronal, or sagittal view (see FIG. 7U); (2) select "Extend from Start" or "Extend from End" (see FIG. 7U), the view will jump to the start or end of the vessel; (3) add (green) dots to extend the vessel (see FIG. 7V); (4) when finished, select the (blue) check mark button, to cancel the extension, select the (red) "x" button (see for example, FIG. 7V). The user interface then extends the vessel according to the changes made by the user. A user can then manually edit the lumen and vessel walls on the SMPR or cross-section views (see for example, FIG. 7W). If the user interface is unable to identify the vessel section which has been added by the user, it will return straight vessel lines connecting the user-added dots. The user can then adjust the centerline.

Figure 7X:
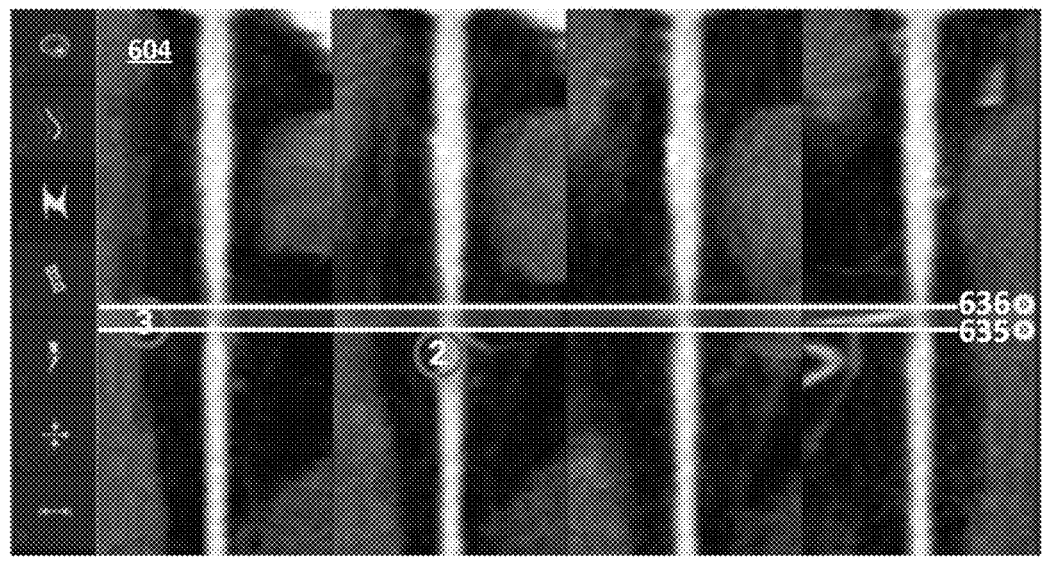
FIG. 7X illustrates an example of a panel that can be displayed while using the chronic total occlusion (CTO) tool, which is used to indicate a portion of artery with 100% stenosis and no detectable blood flow.

The user interface 600 also provides a Chronic Total Occlusion (CTO) tool 709 to identify portions of an artery with a chronic total occlusion (CTO), that is, a portion of artery with 100% stenosis and no detectable blood flow. Since it is likely to contain a large amount of thrombus, the plaque within the CTO is not included in overall plaque quantification. To activate, click on the CTO tool 709 on the editing toolbar 612. To add a CTO, click on the CTO "+" button on the user interface. Two lines (markers) 636, 637 will appear on the MPR view in the second panel 604, as illustrated in FIG. 7X indicating a portion of the vessel of the CTO. The markers 636, 637 can be moved to adjust the extent of the CTO. If more than one CTO is present, additional CTO's can be added by again activating the CTO "+" button on the user interface. A CTO can also be deleted, if necessary. The location of the CTO is stored. In addition, portions of the vessel that are within the designated CTO are not included in the overall plaque calculation, and the plaque quantification determination is re-calculated as necessary after CTO's are identified.

Figure 7Y:
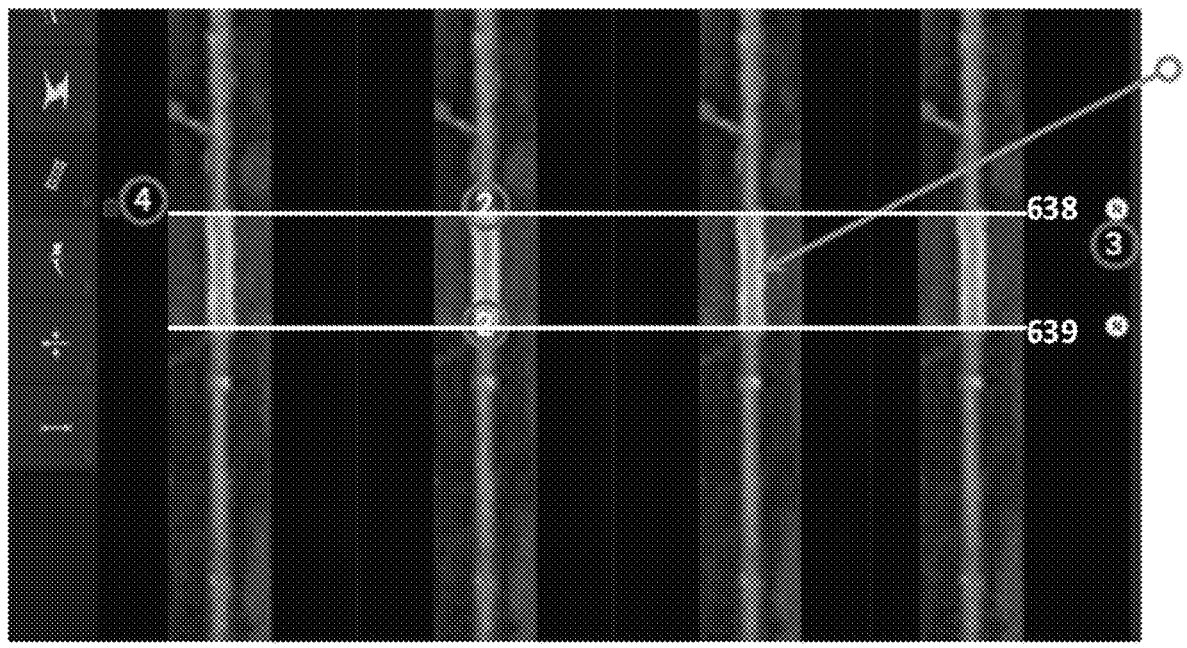
FIG. 7Y illustrates an example of a panel that can be displayed while using the stent tool, which allows a user to mark the extent of a stent in a vessel.

The user interface 600 also provides a Stent tool 710 to indicate where in vessel a stent exists. The Stent tool is activated by a user selection of the Stent tool 710 on the toolbar 612. To add a stent, click on the Stent "+" button provided on the user interface. Two lines 638, 639 (e.g., purple lines) will appear on of the MPR view as illustrated in FIG. 7Y, and the lines 638, 639 can be moved to indicate the extend of the stent by clicking on the individual lines 638, 639 and moving them up and down along the vessel to the ends of the stent. Overlapping with the stent (or the CTO/Exclusion/Stenosis) markers is not permitted by the user interface 600. A stent can also be deleted.

Figure 7Z:
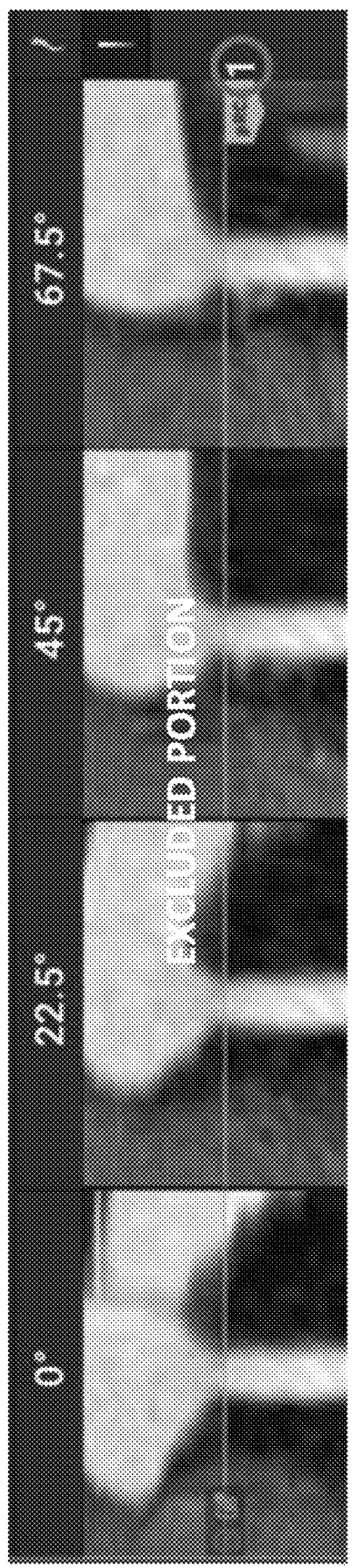
Figure 7A:
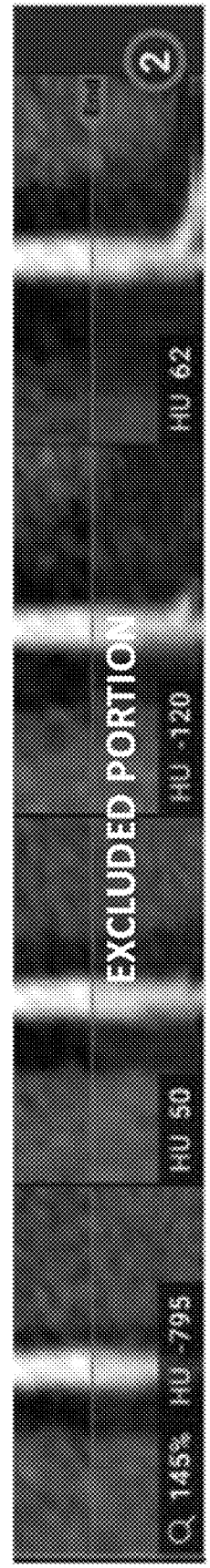
Figure 7A:
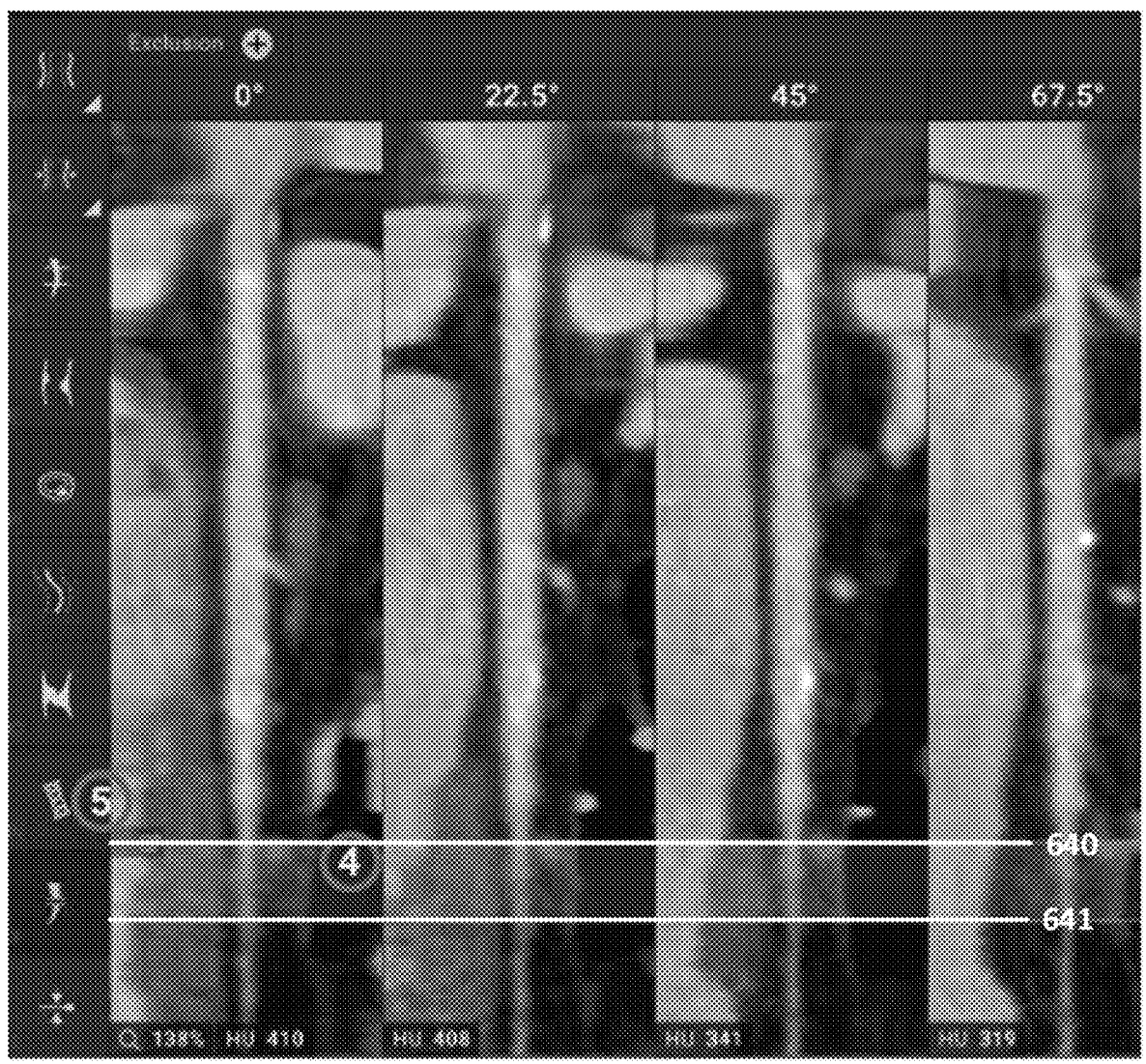
Figure 7A:
Figure 7A:
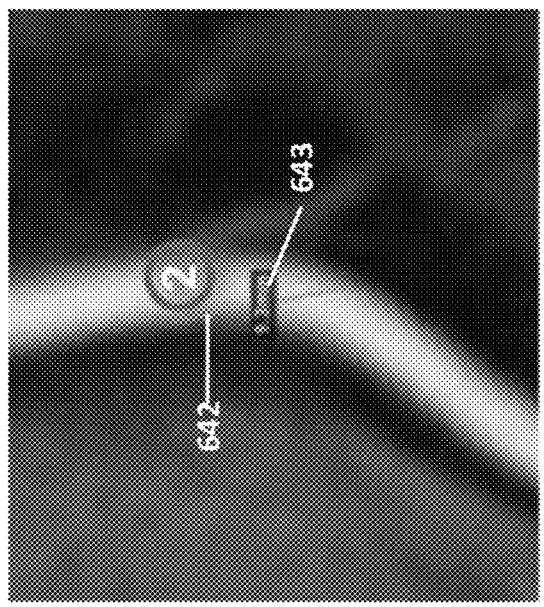
Figure 7A:
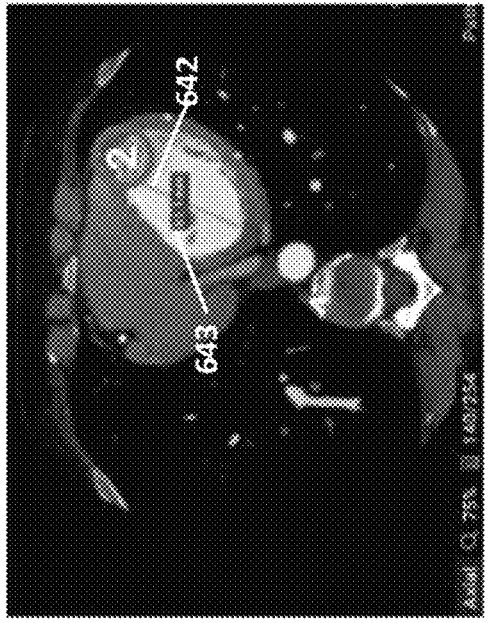
Figure 7A:
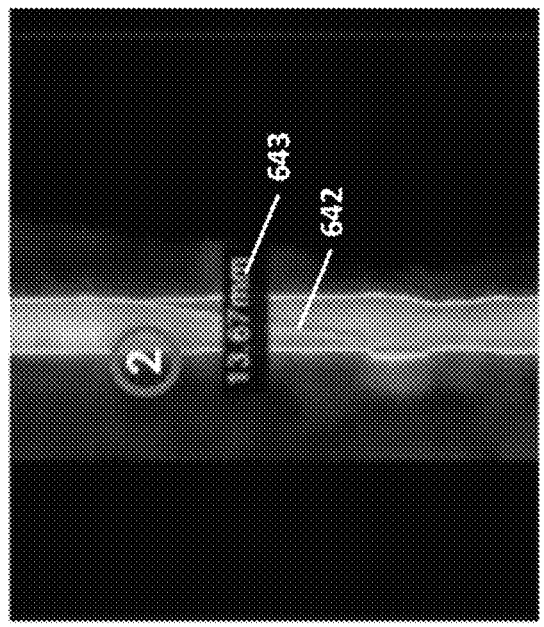
Figure 7A:
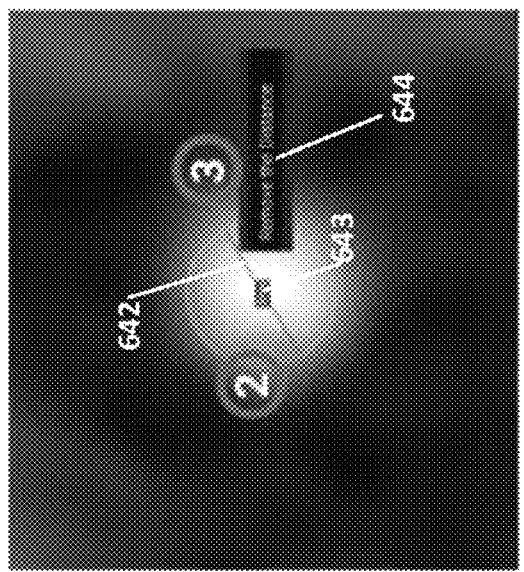
Figure 7A:
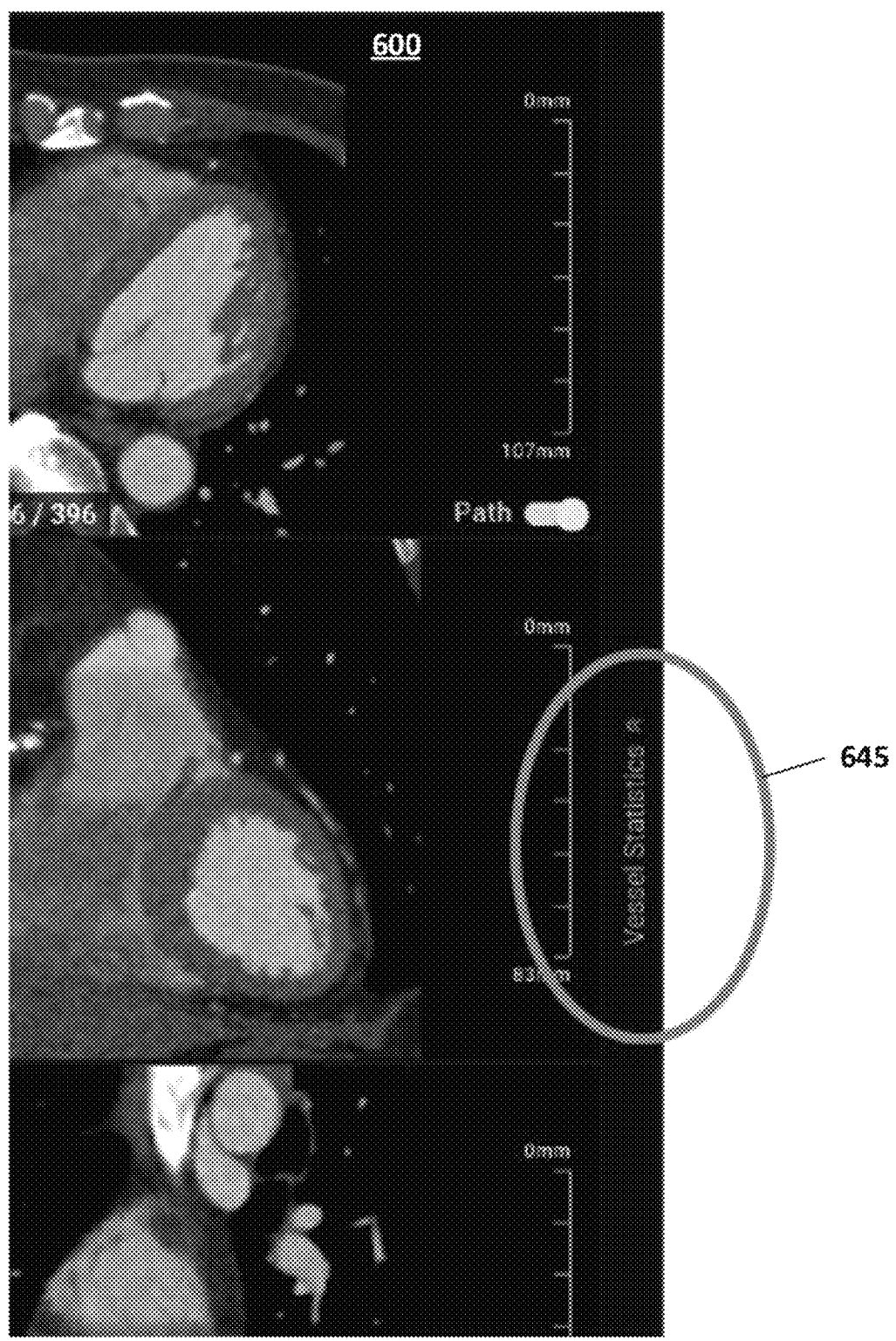
Figure 7A:
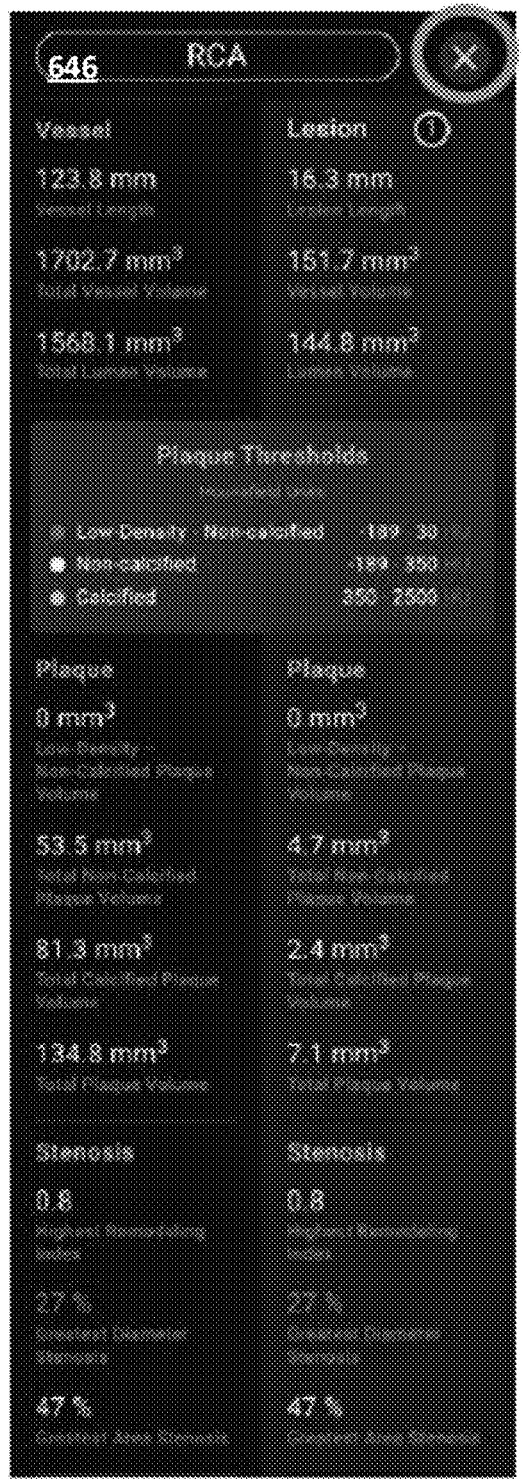
Figure 7A:
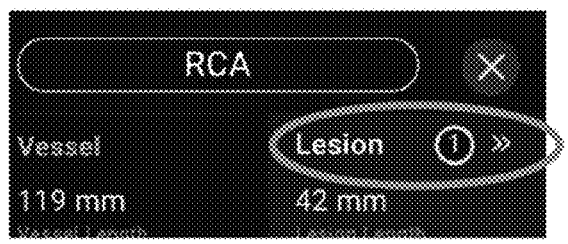
Figure 7A:

The user interface 600 also provides an Exclude tool 711 that is configured to indicate a portion of a vessel to exclude from the analysis due to blurring caused by motion, contrast, misalignment, or other reasons. Excluding poor quality images will improve the overall quality of the results of the analysis for the non-excluded portions of the vessels. To exclude the top or bottom portion of a vessel, activate the segment tool 705 and the exclude tool 711 in the editing toolbar 612. FIG. 7Z illustrates the use of the exclusion tool to exclude a portion from the top of the vessel. FIG. 7AA illustrates the use of the exclusion tool to exclude a bottom portion of the vessel. A first segment marker acts as the exclusion marker for the top portion of the vessel. The area enclosed by exclusion markers is excluded from all vessel statistic calculations. An area can be excluded by dragging the top segment marker to the bottom of the desired area of exclusion. The excluded area will be highlighted. Or the "End" marker can be dragged to the top of the desired area of exclusion. The excluded area will be highlighted, and a user can enter the reason for an exclusion in the user interface (see FIG. 7AC). To add a new exclusion to the center of the vessel, activate the exclude tool 711 on the editing toolbar 612. Click on the Exclusion "+" button. A pop-up window on the user interface will appear for the reason of the exclusion (FIG. 7AC), and the reason can be entered and it is stored in reference to the indicated excluded area. Two markers 640, 641 will appear on the MPR as shown in FIG. 7AB. Move both markers at the same time by clicking inside the highlighted area. The user can move the individual markers by clicking and dragging the lines 640, 641. The user interface 600 tracks the locations of the of the exclusion marker lines 640, 641 (and previously defined features) and prohibits overlap of the area defined by the exclusion lines 640, 641 with any previously indicated portions of the vessel having a CTO, stent or stenosis. The user interface 600 also is configured to delete a designated exclusion.

Now referring to FIGS. 7AD-7AG, the user interface 600 also provides a Distance tool 713, which is used to measure the distance between two points on an image. It is a drag and drop ruler that captures precise measurements. The Distance tool works in the MPR, cross-section, axial, coronal, and sagittal views. To activate, click on the distance tool 713 on the editing toolbar 612. Then, click and drag between the desired two points. A line 642 and measurement 643 will appear on the image displayed on the user interface 600. Delete the measurement by right-clicking on the distance line 642 or measurement 643 and selecting "Remove the Distance" button 644 on the user interface 600 (see FIG. 7AF). FIG. 7AD illustrates an example of measuring a distance of a straightened multiplanar vessel (SMPR). FIG. 7AE illustrates an example of measuring the distance 642 of a curved multiplanar vessel (CMPR). FIG. 7AF illustrates an example of measuring a distance 642 of a cross-section of the vessel. FIG. 7AG illustrates an example of measuring the distance 642 on an Axial View of a patient's anatomy.

An example of a vessel statistics panel of the user interface 600 is described in reference to FIGS. 7AH-7AK. FIG. 7AH illustrates a "vessel statistics" portion 645 of the user interface 600 (e.g., a button) of a panel which can be selected to display the vessel statistics panel 646 (or "tab"), illustrated in FIG. 7AI. FIG. 7AJ illustrates certain functionality on the vessel statistics tab that allows a user to click through the details of multiple lesions. FIG. 7AK further illustrates the vessel panel which the user can use to toggle between vessels. For example, Users can hide the panel by clicking on the "X" on the top right hand side of the panel, illustrated in FIG. 7AI. Statistics are shown at the per-vessel and per-lesion (if present) level, as indicated in FIG. 7AJ.

If more than one lesion is marked by the user, the user can click through each lesion's details. To view the statistics for each vessel, the users can toggle between vessels on the vessel panel illustrated in FIG. 7AK.

General information pertaining to the length and volume are presented for the vessel and lesion (if present) in the vessel statistics panel 646, along with the plaque and stenosis information on a per-vessel and per-lesion level. Users may exclude artifacts from the image they do not want to be considered in the calculations by using the exclusion tool. The following tables indicate certain statistics that are available for vessels, lesions, plaque, and stenosis.

| Vessel | |
| --- | --- |
| Term | Definition |
| Vessel Length (mm) | Length of a linear coronary vessel |
| Total Vessel Volume (mm3) | The volume of consecutive slices of vessel contours. |
| Total Lumen Volume (mm3) | The volume of consecutive slices of lumen contours |

| Lesion | |
| --- | --- |
| Term | Definition |
| Lesion Length (mm) | Linear distance from the start of a coronary lesion to the end of a coronary lesion. |
| Vessel Volume (mm3) | The volume of consecutive slices of vessel contours. |
| Lumen Volume (mm3) | The volume of consecutive slices of lumen contours. |

| Plaque | |
| --- | --- |
| Term | Definition |
| Total Calcified Plaque Volume (mm3) | Calcified plaque is defined as plaque in between the lumen and vessel wall with an attenuation of greater than 350 HU, or as defined by the user, and is reported in absolute measures by plaque volume. Calcified plaques are identified in each coronary artery ≥1.5 mm in mean vessel diameter. |
| Total Non-Calcified Plaque Volume (mm3) | Non-calcified plaque is defined as plaque in between the lumen and vessel wall with an attenuation of less than or equal to 350, or as defined by the user, HU and is reported in absolute measures by plaque volume. The total non-calcified plaque volume is the sum total of all non-calcified plaques identified in each coronary artery ≥1.5 mm in mean vessel diameter. Non-calcified plaque data reported is further broken down into low-density plaque, based on HU density thresholds. |
| Low-Density Non-Calcified Plaque Volume (mm3) | Low-Density-Non-Calcified Plaque is defined as plaque in between the lumen and vessel wall with an attenuation of less than or equal to 30 HU or as defined by the user and is reported in absolute measures by plaque volume. |
| Total Plaque Volume (mm3) | Plaque volume is defined as plaque in between the lumen and vessel wall reported in absolute measures. The total plaque volume is the sum total of all plaque identified in each coronary artery ≥1.5 mm in mean vessel diameter or wherever the user places the "End" marker. |

| Stenosis | |
| --- | --- |
| Term | Definition |
| Remodeling Index | Remodeling Index is defined as the mean vessel diameter at a denoted slice divided by the mean vessel diameter at a reference slice. |
| Greatest Diameter Stenosis (%) | The deviation of the mean lumen diameter at the denoted slice from a reference slice, expressed in percentage. |
| Greatest Area Stenosis (%) | The deviation of the lumen area at the denoted slice to a reference area, expressed in percentage |

A quantitative variable that is used in the system and displayed on various portions of the user interface 600, for example, in reference to low-density non-calcified plaque, non-calcified plaque, and calcified plaque, is the Hounsfield unit (HU). As is known, a Hounsfield Unit scale is a quantitative scale for describing radiation, and is frequently used in reference to CT scans as a way to characterize radiation attenuation and thus making it easier to define what a given finding may represent. A Hounsfield Unit measurement is presented in reference to a quantitative scale. Examples of Hounsfield Unit measurements of certain materials are shown in the following table:

| Material | HU |
| --- | --- |
| Air | −1000 |
| Fat | −50 |
| Distilled Water | 0 |
| Soft Tissue | +40 |
| Blood | +40 to 80 |
| Calcified Plaques | 350-1000+ |
| Bone | +1000 |

Figure 8B:
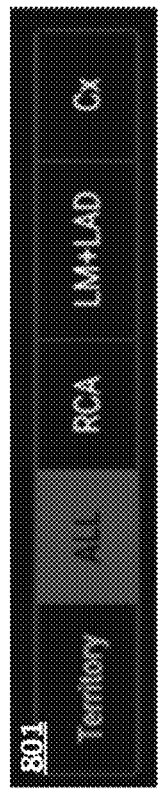
FIG. 8B illustrates an example of a portion of a panel displayed on the user interface that allows selection of a territory or combination of territories (e.g., left main artery (LM), left anterior descending artery (LAD), left circumflex artery (LCx), right coronary artery (RCA), according to various embodiments.
Figure 8A:
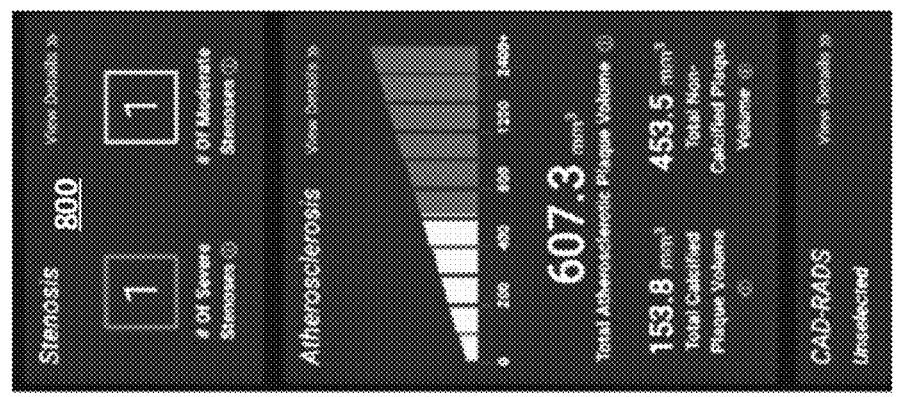
FIG. 8A illustrates an example of a panel of the user interface that shows stenosis, atherosclerosis, and CAD-RADS results of the analysis.
Figure 8C:
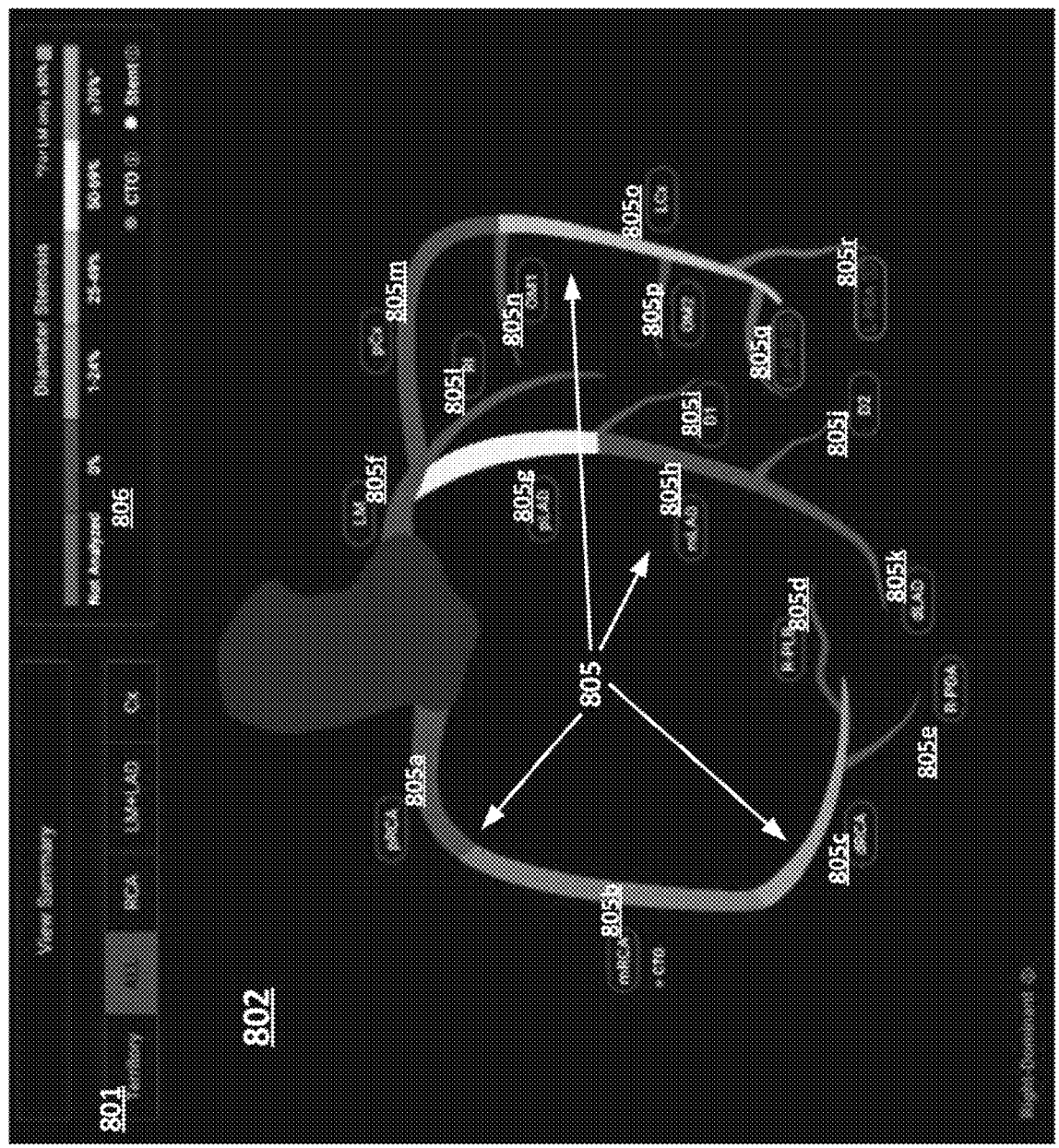
FIG. 8C illustrates an example of a panel that can be displayed on the user interface showing a cartoon representation of a coronary artery tree ("cartoon artery tree").

In an embodiment, information that the system determines relating to stenosis, atherosclerosis, and CAD-RADS details are included on panel 800 of the user interface 600, as illustrated in FIG. 8A. By default, the CAD-RADS score may be unselected and requires the user to manually select the score on the CAD-RADS page. Hovering over the "#" icons causes the user interface 600 to provide more information about the selected output. To view more details about the stenosis, atherosclerosis, and CAD-RADS outputs, click the "View Details" button in the upper right of panel 800—this will navigate to the applicable details page. In an embodiment, in the center of a centerpiece page view of the user interface 600 there is a non-patient specific rendition of a coronary artery tree 805 (a "cartoon artery tree" 805) broken into segments 805a-855r based on the SCCT coronary segmentation, as illustrated in panel 802 in FIG. 8C. All analyzed vessels are displayed in color according to the legend 806 based on the highest diameter stenosis within that vessel. Greyed out segments/vessels in the cartoon artery tree 805, for example, segment 805q and 805r, were not anatomically available or not analyzed in the system (all segments may not exist in all patients). Per-territory and per-segment information can be viewed by clicking the territory above the tree (RCA, LM+LAD, etc.) using, for example, the user interface 600 selection buttons in panel 801, as illustrated in FIGS. 8B and 8C. Or my selecting a segment 805a-805r within the cartoon coronary tree 805.

Figure 8D:
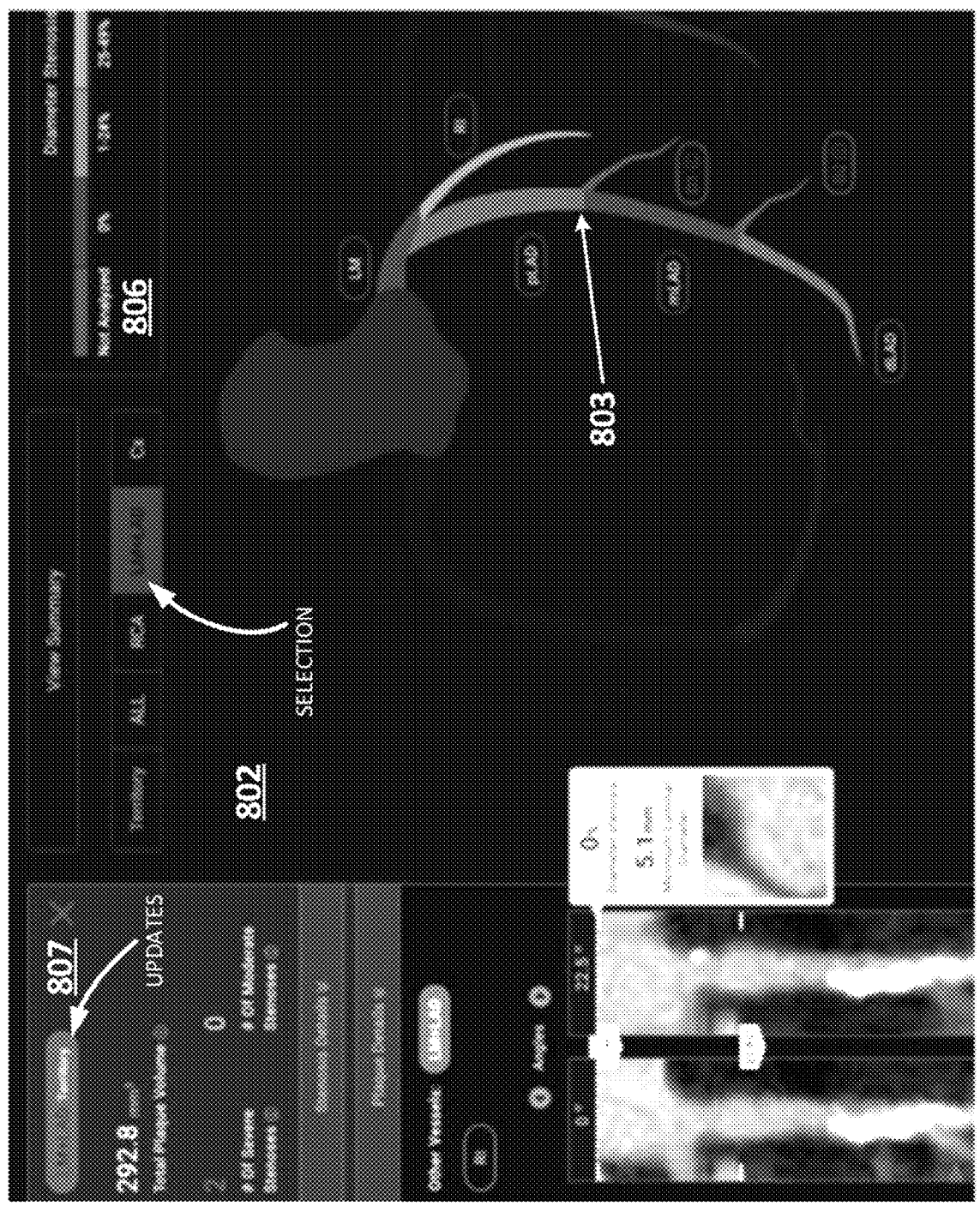
FIG. 8D illustrates an example of a panel that can be displayed on the user interface illustrating territory selection using the cartoon artery tree.
Figure 8F:
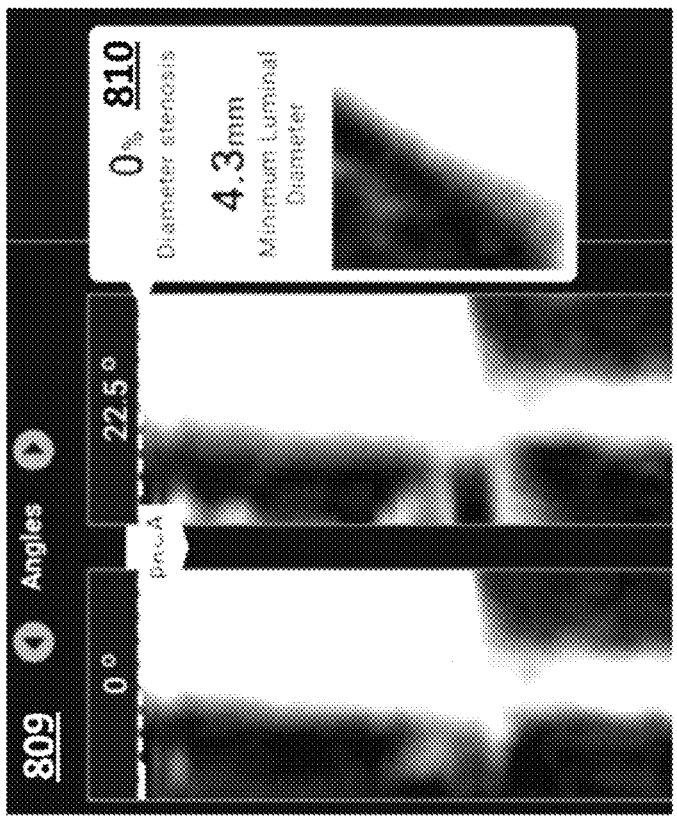
FIG. 8F illustrates an example panel that can be displayed on the user interface showing a SMPR view of a selected vessel, and corresponding statistics of the selected vessel.
Figure 8I:
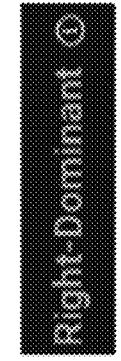
FIG. 8I illustrates an example of a portion of a panel that can be displayed in the user interface indicating left or right dominance of the patient.
Figure 8H:
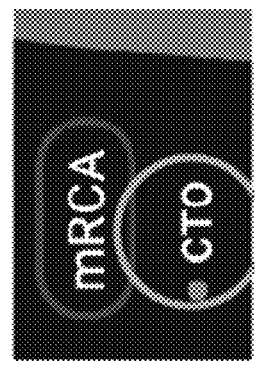
FIG. 8H illustrates an example of a portion of a panel that can be displayed in the user interface indicating CTO presence at the segment level.
Figure 8E:
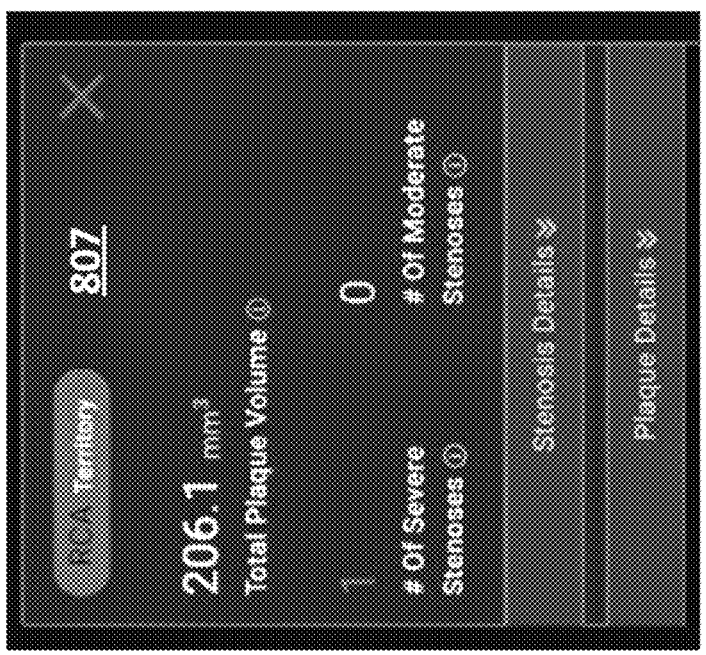
FIG. 8E illustrates an example panel that can be displayed on the user interface showing per-territory summaries.
Figure 8G:
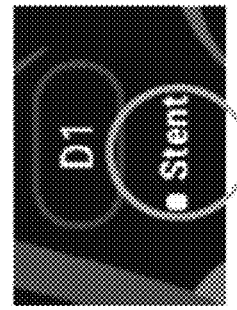
FIG. 8G illustrates an example of a portion of a panel that can be displayed in the user interface indicating the presence of a stent, which is displayed at the segment level.
Figure 8J:
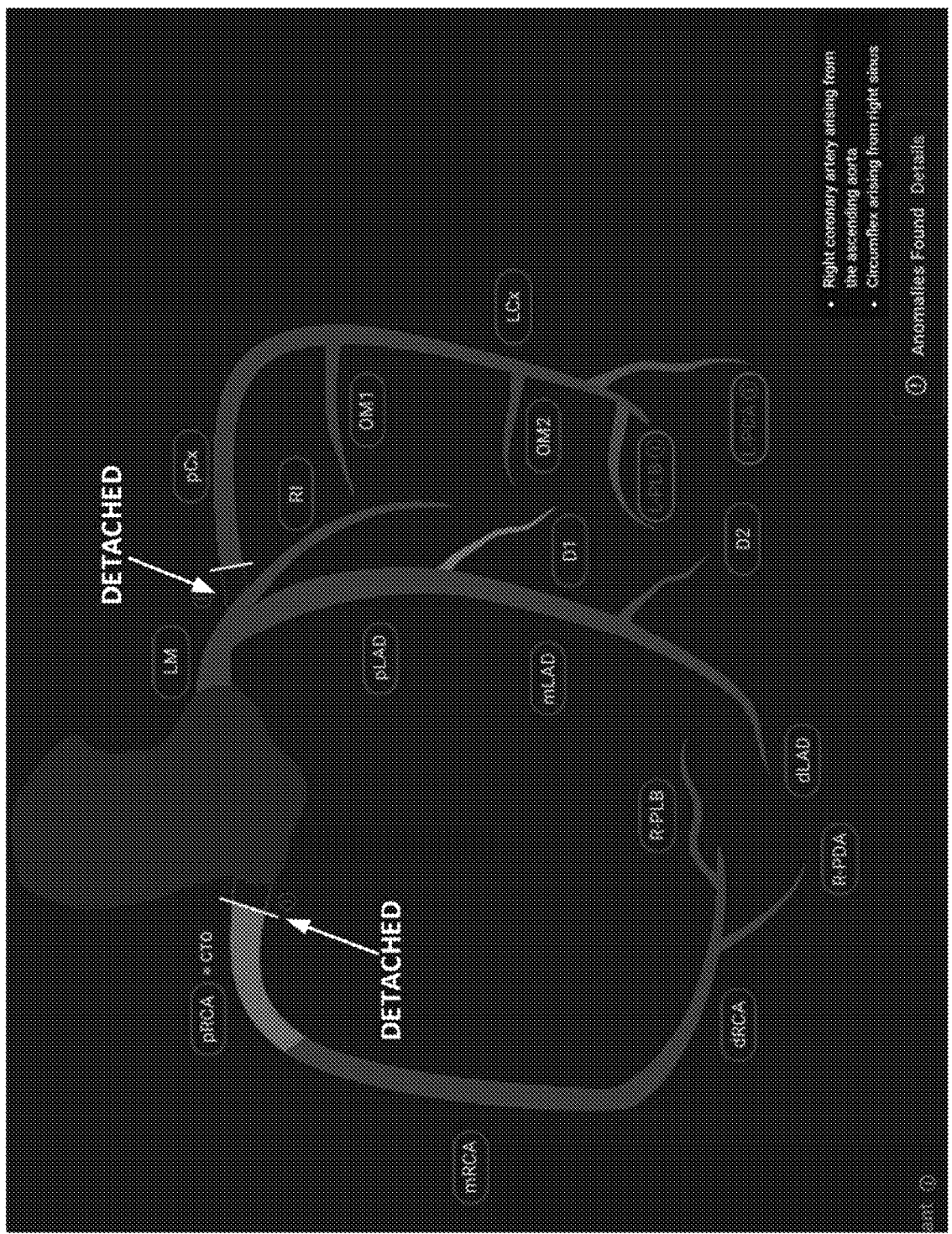
FIG. 8J illustrates an example of a panel that can be displayed on the user interface showing cartoon artery tree with indications of anomalies that were found.
Figure 8K:
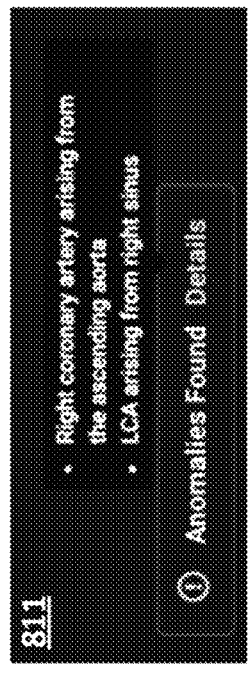
FIG. 8K illustrates an example of a portion of a panel that can be displayed on the panel of FIG. 8J that can be selected to show details of an anomaly.

Stenosis and atherosclerosis data displayed on the user interface in panel 807 will update accordingly as various segments are selected, as illustrated in FIG. 8D. FIG. 8E illustrates an example of a portion of the per-territory summary panel 807 of the user interface. FIG. 8F also illustrates an example of portion of panel 807 showing the SMPR of a selected vessel and its associated statistics along the vessel at indicated locations (e.g., at locations indicated by a pointing device as it is moved along the SMPR visualization). That is, the user interface 600 is configured to provide plaque details and stenosis details in an SMPR visualization in panel 809 and a pop-up panel 810 that displays information as the user interface receives location information long the displayed vessel from the user, e.g., via a pointing device. The presence of a chronic total occlusion (CT)) and/or a stent are indicated at the vessel segment level. For example, FIG. 8G illustrates the presence of a stent in the D1 segment. FIG. 8H indicates the presence of a CTO in the mRCA segment. Coronary dominance and any anomalies can be displayed below the coronary artery tree as illustrated in FIG. 8I. The anomalies that were selected in the analysis can be displayed, for example, by "hovering" with a pointing device over the "details" button. If plaque thresholds were changed in the analysis, an alert can be displayed on the user interface, or on a generated report, that indicates the plaque thresholds were changed. When anomalies are present, the coronary vessel segment 805 associated with each anomaly will appear detached from the aorta as illustrated in FIG. 8J. In an embodiment, a textual summary of the analysis can also be displayed below the coronary tree, for example, as illustrated in the panel 811 in FIG. 8K.

Figure 9A:
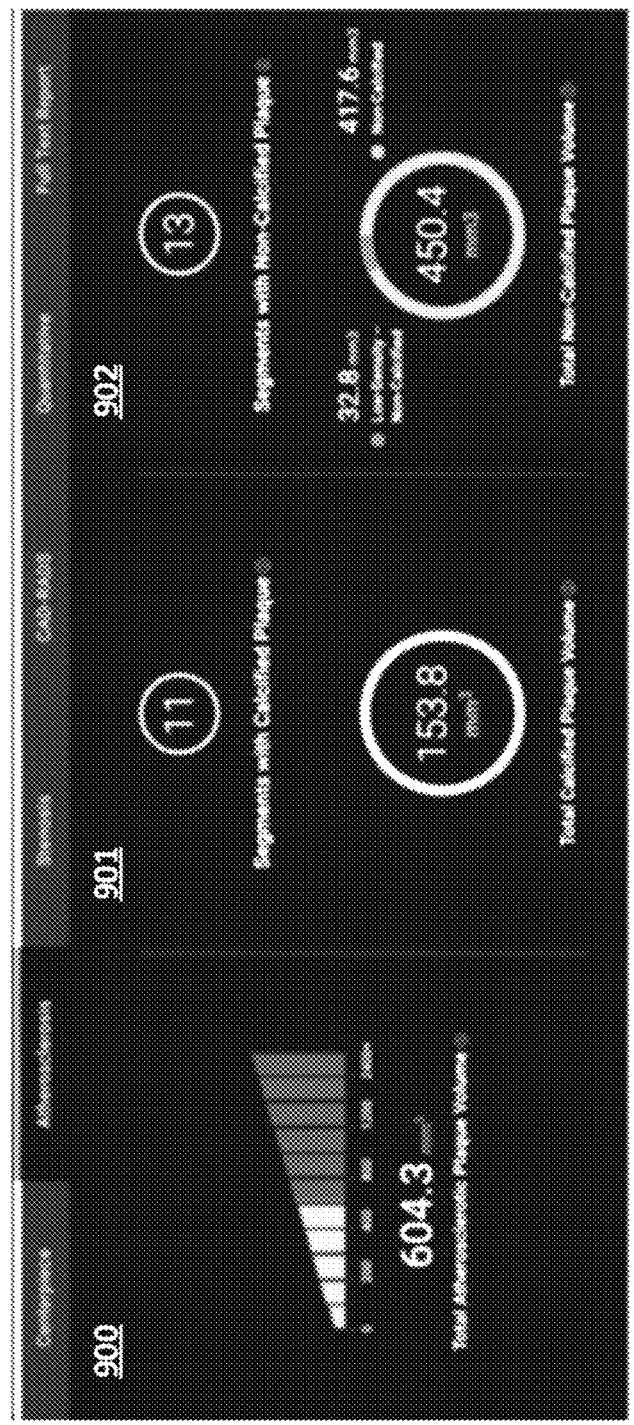
FIG. 9A illustrates an example of an atherosclerosis panel that can be displayed on the user interface which displays a summary of atherosclerosis information based on the analysis.
Figure 9B:
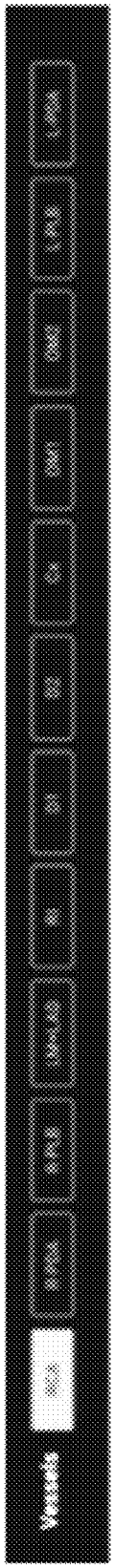
FIG. 9B illustrates an example of a vessel selection panel which can be used to select a vessel such that the summary of atherosclerosis information is displayed on a per segment basis.

FIG. 9A illustrates an atherosclerosis panel 900 that can be displayed on the user interface, which displays a summary of atherosclerosis information based on the analysis. FIG. 9B illustrates the vessel selection panel which can be used to select a vessel such that the summary of atherosclerosis information is displayed on a per segment basis. The top section of the atherosclerosis panel 900 contains per-patient data, as illustrated in FIG. 9A. When a user "hovers' over the "Segments with Calcified Plaque" on panel 901, or hovers over the "Segments with Non-Calcified Plaque" in panel 902, the segment names with the applicable plaque are displayed. Below the patient specific data, users may access per-vessel and per-segment atherosclerosis data by clicking on one of the vessel buttons, illustrated in FIG. 9B.

Figure 9C:
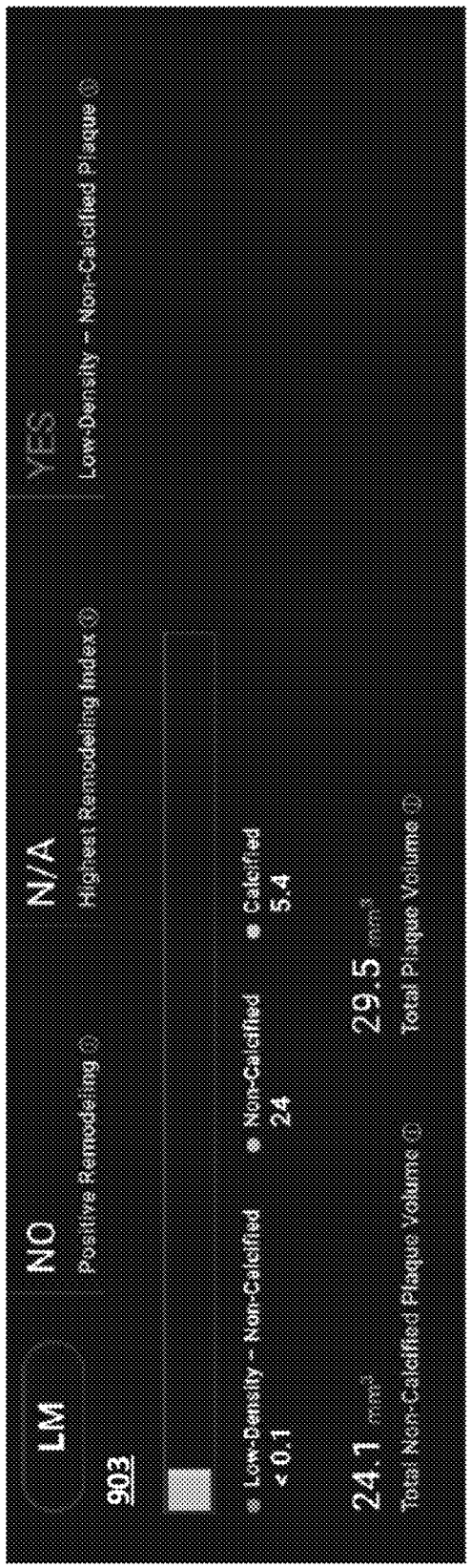
FIG. 9C illustrates an example of a panel that can be displayed on the user interface which shows per segment atherosclerosis information.

FIG. 9C illustrates a panel 903, that can be generated and displayed on the user interface, which shows atherosclerosis information determined by the system on a per segment basis. The presence of positive remodeling, the highest remodeling index, and the presence of Low-Density-Non-Calcified Plaque are reported for each segment in the panel 903 illustrated in FIG. 9C. For example, plaque data can be displayed below on a per-segment basis, and plaque composition volumes can be displayed on a per-segment in the panel 903 illustrated in FIG. 9C.

Figure 9D:
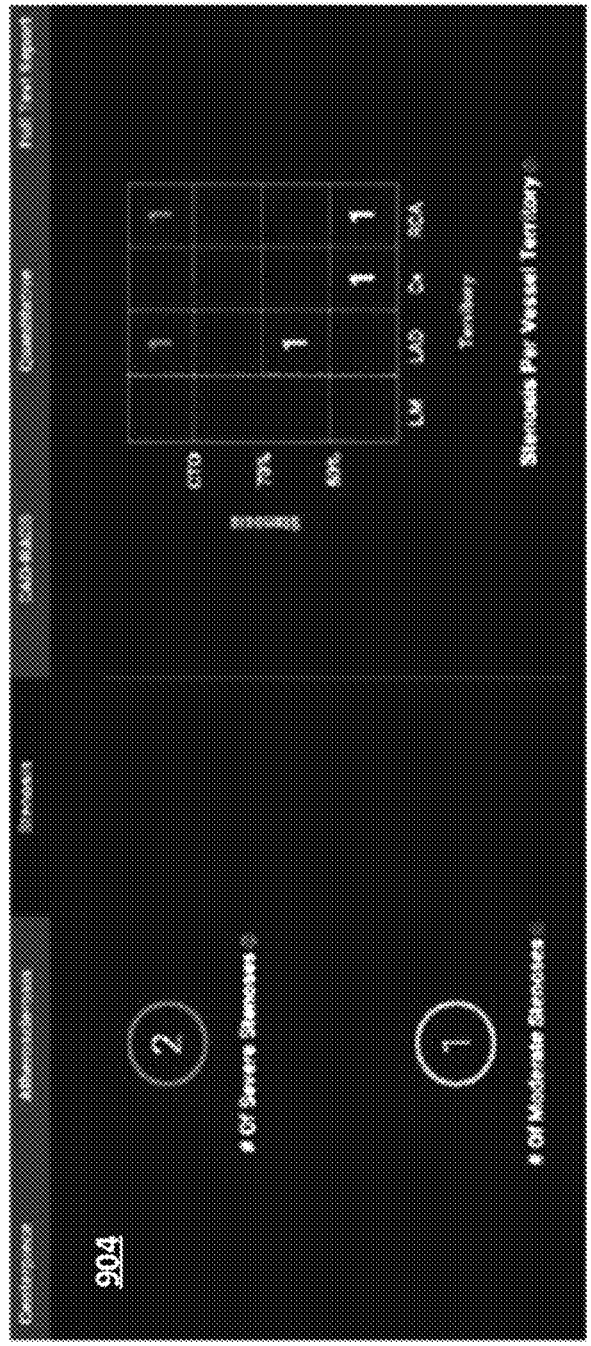
FIG. 9D illustrates an example of a panel that can be displayed on the user interface that contains stenosis per patient data.
Figure 9E:
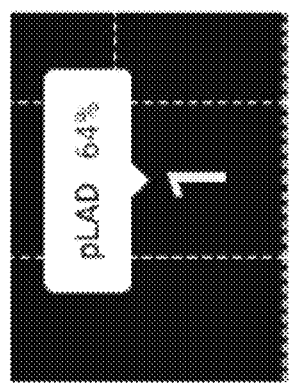
FIG. 9E illustrates an example of a portion of a panel that can be displayed on the user interface that when a count is selected (e.g., by hovering over the number) segment details are displayed.

FIG. 9D illustrates a panel 904 that can be displayed on the user interface that contains stenosis per patient data. The top section of the stenosis panel 904 contains per-patient data. Further details about each count can be displayed by hovering with a pointing device over the numbers, as illustrated in FIG. 9E. Vessels included in each territory are shown in the table below:

| Vessel Territory | Segment Name |
| --- | --- |
| LM (Left Main Artery) | LM |
| LAD (Left Anterior Descending) | pLAD |
| | mLAD |
| | dLAD |
| | D1 |

-continued

| Vessel Territory | Segment Name |
|---|---|
| | D2 |
| | RI |
| LCx (Left Circumflex Artery) | pCx |
| | LCx |
| | OM1 |
| | OM2 |
| | L-PLB |
| | L-PDA |
| RCA (Right Coronary Artery) | pRCA |
| | mRCA |
| | dRCA |
| | R-PLB |
| | R-PDA |

Figure 9F:
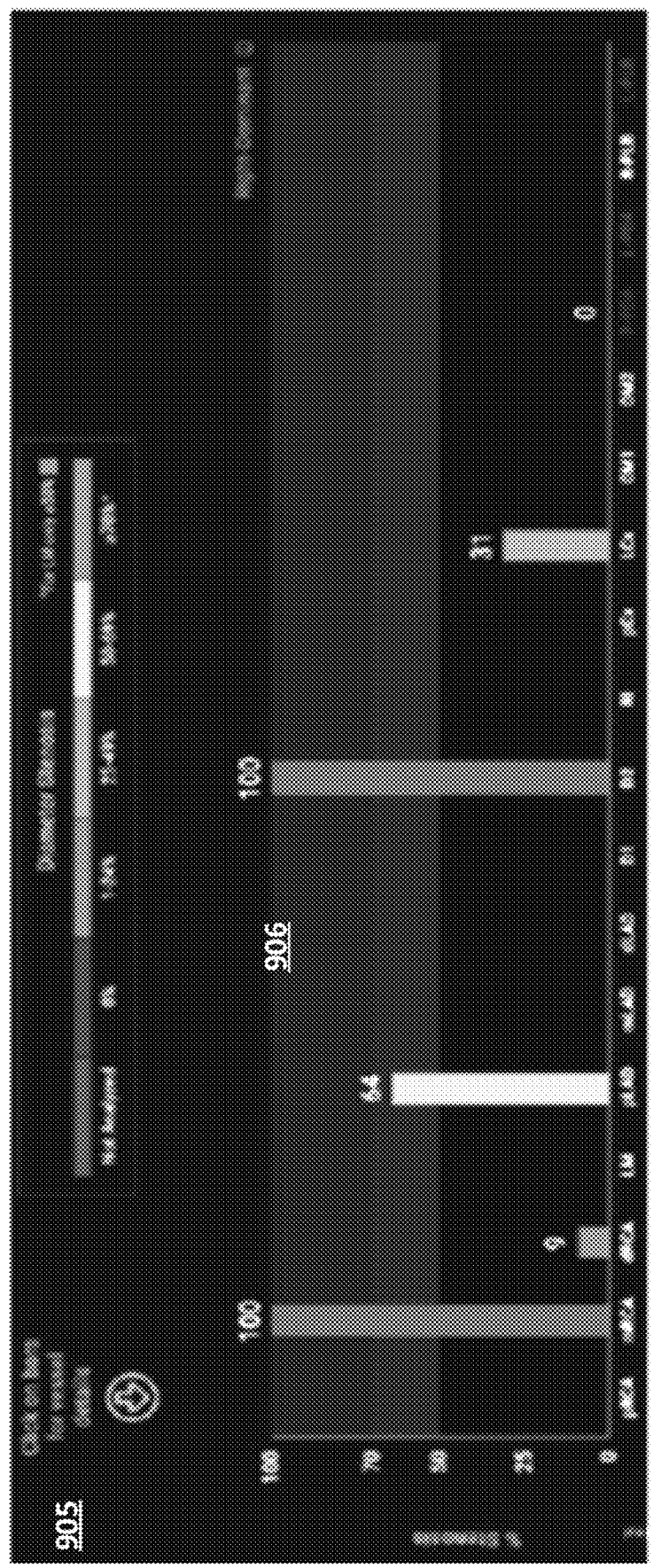
FIG. 9F illustrates an example of a portion of a panel that can be displayed on the user interface that shows stenosis per segment in a graphical format, for example, in a stenosis per segment bar graph.

In an embodiment, a percentage Diameter Stenosis bar graph 906 can be generated and displayed in a panel 905 of the user interface, as illustrated in FIG. 9F. The percentage Diameter Stenosis bar graph 906 displays the greatest diameter stenosis in each segment. If a CTO has been marked on the segment, it will display as a 100% diameter stenosis. If more than one stenosis has been marked on a segment, the highest value outputs are displayed by default and the user can click into each stenosis bar to view stenosis details and interrogate smaller stenosis (if present) within that segment. The user can also scroll through each cross-section by dragging the grey button in the center of a SMPR view of the vessel, and view the lumen diameter and % diameter stenosis at each cross-section at any selected location, as illustrated in FIG. 9G.

FIG. 9H illustrates a panel showing categories of the one or more stenosis marked on the SMPR based on the analysis. Color can be used to enhance the displayed information. In an example, stenosis in the LM>=50% diameter stenosis are marked in red. As illustrated in a panel 907 of the user interface in FIG. 9I, for each segment's greatest percentage diameter stenosis the minimum luminal diameter and lumen diameter at the reference can be displayed when a pointing device is "hovered" above the graphical vessel cross-section representation, as illustrated in FIG. 9J. If a segment was not analyzed or is not anatomically present, the segment will be greyed out and will display "Not Analyzed". If a segment was analyzed but did not have any stenosis marked, the value will display "N/A".

Figure 9K:
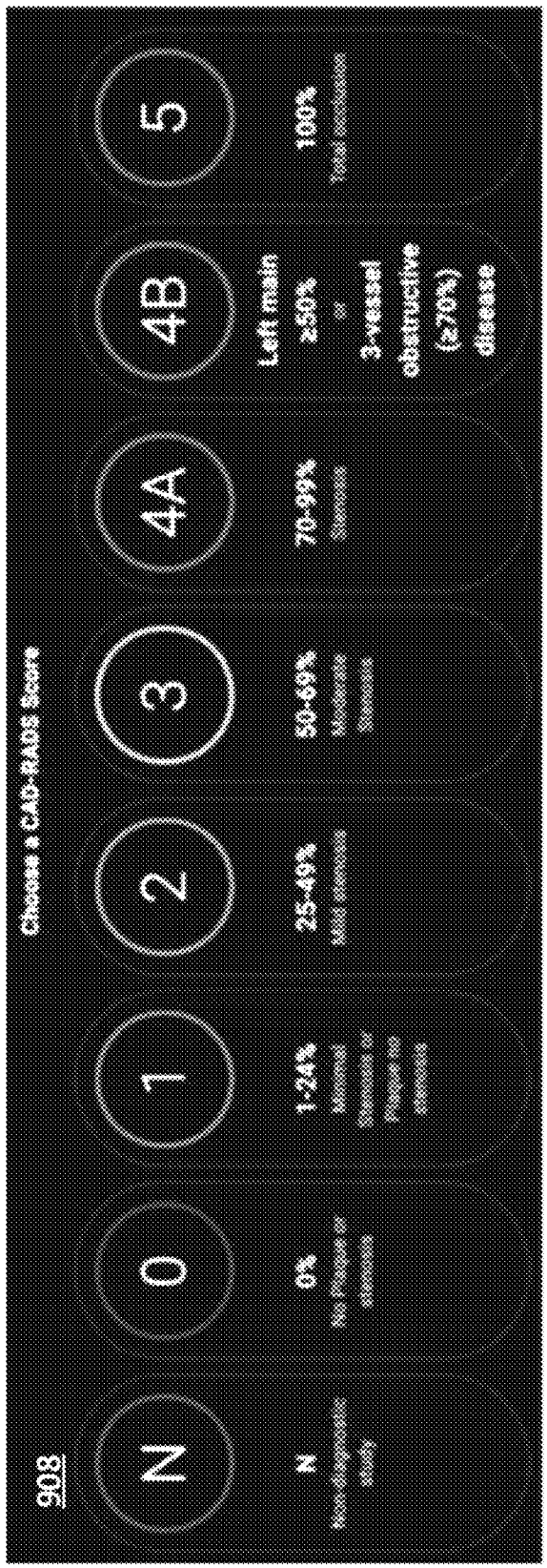
FIG. 9K illustrates an example of a panel that can be displayed in user interface indicating CADS-RADS score selection.
Figure 9L:
FIG. 9L illustrates an example of a panel that can be displayed in the user interface showing further CAD-RADS details generated in the analysis.

FIG. 9K illustrates a panel 908 of the user interface that indicates CADS-RADS score selection. The CAD-RADS panel displays the definitions of CAD-RADS as defined by "Coronary Artery Disease-Reporting and Data System (CAD-RADS) An Expert Consensus Document of SCCT, ACR and NASCI: Endorsed by the ACC". The user is in full control of selecting the CAD-RADS score. In an embodiment, no score will be suggested by the system. In another embodiment, a CAD-RADS score can be suggested. Once a CAD-RADS score is selected on this page, the score will display in both certain user interface panels and full text report pages. Once a CAD-RADS score is selected, the user has the option of selecting modifiers and the presentation of symptoms. Once a presentation is selected, the interpretation, further cardiac investigation and management guidelines can be displayed to the user on the user interface, for example, as illustrated in the panel 909 illustrated in FIG. 9L. These guidelines reproduce the guidelines found in "Coronary Artery Disease-Reporting and Data System (CAD-RADS) An Expert Consensus Document of SCCT, ACR and NASCI: Endorsed by the ACC."

Figure 9M:
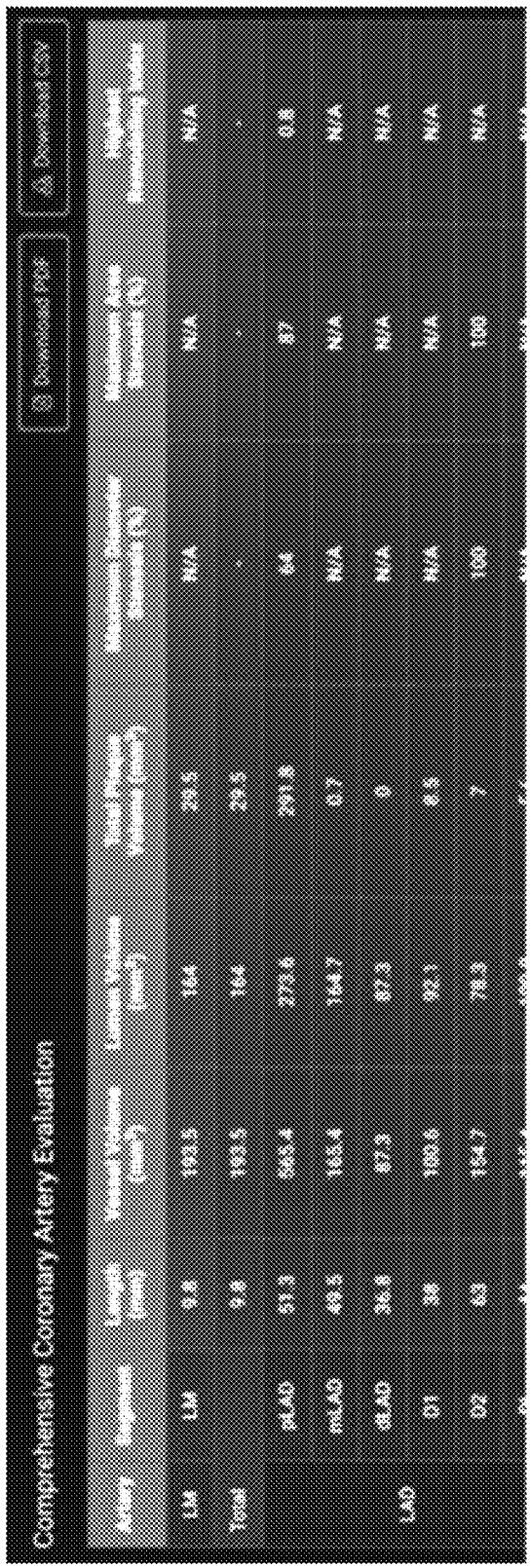
FIG. 9M illustrates an example of a panel that can be displayed in the user interface showing a table indicating quantitative stenosis and vessel outputs which are determined during the analysis.
Figure 9N:
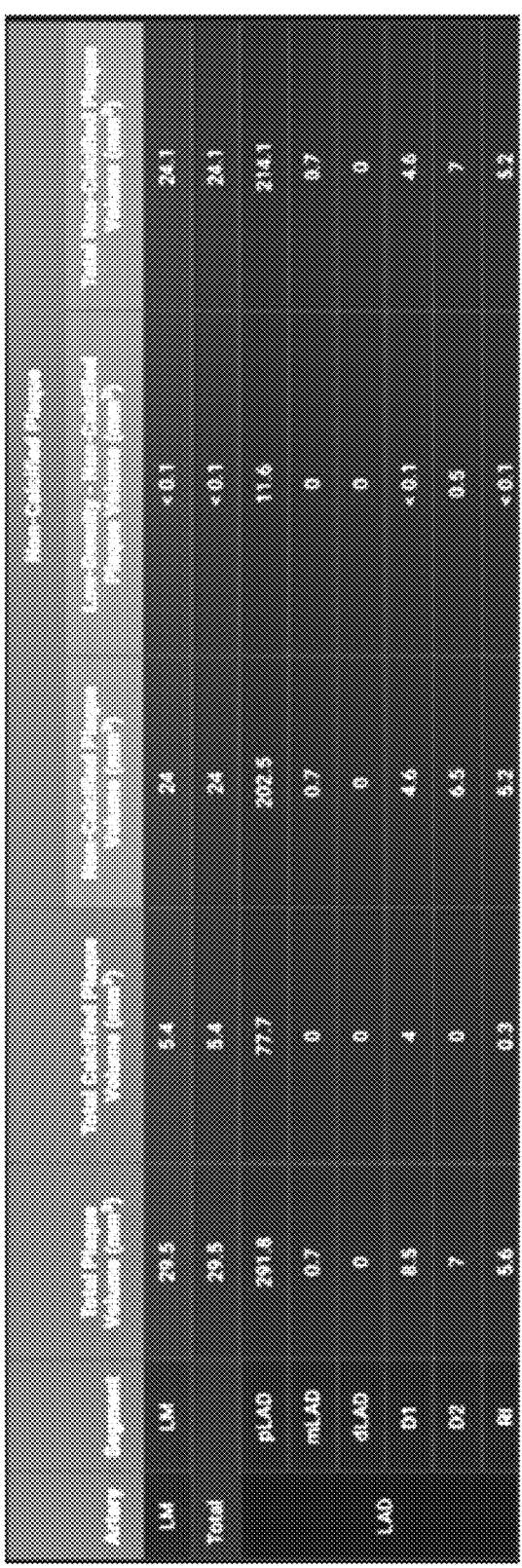
FIG. 9N illustrates an example of a panel that can be displayed in the user interface showing a table indicating quantitative plaque outputs.

FIGS. 9M and 9N illustrate tables that can be generated and displayed on a panel of the user interface, and/or included in a report. FIG. 9M illustrates quantitative stenosis and vessel outputs. FIG. 9N illustrates quantitative plaque outputs. In these quantitative tables, a user can view quantitative per-segment stenosis and atherosclerosis outputs from the system analysis. The quantitative stenosis and vessel outputs table (FIG. 9M) includes information for the evaluated arteries and segments. Totals are given for each vessel territory. Information can include, for example, length, vessel volume, lumen volume, total plaque volume, maximum diameter stenosis, maximum area stenosis, and highest remodeling index. The quantitative plaque outputs table (FIG. 9N) includes information for the evaluated arteries and segments. Information can include, for example, total plaque volume, total calcified plaque volume, non-calcified plaque volume, low-density non-calcified plaque volume, and total non-calcified plaque volume. The user is also able to download a PDF or CSV file of the quantitative outputs is a full text Report. The full text Report presents a textual summary of the atherosclerosis, stenosis, and CAD-RADS measures. The user can edit the report, as desired. Once the user chooses to edit the report, the report will not update the CAD-RADS selection automatically.

Figure 10:
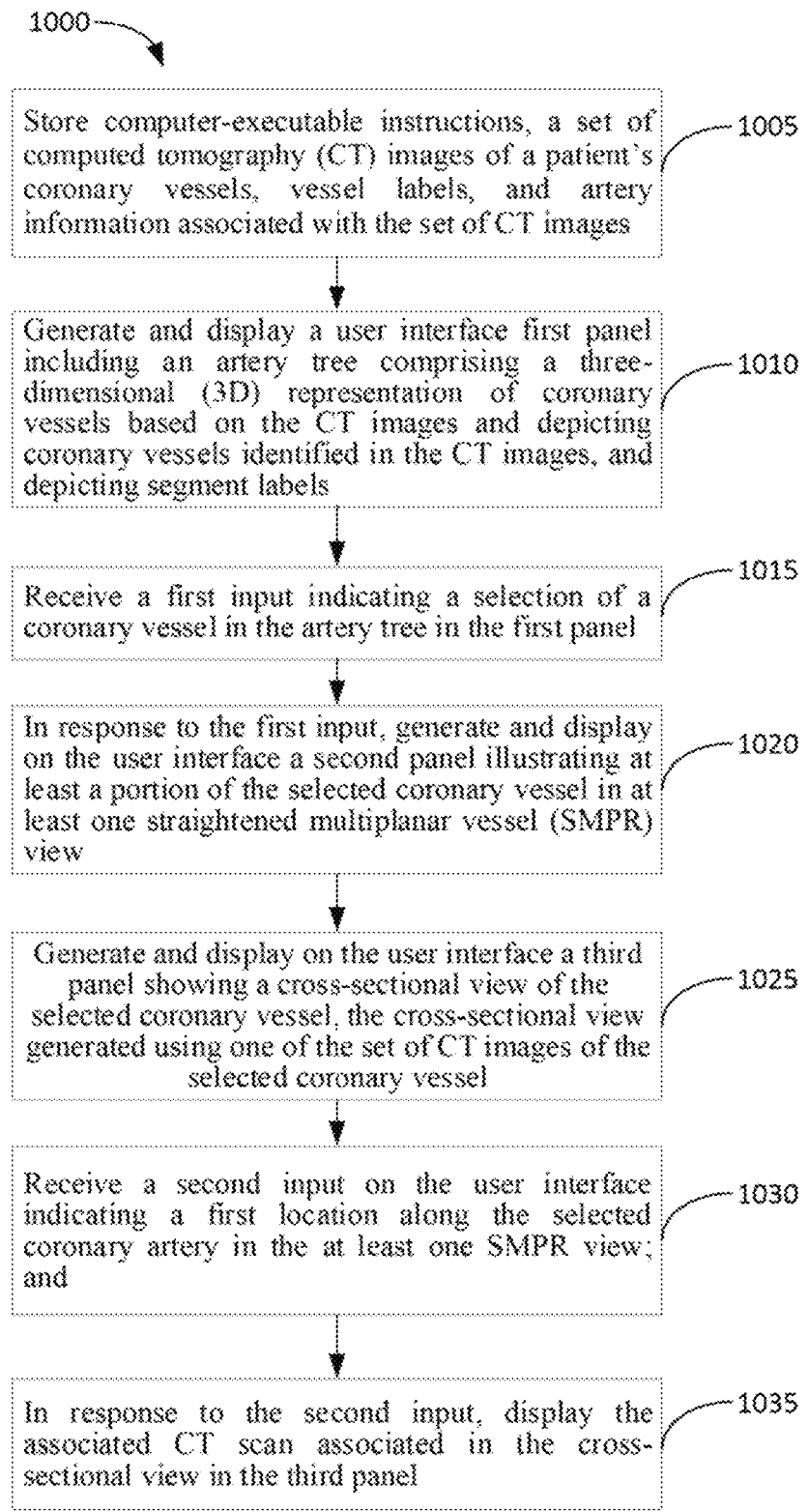
FIG. 10 is a flowchart illustrating a process 1000 for analyzing and displaying CT images and corresponding information.

FIG. 10 is a flowchart illustrating a process 1000 for analyzing and displaying CT images and corresponding information. At block 1005, the process 1000 stores computer-executable instructions, a set of CT images of a patient's coronary vessels, vessel labels, and artery information associated with the set of CT images including information of stenosis, plaque, and locations of segments of the coronary vessels. All of the steps of the process can be performed by embodiments of the system described herein, for example, on embodiments of the systems described in FIG. 13. For example, by one or more computer hardware processors in communication with the one or more non-transitory computer storage mediums, executing the computer-executable instructions stored on one or more non-transitory computer storage mediums. In various embodiments, the user interface can include one or more portions, or panels, that are configured to display one or more of images, in various views (e.g., SMPR, CMPR, cross-sectional, axial, sagittal, coronal, etc.) related to the CT images of a patient's coronary arteries, a graphical representation of coronary arteries, features (e.g., a vessel wall, the lumen, the centerline, the stenosis, plaque, etc.) that have been extracted or revised by machine learning algorithm or by an analyst, and information relating to the CT images that has been determined by the system, by an analyst, or by an analyst interacting with the system (e.g., measurements of features in the CT images. In various embodiments, panels of the user interface can be arranged differently than what is described herein and what is illustrated in the corresponding figures. A user can make an input to the user interface using a pointing device or a user's finger on a touchscreen. In an embodiment, the user interface can receive input by determining the selection of a button/icon/portion of the user interface. In an embodiment, the user interface can receive an input in a defined field of the user interface.

At block 1010, the process 1000 can generate and display in a user interface a first panel including an artery tree comprising a three-dimensional (3D) representation of coronary vessels based on the CT images and depicting coronary vessels identified in the CT images, and depicting segment labels, the artery tree not including heart tissue between branches of the artery tree. An example of such an artery tree 602 is shown in panel 601 in FIG. 6A. In various embodiments, panel 601 can be positioned in locations of the user interface 600 other than what is shown in FIG. 6A.

At block 1015, the process 1000 can receive a first input indicating a selection of a coronary vessel in the artery tree in the first panel. For example, the first input can be received by the user interface 600 of a vessel in the artery tree 602 in panel 601. At block 1020, in response to the first input, the process 1000 can generate and display on the user interface a second panel illustrating at least a portion of the selected coronary vessel in at least one straightened multiplanar vessel (SMPR) view. In an example, the SMPR view is displayed in panel 604 of FIG. 6A.

At block 1025, the process 1000 can generate and display on the user interface a third panel showing a cross-sectional view of the selected coronary vessel, the cross-sectional view generated using one of the set of CT images of the selected coronary vessel. Locations along the at least one SMPR view are each associated with one of the CT images in the set of CT images such that a selection of a particular location along the coronary vessel in the at least one SMPR view displays the associated CT image in the cross-sectional view in the third panel. In an example, the cross-sectional view can be displayed in panel 606 as illustrated in FIG. 6A. At block 1030, the process 1000 can receive a second input on the user interface indicating a first location along the selected coronary artery in the at least one SMPR view. In an example, user may use a pointing device to select a different portion of the vessel shown in the SMPR view in panel 604. At block 1030, the process 1000, in response to the second input, displays the associated CT scan associated in the cross-sectional view in the third panel, panel 606. That is, the cross-sectional view that correspond to the first input is replaced by the cross-sectional view that corresponds to the second input on the SMPR view.

Normalization Device

In some instances, medical images processed and/or analyzed as described throughout this application can be normalized using a normalization device. As will be described in more detail in this section, the normalization device may comprise a device including a plurality of samples of known substances that can be placed in the medical image field of view so as to provide images of the known substances, which can serve as the basis for normalizing the medical images. In some instances, the normalization device allows for direct within image comparisons between patient tissue and/or other substances (e.g., plaque) within the image and known substances within the normalization device.

As mentioned briefly above, in some instances, medical imaging scanners may produce images with different scalable radiodensities for the same object. This, for example, can depend not only on the type of medical imaging scanner or equipment used but also on the scan parameters and/or environment of the particular day and/or time when the scan was taken. As a result, even if two different scans were taken of the same subject, the brightness and/or darkness of the resulting medical image may be different, which can result in less than accurate analysis results processed from that image. To account for such differences, in some embodiments, the normalization device comprising one or more known samples of known materials can be scanned together with the subject, and the resulting image of the one or more known elements can be used as a basis for translating, converting, and/or normalizing the resulting image.

Normalizing the medical images that will be analyzed can be beneficial for several reasons. For example, medical images can be captured under a wide variety of conditions, all of which can affect the resulting medical images. In instances where the medical imager comprises a CT scanner, a number of different variables can affect the resulting image. Variable image acquisition parameters, for example, can affect the resulting image. Variable image acquisition parameters can comprise one or more of a kilovoltage (kV), kilovoltage peak (kVp), a milliamperage (mA), or a method of gating, among others. In some embodiments, methods of gating can include prospective axial triggering, retrospective ECG helical gating, and fast pitch helical, among others. Varying any of these parameters, may produce slight differences in the resulting medical images, even if the same subject is scanned.

Figure 11B:
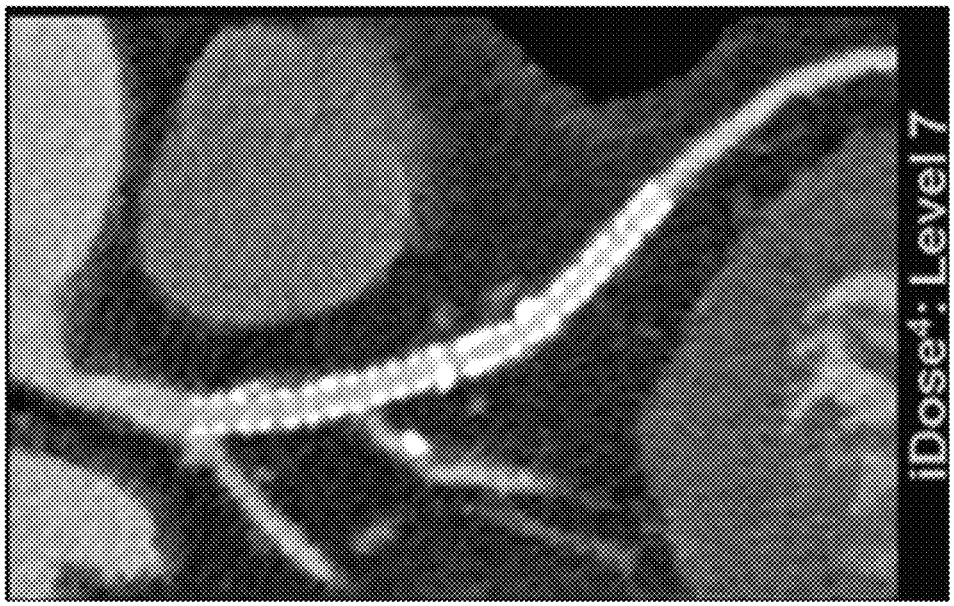
FIGS. 11A and 11B are example CT images illustrating how plaque can appear differently depending on the image acquisition parameters used to capture the CT images.
Figure 11A:
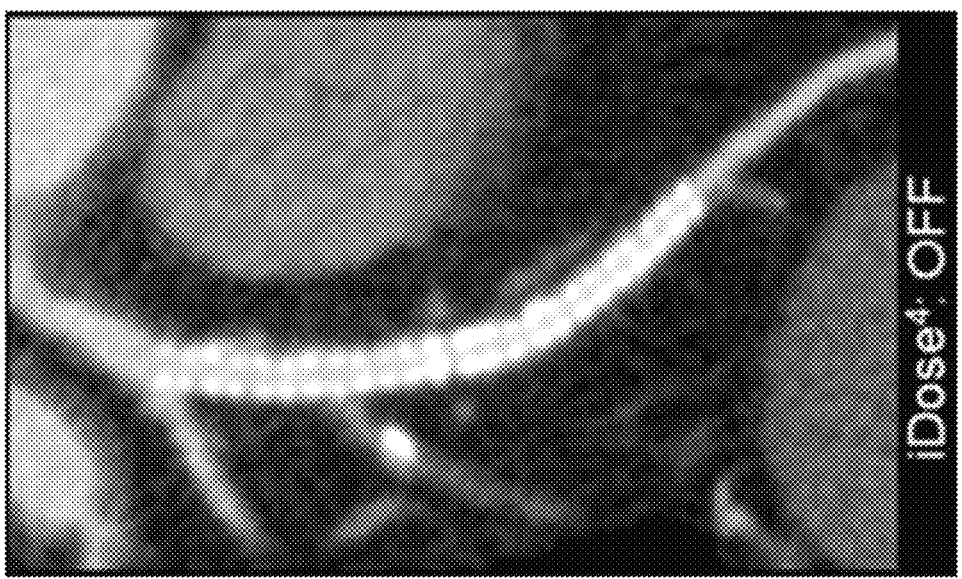
Figure 11C:
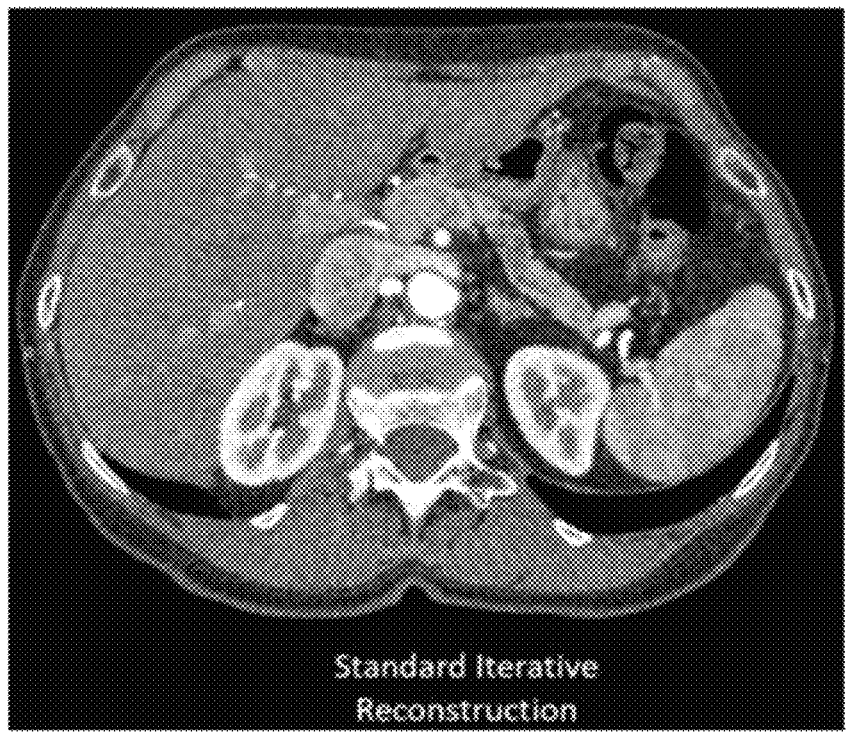
FIGS. 11C and 11D provide another example that illustrates that plaque can appear differently in CT images depending on the image acquisition parameters used to capture the CT images.
Figure 11D:
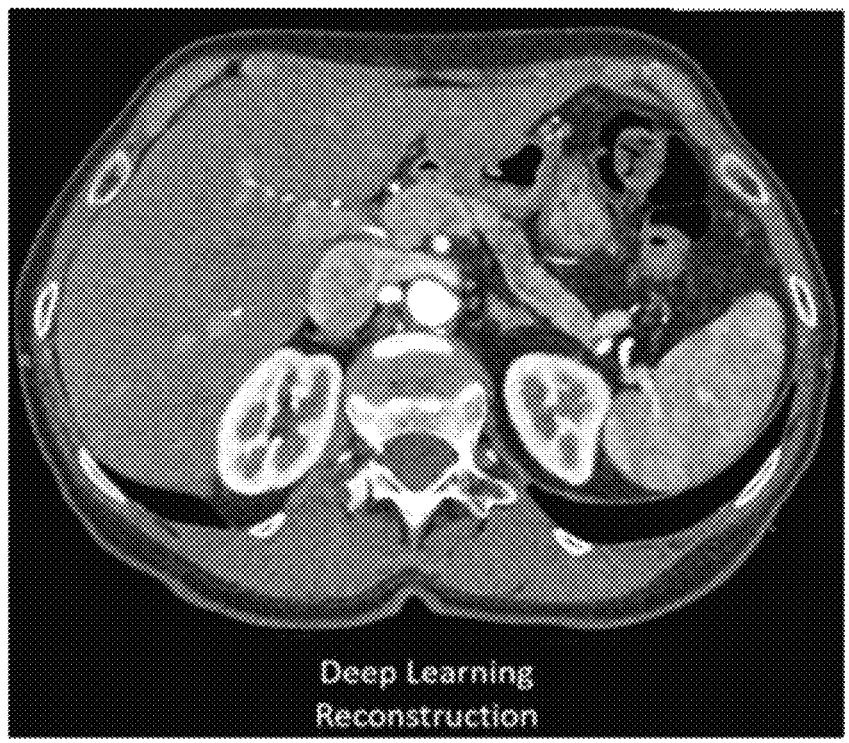

Additionally, the type of reconstruction used to prepare the image after the scan may provide differences in medical images. Example types of reconstruction can include iterative reconstruction, non-iterative reconstruction, machine learning-based reconstruction, and other types of physics-based reconstruction among others. FIGS. 11A-11D illustrate different images reconstructed using different reconstruction techniques. In particular, FIG. 11A illustrates a CT image reconstructed using filtered back projection, while FIG. 11B illustrates the same CT image reconstructed using iterative reconstruction. As shown, the two images appear slightly different. The normalization device described below can be used to help account for these differences by providing a method for normalizing between the two. FIG. 11C illustrates a CT image reconstructed by using iterative reconstruction, while FIG. 11D illustrates the same image reconstructed using machine learning. Again, one can see that the images include slight differences, and the normalization device described herein can advantageously be useful in normalizing the images to account for the two differences.

As another example, various types of image capture technologies can be used to capture the medical images. In instances where the medical imager comprises a CT scanner, such image capture technologies may include a dual source scanner, a single source scanner, dual energy, monochromatic energy, spectral CT, photon counting, and different detector materials, among others. As before, images captured using difference parameters may appear slightly different, even if the same subject is scanned. In addition to CT scanners, other types of medical imagers can also be used to capture medical images. These can include, for example, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS). Use of the normalization device can facilitate normalization of images such that images captured on these different imaging devices can be used in the methods and systems described herein.

Additionally, new types of medical imaging technologies are currently being developed. Use of the normalization device can allow the methods and systems described herein to be used even with medical imaging technologies that are currently being developed or that will be developed in the future. Use of different or emerging medical imaging technologies can also cause slight differences between images.

Another factor that can cause differences in medical images that can be accounted for using the normalization device can be use of different contrast agents during medical imaging. Various contrast agents currently exist, and still others are under development. Use of the normalization device can facilitate normalization of medical images regardless of the type of contrast agent used and even in instances where no contrast agent is used.

These slight differences can, in some instances, negatively impact analysis of the image, especially where analysis of the image is performed by artificial intelligence or machine learning algorithms that were trained or developed using medical images captured under different conditions. In some embodiments, the methods and systems described throughout this application for analyzing medical images can include the use of artificial intelligence and/or machine learning algorithms. Such algorithms can be trained using medical images. In some embodiments, the medical images that are used to train these algorithms can include the normalization device such that the algorithms are trained based on normalized images. Then, by normalizing subsequent images by also including the normalization device in those images, the machine learning algorithms can be used to analyze medical images captured under a wide variety of parameters, such as those described above.

In some embodiments, the normalization device described herein is distinguishable from a conventional phantom. In some instances, conventional phantoms can be used to verify if a CT machine is operating in a correct manner. These conventional phantoms can be used periodically to verify the calibration of the CT machine. For example, in some instances, conventional phantoms can be used prior to each scan, weekly, monthly, yearly, or after maintenance on the CT machine to ensure proper functioning and calibration. Notably, however, the conventional phantoms do not provide a normalization function that allows for normalization of the resulting medical images across different machines, different parameters, different patients, etc.

In some embodiments, the normalization device described herein can provide this functionality. The normalization device can allow for the normalization of CT data or other medical imaging data generated by various machine types and/or for normalization across different patients. For example, different CT devices manufactured by various manufacturers, can produce different coloration and/or different gray scale images. In another example, some CT scanning devices can produce different coloration and/or different gray scale images as the CT scanning device ages or as the CT scanning device is used or based on the environmental conditions surrounding the device during the scanning. In another example, patient tissue types or the like can cause different coloration and/or gray scale levels to appear differently in medical image scan data. Normalization of CT scan data can be important in order to ensure that processing of the CT scan data or other medical imaging data is consistent across various data sets generated by various machines or the same machines used at different times and/or across different patients. In some embodiments, the normalization device needs to be used each time a medical image scan is performed because scanning equipment can change over time and/or patients are different with each scan. In some embodiments, the normalization device is used in performing each and every scan of patient in order to normalize the medical image data of each patient for the AI algorithm(s) used to analyze the medical image data of the patient. In other words, in some embodiments, the normalization device is used to normalize to each patient as opposed to each scanner. In some embodiments, the normalization device may have different known materials with different densities adjacent to each other (e.g., as described with reference to FIG. 12F). This configuration may address an issue present in some CT images where the density of a pixel influences the density of the adjacent pixels and that influence changes with the density of each of the individual pixel. One example of such an embodiment can include different contrast densities in the coronary lumen influencing the density of the plaque pixels. The normalization device can address this issue by having known volumes of known substances to help to correctly evaluate volumes of materials/lesions within the image correcting in some way the influence of the blooming artifact on quantitative CT image analysis/measures. In some instances, the normalization device might have moving known materials with known volume and known and controllable motion. This may allow to exclude or reduce the effect of motion on quantitative CT image analysis/measures.

Accordingly, the normalization device, in some embodiments, is not a phantom in the traditional sense because the normalization device is not just calibrating to a particular scanner but is also normalizing for a specific patient at a particular time in a particular environment for a particular scan, for particular scan image acquisition parameters, and/or for specific contrast protocols. Accordingly, in some embodiments, the normalization device can be considered a reverse phantom. This can be because, rather than providing a mechanism for validating a particular medical imager as a conventional phantom would, the normalization device can provide a mechanism for normalizing or validating a resulting medical image such that it can be compared with other medical images taken under different conditions. In some embodiments, the normalization device is configured to normalize the medical image data being examined with the medical image data used to train, test, and/or validate the AI algorithms used for analyzing the to be examined medical image data.

In some embodiments, the normalization of medical scanning data can be necessary for the AI processing methods disclosed herein because in some instances AI processing methods can only properly process medical scanning data when the medical scanning data is consistent across all medical scanning data being processed. For example, in situations where a first medical scanner produces medical images showing fatty material as dark gray or black, whereas a second medical scanner produces medical image showing the same fatty material as medium or light gray, then the AI processing methodologies of the systems, methods, and devices disclosed herein may misidentify and/or not fully identify the fatty materials in one set or both sets of the medical images produced by the first and second medical scanners. This can be even more problematic as the relationship of specific material densities may not be not constant, and even may change in an non linear way depending on the material and on the scanning parameters. In some embodiments, the normalization device enables the use of AI algorithms trained on certain medical scanner devices to be used on medical images generated by next-generation medical scanner devices that may have not yet even been developed.

Figure 12A:
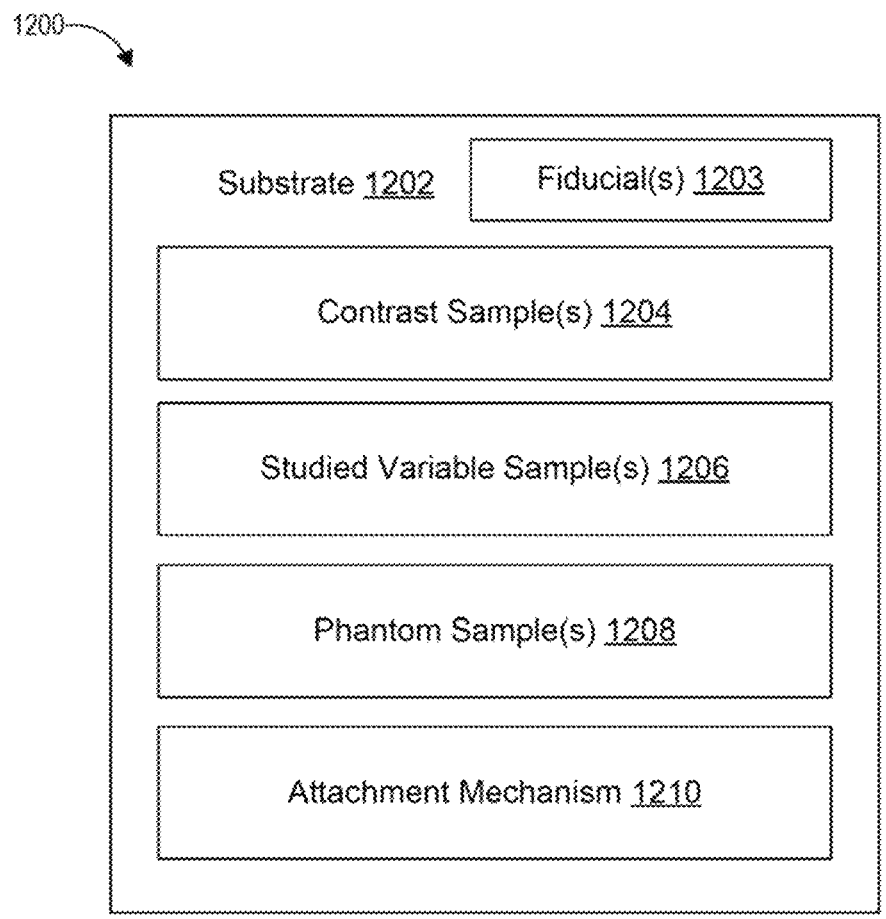
FIG. 12A is a block diagram representative of an embodiment of a normalization device that can be configured to normalize medical images for use with the methods and systems described herein.

FIG. 12A is a block diagram representative of an embodiment of a normalization device 1200 that can be configured to normalize medical images for use with the methods and systems described herein. In the illustrated embodiment, the normalization device 1200 can include a substrate 1202. The substrate 1202 can provide the body or structure for the normalization device 1200. In some embodiments, the normalization device 1200 can comprise a square or rectangular or cube shape, although other shapes are possible. In some embodiments, the normalization device 1200 is configured to be bendable and/or be self-supporting. For example, the substrate 1202 can be bendable and/or self-supporting. A bendable substrate 1202 can allow the normalization device to fit to the contours of a patient's body. In some embodiments, the substrate 1202 can comprise one or more fiducials 1203. The fiducials 1203 can be configured to facilitate determination of the alignment of the normalization device 1200 in an image of the normalization device such that the position in the image of each of the one or more compartments holding samples of known materials can be determined.

The substrate 1202 can also include a plurality of compartments (not shown in FIG. 12A, but see, for example, compartments 1216 of FIGS. 12C-12F). The compartments 1216 can be configured to hold samples of known materials, such as contrast samples 1204, studied variable samples 1206, and phantom samples 1208. In some embodiments, the contrast samples 1204 comprise samples of contrast materials used during capture of the medical image. In some embodiments, the samples of the contrast materials 1204 comprise one or more of iodine, Gad, Tantalum, Tungsten, Gold, Bismuth, or Ytterbium. These samples can be provided within the compartments 1216 of the normalization device 1200 at various concentrations. The studied variable samples 1206 can includes samples of materials representative of materials to be analyzed systems and methods described herein. In some examples, the studied variable samples 1206 comprise one or more of calcium 1000 HU, calcium 220 HU, calcium 150 HU, calcium 130 HU, and a low attenuation (e.g., 30 HU) material. Other studied variable samples 1206 provided at different concentrations can also be included. In general, the studied variable samples 1206 can correspond to the materials for which the medical image is being analyzed. The phantom samples 1208 can comprise samples of one or more phantom materials. In some examples, the phantom samples 1208 comprise one or more of water, fat, calcium, uric acid, air, iron, or blood. Other phantom samples 1208 can also be used.

In some embodiments, the more materials contained in the normalization device 1200, or the more compartments 1216 with different materials in the normalization device 1200, the better the normalization of the data produced by the medical scanner. In some embodiments, the normalization device 1200 or the substrate 1202 thereof is manufactured from flexible and/or bendable plastic. In some embodiments, the normalization device 1200 is adapted to be positioned within or under the coils of an MR scanning device. In some embodiments, the normalization device 1200 or the substrate 1202 thereof is manufactured from rigid plastic.

In the illustrated embodiment of FIG. 12A, the normalization device 1200 also includes an attachment mechanism 1210. The attachment mechanism 1210 can be used to attach the normalization device 1200 to the patient. For example, in some embodiments, the normalization device 1200 is attached to the patient near the coronary region to be imaged prior to image acquisition. In some embodiments, the normalization device 1200 can be adhered to the skin of a patient using an adhesive or Velcro or some other fastener or glue. In some embodiments, the normalization device 1200 can be applied to a patient like a bandage. For example, in some embodiments, a removable Band-Aid or sticker is applied to the skin of the patient, wherein the Band-Aid can comprise a Velcro outward facing portion that allows the normalization device having a corresponding Velcro mating portion to adhere to the Band-Aid or sticker that is affixed to the skin of the patient (see, for example, the normalization device of FIG. 12G, described below).

In some embodiments, the attachment mechanism 1210 can be omitted, such that the normalization device 1200 need not be affixed to the patient. Rather, in some embodiments, the normalization device can be placed in a medical scanner with or without a patient. In some embodiments, the normalization device can be configured to be placed alongside a patient within a medical scanner.

In some embodiments, the normalization device 1200 can be a reusable device or be a disposable one-time use device. In some embodiments, the normalization device 1200 comprises an expiration date, for example, the device can comprise a material that changes color to indicate expiration of the device, wherein the color changes over time and/or after a certain number of scans or an amount of radiation exposure (see, for example, FIGS. 12H and 12I, described below). In some embodiments, the normalization device 1200 requires refrigeration between uses, for example, to preserve one or more of the samples contained therein. In some embodiments, the normalization device 1200 can comprise an indicator, such as a color change indicator, that notifies the user that the device has expired due to heat exposure or failure to refrigerate.

In certain embodiments, the normalization device 1200 comprises a material that allows for heat transfer from the skin of the patient in order for the materials within the normalization device 1200 to reach the same or substantially the same temperature of the skin of the patient because in some cases the temperature of the materials can affect the resulting coloration or gray-scale of the materials produced by the image scanning device. For example, the substrate 1202 can comprise a material with a relatively high heat transfer coefficient to facilitate heat transfer from the patient to the samples within the substrate 1202. In some embodiments, the normalization device 1200 can be removably coupled to a patient's skin by using an adhesive that can allow the device to adhere to the skin of a patient.

In some embodiments, the normalization device 1200 can be used in the imaging field of view or not in the imaging field of view. In some embodiments, the normalization device 1200 can be imaged simultaneously with the patient image acquisition or sequentially. Sequential use can comprise first imaging the normalization device 1200 and the imaging the patient shortly thereafter using the same imaging parameters (or vice versa). In some embodiments, the normalization device 1200 can be static or programmed to be in motion or movement in sync with the image acquisition or the patient's heart or respiratory motion. In some embodiments, the normalization device 1200 can utilize comparison to image domain-based data or projection domain-based data. In some embodiments, the normalization device 1200 can be a 2D (area), or 3D (volume), or 4D (changes with time) device. In some embodiments, two or more normalization devices 1200 can be affixed to and/or positioned alongside a patient during medical image scanning in order to account for changes in coloration and/or gray scale levels at different depths within the scanner and/or different locations within the scanner.

Figure 12B:
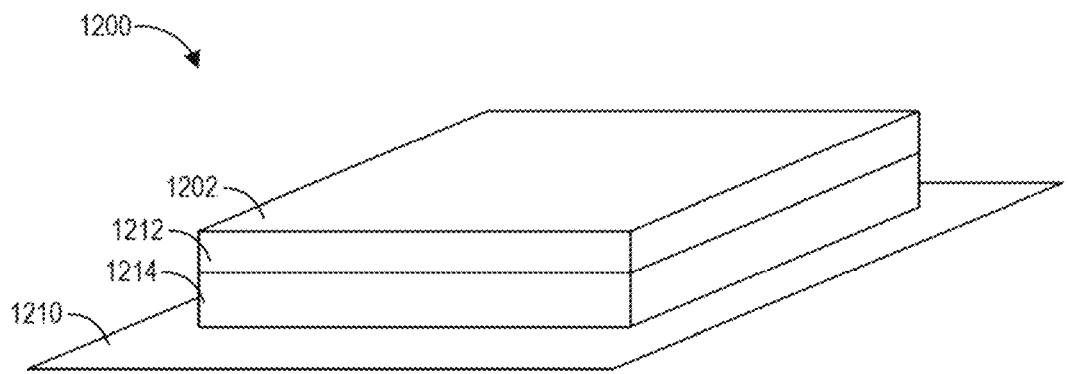
FIG. 12B is a perspective view of an embodiment of a normalization device including a multilayer substrate.
Figure 12C:
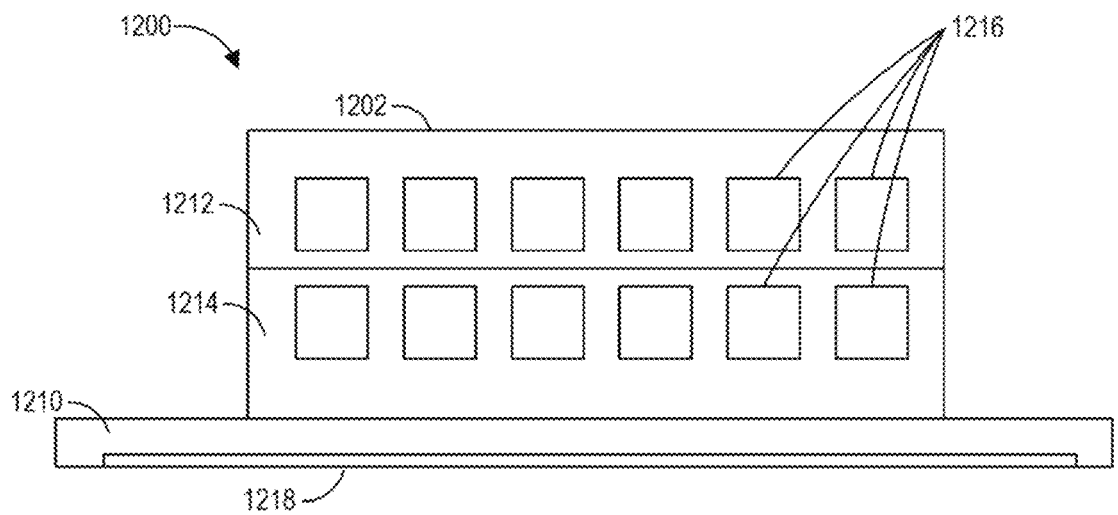
FIG. 12C is a cross-sectional view of the normalization device of FIG. 12B illustrating various compartments positioned therein for holding samples of known materials for use during normalization.

In some embodiments, the normalization device 1200 can comprise one or more layers, wherein each layer comprises compartments for holding the same or different materials as other layers of the device. FIG. 12B, for example, illustrates a perspective view of an embodiment of a normalization device 1200 including a multilayer substrate 1202. in the illustrated embodiment, the substrate 1202 comprises a first layer 1212 and a second layer 1214. The second layer 1214 can be positioned above the first layer 1212. In other embodiments, one or more additional layers may be positioned above the second layer 1214. Each of the layers 1212, 1214 can be configured with compartments for holding the various known samples, as shown in FIG. 12C. In some embodiments, the various layers 1212, 1214 of the normalization device 1200 allow for normalization at various depth levels for various scanning machines that perform three-dimensional scanning, such as MR and ultrasound. In some embodiments, the system can be configured to normalize by averaging of coloration and/or gray scale level changes in imaging characteristics due to changes in depth.

FIG. 12C is a cross-sectional view of the normalization device 1200 of FIG. 12B illustrating various compartments 1216 positioned therein for holding samples of known materials for use during normalization. The compartments 1216 can be configured to hold, for example, the contrast samples 1204, the studied variable samples 1206, and the phantom samples 1208 illustrated in FIG. 12A. The compartments 1216 may comprise spaces, pouches, cubes, spheres, areas, or the like, and within each compartment 1216 there is contained one or more compounds, fluids, substances, elements, materials, and the like. In some embodiments, each of the compartments 1216 can comprise a different substance or material. In some embodiments, each compartment 1216 is air-tight and sealed to prevent the sample, which may be a liquid, from leaking out.

Figure 12D:
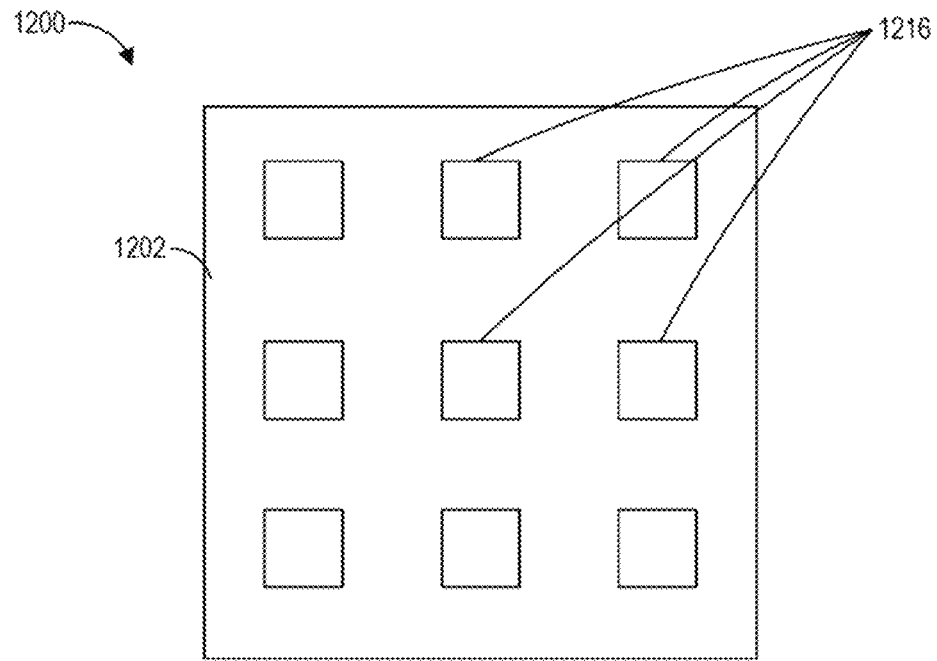
FIG. 12D illustrates a top down view of an example arrangement of a plurality of compartments within a normalization device. In the illustrated embodiment, the plurality of compartments are arranged in a rectangular or grid-like pattern.
Figure 12E:
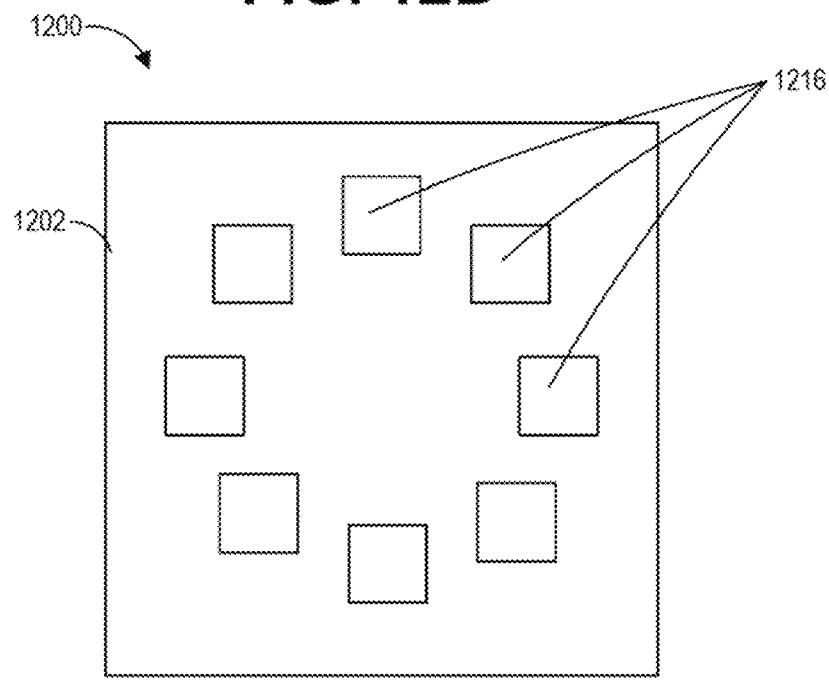
FIG. 12E illustrates a top down view of another example arrangement of a plurality of compartments within a normalization device. In the illustrated embodiment, the plurality of compartments are arranged in a circular pattern.

Within each layer 1212, 1214, or within the substrate 1202, the normalization device 1200 may include different arrangements for the compartments 1216. FIG. 12D illustrates a top down view of an example arrangement of a plurality of compartments 1216 within the normalization device 1200. In the illustrated embodiment, the plurality of compartments 1216 are arranged in a rectangular or grid-like pattern. FIG. 12E illustrates a top down view of another example arrangement of a plurality of compartments 1216 within a normalization device 1200. In the illustrated embodiment, the plurality of compartments 1216 are arranged in a circular pattern. Other arrangements are also possible.

Figure 12F:
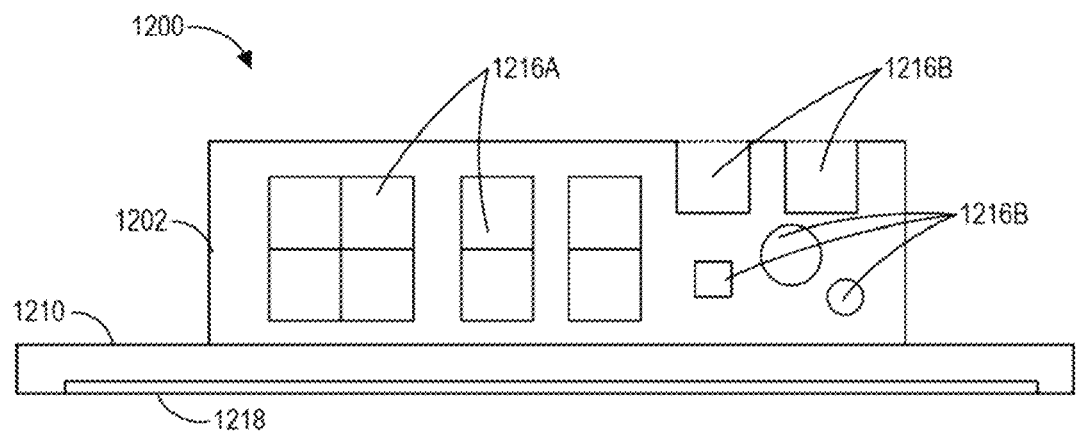
FIG. 12F is a cross-sectional view of another embodiment of a normalization device illustrating various features thereof, including adjacently arranged compartments, self-sealing Tillable compartments, and compartments of various sizes.

FIG. 12F is a cross-sectional view of another embodiment of a normalization device 1200 illustrating various features thereof, including adjacently arranged compartments 1216A, self-sealing fillable compartments 1216B, and compartments of various sizes and shapes 1216C. As shown in FIG. 12F, one or more of the compartments 1216A can be arranged so as to be adjacent to each other so that materials within the compartments 1216A can be in contact with and/or in close proximity to the materials within the adjacent compartments 1216A. In some embodiments, the normalization device 1200 comprises high density materials juxtaposed to low density materials in order to determine how a particular scanning device displays certain materials, thereby allowing normalization across multiple scanning devices. In some embodiments, certain materials are positioned adjacent or near other materials because during scanning certain materials can influence each other. Examples of materials that can be placed in adjacently positioned compartments 1216A can include iodine, air, fat material, tissue, radioactive contrast agent, gold, iron, other metals, distilled water, and/or water, among others.

In some embodiments, the normalization device 1200 is configured receive material and/or fluid such that the normalization device is self-sealing. Accordingly, FIG. 12F illustrates compartments 1216B that are self-sealing. These can allow a material to be injected into the compartment 1216B and then sealed therein. For example, a radioactive contrast agent can be injected in a self-sealing manner into a compartment 1216B of the normalization device 1200, such that the medical image data generated from the scanning device can be normalized over time as the radioactive contrast agent decays over time during the scanning procedure. In some embodiments, the normalization device can be configured to contain materials specific for a patient and/or a type of tissue being analyzed and/or a disease type and/or a scanner machine type.

In some embodiments, the normalization device 1200 can be configured measure scanner resolution and type of resolution by configuring the normalization device 1200 with a plurality of shapes, such as a circle. Accordingly, the compartments 1216C can be provided with different shapes and sizes. FIG. 12F illustrates an example wherein compartments 1216C are provided with different shapes (cubic and spherical) and different sizes. In some embodiments, all compartments 1216 can be the same shape and size.

In some embodiments, the size of one or more compartment 1216 of the normalization device 1200 can be configured or selected to correspond to the resolution of the medical image scanner. For example, in some embodiments, if the spatial resolution of a medical image scanner is 0.5 mm×0.5 mm×0.5 mm, then the dimension of the compartments of the normalization device can also be 0.5 mm×0.5 mm×0.5 mm. In some embodiments, the sizes of the compartments range from 0.5 mm to 0.75 mm. In some embodiments, the width of the compartments of the normalization device can be about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm, about 0.95 mm, about 1.0 mm, and/or within a range defined by two of the aforementioned values. In some embodiments, the length of the compartments of the normalization device can be about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm, about 0.95 mm, about 1.0 mm, and/or within a range defined by two of the aforementioned values. In some embodiments, the height of the compartments of the normalization device can be about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm, about 0.95 mm, about 1.0 mm, and/or within a range defined by two of the aforementioned values.

In some embodiments, the dimensions of each of the compartments 1216 in the normalization device 1200 are the same or substantially the same for all of the compartments 1216. In some embodiments, the dimensions of some or all of the compartments 1216 in the normalization device 1200 can be different from each other in order for a single normalization device 1200 to have a plurality of compartments having different dimensions such that the normalization device 1200 can be used in various medical image scanning devices having different resolution capabilities (for example, as illustrated in FIG. 12F). In some embodiments, a normalization device 1200 having a plurality of compartments 1216 with differing dimensions enable the normalization device to be used to determine the actual resolution capability of the scanning device. In some embodiments, the size of each compartment 1216 may extend up to 10 mm, and the sizes of each compartment may be variable depending upon the material contained within.

Figure 12G:
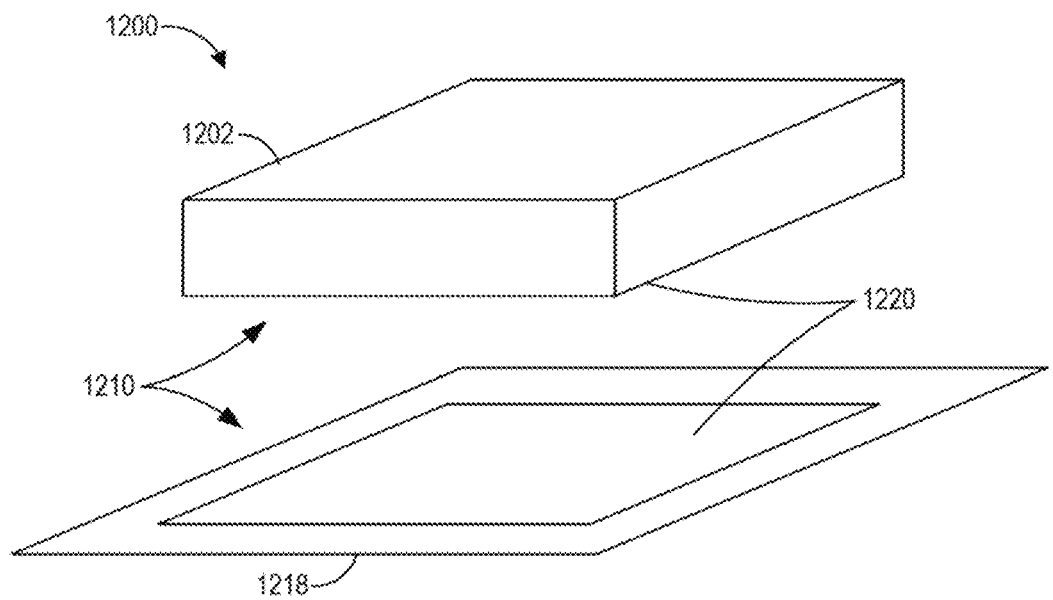
FIG. 12G is a perspective view illustrating an embodiment of an attachment mechanism for a normalization device that uses hook and loop fasteners to secure a substrate of the normalization device to a fastener of the normalization device.

In the illustrated embodiment of FIGS. 12C and 12F, the normalization device 1200 includes an attachment mechanism 1210 which includes an adhesive surface 1218. The adhesive surface 1218 can be configured to affix (e.g., removably affix) the normalization device 1200 to the skin of the patient. FIG. 12G is a perspective view illustrating an embodiment of an attachment mechanism 1210 for a normalization device 1200 that uses hook and loop fasteners 1220 to secure a substrate of the normalization device to a fastener of the normalization device 1200. In the illustrated embodiment, an adhesive surface 1218 can be configured to be affixed to the patient. The adhesive surface 1218 can include a first hook and loop fastener 1220. A corresponding hook and loop fastener 1220 can be provided on a lower surface of the substrate 1202 and used to removably attach the substrate 1202 to the adhesive surface 1218 via the hook and loop fasteners 1220.

Figure 12H:
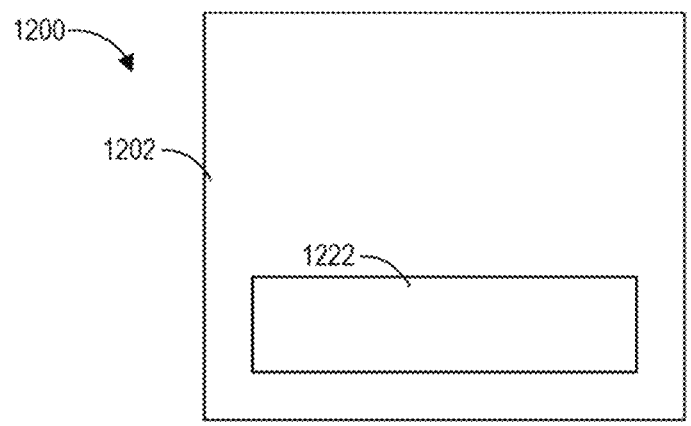
FIGS. 12H and 12I illustrate an embodiment of a normalization device that includes an indicator configured to indicate an expiration status of the normalization device.
Figure 12I:
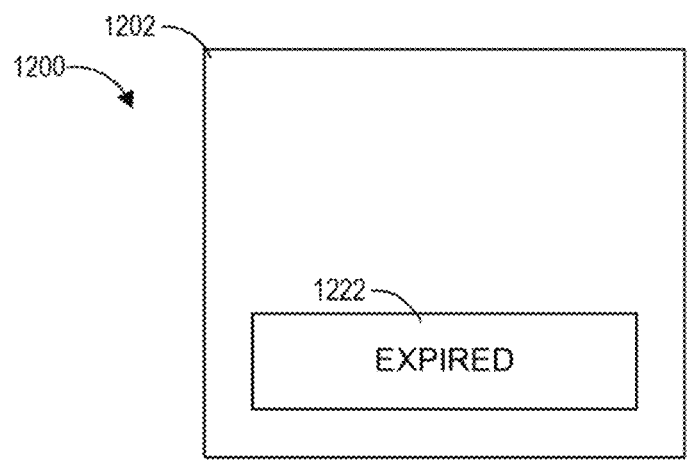

FIGS. 12H and 12I illustrate an embodiment of a normalization device 1200 that includes an indicator 1222 configured to indicate an expiration status of the normalization device 1200. The indicator 1222 can comprise a material that changes color or reveals a word to indicate expiration of the device, wherein the color or text changes or appears over time and/or after a certain number of scans or an amount of radiation exposure. FIG. 12H illustrates the indicator 1222 in a first state representative of a non-expired state, and FIG. 12I illustrates the indicator 1222 in a second state representative of an expired state. In some embodiments, the normalization device 1200 requires refrigeration between uses. In some embodiments, the indicator 1222, such as a color change indicator, can notify the user that the device has expired due to heat exposure or failure to refrigerate.

In some embodiments, the normalization device 1200 can be used with a system configured to set distilled water to a gray scale value of zero, such that if a particular medical image scanning device registers the compartment of the normalization device 1200 comprising distilled water as having a gray scale value of some value other than zero, then the system can utilize an algorithm to transpose or transform the registered value to zero. In some embodiments, the system is configured to generate a normalization algorithm based on known values established for particular substances in the compartments of the normalization device 1200, and on the detected/generated values by a medical image scanning device for the same substances in the compartments 1216 of the normalization device 1200. In some embodiments, the normalization device 1200 can be configured to generate a normalization algorithm based on a linear regression model to normalize medical image data to be analyzed. In some embodiments, the normalization device 1200 can be configured to generate a normalization algorithm based on a non-linear regression model to normalize medical image data to be analyzed. In some embodiments, the normalization device 1200 can be configured to generate a normalization algorithm based on any type of model or models, such as an exponential, logarithmic, polynomial, power, moving average, and/or the like, to normalize medical image data to be analyzed. In some embodiments, the normalization algorithm can comprise a two-dimensional transformation. In some embodiments, the normalization algorithm can comprise a three-dimensional transformation to account for other factors such as depth, time, and/or the like.

By using the normalization device 1200 to scan known substances using different machines or the same machine at different times, the system can normalize CT scan data across various scanning machines and/or the same scanning machine at different times. In some embodiments, the normalization device 1200 disclosed herein can be used with any scanning modality including but not limited to x-ray, ultrasound, echocardiogram, magnetic resonance (MR), optical coherence tomography (OCT), intravascular ultrasound (IVUS) and/or nuclear medicine imaging, including positron-emission tomography (PET) and single photon emission computed tomography (SPECT).

In some embodiments, the normalization device 1200 contains one or more materials that form plaque (e.g., studied variable samples 1206) and one or more materials that are used in the contrast that is given to the patient through a vein during examination (e.g., contrast samples 1204). In some embodiments, the materials within the compartments 1216 include iodine of varying concentrations, calcium of varying densities, non-calcified plaque materials or equivalents of varying densities, water, fat, blood or equivalent density material, iron, uric acid, air, gadolinium, tantalum, tungsten, gold, bismuth, ytterbium, and/or other material. In some embodiments, the training of the AI algorithm can be based at least in part on data relating to the density in the images of the normalization device 1200. As such, in some embodiments, the system can have access to and/or have stored pre-existing data on how the normalization device 1200 behaved or was shown in one or more images during the training of the AI algorithm. In some embodiments, the system can use such prior data as a baseline to determine the difference with how the normalization device 1200 behaves in the new or current CT scan to which the AI algorithm is applied to. In some embodiments, the determined difference can be used to calibrate, normalize, and/or map one or more densities in recently acquired image(s) to one or more images that were obtained and/or used during training of the AI algorithm.

As a non-limiting example, in some embodiments, the normalization device 1200 comprises calcium. If, for example, the calcium in the CT or normalization device 1200 that was used to train the AI algorithm(s) showed a density of 300 Hounsfield Units (HU), and if the same calcium showed a density of 600 HU in one or more images of a new scan, then the system, in some embodiments, may be configured to automatically divide all calcium densities in half to normalize or transform the new CT image(s) to be equivalent to the old CT image(s) used to train the AI algorithm.

In some embodiments, as discussed above, the normalization device 1200 comprises a plurality or all materials that may be relevant, which can be advantageous as different materials can change densities in different amounts across scans. For example, if the density of calcium changes 2X across scans, the density of fat may change around 10% across the same scans. As such, it can be advantageous for the normalization device 1200 to comprise a plurality of materials, such as for example one or more materials that make up plaque, blood, contrast, and/or the like.

As described above, in some embodiments, the system can be configured to normalize, map, and/or calibrate density readings and/or CT images obtained from a particular scanner and/or subject proportionally according to changes or differences in density readings and/or CT images obtained from one or more materials of a normalization device 1200 using a baseline scanner compared to density readings and/or CT images obtained from one or more same materials of a normalization device 1200 using the particular scanner and/or subject. As a non-limiting example, for embodiments in which the normalization device 1200 comprises calcium, the system can be configured to apply the same change in density of known calcium between the baseline scan and the new scan, for example 2×, to all other calcium readings of the new scan to calibrate and/or normalize the readings.

In some embodiments, the system can be configured to normalize, map, and/or calibrate density readings and/or CT images obtained from a particular scanner and/or subject by averaging changes or differences between density readings and/or CT images obtained from one or more materials of a normalization device 1200 using a baseline scanner compared to density readings and/or CT images obtained from one or more materials or areas of a subject using the same baseline scanner. As a non-limiting example, for embodiments in which the normalization device 1200 comprises calcium, the system can be configured to determine a difference, or a ratio thereof, in density readings between calcium in the normalization device 1200 and other areas of calcium in the subject during the baseline scan. In some embodiments, the system can be configured to similarly determine a difference, or a ratio thereof, in density readings between calcium in the normalization device 1200 and other areas of calcium in the subject during the new scan; dividing the value of calcium from the device to the value of calcium anywhere else in the image can cancel out any change as the difference in conditions can affect the same material in the same manner.

In some embodiments, the device will account for scan parameters (such as mA or kVp), type and number of x-ray sources within a scanner (such as single source or dual source), temporal resolution of a scanner, spatial resolution of scanner or image, image reconstruction method (such as adaptive statistical iterative reconstruction, model-based iterative reconstruction, machine learning-based iterative reconstruction or similar); image reconstruction method (such as from different types of kernels, overlapping slices from retrospective ECG-helical studies, non-overlapping slices from prospective axial triggered studies, fast pitch helical studies, or half vs. full scan integral reconstruction); contrast density accounting for internal factors (such as oxygen, blood, temperature, and others); contrast density accounting for external factors (such as contrast density, concentration, osmolality and temporal change during the scan); detection technology (such as material, collimation and filtering); spectral imaging (such as polychromatic, monochromatic and spectral imaging along with material basis decomposition and single energy imaging); photon counting; and/or scanner brand and model.

In some embodiments, the normalization device 1200 can be applied to MM studies, and account for one or more of: type of coil; place of positioning, number of antennas; depth from coil elements; image acquisition type; pulse sequence type and characteristics; field strength, gradient strength, slew rate and other hardware characteristics; magnet vendor, brand and type; imaging characteristics (thickness, matrix size, field of view, acceleration factor, reconstruction methods and characteristics, 2D, 3D, 4D [cine imaging, any change over time], temporal resolution, number of acquisitions, diffusion coefficients, method of populating k-space); contrast (intrinsic [oxygen, blood, temperature, etc.] and extrinsic types, volume, temporal change after administration); static or moving materials; quantitative imaging (including T1 T2 mapping, ADC, diffusion, phase contrast, and others); and/or administration of pharmaceuticals during image acquisition.

In some embodiments, the normalization device 1200 can be applied to ultrasound studies, and account for one or more of: type and machine brands; transducer type and frequency; greyscale, color, and pulsed wave doppler; B- or M-mode doppler type; contrast agent; field of view; depth from transducer; pulsed wave deformity (including elastography), angle; imaging characteristics (thickness, matrix size, field of view, acceleration factor, reconstruction methods and characteristics, 2D, 3D, 4D [cine imaging, any change over time]; temporal resolution; number of acquisitions; gain, and/or focus number and places, amongst others.

In some embodiments, the normalization device 1200 can be applied to nuclear medicine studies, such as PET or SPECT and account for one or more of: type and machine brands; for PET/CT all CT applies; for PET/MR all MR applies; contrast (radiopharmaceutical agent types, volume, temporal change after administration); imaging characteristics (thickness, matrix size, field of view, acceleration factor, reconstruction methods and characteristics, 2D, 3D, 4D [cine imaging, any change over time]; temporal resolution; number of acquisitions; gain, and/or focus number and places, amongst others.

In some embodiments, the normalization device may have different known materials with different densities adjacent to each other. This may address any issue present in some CT images where the density of a pixel influences the density of the adjacent pixels and that influence changes with the density of each of the individual pixel. One example of this embodiment being different contrast densities in the coronary lumen influencing the density of the plaque pixels. In some embodiments, the normalization device may include known volumes of known substances to help to correctly evaluate volumes of materials/lesions within the image in order to correct the influence of the blooming artifact on quantitative CT image analysis/measures. In some embodiments, the normalization device might have moving known materials with known volume and known and controllable motion. This would allow to exclude or reduce the effect of motion on quantitative CT image analysis/measures.

In some embodiments, having a known material on the image in the normalization device might also be helpful for material specific reconstructions from the same image. For example, it can be possible to use only one set of images to display only known materials, not needing multiple kV/spectral image hardware.

Figure 12J:
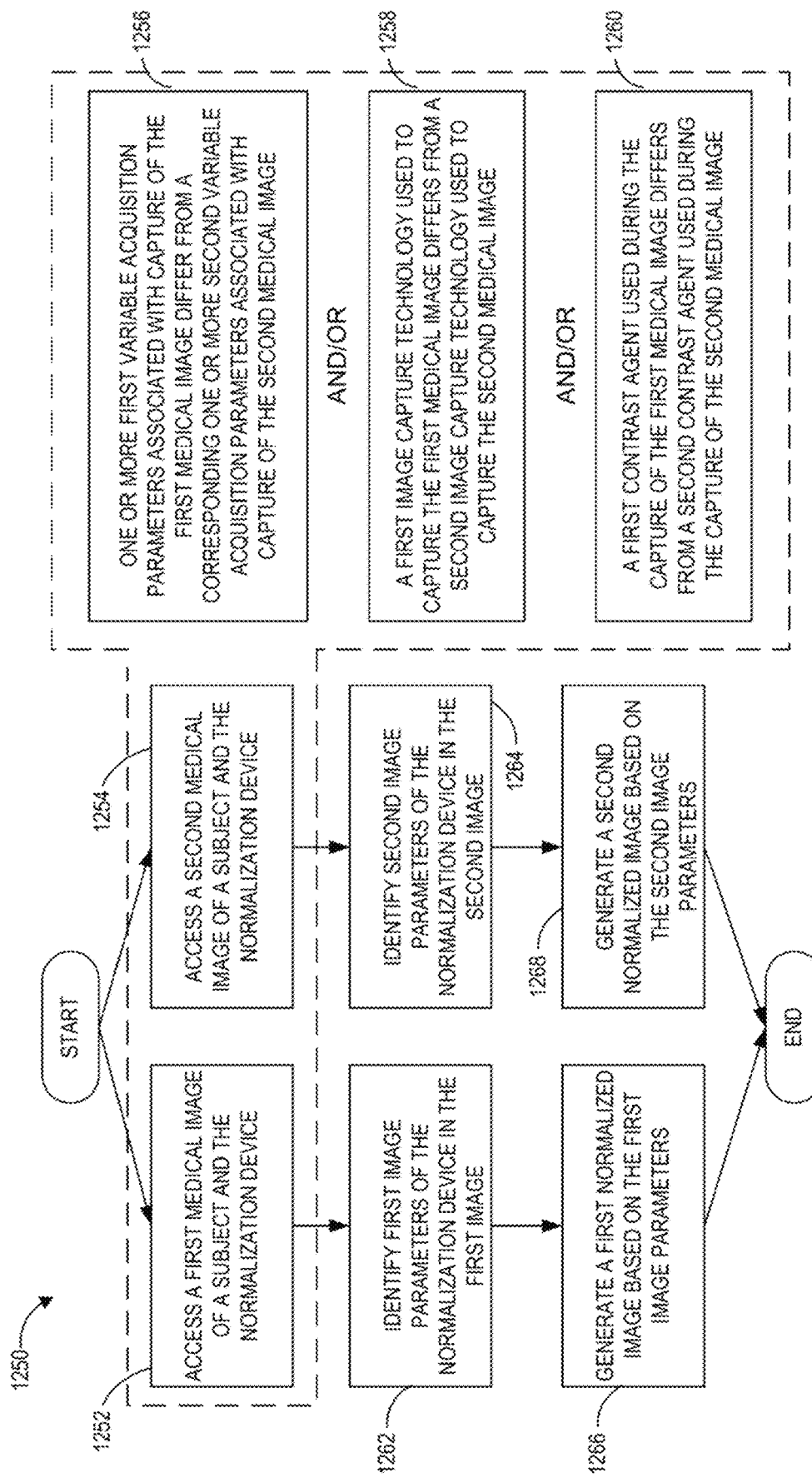
FIG. 12J is a flowchart illustrating an example method for normalizing medical images for an algorithm-based medical imaging analysis, wherein normalization of the medical images improves accuracy of the algorithm-based medical imaging analysis.

FIG. 12J is a flowchart illustrating an example method 1250 for normalizing medical images for an algorithm-based medical imaging analysis such as the analyses described herein. Use of the normalization device can improve accuracy of the algorithm-based medical imaging analysis. The method 1250 can be a computer-implemented method, implemented on a system that comprises a processor and an electronic storage medium. The method 1250 illustrates that the normalization device can be used to normalize medical images captured under different conditions. For example, at block 1252, a first medical image of a coronary region of a subject and the normalization device is accessed. The first medical image can be obtained non-invasively. The normalization device can comprise a substrate comprising a plurality of compartments, each of the plurality of compartments holding a sample of a known material, for example as described above. At block 1254, a second medical image of a coronary region of a subject and the normalization device is captured. The second medical image can be obtained non-invasively. Although the method 1250 is described with reference to a coronary region of a patient, the method is also applicable to all body parts and not only the vessels as the same principles apply to all body parts, all time points and all imaging devices. This can even include "live" type of images such as fluoroscopy or MR real time image.

As illustrated by the portion within the dotted lines, the first medical image and the second medical image can comprise at least one of the following: (1) one or more first variable acquisition parameters associated with capture of the first medical image differ from a corresponding one or more second variable acquisition parameters associated with capture of the second medical image, (2) a first image capture technology used to capture the first medical image differs from a second image capture technology used to capture the second medical image, and (3) a first contrast agent used during the capture of the first medical image differs from a second contrast agent used during the capture of the second medical image.

In some embodiments, the first medical image and the second medical image each comprise a CT image and the one or more first variable acquisition parameters and the one or more second variable acquisition parameters comprise one or more of a kilovoltage (kV), kilovoltage peak (kVp), a milliamperage (mA), or a method of gating. In some embodiments, the method of gating comprises one of prospective axial triggering, retrospective ECG helical gating, and fast pitch helical. In some embodiments, the first image capture technology and the second image capture technology each comprise one of a dual source scanner, a single source scanner, dual energy, monochromatic energy, spectral CT, photon counting, and different detector materials. In some embodiments, the first contrast agent and the second contrast agent each comprise one of an iodine contrast of varying concentration or a non-iodine contrast agent. In some embodiments, the first image capture technology and the second image capture technology each comprise one of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

In some embodiments, a first medical imager that captures the first medical imager is different than a second medical image that capture the second medical image. In some embodiments, the subject of the first medical image is different than the subject of the first medical image. In some embodiments, wherein the subject of the first medical image is the same as the subject of the second medical image. In some embodiments, wherein the subject of the first medical image is different than the subject of the second medical image. In some embodiments, wherein the capture of the first medical image is separated from the capture of the second medical image by at least one day. In some embodiments, wherein the capture of the first medical image is separated from the capture of the second medical image by at least one day. In some embodiments, wherein a location of the capture of the first medical image is geographically separated from a location of the capture of the second medical image.

Accordingly, it is apparent that the first and second medical images can be acquired under different conditions that can cause differences between the two images, even if the subject of each image is the same. The normalization device can help to normalize and account for these differences.

The method 1250 then moves to blocks 1262 and 1264, at which image parameters of the normalization device within the first medical image and which image parameters of the normalization device within the second medical image are identified, respectively. Due to different circumstances under which the first and second medical images were captured, the normalization device may appear differently in each image, even though the normalization device includes the same known samples.

Next, at blocks 1266 and 1268, the method generates a normalized first medical image for the algorithm-based medical imaging analysis based in part on the first identified image parameters of the normalization device within the first medical image and generates a normalized second medical image for the algorithm-based medical imaging analysis based in part on the second identified image parameters of the normalization device within the second medical image, respectively. In these blocks, each image is normalized based on the appearance or determined parameters of the normalization device in each image.

In some embodiments, the algorithm-based medical imaging analysis comprises an artificial intelligence or machine learning imaging analysis algorithm, and the artificial intelligence or machine learning imaging analysis algorithm was trained using images that included the normalization device.

System Overview

Figure 13:
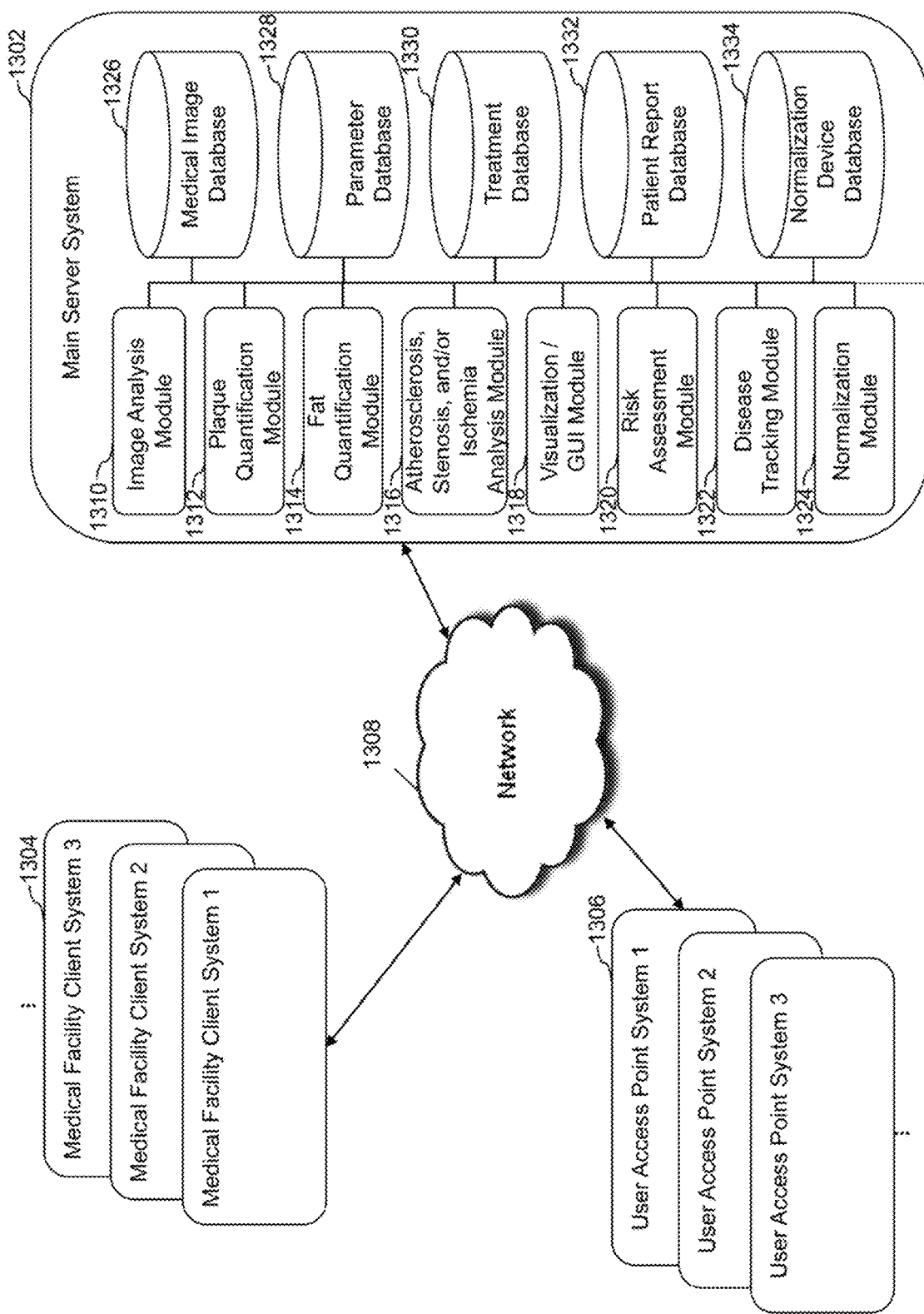
FIG. 13 is a block diagram depicting an embodiment(s) of a system for medical image analysis, visualization, risk assessment, disease tracking, treatment generation, and/or patient report generation.

In some embodiments, the systems, devices, and methods described herein are implemented using a network of one or more computer systems, such as the one illustrated in FIG. 13. FIG. 13 is a block diagram depicting an embodiment(s) of a system for medical image analysis, visualization, risk assessment, disease tracking, treatment generation, and/or patient report generation.

As illustrated in FIG. 13, in some embodiments, a main server system 1302 is configured to perform one or more processes, analytics, and/or techniques described herein, some of which relating to medical image analysis, visualization, risk assessment, disease tracking, treatment generation, and/or patient report generation. In some embodiments, the main server system 1302 is connected via an electronic communications network 1308 to one or more medical facility client systems 1304 and/or one or more user access point systems 1306. For example, in some embodiments, one or more medical facility client systems 1304 can be configured to access a medical image taken at the medical facility of a subject, which can then be transmitted to the main server system 1302 via the network 1308 for further analysis. After analysis, in some embodiments, the analysis results, such as for example quantified plaque parameters, assessed risk of a cardiovascular event, generated report, annotated and/or derived medical images, and/or the like, can be transmitted back to the medical facility client system 1304 via the network 1308. In some embodiments, the analysis results, such as for example quantified plaque parameters, assessed risk of a cardiovascular event, generated report, annotated and/or derived medical images, and/or the like, can be transmitted also to a user access point system 1306, such as a smartphone or other computing device of the patient or subject. As such, in some embodiments, a patient can be allowed to view and/or access a patient-specific report and/or other analyses generated and/or derived by the system from the medical image on the patient's computing device.

In some embodiments, the main server system 1302 can comprise and/or be configured to access one or more modules and/or databases for performing the one or more processes, analytics, and/or techniques described herein. For example, in some embodiments, the main server system 1302 can comprise an image analysis module 1310, a plaque quantification module 1312, a fat quantification module 1314, an atherosclerosis, stenosis, and/or ischemia analysis module 1316, a visualization/GUI module 1318, a risk assessment module 1320, a disease tracking module 1322, a normalization module 1324, a medical image database 1326, a parameter database 1328, a treatment database 1330, a patient report database 1332, a normalization device database 1334, and/or the like.

In some embodiments, the image analysis module 1310 can be configured to perform one or more processes described herein relating to image analysis, such as for example vessel and/or plaque identification from a raw medical image. In some embodiments, the plaque quantification module 1312 can be configured to perform one or more processes described herein relating to deriving or generating quantified plaque parameters, such as for example radiodensity, volume, heterogeneity, and/or the like of plaque from a raw medical image. In some embodiments, the fat quantification module 1314 can be configured to perform one or more processes described herein relating to deriving or generating quantified fat parameters, such as for example radiodensity, volume, heterogeneity, and/or the like of fat from a raw medical image. In some embodiments, the atherosclerosis, stenosis, and/or ischemia analysis module 1316 can be configured to perform one or more processes described herein relating to analyzing and/or generating an assessment or quantification of atherosclerosis, stenosis, and/or ischemia from a raw medical image. In some embodiments, the visualization/GUI module 1318 can be configured to perform one or more processes described herein relating to deriving or generating one or more visualizations and/or GUIs, such as for example a straightened view of a vessel identifying areas of good and/or bad plaque from a raw medical image. In some embodiments, the risk assessment module 1320 can be configured to perform one or more processes described herein relating to deriving or generating risk assessment, such as for example of a cardiovascular event or disease from a raw medical image. In some embodiments, the disease tracking module 1322 can be configured to perform one or more processes described herein relating to tracking a plaque-based disease, such as for example atherosclerosis, stenosis, ischemia, and/or the like from a raw medical image. In some embodiments, the normalization module 1324 can be configured to perform one or more processes described herein relating to normalizing and/or translating a medical image, for example based on a medical image of a normalization device comprising known materials, for further processing and/or analysis.

In some embodiments, the medical image database 1326 can comprise one or more medical images that are used for one or more of the various analysis techniques and processes described herein. In some embodiments, the parameter database 1328 can comprise one or more parameters derived from raw medical images by the system, such as for example one or more vessel morphology parameters, quantified plaque parameters, quantified fat parameters, and/or the like. In some embodiments, the treatment database 1328 can comprise one or more recommended treatments derived from raw medical images by the system. In some embodiments, the patient report database 1332 can comprise one or more patient-specific reports derived from raw medical images by the system and/or one or more components thereof that can be used to generate a patient-specific report based on medical image analysis results. In some embodiments, the normalization database 1334 can comprise one or more historical data points and/or datasets of normalizing various medical images and/or the specific types of medical imaging scanners and/or specific scan parameters used to obtain those images, as well as previously used normalization variables and/or translations for different medical images.

Computer System

Figure 14:
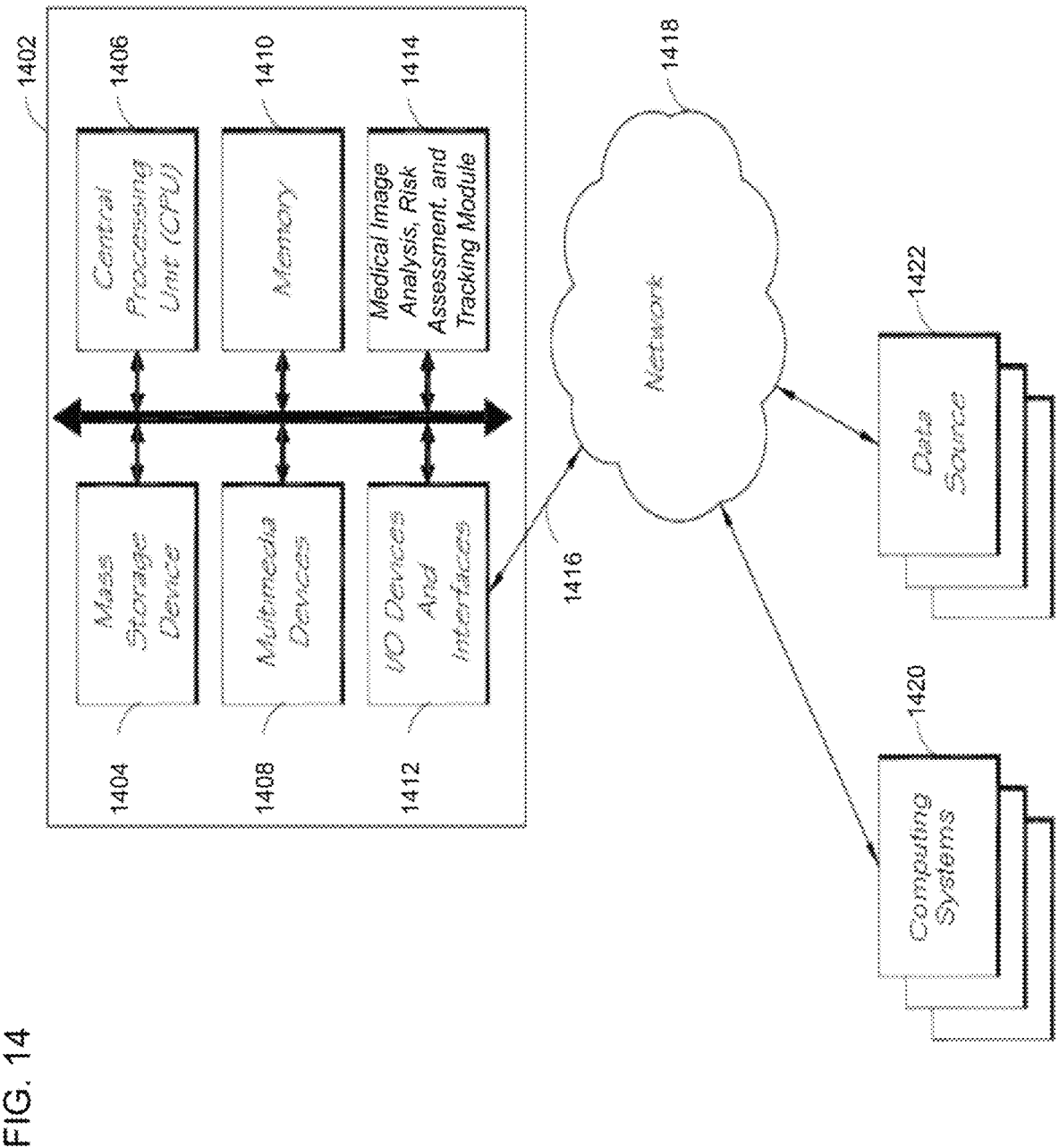
FIG. 14 is a block diagram depicting an embodiment(s) of a computer hardware system configured to run software for implementing one or more embodiments of a system for medical image analysis, visualization, risk assessment, disease tracking, treatment generation, and/or patient report generation.

In some embodiments, the systems, processes, and methods described herein are implemented using a computing system, such as the one illustrated in FIG. 14. The example computer system 1402 is in communication with one or more computing systems 1420 and/or one or more data sources 1422 via one or more networks 1418. While FIG. 14 illustrates an embodiment of a computing system 1402, it is recognized that the functionality provided for in the components and modules of computer system 1402 may be combined into fewer components and modules, or further separated into additional components and modules.

The computer system 1402 can comprise a Medical Analysis, Risk Assessment, and Tracking Module 1414 that carries out the functions, methods, acts, and/or processes described herein. The Medical Analysis, Risk Assessment, and Tracking Module 1414 is executed on the computer system 1402 by a central processing unit 1406 discussed further below.

In general the word "module," as used herein, refers to logic embodied in hardware or firmware or to a collection of software instructions, having entry and exit points. Modules are written in a program language, such as JAVA, C or C++, PYTHON or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems, and may be stored on or within any suitable computer readable medium, or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 1402 includes one or more processing units (CPU) 1406, which may comprise a microprocessor. The computer system 1402 further includes a physical memory 1410, such as random access memory (RAM) for temporary storage of information, a read only memory (ROM) for permanent storage of information, and a mass storage device 1404, such as a backing store, hard drive, rotating magnetic disks, solid state disks (SSD), flash memory, phase-change memory (PCM), 3D XPoint memory, diskette, or optical media storage device. Alternatively, the mass storage device may be implemented in an array of servers. Typically, the components of the computer system 1402 are connected to the computer using a standards based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1402 includes one or more input/output (I/O) devices and interfaces 1412, such as a keyboard, mouse, touch pad, and printer. The I/O devices and interfaces 1412 can include one or more display devices, such as a monitor, that allows the visual presentation of data to a user. More particularly, a display device provides for the presentation of GUIs as application software data, and multi-media presentations, for example. The I/O devices and interfaces 1412 can also provide a communications interface to various external devices. The computer system 1402 may comprise one or more multi-media devices 1408, such as speakers, video cards, graphics accelerators, and microphones, for example.

The computer system 1402 may run on a variety of computing devices, such as a server, a Windows server, a Structure Query Language server, a Unix Server, a personal computer, a laptop computer, and so forth. In other embodiments, the computer system 1402 may run on a cluster computer system, a mainframe computer system and/or other computing system suitable for controlling and/or communicating with large databases, performing high volume transaction processing, and generating reports from large databases. The computing system 1402 is generally controlled and coordinated by an operating system software, such as z/OS, Windows, Linux, UNIX, BSD, SunOS, Solaris, MacOS, or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 1402 illustrated in FIG. 14 is coupled to a network 1418, such as a LAN, WAN, or the Internet via a communication link 1416 (wired, wireless, or a combination thereof). Network 1418 communicates with various computing devices and/or other electronic devices. Network 1418 is communicating with one or more computing systems 1420 and one or more data sources 1422. The Medical Analysis, Risk Assessment, and Tracking Module 1414 may access or may be accessed by computing systems 1420 and/or data sources 1422 through a web-enabled user access point. Connections may be a direct physical connection, a virtual connection, and other connection type. The web-enabled user access point may comprise a browser module that uses text, graphics, audio, video, and other media to present data and to allow interaction with data via the network 1418.

Access to the Medical Analysis, Risk Assessment, and Tracking Module 1414 of the computer system 1402 by computing systems 1420 and/or by data sources 1422 may be through a web-enabled user access point such as the computing systems' 1420 or data source's 1422 personal computer, cellular phone, smartphone, laptop, tablet computer, e-reader device, audio player, or other device capable of connecting to the network 1418. Such a device may have a browser module that is implemented as a module that uses text, graphics, audio, video, and other media to present data and to allow interaction with data via the network 1418.

The output module may be implemented as a combination of an all-points addressable display such as a cathode ray tube (CRT), a liquid crystal display (LCD), a plasma display, or other types and/or combinations of displays. The output module may be implemented to communicate with input devices 1412 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 1402 may comprise a physical or logical connection established between a remote microprocessor and a mainframe host computer for the express purpose of uploading, downloading, or viewing interactive data and databases on-line in real time. The remote microprocessor may be operated by an entity operating the computer system 1402, including the client server systems or the main server system, and/or may be operated by one or more of the data sources 1422 and/or one or more of the computing systems 1420. In some embodiments, terminal emulation software may be used on the microprocessor for participating in the micro-mainframe link.

In some embodiments, computing systems 1420 who are internal to an entity operating the computer system 1402 may access the Medical Analysis, Risk Assessment, and Tracking Module 1414 internally as an application or process run by the CPU 1406.

The computing system 1402 may include one or more internal and/or external data sources (for example, data sources 1422). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 1402 may also access one or more databases 1422. The databases 1422 may be stored in a database or data repository. The computer system 1402 may access the one or more databases 1422 through a network 1418 or may directly access the database or data repository through I/O devices and interfaces 1412. The data repository storing the one or more databases 1422 may reside within the computer system 1402.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

Example Embodiments

The following are non-limiting examples of certain embodiments of systems and methods of characterizing coronary plaque. Other embodiments may include one or more other features, or different features, that are discussed herein.

Embodiment 1: A computer-implemented method of quantifying and classifying coronary plaque within a coronary region of a subject based on non-invasive medical image analysis, the method comprising: accessing, by a computer system, a medical image of a coronary region of a subject, wherein the medical image of the coronary region of the subject is obtained non-invasively; identifying, by the computer system utilizing a coronary artery identification algorithm, one or more coronary arteries within the medical image of the coronary region of the subject, wherein the coronary artery identification algorithm is configured to utilize raw medical images as input; identifying, by the computer system utilizing a plaque identification algorithm, one or more regions of plaque within the one or more coronary arteries identified from the medical image of the coronary region of the subject, wherein the plaque identification algorithm is configured to utilize raw medical images as input; determining, by the computer system, one or more vascular morphology parameters and a set of quantified plaque parameters of the one or more identified regions of plaque from the medical image of the coronary region of the subject, wherein the set of quantified plaque parameters comprises a ratio or function of volume to surface area, heterogeneity index, geometry, and radiodensity of the one or more regions of plaque within the medical image; generating, by the computer system, a weighted measure of the determined one or more vascular morphology parameters and the set of quantified plaque parameters of the one or more regions of plaque; and classifying, by the computer system, the one or more regions of plaque within the medical image as stable plaque or unstable plaque based at least in part on the generated weighted measure of the determined one or more vascular morphology parameters and the determined set of quantified plaque parameters, wherein the computer system comprises a computer processor and an electronic storage medium.

Embodiment 2: The computer-implemented method of Embodiment 1, wherein one or more of the coronary artery identification algorithm or the plaque identification algorithm comprises an artificial intelligence or machine learning algorithm.

Embodiment 3: The computer-implemented method of any one of Embodiments 1 or 2, wherein the plaque identification algorithm is configured to determine the one or more regions of plaque by determining a vessel wall and lumen wall of the one or more coronary arteries and determining a volume between the vessel wall and lumen wall as the one or more regions of plaque.

Embodiment 4: The computer-implemented method of any one of Embodiments 1-3, wherein the one or more coronary arteries are identified by size.

Embodiment 5: The computer-implemented method of any one of Embodiments 1-4, wherein a ratio of volume to surface area of the one or more regions of plaque below a predetermined threshold is indicative of stable plaque.

Embodiment 6: The computer-implemented method of any one of Embodiments 1-5, wherein a radiodensity of the one or more regions of plaque above a predetermined threshold is indicative of stable plaque.

Embodiment 7: The computer-implemented method of any one of Embodiments 1-6, wherein a heterogeneity of the one or more regions of plaque below a predetermined threshold is indicative of stable plaque.

Embodiment 8: The computer-implemented method of any one of Embodiments 1-7, wherein the set of quantified plaque parameters further comprises diffusivity of the one or more regions of plaque.

Embodiment 9: The computer-implemented method of any one of Embodiments 1-8, wherein the set of quantified plaque parameters further comprises a ratio of radiodensity to volume of the one or more regions of plaque.

Embodiment 10: The computer-implemented method of any one of Embodiments 1-9, further comprising generating, by the computer system, a proposed treatment for the subject based at least in part on the classified one or more regions of plaque.

Embodiment 11: The computer-implemented method of any one of Embodiments 1-10, further comprising generating, by the computer system, an assessment of the subject for one or more of atherosclerosis, stenosis, or ischemia based at least in part on the classified one or more regions of plaque.

Embodiment 12: The computer-implemented method of any one of Embodiments 1-11, wherein the medical image comprises a Computed Tomography (CT) image.

Embodiment 13: The computer-implemented method of Embodiment 12, wherein the medical image comprises a non-contrast CT image.

Embodiment 14: The computer-implemented method of Embodiment 12, wherein the medical image comprises a contrast-enhanced CT image.

Embodiment 15: The computer-implemented method of any one of Embodiments 1-11, wherein the medical image comprises a Magnetic Resonance (MR) image.

Embodiment 16: The computer-implemented method of any one of Embodiments 1-11, wherein the medical image is obtained using an imaging technique comprising one or more of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

Embodiment 17: The computer-implemented method of any one of Embodiments 1-16, wherein the heterogeneity index of one or more regions of plaque is determined by generating a three-dimensional histogram of radiodensity values across a geometric shape of the one or more regions of plaque.

Embodiment 18: The computer-implemented method of any one of Embodiments 1-17, wherein the heterogeneity index of one or more regions of plaque is determined by generating spatial mapping of radiodensity values across the one or more regions of plaque.

Embodiment 19: The computer-implemented method of any one of Embodiments 1-18, wherein the set of quantified plaque parameters comprises a percentage composition of plaque comprising different radiodensity values.

Embodiment 20: The computer-implemented method of any one of Embodiments 1-19, wherein the set of quantified plaque parameters comprises a percentage composition of plaque comprising different radiodensity values as a function of volume of plaque.

Embodiment 21: The computer-implemented method of any one of Embodiments 1-20, wherein the geometry of the one or more regions of plaque comprises a round or oblong shape.

Embodiment 22: The computer-implemented method of any one of Embodiments 1-21, wherein the one or more vascular morphology parameters comprises a classification of arterial remodeling.

Embodiment 23: The computer-implemented method of Embodiment 22, wherein the classification of arterial remodeling comprises positive arterial remodeling, negative arterial remodeling, and intermediate arterial remodeling.

Embodiment 24: The computer-implemented method of Embodiment 22, wherein the classification of arterial remodeling is determined based at least in part on a ratio of a largest vessel diameter at the one or more regions of plaque to a normal reference vessel diameter.

Embodiment 25: The computer-implemented method of Embodiment 23, wherein the classification of arterial remodeling comprises positive arterial remodeling, negative arterial remodeling, and intermediate arterial remodeling, and wherein positive arterial remodeling is determined when the ratio of the largest vessel diameter at the one or more regions of plaque to the normal reference vessel diameter is more than 1.1, wherein negative arterial remodeling is determined when the ratio of the largest vessel diameter at the one or more regions of plaque to the normal reference vessel diameter is less than 0.95, and wherein intermediate arterial remodeling is determined when the ratio of the largest vessel diameter at the one or more regions of plaque to the normal reference vessel diameter is between 0.95 and 1.1.

Embodiment 26: The computer-implemented method of any one of Embodiments 1-25, wherein the function of volume to surface area of the one or more regions of plaque comprises one or more of a thickness or diameter of the one or more regions of plaque.

Embodiment 27: The computer-implemented method of any one of Embodiments 1-26, wherein the weighted measure is generated by weighting the one or more vascular morphology parameters and the set of quantified plaque parameters of the one or more regions of plaque equally.

Embodiment 28: The computer-implemented method of any one of Embodiments 1-26, wherein the weighted measure is generated by weighting the one or more vascular morphology parameters and the set of quantified plaque parameters of the one or more regions of plaque differently.

Embodiment 29: The computer-implemented method of any one of Embodiments 1-26, wherein the weighted measure is generated by weighting the one or more vascular morphology parameters and the set of quantified plaque parameters of the one or more regions of plaque logarithmically, algebraically, or utilizing another mathematical transform.

Embodiment 30: A computer-implemented method of quantifying and classifying vascular plaque based on non-invasive medical image analysis, the method comprising: accessing, by a computer system, a medical image of a subject, wherein the medical image of the subject is obtained non-invasively; identifying, by the computer system utilizing an artery identification algorithm, one or more arteries within the medical image of the subject, wherein the artery identification algorithm is configured to utilize raw medical images as input; identifying, by the computer system utilizing a plaque identification algorithm, one or more regions of plaque within the one or more arteries identified from the medical image of the subject, wherein the plaque identification algorithm is configured to utilize raw medical images as input; determining, by the computer system, one or more vascular morphology parameters and a set of quantified plaque parameters of the one or more identified regions of plaque from the medical image of the subject, wherein the set of quantified plaque parameters comprises a ratio or function of volume to surface area, heterogeneity index, geometry, and radiodensity of the one or more regions of plaque from the medical image; generating, by the computer system, a weighted measure of the determined one or more vascular morphology parameters and the set of quantified plaque parameters of the one or more regions of plaque; and classifying, by the computer system, the one or more regions of plaque within the medical image as stable plaque or unstable plaque based at least in part on the generated weighted measure of the determined one or more vascular morphology and the determined set of quantified plaque parameters, wherein the computer system comprises a computer processor and an electronic storage medium.

Embodiment 31: The computer-implemented method of Embodiment 30, wherein the identified one or more arteries comprise one or more of carotid arteries, aorta, renal artery, lower extremity artery, or cerebral artery.

Embodiment 32: A computer-implemented method of determining non-calcified plaque from a non-contrast Computed Tomography (CT) image, the method comprising: accessing, by a computer system, a non-contrast CT image of a coronary region of a subject; identifying, by the computer system, epicardial fat on the non-contrast CT image; segmenting, by the computer system, arteries on the non-contrast CT image using the identified epicardial fat as outer boundaries of the arteries; identifying, by the computer system, a first set of pixels within the arteries on the non-contrast CT image comprising a Hounsfield unit radiodensity value below a predetermined radiodensity threshold; classifying, by the computer system, the first set of pixels as a first subset of non-calcified plaque; identifying, by the computer system, a second set of pixels within the arteries on the non-contrast CT image comprising a Hounsfield unit radiodensity value within a predetermined radiodensity range; determining, by the computer system, a heterogeneity index of the second set of pixels and identifying a subset of the second set of pixels comprising a heterogeneity index above a heterogeneity index threshold;

classifying, by the computer system, the subset of the second set of pixels as a second subset of non-calcified plaque; and determining, by the computer system, non-calcified plaque from the non-contrast CT image by combining the first subset of non-calcified plaque and the second subset of non-calcified plaque, wherein the computer system comprises a computer processor and an electronic storage medium.

Embodiment 33: The computer-implemented method of Embodiment 32, wherein the predetermined radiodensity threshold comprises a Hounsfield unit radiodensity value of 30.

Embodiment 34: The computer-implemented method of any one of Embodiments 32-33, wherein the predetermined radiodensity range comprises Hounsfield unit radiodensity values between 30 and 100.

Embodiment 35: The computer-implemented method of any one of Embodiments 32-34, wherein identifying epicardial fat on the non-contrast CT image further comprises: determining a Hounsfield unit radiodensity value of each pixel within the non-contrast CT image; and classifying as epicardial fat pixels within the non-contrast CT image with a Hounsfield unit radiodensity value within a predetermined epicardial fat radiodensity range, wherein the predetermined epicardial fat radiodensity range comprises a Hounsfield unit radiodensity value of −100.

Embodiment 36: The computer-implemented method of any one of Embodiments 32-35, wherein the heterogeneity index of the second set of pixels is determined by generating spatial mapping of radiodensity values of the second set of pixels.

Embodiment 37: The computer-implemented method of any one of Embodiments 32-36, wherein the heterogeneity index of the second set of pixels is determined by generating a three-dimensional histogram of radiodensity values across a geometric region within the second set of pixels.

Embodiment 38: The computer-implemented method of any one of Embodiments 32-37, further comprising classifying, by the computer system, a subset of the second set of pixels comprising a heterogeneity index below the heterogeneity index threshold as blood.

Embodiment 39: The computer-implemented method of any one of Embodiments 32-38, further comprising generating a quantized color map of the coronary region of the subject by assigning a first color to the identified epicardial fat, assigning a second color to the segmented arteries, and assigning a third color to the determined non-calcified plaque.

Embodiment 40: The computer-implemented method of any one of Embodiments 32-39, further comprising: identifying, by the computer system, a third set of pixels within the arteries on the non-contrast CT image comprising a Hounsfield unit radiodensity value above a predetermined calcified radiodensity threshold; and classifying, by the computer system, the third set of pixels as calcified plaque.

Embodiment 41: The computer-implemented method of any one of Embodiments 32-40, further comprising determining, by the computer system, a proposed treatment based at least in part on the determined non-calcified plaque.

Embodiment 42: A computer-implemented method of determining low-attenuated plaque from a medical image of a subject, the method comprising: accessing, by a computer system, a medical image of a subject; identifying, by the computer system, epicardial fat on the medical image of the subject by: determining a radiodensity value of each pixel within the medical image of the subject; and classifying as epicardial fat pixels within the medical image of the subject with a radiodensity value within a predetermined epicardial fat radiodensity range; segmenting, by the computer system, arteries on the medical image of the subject using the identified epicardial fat as outer boundaries of the arteries; identifying, by the computer system, a first set of pixels within the arteries on the medical image of the subject comprising a radiodensity value below a predetermined radiodensity threshold; classifying, by the computer system, the first set of pixels as a first subset of low-attenuated plaque; identifying, by the computer system, a second set of pixels within the arteries on the non-contrast CT image comprising a radiodensity value within a predetermined radiodensity range; determining, by the computer system, a heterogeneity index of the second set of pixels and identifying a subset of the second set of pixels comprising a heterogeneity index above a heterogeneity index threshold; classifying, by the computer system, the subset of the second set of pixels as a second subset of low-attenuated plaque; and determining, by the computer system, low-attenuated plaque from the medical image of the subject by combining the first subset of low-attenuated plaque and the second subset of low-attenuated plaque, wherein the computer system comprises a computer processor and an electronic storage medium.

Embodiment 43: The computer-implemented method of Embodiment 42, wherein the medical image comprises a Computed Tomography (CT) image.

Embodiment 44: The computer-implemented method of Embodiment 42, wherein the medical image comprises a Magnetic Resonance (MR) image.

Embodiment 45: The computer-implemented method of Embodiment 42, wherein the medical image comprises an ultrasound image.

Embodiment 46: The computer-implemented method of any one of Embodiments 42-45, wherein the medical image comprises an image of a coronary region of the subject.

Embodiment 47: The computer-implemented method of any one of Embodiments 42-46, further comprising determining, by the computer system, a proposed treatment for a disease based at least in part on the determined low-attenuated plaque.

Embodiment 48: The computer-implemented method of Embodiment 47, wherein the disease comprises one or more of arterial disease, renal artery disease, abdominal atherosclerosis, or carotid atherosclerosis.

Embodiment 49: The computer-implemented method of any one of Embodiments 42-48, wherein the heterogeneity index of the second set of pixels is determined by generating spatial mapping of radiodensity values of the second set of pixels.

Embodiment 50: A computer-implemented method of determining non-calcified plaque from a Dual-Energy Computed Tomography (DECT) image or spectral Computed Tomography (CT) image, the method comprising: accessing, by a computer system, a DECT or spectral CT image of a coronary region of a subject; identifying, by the computer system, epicardial fat on the DECT image or spectral CT; segmenting, by the computer system, arteries on the DECT image or spectral CT; identifying, by the computer system, a first set of pixels within the arteries on the DECT or spectral CT image comprising a Hounsfield unit radiodensity value below a predetermined radiodensity threshold; classifying, by the computer system, the first set of pixels as a first subset of non-calcified plaque; identifying, by the computer system, a second set of pixels within the arteries on the DECT or spectral CT image comprising a Hounsfield unit radiodensity value within a predetermined radiodensity range; classifying, by the computer system, a subset of the second set of pixels as a second subset of non-calcified plaque; and determining, by the computer system, non-calcified plaque from the DECT image or spectral CT by combining the first subset of non-calcified plaque and the second subset of non-calcified plaque, wherein the computer system comprises a computer processor and an electronic storage medium.

Embodiment 51: The computer-implemented method of Embodiment 50, wherein the subset of the second set of pixels is identified by determining, by the computer system, a heterogeneity index of the second set of pixels and identifying the subset of the second set of pixels comprising a heterogeneity index above a heterogeneity index threshold.

Embodiment 52: A computer-implemented method of assessing risk of a cardiovascular event for a subject based on non-invasive medical image analysis, the method comprising: accessing, by a computer system, a medical image of a coronary region of a subject, wherein the medical image of the coronary region of the subject is obtained non-invasively; identifying, by the computer system utilizing a coronary artery identification algorithm, one or more coronary arteries within the medical image of the coronary region of the subject, wherein the coronary artery identification algorithm is configured to utilize raw medical images as input; identifying, by the computer system utilizing a plaque identification algorithm, one or more regions of plaque within the one or more coronary arteries identified from the medical image of the coronary region of the subject, wherein the plaque identification algorithm is configured to utilize raw medical images as input; determining, by the computer system, one or more vascular morphology parameters and a set of quantified plaque parameters of the one or more identified regions of plaque from the medical image of the coronary region of the subject, wherein the set of quantified plaque parameters comprises a ratio or function of volume to surface area, heterogeneity index, geometry, and radiodensity of the one or more regions of plaque within the medical image; generating, by the computer system, a weighted measure of the determined one or more vascular morphology parameters and the set of quantified plaque parameters of the one or more regions of plaque; classifying, by the computer system, the one or more regions of plaque within the medical image as stable plaque or unstable plaque based at least in part on the generated weighted measure of the determined one or more vascular morphology parameters and the determined set of quantified plaque parameters; generating, by the computer system, a risk of cardiovascular event for the subject based at least in part on the one or more regions of plaque classified as stable plaque or unstable plaque; accessing, by the computer system, a coronary values database comprising one or more known datasets of coronary values derived from one or more other subjects and comparing the one or more regions of plaque classified as stable plaque or unstable plaque to the one or more known datasets of coronary values; updating, by the computer system, the generated risk of cardiovascular event for the subject based at least in part on the comparison of the one or more regions of plaque classified as stable plaque or unstable plaque to the one or more known datasets of coronary values; and generating, by the computer system, a proposed treatment for the subject based at least in part on the comparison of the one or more regions of plaque classified as stable plaque or unstable plaque to the one or more known datasets of coronary values, wherein the computer system comprises a computer processor and an electronic storage medium.

Embodiment 53: The computer-implemented method of Embodiment 52, wherein the cardiovascular event comprises one or more of a Major Adverse Cardiovascular Event (MACE), rapid plaque progression, or non-response to medication.

Embodiment 54: The computer-implemented method of any one of Embodiments 52-53, wherein the one or more known datasets of coronary values comprises one or more parameters of stable plaque and unstable plaque derived from medical images of healthy subjects.

Embodiment 55: The computer-implemented method of any one of Embodiments 52-54, wherein the one or more other subjects are healthy.

Embodiment 56: The computer-implemented method of any one of Embodiments 52-55, wherein the one or more other subjects have a heightened risk of a cardiovascular event.

Embodiment 57: The computer-implemented method of any one of Embodiments 52-57, further comprising: identifying, by the computer system, one or more additional cardiovascular structures within the medical image, wherein the one or more additional cardiovascular structures comprise one or more of the left ventricle, right ventricle, left atrium, right atrium, aortic valve, mitral valve, tricuspid valve, pulmonic valve, aorta, pulmonary artery, inferior and superior vena cava, epicardial fat, or pericardium; determining, by the computer system, one or more parameters associated with the identified one or more additional cardiovascular structures; classifying, by the computer system, the one or more additional cardiovascular structures based at least in part on the determined one or more parameters; accessing, by the computer system, a cardiovascular structures values database comprising one or more known datasets of cardiovascular structures parameters derived from medical images of one or more other subjects and comparing the classified one or more additional cardiovascular structures to the one or more known datasets of cardiovascular structures parameters; and updating, by the computer system, the generated risk of cardiovascular event for the subject based at least in part on the comparison of the classified one or more additional cardiovascular structures to the one or more known datasets of cardiovascular structures parameters.

Embodiment 58: The computer-implemented method of Embodiment 57, wherein the one or more additional cardiovascular structures are classified as normal or abnormal.

Embodiment 59: The computer-implemented method of Embodiment 57, wherein the one or more additional cardiovascular structures are classified as increased or decreased.

Embodiment 60: The computer-implemented method of Embodiment 57, wherein the one or more additional cardiovascular structures are classified as static or dynamic over time.

Embodiment 61: The computer-implemented method of any one of Embodiments 57-60, further comprising generating, by the computer system, a quantized color map for the additional cardiovascular structures.

Embodiment 62: The computer-implemented method of any one of Embodiments 57-61, further comprising updating, by the computer system, the proposed treatment for the subject based at least in part on the comparison of the classified one or more additional cardiovascular structures to the one or more known datasets of cardiovascular structures parameters.

Embodiment 63: The computer-implemented method of any one of Embodiments 57-62, further comprising: identifying, by the computer system, one or more non-cardiovascular structures within the medical image, wherein the one or more non-cardiovascular structures comprise one or more of the lungs, bones, or liver; determining, by the computer system, one or more parameters associated with the identified one or more non-cardiovascular structures; classifying, by the computer system, the one or more non-cardiovascular structures based at least in part on the determined one or more parameters; accessing, by the computer system, a non-cardiovascular structures values database comprising one or more known datasets of non-cardiovascular structures parameters derived from medical images of one or more other subjects and comparing the classified one or more non-cardiovascular structures to the one or more known datasets of non-cardiovascular structures parameters; and updating, by the computer system, the generated risk of cardiovascular event for the subject based at least in part on the comparison of the classified one or more non-cardiovascular structures to the one or more known datasets of non-cardiovascular structures parameters.

Embodiment 64: The computer-implemented method of Embodiment 63, wherein the one or more non-cardiovascular structures are classified as normal or abnormal.

Embodiment 65: The computer-implemented method of Embodiment 63, wherein the one or more non-cardiovascular structures are classified as increased or decreased.

Embodiment 66: The computer-implemented method of Embodiment 63, wherein the one or more non-cardiovascular structures are classified as static or dynamic over time.

Embodiment 67: The computer-implemented method of any one of Embodiments 63-66, further comprising generating, by the computer system, a quantized color map for the non-cardiovascular structures.

Embodiment 68: The computer-implemented method of any one of Embodiments 63-67, further comprising updating, by the computer system, the proposed treatment for the subject based at least in part on the comparison of the classified one or more non-cardiovascular structures to the one or more known datasets of non-cardiovascular structures parameters.

Embodiment 69: The computer-implemented method of any one of Embodiments 63-68, wherein the one or more parameters associated with the identified one or more non-cardiovascular structures comprises one or more of ratio of volume to surface area, heterogeneity, radiodensity, or geometry of the identified one or more non-cardiovascular structures.

Embodiment 70: The computer-implemented method of any one of Embodiments 52-69, wherein the medical image comprises a Computed Tomography (CT) image.

Embodiment 71: The computer-implemented method of any one of Embodiments 52-69, wherein the medical image comprises a Magnetic Resonance (MR) image.

Embodiment 72: A computer-implemented method of quantifying and classifying coronary atherosclerosis within a coronary region of a subject based on non-invasive medical image analysis, the method comprising: accessing, by a computer system, a medical image of a coronary region of a subject, wherein the medical image of the coronary region of the subject is obtained non-invasively; identifying, by the computer system utilizing a coronary artery identification algorithm, one or more coronary arteries within the medical image of the coronary region of the subject, wherein the coronary artery identification algorithm is configured to utilize raw medical images as input; identifying, by the computer system utilizing a plaque identification algorithm, one or more regions of plaque within the one or more coronary arteries identified from the medical image of the coronary region of the subject, wherein the plaque identification algorithm is configured to utilize raw medical images as input; determining, by the computer system, one or more vascular morphology parameters and a set of quantified plaque parameters of the one or more identified regions of plaque from the medical image of the coronary region of the subject, wherein the set of quantified plaque parameters comprises a ratio or function of volume to surface area, heterogeneity index, geometry, and radiodensity of the one or more regions of plaque within the medical image; generating, by the computer system, a weighted measure of the determined one or more vascular morphology parameters and the set of quantified plaque parameters of the one or more regions of plaque; quantifying, by the computer system, coronary atherosclerosis of the subject based at least in part on the set of generated weighted measure of the determined one or more vascular morphology parameters and the determined quantified plaque parameters; and classifying, by the computer system, coronary atherosclerosis of the subject as one or more of high risk, medium risk, or low risk based at least in part on the quantified coronary atherosclerosis of the subject, wherein the computer system comprises a computer processor and an electronic storage medium.

Embodiment 73: The computer-implemented method of Embodiment 72, wherein one or more of the coronary artery identification algorithm or the plaque identification algorithm comprises an artificial intelligence or machine learning algorithm.

Embodiment 74: The computer-implemented method of any one of Embodiments 72 or 73, further comprising determining a numerical calculation of coronary stenosis of the subject based at least in part on the one or more vascular morphology parameters and/or set of quantified plaque parameters determined from the medical image of the coronary region of the subject.

Embodiment 75: The computer-implemented method of any one of Embodiments 72-74, further comprising assessing a risk of ischemia for the subject based at least in part on the one or more vascular morphology parameters and/or set of quantified plaque parameters determined from the medical image of the coronary region of the subject.

Embodiment 76: The computer-implemented method of any one of Embodiments 72-75, wherein the plaque identification algorithm is configured to determine the one or more regions of plaque by determining a vessel wall and lumen wall of the one or more coronary arteries and determining a volume between the vessel wall and lumen wall as the one or more regions of plaque.

Embodiment 77: The computer-implemented method of any one of Embodiments 72-76, wherein the one or more coronary arteries are identified by size.

Embodiment 78: The computer-implemented method of any one of Embodiments 72-77, wherein a ratio of volume to surface area of the one or more regions of plaque below a predetermined threshold is indicative of low risk.

Embodiment 79: The computer-implemented method of any one of Embodiments 72-78, wherein a radiodensity of the one or more regions of plaque above a predetermined threshold is indicative of low risk.

Embodiment 80: The computer-implemented method of any one of Embodiments 72-79, wherein a heterogeneity of the one or more regions of plaque below a predetermined threshold is indicative of low risk.

Embodiment 81: The computer-implemented method of any one of Embodiments 72-80, wherein the set of quantified plaque parameters further comprises diffusivity of the one or more regions of plaque.

Embodiment 82: The computer-implemented method of any one of Embodiments 72-81, wherein the set of quantified plaque parameters further comprises a ratio of radiodensity to volume of the one or more regions of plaque.

Embodiment 83: The computer-implemented method of any one of Embodiments 72-82, further comprising generating, by the computer system, a proposed treatment for the subject based at least in part on the classified atherosclerosis.

Embodiment 84: The computer-implemented method of any one of Embodiments 72-83, wherein the coronary atherosclerosis of the subject is classified by the computer system using a coronary atherosclerosis classification algorithm, wherein the coronary atherosclerosis classification algorithm is configured to utilize a combination of the ratio of volume of surface area, volume, heterogeneity index, and radiodensity of the one or more regions of plaque as input.

Embodiment 85: The computer-implemented method of any one of Embodiments 72-84, wherein the medical image comprises a Computed Tomography (CT) image.

Embodiment 86: The computer-implemented method of Embodiment 85, wherein the medical image comprises a non-contrast CT image.

Embodiment 87: The computer-implemented method of Embodiment 85, wherein the medical image comprises a contrast CT image.

Embodiment 88: The computer-implemented method of any one of Embodiments 72-84, wherein the medical image is obtained using an imaging technique comprising one or more of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

Embodiment 89: The computer-implemented method of any one of Embodiments 72-88, wherein the heterogeneity index of one or more regions of plaque is determined by generating a three-dimensional histogram of radiodensity values across a geometric shape of the one or more regions of plaque.

Embodiment 90: The computer-implemented method of any one of Embodiments 72-89, wherein the heterogeneity index of one or more regions of plaque is determined by generating spatial mapping of radiodensity values across the one or more regions of plaque.

Embodiment 91: The computer-implemented method of any one of Embodiments 72-90, wherein the set of quantified plaque parameters comprises a percentage composition of plaque comprising different radiodensity values.

Embodiment 92: The computer-implemented method of any one of Embodiments 72-91, wherein the set of quantified plaque parameters comprises a percentage composition of plaque comprising different radiodensity values as a function of volume of plaque.

Embodiment 93: The computer-implemented method of any one of Embodiments 72-92, wherein the weighted measure of the determined one or more vascular morphology parameters and the set of quantified plaque parameters of the one or more regions of plaque is generated based at least in part by comparing the determined set of quantified plaque parameters to one or more predetermined sets of quantified plaque parameters.

Embodiment 94: The computer-implemented method of Embodiment 93, wherein the one or more predetermined sets of quantified plaque parameters are derived from one or more medical images of other subjects.

Embodiment 95: The computer-implemented method of Embodiment 93, wherein the one or more predetermined sets of quantified plaque parameters are derived from one or more medical images of the subject.

Embodiment 96: The computer-implemented method of any one of Embodiments 72-95, wherein the geometry of the one or more regions of plaque comprises a round or oblong shape.

Embodiment 97: The computer-implemented method of any one of Embodiments 72-96, wherein the one or more vascular morphology parameters comprises a classification of arterial remodeling.

Embodiment 98: The computer-implemented method of Embodiment 97, wherein the classification of arterial remodeling comprises positive arterial remodeling, negative arterial remodeling, and intermediate arterial remodeling.

Embodiment 99: The computer-implemented method of Embodiment 97, wherein the classification of arterial remodeling is determined based at least in part on a ratio of a largest vessel diameter at the one or more regions of plaque to a normal reference vessel diameter.

Embodiment 100: The computer-implemented method of Embodiment 99, wherein the classification of arterial remodeling comprises positive arterial remodeling, negative arterial remodeling, and intermediate arterial remodeling, and wherein positive arterial remodeling is determined when the ratio of the largest vessel diameter at the one or more regions of plaque to the normal reference vessel diameter is more than 1.1, wherein negative arterial remodeling is determined when the ratio of the largest vessel diameter at the one or more regions of plaque to the normal reference vessel diameter is less than 0.95, and wherein intermediate arterial remodeling is determined when the ratio of the largest vessel diameter at the one or more regions of plaque to the normal reference vessel diameter is between 0.95 and 1.1.

Embodiment 101: The computer-implemented method of any one of Embodiments 72-100, wherein the function of volume to surface area of the one or more regions of plaque comprises one or more of a thickness or diameter of the one or more regions of plaque.

Embodiment 102: The computer-implemented method of any one of Embodiments 72-101, wherein the weighted measure is generated by weighting the one or more vascular morphology parameters and the set of quantified plaque parameters of the one or more regions of plaque equally.

Embodiment 103: The computer-implemented method of any one of Embodiments 72-101, wherein the weighted measure is generated by weighting the one or more vascular morphology parameters and the set of quantified plaque parameters of the one or more regions of plaque differently.

Embodiment 104: The computer-implemented method of any one of Embodiments 72-101, wherein the weighted measure is generated by weighting the one or more vascular morphology parameters and the set of quantified plaque parameters of the one or more regions of plaque logarithmically, algebraically, or utilizing another mathematical transform.

Embodiment 105: A computer-implemented method of quantifying a state of coronary artery disease based on quantification of plaque, ischemia, and fat inflammation based on non-invasive medical image analysis, the method comprising: accessing, by a computer system, a medical image of a coronary region of a subject, wherein the medical image of the coronary region of the subject is obtained non-invasively; identifying, by the computer system utilizing a coronary artery identification algorithm, one or more coronary arteries within the medical image of the coronary region of the subject, wherein the coronary artery identification algorithm is configured to utilize raw medical images as input; identifying, by the computer system utilizing a plaque identification algorithm, one or more regions of plaque within the one or more coronary arteries identified from the medical image of the coronary region of the subject, wherein the plaque identification algorithm is configured to utilize raw medical images as input; identifying, by the computer system utilizing a fat identification algorithm, one or more regions of fat within the medical image of the coronary region of the subject, wherein the fat identification algorithm is configured to utilize raw medical images as input; determining, by the computer system, one or more vascular morphology parameters and a set of quantified plaque parameters of the one or more identified regions of plaque from the medical image of the coronary region of the subject, wherein the set of quantified plaque parameters comprises a ratio or function of volume to surface area, heterogeneity index, geometry, and radiodensity of the one or more regions of plaque within the medical image; quantifying, by the computer system, coronary stenosis based at least in part on the set of quantified plaque parameters determined from the medical image of the coronary region of the subject; and determining, by the computer system, a presence or risk of ischemia based at least in part on the set of quantified plaque parameters determined from the medical image of the coronary region of the subject; determining, by the computer system, a set of quantified fat parameters of the one or more identified regions of fat within the medical image of the coronary region of the subject, wherein the set of quantified fat parameters comprises volume, geometry, and radiodensity of the one or more regions of fat within the medical image; generating, by the computer system, a weighted measure of the determined one or more vascular morphology parameters, the set of quantified plaque parameters of the one or more regions of plaque, the quantified coronary stenosis, the determined presence or risk of ischemia, and the determined set of quantified fat parameters; and generating, by the computer system, a risk assessment of coronary disease of the subject based at least in part on the generated weighted measure of the determined one or more vascular morphology parameters, the set of quantified plaque parameters of the one or more regions of plaque, the quantified coronary stenosis, the determined presence or risk of ischemia, and the determined set of quantified fat parameters, wherein the computer system comprises a computer processor and an electronic storage medium.

Embodiment 106: The computer-implemented method of Embodiment 105, wherein one or more of the coronary artery identification algorithm, plaque identification algorithm, or fat identification algorithm comprises an artificial intelligence or machine learning algorithm.

Embodiment 107: The computer-implemented method of any one of Embodiments 105 or 106, further comprising automatically generating, by the computer system, a Coronary Artery Disease Reporting & Data System (CAD-RADS) classification score of the subject based at least in part on the quantified coronary stenosis.

Embodiment 108: The computer-implemented method of any one of Embodiments 105-107, further comprising automatically generating, by the computer system, a CAD-RADS modifier of the subject based at least in part on one or more of the determined one or more vascular morphology parameters, the set of quantified plaque parameters of the one or more regions of plaque, the quantified coronary stenosis, the determined presence or risk of ischemia, and the determined set of quantified fat parameters, wherein the CAD-RADS modifier comprises one or more of nondiagnostic (N), stent (S), graft (G), or vulnerability (V).

Embodiment 109: The computer-implemented method of any one of Embodiments 105-108, wherein the coronary stenosis is quantified on a vessel-by-vessel basis.

Embodiment 110: The computer-implemented method of any one of Embodiments 105-109, wherein the presence or risk of ischemia is determined on a vessel-by-vessel basis.

Embodiment 111: The computer-implemented method of any one of Embodiments 105-110, wherein the one or more regions of fat comprises epicardial fat.

Embodiment 112: The computer-implemented method of any one of Embodiments 105-111, further comprising generating, by the computer system, a proposed treatment for the subject based at least in part on the generated risk assessment of coronary disease.

Embodiment 113: The computer-implemented method of any one of Embodiments 105-112, wherein the medical image comprises a Computed Tomography (CT) image.

Embodiment 114: The computer-implemented method of Embodiment 113, wherein the medical image comprises a non-contrast CT image.

Embodiment 115: The computer-implemented method of Embodiment 113, wherein the medical image comprises a contrast CT image.

Embodiment 116: The computer-implemented method of any one of Embodiments 113-115, wherein the determined set of plaque parameters comprises one or more of a percentage of higher radiodensity calcium plaque or lower radiodensity calcium plaque within the one or more regions of plaque, wherein higher radiodensity calcium plaque comprises a Hounsfield radiodensity unit of above 1000, and wherein lower radiodensity calcium plaque comprises a Hounsfield radiodensity unit of below 1000.

Embodiment 117: The computer-implemented method of any one of Embodiments 105-112, wherein the medical image comprises a Magnetic Resonance (MR) image.

Embodiment 118: The computer-implemented method of any one of Embodiments 105-112, wherein the medical image comprises an ultrasound image.

Embodiment 119: The computer-implemented method of any one of Embodiments 105-112, wherein the medical image is obtained using an imaging technique comprising one or more of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

Embodiment 120: The computer-implemented method of any one of Embodiments 105-119, wherein the heterogeneity index of one or more regions of plaque is determined by generating a three-dimensional histogram of radiodensity values across a geometric shape of the one or more regions of plaque.

Embodiment 121: The computer-implemented method of any one of Embodiments 105-119, wherein the heterogeneity index of one or more regions of plaque is determined by generating spatial mapping of radiodensity values across the one or more regions of plaque.

Embodiment 122: The computer-implemented method of any one of Embodiments 105-121, wherein the set of quantified plaque parameters comprises a percentage composition of plaque comprising different radiodensity values.

Embodiment 123: The computer-implemented method of any one of Embodiments 105-122, wherein the set of quantified plaque parameters further comprises diffusivity of the one or more regions of plaque.

Embodiment 124: The computer-implemented method of any one of Embodiments 105-123, wherein the set of quantified plaque parameters further comprises a ratio of radiodensity to volume of the one or more regions of plaque.

Embodiment 125: The computer-implemented method of any one of Embodiments 105-124, wherein the plaque identification algorithm is configured to determine the one or more regions of plaque by determining a vessel wall and lumen wall of the one or more coronary arteries and determining a volume between the vessel wall and lumen wall as the one or more regions of plaque.

Embodiment 126: The computer-implemented method of any one of Embodiments 105-125, wherein the one or more coronary arteries are identified by size.

Embodiment 127: The computer-implemented method of any one of Embodiments 105-126, wherein the generated risk assessment of coronary disease of the subject comprises a risk score.

Embodiment 128: The computer-implemented method of any one of Embodiments 105-127, wherein the geometry of the one or more regions of plaque comprises a round or oblong shape.

Embodiment 129: The computer-implemented method of any one of Embodiments 105-128, wherein the one or more vascular morphology parameters comprises a classification of arterial remodeling.

Embodiment 130: The computer-implemented method of Embodiment 129, wherein the classification of arterial remodeling comprises positive arterial remodeling, negative arterial remodeling, and intermediate arterial remodeling.

Embodiment 131: The computer-implemented method of Embodiment 129, wherein the classification of arterial remodeling is determined based at least in part on a ratio of a largest vessel diameter at the one or more regions of plaque to a normal reference vessel diameter.

Embodiment 132: The computer-implemented method of Embodiment 131, wherein the classification of arterial remodeling comprises positive arterial remodeling, negative arterial remodeling, and intermediate arterial remodeling, and wherein positive arterial remodeling is determined when the ratio of the largest vessel diameter at the one or more regions of plaque to the normal reference vessel diameter is more than 1.1, wherein negative arterial remodeling is determined when the ratio of the largest vessel diameter at the one or more regions of plaque to the normal reference vessel diameter is less than 0.95, and wherein intermediate arterial remodeling is determined when the ratio of the largest vessel diameter at the one or more regions of plaque to the normal reference vessel diameter is between 0.95 and 1.1.

Embodiment 133: The computer-implemented method of any of Embodiments 105-132, wherein the function of volume to surface area of the one or more regions of plaque comprises one or more of a thickness or diameter of the one or more regions of plaque.

Embodiment 134: The computer-implemented method of any one of Embodiments 105-133, wherein the weighted measure is generated by weighting the one or more vascular morphology parameters, the set of quantified plaque parameters of the one or more regions of plaque, the quantified coronary stenosis, the determined presence or risk of ischemia, and the determined set of quantified fat parameters equally.

Embodiment 135: The computer-implemented method of any one of Embodiments 105-133, wherein the weighted measure is generated by weighting the one or more vascular morphology parameters, the set of quantified plaque parameters of the one or more regions of plaque, the quantified coronary stenosis, the determined presence or risk of ischemia, and the determined set of quantified fat parameters differently.

Embodiment 136: The computer-implemented method of any one of Embodiments 105-133, wherein the weighted measure is generated by weighting the one or more vascular morphology parameters, the set of quantified plaque parameters of the one or more regions of plaque, the quantified coronary stenosis, the determined presence or risk of ischemia, and the determined set of quantified fat parameters logarithmically, algebraically, or utilizing another mathematical transform.

Embodiment 137: A computer-implemented method of tracking a plaque-based disease based at least in part on determining a state of plaque progression of a subject using non-invasive medical image analysis, the method comprising: accessing, by a computer system, a first set of plaque parameters associated with a region of a subject, wherein the first set of plaque parameters are derived from a first medical image of the subject, wherein the first medical image of the subject is obtained non-invasively at a first point in time; accessing, by a computer system, a second medical image of the subject, wherein the second medical image of the subject is obtained non-invasively at a second point in time, the second point in time being later than the first point in time; identifying, by the computer system, one or more regions of plaque from the second medical image; determining, by the computer system, a second set of plaque parameters associated with the region of the subject by analyzing the second medical image and the identified one or more regions of plaque from the second medical image; analyzing, by the computer system, a change in one or more plaque parameters by comparing one or more of the first set of plaque parameters against one or more of the second set of plaque parameters; determining, by the computer system, a state of plaque progression associated with a plaque-based disease for the subject based at least in part on the analyzed change in the one or more plaque parameters, wherein the determined state of plaque progression comprises one or more of rapid plaque progression, non-rapid calcium dominant mixed response, non-rapid non-calcium dominant mixed response, or plaque regression; and tracking, by the computer system, progression of the plaque-based disease based at least in part on the determined state of plaque progression, wherein the computer system comprises a computer processor and an electronic storage medium.

Embodiment 138: The computer-implemented method of Embodiment 137, wherein rapid plaque progression is determined when a percent atheroma volume increase of the subject is more than 1% per year, wherein non-rapid calcium dominant mixed response is determined when a percent atheroma volume increase of the subject is less than 1% per year and calcified plaque represents more than 50% of total new plaque formation, wherein non-rapid non-calcium dominant mixed response is determined when a percent atheroma volume increase of the subject is less than 1% per year and non-calcified plaque represents more than 50% of total new plaque formation, and wherein plaque regression is determined when a decrease in total percent atheroma volume is present.

Embodiment 139: The computer-implemented method of any one of Embodiments 137-138, further comprising generating, by the computer system, a proposed treatment for the subject based at least in part on the determined state of plaque progression of the plaque-based disease.

Embodiment 140: The computer-implemented method of any one of Embodiments 137-139, wherein the medical image comprises a Computed Tomography (CT) image.

Embodiment 141: The computer-implemented method of Embodiment 140, wherein the medical image comprises a non-contrast CT image.

Embodiment 142: The computer-implemented method of Embodiment 140, wherein the medical image comprises a contrast CT image.

Embodiment 143: The computer-implemented method of any one of Embodiments 140-142, wherein the determined state of plaque progression further comprises one or more of a percentage of higher radiodensity plaques or lower radiodensity plaques, wherein higher radiodensity plaques comprise a Hounsfield unit of above 1000, and wherein lower radiodensity plaques comprise a Hounsfield unit of below 1000.

Embodiment 144: The computer-implemented method of any one of Embodiments 137-139, wherein the medical image comprises a Magnetic Resonance (MR) image.

Embodiment 145: The computer-implemented method of any one of Embodiments 137-139, wherein the medical image comprises an ultrasound image.

Embodiment 146: The computer-implemented method of any one of Embodiments 137-145, wherein the region of the subject comprises a coronary region of the subject.

Embodiment 147: The computer-implemented method of any one of Embodiments 137-145, wherein the region of the subject comprises one or more of carotid arteries, renal arteries, abdominal aorta, cerebral arteries, lower extremities, or upper extremities.

Embodiment 148: The computer-implemented method of any one of Embodiments 137-147, wherein the plaque-based disease comprises one or more of atherosclerosis, stenosis, or ischemia.

Embodiment 149: The computer-implemented method of any one of Embodiments 137-148, further comprising: determining, by the computer system, a first Coronary Artery Disease Reporting & Data System (CAD-RADS) classification score of the subject based at least in part on the first set of plaque parameters; determining, by the computer system, a second CAD-RADS classification score of the subject based at least in part on the second set of plaque parameters; and tracking, by the computer system, progression of a CAD-RADS classification score of the subject based on comparing the first CAD-RADS classification score and the second CAD-RADS classification score.

Embodiment 150: The computer-implemented method of any one of Embodiments 137-149, wherein the plaque-based disease is further tracked by the computer system by analyzing one or more of serum biomarkers, genetics, omics, transcriptomics, microbiomics, or metabolomics.

Embodiment 151: The computer-implemented method of any one of Embodiments 137-150, wherein the first set of plaque parameters comprises one or more of a volume, surface area, geometric shape, location, heterogeneity index, and radiodensity of one or more regions of plaque within the first medical image.

Embodiment 152: The computer-implemented method of any one of Embodiments 137-151, wherein the second set of plaque parameters comprises one or more of a volume, surface area, geometric shape, location, heterogeneity index, and radiodensity of one or more regions of plaque within the second medical image.

Embodiment 153: The computer-implemented method of any one of Embodiments 137-152, wherein the first set of plaque parameters and the second set of plaque parameters comprise a ratio of radiodensity to volume of one or more regions of plaque.

Embodiment 154: The computer-implemented method of any one of Embodiments 137-153, wherein the first set of plaque parameters and the second set of plaque parameters comprise a diffusivity of one or more regions of plaque.

Embodiment 155: The computer-implemented method of any one of Embodiments 137-154, wherein the first set of plaque parameters and the second set of plaque parameters comprise a volume to surface area ratio of one or more regions of plaque.

Embodiment 156: The computer-implemented method of any one of Embodiments 137-155, wherein the first set of plaque parameters and the second set of plaque parameters comprise a heterogeneity index of one or more regions of plaque.

Embodiment 157: The computer-implemented method of Embodiment 156, wherein the heterogeneity index of one or more regions of plaque is determined by generating a three-dimensional histogram of radiodensity values across a geometric shape of the one or more regions of plaque.

Embodiment 158: The computer-implemented method of Embodiment 156, wherein the heterogeneity index of one or more regions of plaque is determined by generating spatial mapping of radiodensity values across the one or more regions of plaque.

Embodiment 159: The computer-implemented method of any one of Embodiments 137-158, wherein the first set of plaque parameters and the second set of plaque parameters comprise a percentage composition of plaque comprising different radiodensity values.

Embodiment 160: The computer-implemented method of any one of Embodiments 137-159, wherein the first set of plaque parameters and the second set of plaque parameters comprise a percentage composition of plaque comprising different radiodensity values as a function of volume of plaque.

Embodiment 161: A computer-implemented method of characterizing a change in coronary calcium score of a subject, the method comprising: accessing, by the computer system, a first coronary calcium score of a subject and a first set of plaque parameters associated with a coronary region of a subject, the first coronary calcium score and the first set of parameters obtained at a first point in time, wherein the first set of plaque parameters comprises volume, surface area, geometric shape, location, heterogeneity index, and radiodensity for one or more regions of plaque within the coronary region of the subject; generating, by the computer system, a first weighted measure of the accessed first set of plaque parameters; accessing, by a computer system, a second coronary calcium score of the subject and one or more medical images of the coronary region of the subject, the second coronary calcium score and the one or more medical images obtained at a second point in time, the second point in time being later than the first point in time, wherein the one or more medical images of the coronary region of the subject comprises the one or more regions of plaque; determining, by the computer system, a change in coronary calcium score of the subject by comparing the first coronary calcium score and the second coronary calcium score; identifying, by the computer system, the one or more regions of plaque from the one or more medical images; determining, by the computer system, a second set of plaque parameters associated with the coronary region of the subject by analyzing the one or more medical images, wherein the second set of plaque parameters comprises volume, surface area, geometric shape, location, heterogeneity index, and radiodensity for the one or more regions of plaque; generating, by the computer system, a second weighted measure of the determined second set of plaque parameters; analyzing, by the computer system, a change in the first weighted measure of the accessed first set of plaque parameters and the second weighted measure of the determined second set of plaque parameters; and characterizing, by the computer system, the change in coronary calcium score of the subject based at least in part on the identified one or more regions of plaque and the analyzed change in the first weighted measure of the accessed first set of plaque parameters and the second weighted measure of the determined second set of plaque parameters, wherein the change in coronary in coronary calcium score is characterized as positive, neutral, or negative, wherein the computer system comprises a computer processor and an electronic storage medium.

Embodiment 162: The computer-implemented method of Embodiment 161, wherein radiodensity of the one or more regions of plaque is determined from the one or more medical images by analyzing a Hounsfield unit of the identified one or more regions of plaque.

Embodiment 163: The computer-implemented method of any one of Embodiments 161-162, further comprising determining a change in ratio between volume and radiodensity of the one or more regions of plaque within the coronary region of the subject, and wherein the change in coronary calcium score of the subject is further characterized based at least in part the determined change in ratio between volume and radiodensity of one or more regions of plaque within the coronary region of the subject.

Embodiment 164: The computer-implemented method of any one of Embodiments 161-163, wherein the change in coronary calcium score of the subject is characterized for each vessel.

Embodiment 165: The computer-implemented method of any one of Embodiments 161-164, wherein the change in coronary calcium score of the subject is characterized for each segment.

Embodiment 166: The computer-implemented method of any one of Embodiments 161-165, wherein the change in coronary calcium score of the subject is characterized for each plaque.

Embodiment 167: The computer-implemented method of any one of Embodiments 161-166, wherein the first set of plaque parameters and the second set of plaque parameters further comprise a diffusivity of the one or more regions of plaque.

Embodiment 168: The computer-implemented method of any one of Embodiments 161-167, wherein the change in coronary calcium score of the subject is characterized as positive when the radiodensity of the one or more regions of plaque is increased.

Embodiment 169: The computer-implemented method of any one of Embodiments 161-168, wherein the change in coronary calcium score of the subject is characterized as negative when one or more new regions of plaque are identified from the one or more medical images.

Embodiment 170: The computer-implemented method of any one of Embodiments 161-169, wherein the change in coronary calcium score of the subject is characterized as positive when a volume to surface area ratio of the one or more regions of plaque is decreased.

Embodiment 171: The computer-implemented method of any one of Embodiments 161-170, wherein the heterogeneity index of the one or more regions of plaque is determined by generating a three-dimensional histogram of radiodensity values across a geometric shape of the one or more regions of plaque.

Embodiment 172: The computer-implemented method of any one of Embodiments 161-171, wherein the change in coronary calcium score of the subject is characterized as positive when the heterogeneity index of the one or more regions of plaque is decreased.

Embodiment 173: The computer-implemented method of any one of Embodiments 161-172, wherein the second coronary calcium score of the subject is determined by analyzing the one or more medical images of the coronary region of the subject.

Embodiment 174: The computer-implemented method of any one of Embodiments 161-172, wherein the second coronary calcium score of the subject is accessed from a database.

Embodiment 175: The computer-implemented method of any one of Embodiments 161-174, wherein the one or more medical images of the coronary region of the subject comprises an image obtained from a non-contrast Computed Tomography (CT) scan.

Embodiment 176: The computer-implemented method of any one of Embodiments 161-174, wherein the one or more medical images of the coronary region of the subject comprises an image obtained from a contrast-enhanced CT scan.

Embodiment 177: The computer-implemented method of Embodiment 176, wherein the one or more medical images of the coronary region of the subject comprises an image obtained from a contrast-enhanced CT angiogram.

Embodiment 178: The computer-implemented method of any one of Embodiments 161-177, wherein a positive characterization of the change in coronary in coronary calcium score is indicative of plaque stabilization.

Embodiment 179: The computer-implemented method of any one of Embodiments 161-178, wherein the first set of plaque parameters and the second set of plaque parameters further comprise radiodensity of a volume around plaque Embodiment 180: The computer-implemented method of any one of Embodiments 161-179, wherein the change in coronary calcium score of the subject is characterized by a machine learning algorithm utilized by the computer system.

Embodiment 181: The computer-implemented method of any one of Embodiments 161-180, wherein the first weighted measure is generated by weighting the accessed first set of plaque parameters equally.

Embodiment 182: The computer-implemented method of any one of Embodiments 161-180, wherein the first weighted measure is generated by weighting the accessed first set of plaque parameters differently.

Embodiment 183: The computer-implemented method of any one of Embodiments 161-180, wherein the first weighted measure is generated by weighting the accessed first set of plaque parameters logarithmically, algebraically, or utilizing another mathematical transform.

Embodiment 184: A computer-implemented method of generating prognosis of a cardiovascular event for a subject based on non-invasive medical image analysis, the method comprising: accessing, by a computer system, a medical image of a coronary region of a subject, wherein the medical image of the coronary region of the subject is obtained non-invasively; identifying, by the computer system utilizing a coronary artery identification algorithm, one or more coronary arteries within the medical image of the coronary region of the subject, wherein the coronary artery identification algorithm is configured to utilize raw medical images as input; identifying, by the computer system utilizing a plaque identification algorithm, one or more regions of plaque within the one or more coronary arteries identified from the medical image of the coronary region of the subject, wherein the plaque identification algorithm is configured to utilize raw medical images as input; determining, by the computer system, a set of quantified plaque parameters of the one or more identified regions of plaque within the medical image of the coronary region of the subject, wherein the set of quantified plaque parameters comprises volume, surface area, ratio of volume to surface area, heterogeneity index, geometry, and radiodensity of the one or more regions of plaque within the medical image; classifying, by the computer system, the one or more regions of plaque within the medical image as stable plaque or unstable plaque based at least in part on the determined set of quantified plaque parameters; determining, by the computer system, a volume of unstable plaque classified within the medical image and a total volume of the one or more coronary arteries within the medical image; determining, by the computer system, a ratio of volume of unstable plaque to the total volume of the one or more coronary arteries; generating, by the computer system, a prognosis of a cardiovascular event for the subject based at least in part on analyzing the ratio of volume of unstable plaque to the total volume of the one or more coronary arteries, the volume of the one or more regions of plaque, and the volume of unstable plaque classified within the medical image, wherein the analyzing comprises conducting a comparison to a known dataset of one or more ratios of volume of unstable plaque to total volume of one or more coronary arteries, volume of one or more regions of plaque, and volume of unstable plaque, wherein the known dataset is collected from other subjects; and generating, by the computer system, treatment plan for the subject based at least in part on the generated prognosis of cardiovascular event for the subject, wherein the computer system comprises a computer processor and an electronic storage medium.

Embodiment 185: The computer-implemented method of Embodiment 184, further comprising generating, by the computer system, a weighted measure of the ratio of volume of unstable plaque to the total volume of the one or more coronary arteries, the volume of the one or more regions of plaque, and the volume of unstable plaque classified within the medical image, wherein the prognosis of cardiovascular event is further generated by comparing the weighted measure to one or more weighted measures derived from the known dataset.

Embodiment 186: The computer-implemented method of Embodiment 185, wherein the weighted measure is generated by weighting the ratio of volume of unstable plaque to the total volume of the one or more coronary arteries, the volume of the one or more regions of plaque, and the volume of unstable plaque classified within the medical image equally.

Embodiment 187: The computer-implemented method of Embodiment 185, wherein the weighted measure is generated by weighting the ratio of volume of unstable plaque to the total volume of the one or more coronary arteries, the volume of the one or more regions of plaque, and the volume of unstable plaque classified within the medical image differently.

Embodiment 188: The computer-implemented method of Embodiment 185, wherein the weighted measure is generated by weighting the ratio of volume of unstable plaque to the total volume of the one or more coronary arteries, the volume of the one or more regions of plaque, and the volume of unstable plaque classified within the medical image logarithmically, algebraically, or utilizing another mathematical transform.

Embodiment 189: The computer-implemented method of any one of Embodiments 184-188, further comprising analyzing, by the computer system, a medical image of a non-coronary cardiovascular system of the subject, and wherein the prognosis of a cardiovascular event for the subject is further generated based at least in part on the analyzed medical image of the non-coronary cardiovascular system of the subject.

Embodiment 190: The computer-implemented method of any one of Embodiments 184-189, further comprising accessing, by the computer system, results of a blood chemistry or biomarker test of the subject, and wherein the prognosis of a cardiovascular event for the subject is further generated based at least in part on the results of the blood chemistry or biomarker test of the subject.

Embodiment 191: The computer-implemented method of any one of Embodiments 184-190, wherein the generated prognosis of a cardiovascular event for the subject comprises a risk score of a cardiovascular event for the subject.

Embodiment 192: The computer-implemented method of any one of Embodiments 184-191, wherein the prognosis of a cardiovascular event is generated by the computer system utilizing an artificial intelligence or machine learning algorithm.

Embodiment 193: The computer-implemented method of any one of Embodiments 184-192, wherein the cardiovascular event comprises one or more of atherosclerosis, stenosis, or ischemia.

Embodiment 194: The computer-implemented method of any one of Embodiments 184-193, wherein the generated treatment plan comprises one or more of use of statins, lifestyle changes, or surgery.

Embodiment 195: The computer-implemented method of any one of Embodiments 184-194, wherein one or more of the coronary artery identification algorithm or the plaque identification algorithm comprises an artificial intelligence or machine learning algorithm.

Embodiment 196: The computer-implemented method of any one of Embodiments 184-195, wherein the plaque identification algorithm is configured to determine the one or more regions of plaque by determining a vessel wall and lumen wall of the one or more coronary arteries and determining a volume between the vessel wall and lumen wall as the one or more regions of plaque.

Embodiment 197: The computer-implemented method of any one of Embodiments 184-196, wherein the medical image comprises a Computed Tomography (CT) image.

Embodiment 198: The computer-implemented method of Embodiment 197, wherein the medical image comprises a non-contrast CT image.

Embodiment 199: The computer-implemented method of Embodiment 197, wherein the medical image comprises a contrast CT image.

Embodiment 200: The computer-implemented method of any one of Embodiments 184-196, wherein the medical image comprises a Magnetic Resonance (MR) image.

Embodiment 201: The computer-implemented method of any one of Embodiments 184-196, wherein the medical image is obtained using an imaging technique comprising one or more of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

Embodiment 202: A computer-implemented method of determining patient-specific stent parameters and guidance for implantation based on non-invasive medical image analysis, the method comprising: accessing, by a computer system, a medical image of a coronary region of a patient, wherein the medical image of the coronary region of the patient is obtained non-invasively; identifying, by the computer system utilizing a coronary artery identification algorithm, one or more coronary arteries within the medical image of the coronary region of the patient, wherein the coronary artery identification algorithm is configured to utilize raw medical images as input; identifying, by the computer system utilizing a plaque identification algorithm, one or more regions of plaque within the one or more coronary arteries identified from the medical image of the coronary region of the patient, wherein the plaque identification algorithm is configured to utilize raw medical images as input; determining, by the computer system, a set of quantified plaque parameters of the one or more identified regions of plaque from the medical image of the coronary region of the patient, wherein the set of quantified plaque parameters comprises a ratio or function of volume to surface area, heterogeneity index, location, geometry, and radiodensity of the one or more regions of plaque within the medical image; determining, by the computer system, a set of stenosis vessel parameters of the one or more coronary arteries within the medical image of the coronary region of the patient, wherein the set of vessel parameters comprises volume, curvature, vessel wall, lumen wall, and diameter of the one or more coronary arteries within the medical image in the presence of stenosis; determining, by the computer system, a set of normal vessel parameters of the one or more coronary arteries within the medical image of the coronary region of the patient, wherein the set of vessel parameters comprises volume, curvature, vessel wall, lumen wall, and diameter of the one or more coronary arteries within the medical image without stenosis, wherein the set of normal vessel parameters are determined by graphically removing from the medical image of the coronary region of the patient the identified one or more regions of plaque; determining, by the computer system, a predicted effectiveness of stent implantation for the patient based at least in part on the set of quantified plaque parameters and the set of vessel parameters; generating, by the computer system, patient-specific stent parameters for the patient when the predicted effectiveness of stent implantation for the patient is above a predetermined threshold, wherein the patient-specific stent parameters are generated based at least in part on the set of quantified plaque parameters, the set of vessel parameters, and the set of normal vessel parameters; and generating, by the computer system, guidance for implantation of a patient-specific stent comprising the patient-specific stent parameters, wherein the guidance for implantation of the patient-specific stent is generated based at least in part on the set of quantified plaque parameters and the set of vessel parameters, wherein the generated guidance for implantation of the patient-specific stent comprises insertion of guidance wires and positioning of the patient-specific stent, wherein the computer system comprises a computer processor and an electronic storage medium.

Embodiment 203: The computer-implemented method of Embodiment 202, further comprising accessing, by the computer system, a post-implantation medical image of the coronary region of the patient and performing post-implantation analysis.

Embodiment 204: The computer-implemented method of Embodiment 203, further comprising generating, by the computer system, a treatment plan for the patient based at least in part on the post-implantation analysis.

Embodiment 205: The computer-implemented method of Embodiment 204, wherein the generated treatment plan comprises one or more of use of statins, lifestyle changes, or surgery.

Embodiment 206: The computer-implemented method of any one of Embodiments 202-205, wherein the set of stenosis vessel parameters comprises a location, curvature, and diameter of bifurcation of the one or more coronary arteries.

Embodiment 207: The computer-implemented method of any one of Embodiments 202-206, wherein the patient-specific stent parameters comprise a diameter of the patient-specific stent.

Embodiment 208: The computer-implemented method of Embodiment 207, wherein the diameter of the patient-specific stent is substantially equal to the diameter of the one or more coronary arteries without stenosis.

Embodiment 209: The computer-implemented method of Embodiment 207, wherein the diameter of the patient-specific stent is less than the diameter of the one or more coronary arteries without stenosis.

Embodiment 210: The computer-implemented method of any one of Embodiments 202-209, wherein the predicted effectiveness of stent implantation for the patient is determined by the computer system utilizing an artificial intelligence or machine learning algorithm.

Embodiment 211: The computer-implemented method of any one of Embodiments 202-210, wherein the patient-specific stent parameters for the patient are generated by the computer system utilizing an artificial intelligence or machine learning algorithm.

Embodiment 212: The computer-implemented method of any one of Embodiments 202-211, wherein one or more of the coronary artery identification algorithm or the plaque identification algorithm comprises an artificial intelligence or machine learning algorithm.

Embodiment 213: The computer-implemented method of any one of Embodiments 202-212, wherein the plaque identification algorithm is configured to determine the one or more regions of plaque by determining a vessel wall and lumen wall of the one or more coronary arteries and determining a volume between the vessel wall and lumen wall as the one or more regions of plaque.

Embodiment 214: The computer-implemented method of any one of Embodiments 202-213, wherein the medical image comprises a Computed Tomography (CT) image.

Embodiment 215: The computer-implemented method of Embodiment 214, wherein the medical image comprises a non-contrast CT image.

Embodiment 216: The computer-implemented method of Embodiment 214, wherein the medical image comprises a contrast CT image.

Embodiment 217: The computer-implemented method of any one of Embodiments 202-213, wherein the medical image comprises a Magnetic Resonance (MR) image.

Embodiment 218: The computer-implemented method of any one of Embodiments 202-213, wherein the medical image is obtained using an imaging technique comprising one or more of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

Embodiment 219: A computer-implemented method of generating a patient-specific report on coronary artery disease for a patient based on non-invasive medical image analysis, the method comprising: accessing, by a computer system, a medical image of a coronary region of a patient, wherein the medical image of the coronary region of the patient is obtained non-invasively; identifying, by the computer system utilizing a coronary artery identification algorithm, one or more coronary arteries within the medical image of the coronary region of the patient, wherein the coronary artery identification algorithm is configured to utilize raw medical images as input; identifying, by the computer system utilizing a plaque identification algorithm, one or more regions of plaque within the one or more coronary arteries identified from the medical image of the coronary region of the patient, wherein the plaque identification algorithm is configured to utilize raw medical images as input; determining, by the computer system, one or more vascular morphology parameters and a set of quantified plaque parameters of the one or more identified regions of plaque from the medical image of the coronary region of the patient, wherein the set of quantified plaque parameters comprises a ratio or function of volume to surface area, volume, heterogeneity index, location, geometry, and radiodensity of the one or more regions of plaque within the medical image; quantifying, by the computer system, stenosis and atherosclerosis of the patient based at least in part on the set of quantified plaque parameters determined from the medical image; generating, by the computer system, one or more annotated medical images based at least in part on the medical image, the quantified stenosis and atherosclerosis of the patient, and the set of quantified plaque parameters determined from the medical image; determining, by the computer system, a risk of coronary artery disease for the patient based at least in part by comparing the quantified stenosis and atherosclerosis of the patient and the set of quantified plaque parameters determined from the medical image to a known dataset of one or more quantified stenosis and atherosclerosis and one or more quantified plaque parameters derived from one or more medial images of healthy subjects within an age group of the patient; dynamically generating, by the computer system, a patient-specific report on coronary artery disease for the patient, wherein the generated patient-specific report comprises the one or more annotated medical images, one or more of the set of quantified plaque parameters, and determined risk of coronary artery disease, wherein the computer system comprises a computer processor and an electronic storage medium.

Embodiment 220: The computer-implemented method of Embodiment 219, wherein the patient-specific report comprises a cinematic report.

Embodiment 221: The computer-implemented method of Embodiment 220, wherein the patient-specific report comprises content configured to provide an Augmented Reality (AR) or Virtual Reality (VR) experience.

Embodiment 222: The computer-implemented method of any one of Embodiments 219-221, wherein the patient-specific report comprises audio dynamically generated for the patient based at least in part on the quantified stenosis and atherosclerosis of the patient, the set of quantified plaque parameters determined from the medical image, and determined risk of coronary artery disease.

Embodiment 223: The computer-implemented method of any one of Embodiments 219-222, wherein the patient-specific report comprises phrases dynamically generated for the patient based at least in part on the quantified stenosis and atherosclerosis of the patient, the set of quantified plaque parameters determined from the medical image, and determined risk of coronary artery disease.

Embodiment 224: The computer-implemented method of any one of Embodiments 219-223, further comprising generating, by the computer system, a treatment plan for the patient based at least in part on the quantified stenosis and atherosclerosis of the patient, the set of quantified plaque parameters determined from the medical image, and determined risk of coronary artery disease, wherein the patient-specific report comprises the generated treatment plan.

Embodiment 225: The computer-implemented method of Embodiment 224, wherein the generated treatment plan comprises one or more of use of statins, lifestyle changes, or surgery.

Embodiment 226: The computer-implemented method of any one of Embodiments 219-225, further comprising tracking, by the computer system, progression of coronary artery disease for the patient based at least in part on comparing one or more of the set of quantified plaque parameters determined from the medical image against one or more previous quantified plaque parameters derived from a previous medical image of the patient, wherein the patient-specific report comprises the tracked progression of coronary artery disease.

Embodiment 227: The computer-implemented method of any one of Embodiments 219-226, wherein one or more of the coronary artery identification algorithm or the plaque identification algorithm comprises an artificial intelligence or machine learning algorithm.

Embodiment 228: The computer-implemented method of any one of Embodiments 219-227, wherein the plaque identification algorithm is configured to determine the one or more regions of plaque by determining a vessel wall and lumen wall of the one or more coronary arteries and determining a volume between the vessel wall and lumen wall as the one or more regions of plaque.

Embodiment 229: The computer-implemented method of any one of Embodiments 219-228, wherein the medical image comprises a Computed Tomography (CT) image.

Embodiment 230: The computer-implemented method of Embodiment 229, wherein the medical image comprises a non-contrast CT image.

Embodiment 231: The computer-implemented method of Embodiment 229, wherein the medical image comprises a contrast CT image.

Embodiment 232: The computer-implemented method of any one of Embodiments 219-228, wherein the medical image comprises a Magnetic Resonance (MR) image.

Embodiment 233: The computer-implemented method of any one of Embodiments 219-228, wherein the medical image is obtained using an imaging technique comprising one or more of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

Embodiment 234: A system comprising: at least one non-transitory computer storage medium configured to at least store computer-executable instructions, a set of computed tomography (CT) images of a patient's coronary vessels, vessel labels, and artery information associated with the set of CT images including information of stenosis, plaque, and locations of segments of the coronary vessels; one or more computer hardware processors in communication with the at least one non-transitory computer storage medium, the one or more computer hardware processors configured to execute the computer-executable instructions to at least: generate and display a user interface a first panel including an artery tree comprising a three-dimensional (3D) representation of coronary vessels depicting coronary vessels identified in the CT images, and including segment labels related to the artery tree, the artery tree not including heart tissue between branches of the artery tree; in response to an input on the user interface indicating the selection of a coronary vessel in the artery tree in the first panel, generate and display on the user interface a second panel illustrating at least a portion of the selected coronary vessel in at least one straightened multiplanar vessel (SMPR) view; generate and display on the user interface a third panel showing a cross-sectional view of the selected coronary vessel, the cross-sectional view generated using one of the set of CT images of the selected coronary vessel, wherein locations along the at least one SMPR view are each associated with one of the CT images in the set of CT images such that a selection of a particular location along the coronary vessel in the at least one SMPR view displays the associated CT image in the cross-sectional view in the third panel; and in response to an input on the third panel indicating a first location along the selected coronary artery in the at least one SMPR view, display a cross-sectional view associated with the selected coronary artery at the first location in the third panel.

Embodiment 235: The system of embodiment 234, wherein the one or more computer hardware processors are further configured to execute the computer-executable instructions to, in response to an input on the second panel pf the user interface indicating a second location along the selected coronary artery in the at least one SMPR view, display the associated CT scan associated with the second location in a cross-sectional view in the third panel.

Embodiment 236: The system of embodiment 234, wherein the one or more computer hardware processors are further configured to execute the computer-executable instructions to: in response to a second input on the user interface indicating the selection of a second coronary vessel in the artery tree displayed in the first panel, generate and display in the second panel least a portion of the selected second coronary vessel in at least one straightened multiplanar vessel (SMPR) view, and generate and display on the third panel a cross-sectional view of the selected second coronary vessel, the cross-sectional view generated using one of the set of CT images of the selected second coronary vessel, wherein locations along the selected second coronary artery in the at least one SMPR view are each associated with one of the CT images in the set of CT images such that a selection of a particular location along the second coronary vessel in the at least one SMPR view displays the associated CT image in the cross-sectional view in the third panel.

Embodiment 237: The system of embodiment 234, wherein the one or more computer hardware processors are further configured to identify the vessel segments using a machine learning algorithm that processes the CT images prior to storing the artery information on the at least one non-transitory computer storage medium.

Embodiment 238: The system of embodiment 234, wherein the one or more computer hardware processors are further configured to execute the computer-executable instructions to generate and display on the user interface in a fourth panel a cartoon artery tree, the cartoon artery tree comprising a non-patient specific graphical representation of a coronary artery tree, and wherein in response to a selection of a vessel segment in the cartoon artery tree, a view of the selected vessel segment is displayed in a panel of the user interface in a SMPR view, and upon selection of a location of the vessel segment displayed in the SMPR view, generate and display in the user interface a panel that displays information about the selected vessel at the selected location.

Embodiment 239: The system of embodiment 238, wherein the displayed information includes information relating to stenosis and plaque of the selected vessel.

Embodiment 240: The system of embodiment 234, wherein the one or more computer hardware processors are further configured to execute the computer-executable instructions to generate and segment name labels, proximal to a respective segment on the artery tree, indicative of the name of the segment.

Embodiment 241: The system of embodiment 240, wherein the one or more computer hardware processors are further configured to execute the computer-executable instructions to, in response to an input selection of a first segment name label displayed on the user interface, generate and display on the user interface a panel having a list of vessel segment names and indicating the current name of the selected vessel segment; and in response to an input selection of a second segment name label on the list, replace the first segment name label with the second segment name label of the displayed artery tree in the user interface.

Embodiment 242: The system of embodiment 234, wherein the at least one SMPR view of the selected coronary vessel comprises at least two SMPR views of the selected coronary vessel displayed adjacently at a rotational interval.

Embodiment 243: The system of embodiment 234, wherein the at least one SMPR view include four SMPR views displayed at a relative rotation of 0°, 22.5°, 45°, and 67.5°.

Embodiment 244: The system of embodiment 234, wherein the one or more computer hardware processors are further configured to execute the computer-executable instructions to, in response to a user input, rotate the at least one SMPR view in increments of 1°.

Embodiment 245: The system of embodiment 234, wherein the artery tree, the at least one SMPR view, and the cross-sectional view are displayed concurrently on the user interface.

Embodiment 246: The system of embodiment 245, wherein the artery tree is displayed in a center portion of the user panel, the cross-sectional view is displayed in a center portion of the user interface above or below the artery tree, and the at least one SMPR view are displayed on one side of the center portion of the user interface.

Embodiment 247: The system of embodiment 246, wherein the one or more computer hardware processors are further configured to generate and display, on one side of the center portion of the user interface, one or more anatomical plane views corresponding to the selected coronary artery, the anatomical plane views of the selected coronary vessel based on the CT images Embodiment 248: The system of embodiment 247, wherein the anatomical plane views comprise three anatomical plane views.

Embodiment 249: The system of embodiment 247, wherein the anatomical plane views comprise at least one of an axial plane view, a coronal plane view, or a sagittal plane view.

Embodiment 250: The system of embodiment 234, wherein the one or more computer hardware processors are further configured to receive a rotation input on the user interface, and rotate the at least one SMPR views incrementally based on the rotation input.

Embodiment 251: The system of embodiment 234, wherein the at least one non-transitory computer storage medium is further configured to at least store vessel wall information including information indicative of the lumen and the vessel walls of the coronary artery vessels, and wherein the one or more computer hardware processors are further configured to graphically display lumen and vessel wall information corresponding to the coronary vessel displayed in the cross-sectional view in the third panel.

Embodiment 252: The system of embodiment 251, wherein and one or more computer hardware processors are further configured to display information of the lumen and the vessel wall on the user interface based on the selected portion of the coronary vessel in the at least one SMPR view.

Embodiment 253: The system of embodiment 251, wherein and one or more computer hardware processors are further configured to display information of plaque based on the selected portion of the coronary vessel in the at least one SMPR view.

Embodiment 254: The system of embodiment 251, wherein and one or more computer hardware processors are further configured to display information of stenosis based on the selected portion of the coronary vessel in the at least one SMPR view.

Embodiment 255: The system of embodiment 234, wherein the one or more computer hardware processors are further configured to execute the computer-executable instructions to generate and display on the user interface a cartoon artery tree, the cartoon artery tree being a non-patient specific graphical representation of an artery tree, wherein portions of the artery tree are displayed in a color that corresponds to a risk level.

Embodiment 256: The system of embodiment 255, wherein the risk level is based on stenosis.

Embodiment 257: The system of embodiment 255, wherein the risk level is based on a plaque.

Embodiment 258: The system of embodiment 255, wherein the risk level is based on ischemia.

Embodiment 259: The system of embodiment 255, wherein the one or more computer hardware processors are further configured to execute the computer-executable instructions to, in response to selecting a portion of the cartoon artery tree, displaying on the second panel a SMPR view of the vessel corresponding to the selected portion of the cartoon artery tree, and displaying on the third panel a cross-sectional view of corresponding to the selected portion of the cartoon artery tree.

Embodiment 269: A system comprising: means for storing computer-executable instructions, a set of computed tomography (CT) images of a patient's coronary vessels, vessel labels, and artery information associated with the set of CT images including information of stenosis, plaque, and locations of segments of the coronary vessels; and means for executing the computer-executable instructions to at least: generate and display a user interface a first panel including an artery tree comprising a three-dimensional (3D) representation of coronary vessels based on the CT images and depicting coronary vessels identified in the CT images, and depicting segment labels, the artery tree not including heart tissue between branches of the artery tree; in response to an input on the user interface indicating the selection of a coronary vessel in the artery tree in the first panel, generate and display on the user interface a second panel illustrating at least a portion of the selected coronary vessel in at least one straightened multiplanar vessel (SMPR) view; generate and display on the user interface a third panel showing a cross-sectional view of the selected coronary vessel, the cross-sectional view generated using one of the set of CT images of the selected coronary vessel, wherein locations along the at least one SMPR view are each associated with one of the CT images in the set of CT images such that a selection of a particular location along the coronary vessel in the at least one SMPR view displays the associated CT image in the cross-sectional view in the third panel; and in response to an input on the user interface indicating a first location along the selected coronary artery in the at least one SMPR view, display the associated CT scan associated with the in the cross-sectional view in the third panel.

Embodiment 261: A method for analyzing CT images and corresponding information, the method comprising: storing computer-executable instructions, a set of computed tomography (CT) images of a patient's coronary vessels, vessel labels, and artery information associated with the set of CT images including information of stenosis, plaque, and locations of segments of the coronary vessels; generating and displaying in a user interface a first panel including an artery tree comprising a three-dimensional (3D) representation of coronary vessels based on the CT images and depicting coronary vessels identified in the CT images, and depicting segment labels, the artery tree not including heart tissue between branches of the artery tree; receiving a first input indicating a selection of a coronary vessel in the artery tree in the first panel; in response to the first input, generating and displaying on the user interface a second panel illustrating at least a portion of the selected coronary vessel in at least one straightened multiplanar vessel (SMPR) view; generating and displaying on the user interface a third panel showing a cross-sectional view of the selected coronary vessel, the cross-sectional view generated using one of the set of CT images of the selected coronary vessel, wherein locations along the at least one SMPR view are each associated with one of the CT images in the set of CT images such that a selection of a particular location along the coronary vessel in the at least one SMPR view displays the associated CT image in the cross-sectional view in the third panel; receiving a second input on the user interface indicating a first location along the selected coronary artery in the at least one SMPR view; and in response to the second input, displaying the associated CT scan associated in the cross-sectional view in the third panel, wherein the method is performed by one or more computer hardware processors executing computer-executable instructions in communication stored on one or more non-transitory computer storage mediums.

Embodiment 262: The method of embodiment 261, further comprising, in response to an input on the second panel pf the user interface indicating a second location along the selected coronary artery in the at least one SMPR view, display the associated CT scan associated with the second location in a cross-sectional view in the third panel.

Embodiment 263: The method of any one of embodiments 261 and 262, further comprising: in response to a second input on the user interface indicating the selection of a second coronary vessel in the artery tree displayed in the first panel, generating and displaying in the second panel least a portion of the selected second coronary vessel in at least one straightened multiplanar vessel (SMPR) view, and generating and displaying on the third panel a cross-sectional view of the selected second coronary vessel, the cross-sectional view generated using one of the set of CT images of the selected second coronary vessel, wherein locations along the selected second coronary artery in the at least one SMPR view are each associated with one of the CT images in the set of CT images such that a selection of a particular location along the second coronary vessel in the at least one SMPR view displays the associated CT image in the cross-sectional view in the third panel.

Embodiment 264: The method of any one embodiments 261-263, further comprising generating and displaying on the user interface in a fourth panel a cartoon artery tree, the cartoon artery tree comprising a non-patient specific graphical representation of a coronary artery tree, and wherein in response to a selection of a vessel segment in the cartoon artery tree, a view of the selected vessel segment is displayed in a panel of the user interface in a SMPR view, and upon selection of a location of the vessel segment displayed in the SMPR view, generating and displaying in the user interface a panel that displays information about the selected vessel at the selected location.

Embodiment 265: The method of embodiment 264, wherein the displayed information includes information relating to stenosis and plaque of the selected vessel.

Embodiment 266: The method of any one of embodiments 261-265, further comprising generating and displaying segment name labels, proximal to a respective segment on the artery tree, indicative of the name of the segment, using the stored artery information.

Embodiment 267: The method of any one of embodiments 261-266, further comprising, in response to an input selection of a first segment name label displayed on the user interface, generating and displaying on the user interface a panel having a list of vessel segment names and indicating the current name of the selected vessel segment, and in response to an input selection of a second segment name label on the list, replacing the first segment name label with the second segment name label of the displayed artery tree in the user interface.

Embodiment 268: The method of any one of embodiments 261-267, further comprising generating and displaying a tool bar on a fourth panel of the user interface, the tool bar comprising tools to add, delete, or revise artery information displayed on the user interface.

Embodiment 269: The method of embodiment 268, wherein the tools on the toolbar include a lumen wall tool, a snap to vessel wall tool, a snap to lumen wall tool, vessel wall tool, a segment tool, a stenosis tool, a plaque overlay tool a snap to centerline tool, chronic total occlusion tool, stent tool, an exclude tool, a tracker tool, or a distance measurement tool.

Embodiment 270: The method of embodiment 268, wherein the tools on the toolbar include a lumen wall tool, a snap to vessel wall tool, a snap to lumen wall tool, vessel wall tool, a segment tool, a stenosis tool, a plaque overlay tool a snap to centerline tool, chronic total occlusion tool, stent tool, an exclude tool, a tracker tool, and a distance measurement tool.

Embodiment 271: A normalization device configured to facilitate normalization of medical images of a coronary region of a subject for an algorithm-based medical imaging analysis, the normalization device comprising: a substrate having a width, a length, and a depth dimension, the substrate having a proximal surface and a distal surface, the proximal surface adapted to be placed adjacent to a surface of a body portion of a patient; a plurality of compartments positioned within the substrate, each of the plurality of compartments configured to hold a sample of a known material, wherein: a first subset of the plurality of compartments hold samples of a contrast material with different concentrations, a second subset of the plurality of compartments hold samples of materials representative of materials to be analyzed by the algorithm-based medical imaging analysis, and a third subset of the plurality of compartments hold samples of phantom materials.

Embodiment 272: The normalization device of Embodiment 271, wherein the contrast material comprises one of iodine, Gad, Tantalum, Tungsten, Gold, Bismuth, or Ytterbium.

Embodiment 273: The normalization device of any of Embodiments 271-272, wherein the samples of materials representative of materials to be analyzed by the algorithm-based medical imaging analysis comprise at least two of calcium 1000 HU, calcium 220 HU, calcium 150 HU, calcium 130 HU, and a low attenuation (e.g., 30 HU) material.

Embodiment 274: The normalization device of any of Embodiments 271-273, wherein the samples of phantom materials comprise one more of water, fat, calcium, uric acid, air, iron, or blood.

Embodiment 275: The normalization device of any of Embodiments 271-274, further comprising one or more fiducials positioned on or in the substrate for determining the alignment of the normalization device in an image of the normalization device such that the position in the image of each of the one or more compartments in the first arrangement can be determined using the one or more fiducials.

Embodiment 276: The normalization device of any of Embodiments 271-275, wherein the substrate comprises a first layer, and at least some of the plurality of compartments are positioned in the first layer in a first arrangement.

Embodiment 277: The normalization device of Embodiment 276, wherein the substrate further comprises a second layer positioned above the first layer, and at least some of the plurality of compartments are positioned in the second layer including in a second arrangement.

Embodiment 278: The normalization device of Embodiment 277, further comprising one or more additional layers positioned above the second layer, and at least some of the plurality of compartments are positioned within the one or more additional layers.

Embodiment 279: The normalization device of any one of Embodiments 271-278, wherein at least one of the compartments is configured to be self-sealing such that the material can be injected into the self-sealing compartment and the compartment seals to contain the injected material.

Embodiment 280: The normalization device of any of Embodiments 271-279, further comprising an adhesive on the proximal surface of the substrate and configured to adhere the normalization device to the body portion patient.

Embodiment 281: The normalization device of any of Embodiments 271-280, further comprising a heat transfer material designed to transfer heat from the body portion of the patient to the material in the one or more compartments.

Embodiment 282: The normalization device of any of Embodiments 271-280, further comprising an adhesive strip having a proximal side and a distal side, the proximal side configured to adhere to the body portion, the adhesive strip including a fastener configured to removably attach to the proximal surface of the substrate.

Embodiment 283: The normalization device of Embodiment 282, wherein the fastener comprises a first part of a hook-and-loop fastener, and the first layer comprises a corresponding second part of the hook-and-loop fastener.

Embodiment 284: The normalization device of any of Embodiments 271-283, wherein substrate a flexible material to allow the substrate to conform to the shape of the body portion.

Embodiment 285: The normalization device of any of Embodiments 271-284, wherein the first arrangement includes a circular-shaped arrangements of the compartments.

Embodiment 286: The normalization device of any of Embodiments 271-284, wherein the first arrangement includes a rectangular-shaped arrangements of the compartments.

Embodiment 287: The normalization device of any of Embodiments 271-286, wherein the material in at least two compartments is the same.

Embodiment 288: The normalization device of any of Embodiments 271-287, wherein at least one of a length, a width or a depth dimension of a compartment is less than 0.5 mm.

Embodiment 289: The normalization device of any of Embodiments 271-287, wherein a width dimension the compartments is between 0.1 mm and 1 mm.

Embodiment 290: The normalization device of Embodiment 289, wherein a length dimension the compartments is between 0.1 mm and 1 mm.

Embodiment 291: The normalization device of Embodiment 290, wherein a depth dimension the compartments is between 0.1 mm and 1 mm.

Embodiment 292: The normalization device of any of Embodiments 271-287, wherein at least one of the length, width or depth dimension of a compartment is greater than 1.0 mm.

Embodiment 293: The normalization device of any of Embodiments 271-287, wherein dimensions of some or all of the compartments in the normalization device are different from each other allowing a single normalization device to have a plurality of compartments having different dimensions such that the normalization device can be used in various medical image scanning devices having different resolution capabilities.

Embodiment 294: The normalization device of any of Embodiments 271-287, wherein the normalization device includes a plurality of compartments with differing dimensions such that the normalization device can be used to determine the actual resolution capability of the scanning device.

Embodiment 295: A normalization device, comprising: a first layer having a width, length, and depth dimension, the first layer having a proximal surface and a distal surface, the proximal surface adapted to be placed adjacent to a surface of a body portion of a patient, the first layer including one or more compartments positioned in the first layer in a first arrangement, each of the one or more compartments containing a known material; and one or more fiducials for determining the alignment of the normalization device in an image of the normalization device such that the position in the image of each of the one or more compartments in the first arrangement be the determined using the one or more fiducials.

Embodiment 296: The normalization device of Embodiment 295, further comprising a second layer having a width, length, and depth dimension, the second layer having a proximal surface and a distal surface, the proximal surface adjacent to the distal surface of the first layer, the second layer including one or more compartments positioned in the second layer in a second arrangement, each of the one or more compartments of the second layer containing a known material.

Embodiment 297: The normalization device of Embodiment 296, further comprising one or more additional layers each having a width, length, and depth dimension, the one or more additional layers having a proximal surface and a distal surface, the proximal surface facing the second layer and each of the one or more layers positioned such that the second layer is between the first layer and the one or more additional layers, each of the one or more additional layers respectively including one or more compartments positioned in each respective one or more additional layers layer in a second arrangement, each of the one or more compartments of the one or more additional layers containing a known material.

Embodiment 298: The normalization device of any one of Embodiments 295-297, wherein at least one of the compartments is configured to be self-sealing such that the material can be injected into the self-sealing compartment and the compartment seals to contain the injected material.

Embodiment 299: The normalization device of Embodiment 295, further comprising an adhesive on the proximal surface of the first layer.

Embodiment 300: The normalization device of Embodiment 295, further comprising a heat transfer material designed to transfer heat from the body portion of the patient to the material in the one or more compartments.

Embodiment 301: The normalization device of Embodiment 295, further comprising an adhesive strip having a proximal side and a distal side, the proximal side configured to adhere to the body portion, the adhesive strip including a fastener configured to removably attach to the proximal surface of the first layer.

Embodiment 302: The normalization device of Embodiment 301, wherein the fastener comprises a first part of a hook-and-loop fastener, and the first layer comprises a corresponding second part of the hook-and-loop fastener.

Embodiment 303: The normalization device of Embodiment 295, wherein the normalization device comprises a flexible material to allow the normalization device to conform to the shape of the body portion.

Embodiment 304: The normalization device of Embodiment 295, wherein the first arrangement includes a circular-shaped arrangements of the compartments.

Embodiment 305: The normalization device of Embodiment 295, wherein the first arrangement includes a rectangular-shaped arrangements of the compartments.

Embodiment 306: The normalization device of Embodiment 295, wherein the material in at least two compartments of the first layer is the same.

Embodiment 307: The normalization device of any of Embodiments 296 or 297, wherein the material in at least two compartments of any of the layers is the same.

Embodiment 308: The normalization device of Embodiment 295, wherein at least one of the one or more compartments include a contrast material.

Embodiment 309: The normalization device of Embodiment 308, wherein the contrast material comprises one of iodine, Gad, Tantalum, Tungsten, Gold, Bismuth, or Ytterbium.

Embodiment 310: The normalization device of Embodiment 295, wherein at least one of the one or more compartments include a material representative of a studied variable.

Embodiment 311: The normalization device of Embodiment 309, wherein the studied variable is representative of calcium 1000 HU, calcium 220 HU, calcium 150 HU, calcium 130 HU, or a low attenuation (e.g., 30 HU) material.

Embodiment 312: The normalization device of Embodiment 295, wherein at least one of the one or more compartments include a phantom.

Embodiment 313: The normalization device of Embodiment 312, wherein the phantom comprises one of water, fat, calcium, uric acid, air, iron, or blood.

Embodiment 314: The normalization device of Embodiment 295, wherein the first arrangement includes at least one compartment that contains a contrast agent, at least one compartment that includes a studied variable and at least one compartment that includes a phantom.

Embodiment 315: The normalization device of Embodiment 295, wherein the first arrangement includes at least one compartment that contains a contrast agent and at least one compartment that includes a studied variable.

Embodiment 316: The normalization device of Embodiment 295, wherein the first arrangement includes at least one compartment that contains a contrast agent and at least one compartment that includes a phantom.

Embodiment 317: The normalization device of Embodiment 295, wherein the first arrangement includes at least one compartment that contains a studied variable and at least one compartment that includes a phantom.

Embodiment 318: The normalization device of Embodiment 271, wherein the first arrangement of the first layer includes at least one compartment that contains a contrast agent, at least one compartment that includes a studied variable and at least one compartment that includes a phantom, and the second arrangement of the second layer includes at least one compartment that contains a contrast agent, at least one compartment that includes a studied variable and at least one compartment that includes a phantom.

Embodiment 319: The normalization device of Embodiment 295, wherein at least one of the length, width or depth dimension of a compartment is less than 0.5 mm.

Embodiment 320: The normalization device of Embodiment 295, wherein the width dimension the compartments is between 0.1 mm and 1 mm.

Embodiment 321: The normalization device of Embodiment 295, wherein the length dimension the compartments is between 0.1 mm and 1 mm.

Embodiment 322: The normalization device of Embodiment 295, wherein the depth (or height) dimension the compartments is between 0.1 mm and 1 mm.

Embodiment 323: The normalization device of Embodiment 295, wherein at least one of the length, width or depth dimension of a compartment is greater than 1.0 mm.

Embodiment 324: The normalization device of any one of Embodiments 295-297, wherein the dimensions of some or all of the compartments in the normalization device are different from each other allowing a single normalization device to have a plurality of compartments having different dimension such that the normalization device can be used in various medical image scanning devices having different resolution capabilities.

Embodiment 325: The normalization device of any one of Embodiments 295-297, wherein the normalization device includes a plurality of compartments with differing dimensions such that the normalization device can be used to determine the actual resolution capability of the scanning device.

Embodiment 326: A computer-implemented method for normalizing medical images for an algorithm-based medical imaging analysis, wherein normalization of the medical images improves accuracy of the algorithm-based medical imaging analysis, the method comprising: accessing, by a computer system, a first medical image of a region of a subject and the normalization device, wherein the first medical image is obtained non-invasively, and wherein the normalization device comprises a substrate comprising a plurality of compartments, each of the plurality of compartments holding a sample of a known material; accessing, by the computer system, a second medical image of a region of a subject and the normalization device, wherein the second medical image is obtained non-invasively, and wherein the first medical image and the second medical image comprise at least one of the following: one or more first variable acquisition parameters associated with capture of the first medical image differ from a corresponding one or more second variable acquisition parameters associated with capture of the second medical image, a first image capture technology used to capture the first medical image differs from a second image capture technology used to capture the second medical image, and a first contrast agent used during the capture of the first medical image differs from a second contrast agent used during the capture of the second medical image; identifying, by the computer system, image parameters of the normalization device within the first medical image; generating a normalized first medical image for the algorithm-based medical imaging analysis based in part on the first identified image parameters of the normalization device within the first medical image; identifying, by the computer system, image parameters of the normalization device within the second medical image; and generating a normalized second medical image for the algorithm-based medical imaging analysis based in part on the second identified image parameters of the normalization device within the second medical image, wherein the computer system comprises a computer processor and an electronic storage medium.

Embodiment 327: The computer-implemented method of Embodiment 326, wherein the algorithm-based medical imaging analysis comprises an artificial intelligence or machine learning imaging analysis algorithm, and wherein the artificial intelligence or machine learning imaging analysis algorithm was trained using images that included the normalization device.

Embodiment 328: The computer-implemented method of any of Embodiments 326-327, wherein the first medical image and the second medical image each comprise a CT image and the one or more first variable acquisition parameters and the one or more second variable acquisition parameters comprise one or more of a kilovoltage (kV), kilovoltage peak (kVp), a milliamperage (mA), or a method of gating.

Embodiment 329: The computer-implemented method of Embodiment 328, wherein the method of gating comprises one of prospective axial triggering, retrospective ECG helical gating, and fast pitch helical.

Embodiment 330: The computer-implemented method of any of Embodiments 326-329, wherein the first image capture technology and the second image capture technology each comprise one of a dual source scanner, a single source scanner, Dual source vs. single source scanners dual energy, monochromatic energy, spectral CT, photon counting, and different detector materials.

Embodiment 331: The computer-implemented method of any of Embodiments 326-330, wherein the first contrast agent and the second contrast agent each comprise one of an iodine contrast of varying concentration or a non-iodine contrast agent.

Embodiment 332: The computer-implemented method of any of Embodiments 326-327, wherein the first image capture technology and the second image capture technology each comprise one of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

Embodiment 333: The computer-implemented method of any of Embodiments 326-332, wherein a first medical imager that captures the first medical imager is different than a second medical image that capture the second medical image.

Embodiment 334: The computer-implemented method of any of Embodiments 326-333, wherein the subject of the first medical image is different than the subject of the first medical image.

Embodiment 335: The computer-implemented method of any of Embodiments 326-333, wherein the subject of the first medical image is the same as the subject of the second medical image.

Embodiment 336: The computer-implemented method of any of Embodiments 326-333, wherein the subject of the first medical image is different than the subject of the second medical image.

Embodiment 337: The computer-implemented method of any of Embodiments 326-336, wherein the capture of the first medical image is separated from the capture of the second medical image by at least one day.

Embodiment 338: The computer-implemented method of any of Embodiments 326-337, wherein the capture of the first medical image is separated from the capture of the second medical image by at least one day.

Embodiment 339: The computer-implemented method of any of Embodiments 326-338, wherein a location of the capture of the first medical image is geographically separated from a location of the capture of the second medical image.

Embodiment 340: The computer-implemented method of any of Embodiments 326-339, wherein the normalization device comprises the normalization device of any of Embodiments 271-325.

Embodiment 340: The computer-implemented method of any of Embodiments 326-339, wherein the normalization device comprises the normalization device of any of Embodiments 271-325.

Embodiment 341: The computer-implemented method of any of Embodiments 326-340, wherein the region of the subject comprises a coronary region of the subject.

Embodiment 342: The computer-implemented method of any of Embodiments 326-341, wherein the region of the subject comprises one or more coronary arteries of the subject.

Embodiment 343: The computer-implemented method of any of Embodiments 326-340, wherein the region of the subject comprises one or more of carotid arteries, renal arteries, abdominal aorta, cerebral arteries, lower extremities, or upper extremities of the subject.

OTHER EMBODIMENT(S)

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present.

What is claimed is:

1. A computer-implemented method of tracking a plaque-based disease based on non-invasive medical image analysis of a medical image of a coronary artery region of a subject to determine a state of plaque progression of the subject, the method comprising:
  accessing, by a computer system, a first set of plaque parameters and a first set of vascular parameters associated with a coronary artery region of a subject, wherein the first set of plaque parameters and the first set of vascular parameters are derived from a first medical image of the coronary artery region of the subject comprising one or more regions of plaque, wherein the first medical image of the coronary artery region of the subject is obtained non-invasively at a first point in time, wherein the first set of plaque parameters comprises a ratio or function of volume or surface area, heterogeneity index, geometry, location and density of the one or more regions of plaque at the first point in time, and wherein the first set of vascular parameters comprises one or more measures of narrowing or remodeling of a vasculature at the first point in time;
  generating, by the computer system, a first weighted measure of the accessed first set of plaque parameters and the first set of vascular parameters;
  accessing, by the computer system, a second medical image of the coronary artery region of the subject, wherein the second medical image of the coronary artery region of the subject is obtained non-invasively at a second point in time, the second point in time being later than the first point in time, wherein the second medical image of the coronary artery region of the subject comprises the one or more regions of plaque;
  identifying, by the computer system, the one or more regions of plaque from the second medical image;
  determining, by the computer system, a second set of plaque parameters and a second set of vascular parameters associated with the coronary artery region of the subject by analyzing the one or more regions of plaque from the second medical image, wherein the second set of plaque parameters comprises a ratio or function of volume or surface area, heterogeneity index, geometry, location, and density of the one or more regions of plaque at the second point in time, and wherein the second set of vascular parameters comprises one or more measures of narrowing or remodeling of the vasculature at the second point in time;
  generating, by the computer system, a second weighted measure of the determined second set of plaque parameters and the second set of vascular parameters;
  analyzing, by the computer system, a change between the first weighted measure of the accessed first set of plaque parameters and the first set of vascular parameters and the second weighted measure of the determined second set of plaque parameters and the second set of vascular parameters;
  determining, by the computer system, a state of plaque progression associated with a plaque-based disease for the subject based at least in part on the analyzed change between the first weighted measure of the accessed first set of plaque parameters and the first set of vascular parameters and the second weighted measure of the determined second set of plaque parameters and the second set of vascular parameters, wherein the determined state of plaque progression comprises one of rapid plaque progression, non-rapid calcium dominant mixed response progression, non-rapid non-calcium dominant mixed response progression, or plaque regression; and
  tracking, by the computer system, progression of the plaque-based disease based at least in part on the determined state of plaque progression,
  wherein the computer system comprises a computer processor and an electronic storage medium.

2. The computer-implemented method of claim 1, wherein the heterogeneity index of the one or more regions of plaque is determined by generating a spatial mapping of density values within the one or more regions of plaque.

3. The computer-implemented method of claim 1, wherein the heterogeneity index of the one or more regions of plaque is determined by generating a three-dimensional histogram of density values within a geometric shape of the one or more regions of plaque.

4. The computer-implemented method of claim 1, wherein the density of the one or more regions of plaque comprises one or more of radiodensity or absolute material density of the one or more regions of plaque.

5. The computer-implemented method of claim 1, further comprising:
  accessing, by the computer system, a third medical image of the coronary artery region of the subject, wherein the third medical image of the coronary artery region of the subject is obtained non-invasively at a third point in time, the third point in time being later than the second point in time, wherein the third medical image of the coronary artery region of the subject comprises the one or more regions of plaque;
  identifying, by the computer system, the one or more regions of plaque from the third medical image;
  determining, by the computer system, a third set of plaque parameters and a third set of vascular parameters associated with the coronary artery region of the subject by analyzing the one or more regions of plaque from the third medical image, wherein the third set of plaque parameters comprises a ratio or function of volume or surface area, heterogeneity index, geometry, location and density of the one or more regions of plaque at the third point in time, and wherein the third set of vascular parameters comprises one or more measures of narrowing or remodeling of the vasculature at the third point in time;

generating, by the computer system, a third weighted measure of the determined third set of plaque parameters and the third set of vascular parameters;

analyzing, by the computer system, a change between the second weighted measure of the accessed second set of plaque parameters and the second set of vascular parameters and the third weighted measure of the determined third set of plaque parameters and the third set of vascular parameters;

determining, by the computer system, an updated state of plaque progression associated with the plaque-based disease for the subject based at least in part on the analyzed change between the second weighted measure of the accessed second set of plaque parameters and the second set of vascular parameters and the third weighted measure of the determined third set of plaque parameters and the third set of vascular parameters, wherein the determined state of plaque progression comprises one of rapid plaque progression, non-rapid calcium dominant mixed response progression, non-rapid non-calcium dominant mixed response progression, or plaque regression; and tracking, by the computer system, progression of the plaque-based disease based at least in part on the determined updated state of plaque progression.

6. The computer-implemented method of claim 1, wherein the state of plaque progression is determined as rapid plaque progression when a percent atheroma volume increase of the subject is more than 1% per year, wherein the state of plaque progression is determined as non-rapid calcium dominant mixed response when a percent atheroma volume increase of the subject is less than 1% per year and calcified plaque represents more than 50% of total new plaque formation, wherein the state of plaque progression is determined as non-rapid non-calcium dominant mixed response when a percent atheroma volume increase of the subject is less than 1% per year and non-calcified plaque represents more than 50% of total new plaque formation, and wherein the state of plaque progression is determined as plaque regression when a decrease in total percent atheroma volume is present.

7. The computer-implemented method of claim 1, further comprising generating, by the computer system, a proposed treatment for the subject based at least in part on one or more of the determined state of plaque progression of the plaque-based disease or the tracked progression of the plaque-based disease.

8. The computer-implemented method of claim 1, wherein the medical image comprises a Computed Tomography (CT) image.

9. The computer-implemented method of claim 8, wherein the medical image comprises a non-contrast CT image.

10. The computer-implemented method of claim 1, wherein the state of plaque progression is further determined based at least in part on one or more of a percentage of higher radiodensity plaque or lower radiodensity plaque within the one or more regions of plaque, wherein the higher radiodensity plaque comprises pixels with a Hounsfield unit of above 1000, and wherein lower radiodensity plaque comprises pixels with a Hounsfield unit of below 1000.

11. The computer-implemented method of claim 1, wherein the medical image is obtained using an imaging technique comprising one or more of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

12. The computer-implemented method of claim 1, wherein the plaque-based disease comprises one or more of atherosclerosis, stenosis, or ischemia.

13. The computer-implemented method of claim 1, further comprising:

determining, by the computer system, a first Coronary Artery Disease Reporting & Data System (CAD-RADS) classification score of the subject at the first point in time based at least in part on one or more of the first set of plaque parameters;

determining, by the computer system, a second CAD-RADS classification score of the subject at the second point in time based at least in part on one or more of the second set of plaque parameters; and tracking, by the computer system, progression of a CAD-RADS classification score of the subject over time based on comparing the first CAD-RADS classification score and the second CAD-RADS classification score.

14. The computer-implemented method of claim 1, wherein the plaque-based disease is further tracked by analyzing one or more of serum biomarkers, genetics, transcriptomics, microbiomics, metabolomics, omic markers, biometric markers, or clinical parameters.

15. The computer-implemented method of claim 1, wherein the first set of plaque parameters and the second set of plaque parameters further comprise a ratio of radiodensity to volume of the one or more regions of plaque.

16. The computer-implemented method of claim 1, wherein the first set of plaque parameters and the second set of plaque parameters further comprise a diffuseness of the one or more regions of plaque.

17. The computer-implemented method of claim 1, wherein the first set of plaque parameters and the second set of plaque parameters comprise a percentage composition of plaque comprising different radiodensity values.

18. The computer-implemented method of claim 1, wherein the first set of plaque parameters and the second set of plaque parameters further comprise a percentage composition of plaque comprising different radiodensity values as a function of volume of plaque.

19. A computer-implemented method of tracking a plaque-based disease based on non-invasive medical image analysis of a medical image of a subject to determine a state of plaque progression of the subject, the method comprising:

accessing, by a computer system, a first set of plaque parameters and a first set of vascular parameters associated with a subject, wherein the first set of plaque parameters and the first set of vascular parameters are derived from a first medical image of the subject comprising one or more regions of plaque, wherein the first medical image of the subject is obtained non-invasively at a first point in time, wherein the first set of plaque parameters comprises a volume, surface area, heterogeneity index, geometry, location and density of one or more regions of plaque from the medical image of the subject at the first point in time, and wherein the first set of vascular parameters comprises one or more measures of narrowing or remodeling of a vasculature at the first point in time;

generating, by the computer system, a first weighted measure of the accessed first set of plaque parameters and the first set of vascular parameters;

accessing, by the computer system, a second medical image of the subject, wherein the second medical image of the subject is obtained non-invasively at a second point in time, the second point in time being later than the first point in time, wherein the second medical image of the subject comprises the one or more regions of plaque;

identifying, by the computer system, the one or more regions of plaque from the second medical image;

determining, by the computer system, a second set of plaque parameters and a second of vascular parameters associated with the subject by analyzing the one or more regions of plaque from the second medical image, wherein the second set of plaque parameters comprises a volume, surface area, heterogeneity index, geometry, location and density of the one or more regions of plaque at the second point in time, and wherein the second set of vascular parameters comprises one or more measures of narrowing or remodeling of the vasculature at the second point in time;

generating, by the computer system, a second weighted measure of the determined second set of plaque parameters and the second set of vascular parameters;

analyzing, by the computer system, a change between the first weighted measure of the accessed first set of plaque parameters and the first set of vascular parameters and the second weighted measure of the determined second set of plaque parameters and the second set of vascular parameters;

determining, by the computer system, a state of plaque progression associated with a plaque-based disease for the subject based at least in part on the analyzed change between the first weighted measure of the accessed first set of plaque parameters and the first set of vascular parameters and the second weighted measure of the determined second set of plaque parameters and the second set of vascular parameters, wherein the determined state of plaque progression comprises one or more of rapid plaque progression, non-rapid plaque progression, plaque stabilization, plaque destabilization, or plaque regression; and tracking, by the computer system, progression of the plaque-based disease based at least in part on the determined state of plaque progression, wherein the computer system comprises a computer processor and an electronic storage medium.

20. The computer-implemented method of claim 19, wherein the heterogeneity index of the one or more regions of plaque is determined by generating a spatial mapping of density within the one or more regions of plaque.

21. The computer-implemented method of claim 19, wherein the heterogeneity index of the one or more regions of plaque is determined by generating a three-dimensional histogram of density within a geometric shape of the one or more regions of plaque.

22. The computer-implemented method of claim 19, wherein the state of plaque progression is further determined based at least in part on an increase or decrease in density of the one or more regions of plaque between the first point in time and the second point in time, wherein increase in density of the one or more regions of plaque is indicative of plaque stabilization, and wherein decrease in density of the one or more regions of plaque is indicative of plaque destabilization.

23. The computer-implemented method of claim 19, wherein the state of plaque progression is determined as rapid plaque progression when the volume of the one or more regions of plaque is increased by more than 20% between the first point in time and the second point in time, wherein the state of plaque progression is determined as non-rapid plaque progression when the volume of the one or more regions of plaque is increased by less than 20% between the first point in time and the second point in time, and wherein the state of plaque progression is determined as plaque regression when the volume of the one or more regions of plaque is decreased between the first point in time and the second point in time.

24. The computer-implemented method of claim 19, further comprising generating, by the computer system, a proposed treatment for the subject based at least in part on one or more of the determined state of plaque progression of the plaque-based disease or the tracked progression of the plaque-based disease.

25. The computer-implemented method of claim 19, wherein the medical image of the subject comprises a coronary artery region of the subject.

26. The computer-implemented method of claim 19, wherein the medical image of the subject comprises one or more of carotid arteries, renal arteries, abdominal aorta, cerebral arteries, lower extremities, or upper extremities.

27. The computer-implemented method of claim 19, wherein the medical image comprises a Computed Tomography (CT) image.

28. The computer-implemented method of claim 19, wherein the medical image is obtained using an imaging technique comprising one or more of CT, x-ray, ultrasound, echocardiography, intravascular ultrasound (IVUS), MR imaging, optical coherence tomography (OCT), nuclear medicine imaging, positron-emission tomography (PET), single photon emission computed tomography (SPECT), or near-field infrared spectroscopy (NIRS).

29. A system for tracking a plaque-based disease based on non-invasive medical image analysis of a medical image of a subject to determine a state of plaque progression of the subject, the system comprising:

one or more computer readable storage devices configured to store a plurality of computer executable instructions; and one or more hardware computer processors in communication with the one or more computer readable storage devices and configured to execute the plurality of computer executable instructions in order to cause the system to:

access a first set of plaque parameters and a first set of vascular parameters associated with a subject, wherein the first set of plaque parameters and the first set of vascular parameters are derived from a first medical image of the subject comprising one or more regions of plaque, wherein the first medical image of the subject is obtained non-invasively at a first point in time, wherein the first set of plaque parameters comprises one or more of a gradient or mathematical transformation of volume or surface area, heterogeneity index, geometry, location or density of one or more regions of plaque from the medical image of the subject at the first point in time, and wherein the first set of vascular parameters comprises one or more measures of narrowing or remodeling of a vasculature at the first point in time;

generate a first weighted measure of the accessed first set of plaque parameters and the first set of vascular parameters;

access a second medical image of the subject, wherein the second medical image of the subject is obtained non-invasively at a second point in time, the second point in time being later than the first point in time, wherein the second medical image of the subject comprises the one or more regions of plaque;

identify the one or more regions of plaque from the second medical image;

determine a second set of plaque parameters and a second set of vascular parameters associated with the subject by analyzing the one or more regions of plaque from the second medical image, wherein the second set of plaque parameters comprises one or more of a gradient or mathematical transformation of volume and surface area, heterogeneity index, geometry, location or density of the one or more regions of plaque at the second point in time, and wherein the second set of vascular parameters comprises one or more measures of narrowing or remodeling of the vasculature at the second point in time;

generate a second weighted measure of the determined second set of plaque parameters and the second set of vascular parameters;

analyze a change between the first weighted measure of the accessed first set of plaque parameters and the first set of vascular parameters and the second weighted measure of the determined second set of plaque parameters and the second set of vascular parameters;

determine a state of plaque progression associated with a plaque-based disease for the subject based at least in part on the analyzed change between the first weighted measure of the accessed first set of plaque parameters and the first set of vascular parameters and the second weighted measure of the determined second set of plaque parameters and the second set of vascular parameters, wherein the determined state of plaque progression comprises one or more of increase in plaque density, decrease in plaque density, stabilization of plaque density, increase in vascular size, decrease in vascular size, or stabilization of vascular size; and track progression of the plaque-based disease based at least in part on the determined state of plaque progression.

30. The system of claim 29, wherein the heterogeneity index of the one or more regions of plaque is determined by generating a spatial mapping of density within the one or more regions of plaque.

* * * * *

UNITED STATES PATENT AND TRADEMARK OFFICE
CERTIFICATE OF CORRECTION

| | | |
|---|---|---|
| PATENT NO. | : 11,094,060 B1 | Page 1 of 7 |
| APPLICATION NO. | : 17/213966 | |
| DATED | : August 17, 2021 | |
| INVENTOR(S) | : James K. Min | |

It is certified that error appears in the above-identified patent and that said Letters Patent is hereby corrected as shown below:

On the Title Page

On page 3, in Column 2, item (56), Other Publications, Line 10, delete "vunerability" and insert --vulnerability--.

On page 3, in Column 2, item (56), Other Publications, Line 13, delete "JACCL" and insert --JACC--.

On page 3, in Column 2, item (56), Other Publications, Line 26, delete "Amercan Heart Assocation," and insert --American Heart Association,--.

On page 3, in Column 2, item (56), Other Publications, Line 34, delete "Predictiong" and insert --Predicting--.

On page 3, in Column 2, item (56), Other Publications, Line 43, delete "Halftsone" and insert --Halftone--.

On page 4, in Column 1, item (56), Other Publications, Line 11, delete "professinals" and insert --professionals--.

On page 4, in Column 1, item (56), Other Publications, Line 59, delete "Quantatitive" and insert --Quantitative--.

On page 4, in Column 2, item (56), Other Publications, Line 1, delete "Quantitiative" and insert --Quantitative--.

On page 4, in Column 2, item (56), Other Publications, Line 9, delete "Instanteous" and insert --Instantaneous--.

On page 4, in Column 2, item (56), Other Publications, Line 13, delete "Franctional" and insert --Fractional--.

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,094,060 B1

On page 4, in Column 2, item (56), Other Publications, Line 17, delete "invasice" and insert --invasive--.

On page 4, in Column 2, item (56), Other Publications, Line 31, delete "Statble" and insert --Stable--.

On page 5, in Column 1, item (56), Other Publications, Line 6, delete "2016." and insert --2016].--.

On page 5, in Column 1, item (56), Other Publications, Line 9, delete "Progostic" and insert --Prognostic--.

On page 5, in Column 1, item (56), Other Publications, Line 15, delete "clas" and insert --class--.

On page 5, in Column 1, item (56), Other Publications, Line 34, delete "(AIRC)" and insert --(ARIC)--.

On page 5, in Column 1, item (56), Other Publications, Line 53, delete "ariability" and insert --variability--.

On page 5, in Column 2, item (56), Other Publications, Line 4, delete "Quantitiative" and insert --Quantitative--.

On page 5, in Column 2, item (56), Other Publications, Line 20, delete "(Progession" and insert --(Progression--.

On page 5, in Column 2, item (56), Other Publications, Line 27, delete "Progession" and insert --Progression--.

On page 6, in Column 1, item (56), Other Publications, Line 22, delete "Evalution" and insert --Evaluation--.

On page 6, in Column 1, item (56), Other Publications, Line 31, delete "2013;34(35:" and insert --2013; 34 (35):--.

On page 6, in Column 1, item (56), Other Publications, Line 58, delete "indentification" and insert --identification--.

On page 6, in Column 2, item (56), Other Publications, Line 45, delete "Tomorgraphy" and insert --Tomography--.

On page 6, in Column 2, item (56), Other Publications, Line 49, delete "Toogr," and insert --Tomogr,--.

On page 6, in Column 2, item (56), Other Publications, Line 51, delete "plaqie" and insert --plaque--.

On page 6, in Column 2, item (56), Other Publications, Line 54, delete "Reproductibility" and insert --Reproducibility--.

On page 7, in Column 1, item (56), Other Publications, Line 18, delete "departement."" and insert --department."--.

On page 7, in Column 1, item (56), Other Publications, Line 28, delete "Three-Dimentional" and insert --Three-Dimensional--.

On page 7, in Column 1, item (56), Other Publications, Line 29, delete "Transactons" and insert --Transactions--.

On page 7, in Column 1, item (56), Other Publications, Line 38, delete "Circuliation," and insert --Circulation,--.

On page 7, in Column 1, item (56), Other Publications, Line 62, delete "JAAC" and insert --JACC--.

On page 7, in Column 2, item (56), Other Publications, Line 6, delete "Heatlh" and insert --Health--.

On page 7, in Column 2, item (56), Other Publications, Line 11, delete "stucy" and insert --study--.

On page 7, in Column 2, item (56), Other Publications, Line 58, delete "diseae" and insert --disease--.

On page 7, in Column 2, item (56), Other Publications, Line 62, delete "hemorrage."" and insert --hemorrhage."--.

On page 8, in Column 1, item (56), Other Publications, Line 2, delete "progession" and insert --progression--.

On page 8, in Column 1, item (56), Other Publications, Line 7, delete "Chracteristics" and insert --Characteristics--.

On page 8, in Column 2, item (56), Other Publications, Line 2, delete "Imaging)" and insert --Imaging--.

On page 8, in Column 2, item (56), Other Publications, Line 4, delete "quanititive" and insert --quantitative--.

On page 8, in Column 2, item (56), Other Publications, Line 10, delete "Cardiocascular" and insert --Cardiovascular--.

In the Drawings

In sheet 3 of 66, FIG. 2B, reference numeral 242, Line 1, delete "Second" and insert --2$^{nd}$--.

In sheet 56 of 66, FIG. 10, reference numeral 1020, Line 4, after "multiplanar" insert --reformat--.

CERTIFICATE OF CORRECTION (continued)
U.S. Pat. No. 11,094,060 B1

In the Specification

In Column 5, Line 42, after "multiplanar" insert --reformat--.

In Column 6, Line 48, delete "a the" and insert --the--.

In Column 8, Line 62, after "multiplanar" insert --reformat--.

In Column 9, Line 36, delete "7 AB" and insert --7AB--.

In Column 9, Line 64, delete "(e.g.," and insert --e.g.,--.

In Column 11, Line 49, delete "Tillable" and insert --fillable--.

In Column 11, Line 56, delete "121" and insert --12I--.

In Column 22, Line 45, after "or" insert --more--.

In Column 29, Line 13, delete "icosopent" and insert --icosapent--.

In Column 29, Line 15, delete "rivoroxaban" and insert --rivaroxaban--.

In Column 40, Line 1, delete ">vs." and insert --> vs.--.

In Column 61, Line 25, delete "two dimensional" and insert --two-dimensional--.

In Column 61, Line 27, delete "three dimensional" and insert --three-dimensional--.

In Column 62, Line 60, delete ""la")" and insert --"1a")--.

In Column 63, Line 2, after "multiplanar" insert --reformat--.

In Column 63, Line 5, after "multiplanar" insert --reformat--.

In Column 63, Line 43, delete "(e.g.," and insert --e.g.,--.

In Columns 65-66, Line 38 (approx.), table, delete "LUMEN" and insert --LUMEN.--.

In Columns 65-66, Line 41 (approx.), table, delete "AREAS" and insert --AREAS.--.

In Columns 65-66, Line 43 (approx.), table, delete "EXTEROR" and insert --EXTERIOR--.

In Columns 65-66, Line 43 (approx.), table, delete "WALL" and insert --WALL.--.

In Columns 65-66, Line 44 (approx.), table, delete "SHADEID" and insert --SHADED--.

CERTIFICATE OF CORRECTION (continued)
U.S. Pat. No. 11,094,060 B1

In Columns 65-66, Line 46 (approx.), table, delete "AREAS" and insert --AREAS.--.

In Columns 65-66, Line 55 (approx.), table, delete "CROSS SECTION" and insert --CROSS-SECTION--.

In Columns 65-66, Line 57 (approx.), table, delete "ATTENUATION" and insert --ATTENUATION.--.

In Columns 65-66, Line 63 (approx.), table, delete "ISTOTALLY" and insert --IS TOTALLY--.

In Columns 65-66, Line 66 (approx.), table, delete "CORNARY" and insert --CORONARY--.

In Columns 67-68, Line 8 (approx.), table, delete "SAGITIAL," and insert --SAGITTAL,--.

In Columns 67-68, Line 13 (approx.), table, delete "INTEREST" and insert --INTEREST.--.

In Column 67, Line 45, delete "(e.g.," and insert --e.g.,--.

In Column 68, Line 39, delete "Figure" and insert --FIG.--.

In Column 69, Line 1, after "multiplanar" insert --reformat--.

In Column 70, Line 7, delete "quantification." and insert --quantification,--.

In Column 71, Line 27, delete "of the of the" and insert --of the--.

In Column 71, Line 47, after "multiplanar" insert --reformat--.

In Column 71, Line 49, after "multiplanar" insert --reformat--.

In Column 73, Line 11 (approx.), delete "percentage" and insert --percentage.--.

In Column 73, Line 51, delete "805a-855r" and insert --805a-805r--.

In Column 74, Line 12 (approx.), delete "(CT))" and insert --(CT)--.

In Column 74, Line 35 (approx.), delete ""hovers"" and insert --"hovers"--.

In Column 76, Line 50, delete "(e.g.," and insert --e.g.,--.

In Column 77, Line 11, after "multiplanar" insert --reformat--.

In Column 77, Line 30, delete "1030," and insert --1035,--.

In Column 80, Line 48, after "be" delete "not".

CERTIFICATE OF CORRECTION (continued)
U.S. Pat. No. 11,094,060 B1

In Column 80, Line 49, delete "non linear" and insert --non-linear--.

In Column 82, Line 15, delete "121," and insert --12I,--.

In Column 82, Line 63, delete "in" and insert --In--.

In Column 85, Line 18, delete "121" and insert --12I--.

In Column 86, Line 50, delete "2X" and insert --2×--.

In Column 87, Line 48, delete "MM" and insert --MRI--.

In Column 88, Line 3, delete "(thickness," and insert --thickness,--.

In Column 88, Line 15, delete "(thickness," and insert --thickness,--.

In Column 92, Line 24, delete "PYPHON" and insert --PYTHON--.

In Column 92, Line 27, delete "Python." and insert --PYTHON.--.

In Column 107, Line 60, delete "Disease Reporting" and insert --Disease-Reporting--.

In Column 111, Line 48, delete "Disease Reporting" and insert --Disease-Reporting--.

In Column 114, Line 46, delete "plaque" and insert --plaque.--.

In Column 121, Line 23, after "multiplanar" insert --reformat--.

In Column 121, Line 54, after "multiplanar" insert --reformat--.

In Column 122, Line 67, delete "images" and insert --images.--.

In Column 123, Line 60, delete "269:" and insert --260:--.

In Column 124, Line 10, after "multiplanar" insert --reformat--.

In Column 124, Line 41, after "multiplanar" insert --reformat--.

In Column 125, Line 4, after "multiplanar" insert --reformat--.

In Column 125, Line 15, after "one" insert --of--.

In Column 127, Line 27, after "dimension" insert --of--.

In Column 127, Line 30, after "dimension" insert --of--.

CERTIFICATE OF CORRECTION (continued)
U.S. Pat. No. 11,094,060 B1

In Column 127, Line 33, after "dimension" insert --of--.

In Column 129, Line 46, after "dimension" insert --of--.

In Column 129, Line 49, after "dimension" insert --of--.

In Column 129, Line 52, after "dimension" insert --of--.

In the Claims

In Column 136, Line 9, Claim 13, delete "Disease Reporting" and insert --Disease-Reporting--.

In Column 137, Line 8, Claim 19, after "second" insert --set--.